(12) United States Patent
Hartwell et al.

(10) Patent No.: US 11,344,665 B2
(45) Date of Patent: May 31, 2022

(54) COLLAPSIBLE DRESSING FOR NEGATIVE PRESSURE WOUND TREATMENT

(71) Applicant: Smith & Nephew PLC, Watford (GB)

(72) Inventors: Edward Yerbury Hartwell, Hull (GB); Varuni Rachindra Brownhill, Swanland (GB); John Gowans, York (GB)

(73) Assignee: Smith & Nephew PLC, Watford (GB)

( * ) Notice: Subject to any disclaimer, the term of this patent is extended or adjusted under 35 U.S.C. 154(b) by 170 days.

(21) Appl. No.: 16/265,738

(22) Filed: Feb. 1, 2019

(65) Prior Publication Data

US 2019/0240385 A1 Aug. 8, 2019

Related U.S. Application Data

(63) Continuation of application No. 15/113,404, filed as application No. PCT/EP2015/050963 on Jan. 20, 2015, now Pat. No. 10,201,642.
(Continued)

(51) Int. Cl.
*A61M 1/00* (2006.01)
*A61F 13/00* (2006.01)
(Continued)

(52) U.S. Cl.
CPC .......... *A61M 1/90* (2021.05); *A61F 13/00059* (2013.01); *A61F 13/00068* (2013.01);
(Continued)

(58) Field of Classification Search
CPC ............ A61M 1/00; A61M 5/00; A61M 5/32; A61M 25/00; A61M 35/00; A61M 5/178;
(Continued)

(56) References Cited

U.S. PATENT DOCUMENTS 3,194,239 A 7/1965 Sullivan
3,789,851 A 2/1974 Leveen
(Continued)

FOREIGN PATENT DOCUMENTS

AU 2012261793 B2 11/2014
AU 2013206230 B2 5/2016
(Continued)

OTHER PUBLICATIONS

"Definition of Oculiform," Webster's Revised Unabridged Dictionary, accessed from The Free Dictionary on May 30, 2018 from URL: https://www.thefreedictionary.com/Oculiform, 1913, 1 page.
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

Embodiments disclosed herein are directed to negative pressure treatment systems and wound dressing systems, apparatuses, and methods that may be used for the treatment of wounds. In particular, some embodiments are directed to improved wound dressings comprising an obscuring layer that may hide fluid contained therein and a stabilizing structure that may aid in wound closure.

17 Claims, 91 Drawing Sheets

Related U.S. Application Data

(60) Provisional application No. 61/929,870, filed on Jan. 21, 2014.

(51) Int. Cl.
| | |
|---|---|
| *A61F 13/02* | (2006.01) |
| *A61M 5/00* | (2006.01) |
| *A61M 5/32* | (2006.01) |
| *A61M 25/00* | (2006.01) |
| *A61M 35/00* | (2006.01) |
| *A61M 5/178* | (2006.01) |
| *A61F 7/00* | (2006.01) |
| *B32B 3/12* | (2006.01) |

(52) U.S. Cl.
CPC ........ *A61F 13/022* (2013.01); *A61F 13/0206* (2013.01); *A61F 13/0209* (2013.01); *A61F 13/0216* (2013.01); *A61F 13/0223* (2013.01); *A61F 2013/00182* (2013.01); *B32B 3/12* (2013.01)

(58) Field of Classification Search
CPC ...... A61F 13/00; A61F 7/00; A61F 13/00059; A61F 13/00068; A61F 13/0206; A61F 13/0209; A61F 13/0216; A61F 13/022; A61F 13/0223; A61F 2013/00182
See application file for complete search history.

(56) References Cited

U.S. PATENT DOCUMENTS

| | | | |
|---|---|---|---|
| 4,467,805 A | 8/1984 | Fukuda |
| 4,608,041 A | 8/1986 | Nielsen |
| 4,699,134 A | 10/1987 | Samuelsen |
| 4,815,468 A | 3/1989 | Annand |
| 5,176,663 A | 1/1993 | Svedman et al. |
| 5,264,218 A | 11/1993 | Rogozinski |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 5,960,497 A | 10/1999 | Castellino et al. |
| 6,080,168 A | 6/2000 | Levin et al. |
| 6,086,591 A | 7/2000 | Bojarski |
| 6,142,982 A | 11/2000 | Hunt et al. |
| 6,176,868 B1 | 1/2001 | Detour |
| 6,503,208 B1 | 1/2003 | Skovlund |
| 6,548,727 B1 | 4/2003 | Swenson |
| 6,553,998 B2 | 4/2003 | Heaton et al. |
| 6,566,575 B1 | 5/2003 | Stickels et al. |
| 6,685,681 B2 | 2/2004 | Lockwood et al. |
| 6,695,823 B1 | 2/2004 | Lina et al. |
| 6,712,830 B2 | 3/2004 | Esplin |
| 6,767,334 B1 | 7/2004 | Randolph |
| 6,770,794 B2 | 8/2004 | Fleischmann |
| 6,787,682 B2 | 9/2004 | Gilman |
| 6,893,452 B2 | 5/2005 | Jacobs |
| 6,936,037 B2 | 8/2005 | Bubb et al. |
| 6,951,553 B2 | 10/2005 | Bubb et al. |
| 6,977,323 B1 | 12/2005 | Swenson |
| 6,994,702 B1 | 2/2006 | Johnson |
| 7,004,915 B2 | 2/2006 | Boynton et al. |
| 7,025,755 B2 | 4/2006 | Epstein et al. |
| 7,070,584 B2 | 7/2006 | Johnson et al. |
| 7,128,735 B2 | 10/2006 | Weston et al. |
| 7,144,390 B1 | 12/2006 | Hannigan et al. |
| 7,153,312 B1 | 12/2006 | Torrie et al. |
| 7,156,862 B2 | 1/2007 | Jacobs et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| D544,092 S | 6/2007 | Lewis |
| 7,262,174 B2 | 8/2007 | Jiang et al. |
| 7,279,612 B1 | 10/2007 | Heaton et al. |
| 7,315,183 B2 | 1/2008 | Hinterscher |
| 7,351,250 B2 | 4/2008 | Zamierowski |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,413,571 B2 | 8/2008 | Zamierowski |
| 7,438,705 B2 | 10/2008 | Karpowicz et al. |
| 7,494,482 B2 | 2/2009 | Orgill et al. |
| 7,534,240 B1 | 5/2009 | Johnson |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,612,248 B2 | 11/2009 | Burton et al. |
| 7,615,036 B2 | 11/2009 | Joshi et al. |
| 7,618,382 B2 | 11/2009 | Vogel et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,678,102 B1 | 3/2010 | Heaton |
| 7,683,667 B2 | 3/2010 | Kim et al. |
| 7,699,823 B2 | 4/2010 | Haggstrom et al. |
| 7,699,830 B2 | 4/2010 | Martin et al. |
| 7,699,831 B2 | 4/2010 | Bengtson et al. |
| 7,700,819 B2 | 4/2010 | Ambrosio et al. |
| 7,708,724 B2 | 5/2010 | Weston et al. |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,754,937 B2 | 7/2010 | Boehringer et al. |
| 7,776,028 B2 | 8/2010 | Miller et al. |
| 7,777,522 B2 | 8/2010 | Yang et al. |
| 7,779,625 B2 | 8/2010 | Joshi et al. |
| 7,815,616 B2 | 10/2010 | Boehringer et al. |
| 7,846,141 B2 | 12/2010 | Weston |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston et al. |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 8,030,534 B2 | 10/2011 | Radl et al. |
| 8,057,447 B2 | 11/2011 | Olson et al. |
| 8,062,272 B2 | 11/2011 | Weston et al. |
| 8,062,331 B2 | 11/2011 | Zamierowski |
| 8,067,662 B2 | 11/2011 | Aali et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,197,467 B2 | 6/2012 | Heaton et al. |
| 8,235,955 B2 | 8/2012 | Blott et al. |
| 8,246,590 B2 | 8/2012 | Hu et al. |
| 8,257,328 B2 | 9/2012 | Augustine et al. |
| 8,273,105 B2 | 9/2012 | Cohen et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |

(56) References Cited

U.S. PATENT DOCUMENTS

| | | |
|---|---|---|
| 8,376,972 B2 | 2/2013 | Fleischmann |
| 8,430,867 B2 | 4/2013 | Robinson et al. |
| 8,444,392 B2 | 5/2013 | Turner et al. |
| 8,447,375 B2 | 5/2013 | Shuler |
| 8,454,990 B2 | 6/2013 | Canada et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,776 B2 | 8/2013 | Ebner |
| 8,535,296 B2 | 9/2013 | Blott et al. |
| 8,608,776 B2 | 12/2013 | Coward et al. |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,715,256 B2 | 5/2014 | Greener |
| 8,721,629 B2 | 5/2014 | Hardman et al. |
| 8,746,662 B2 | 6/2014 | Poppe |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,821,535 B2 | 9/2014 | Greener |
| 8,843,327 B2 | 9/2014 | Vernon-Harcourt et al. |
| 8,945,030 B2 | 2/2015 | Weston et al. |
| 8,951,235 B2 | 2/2015 | Allen et al. |
| 9,044,579 B2 | 6/2015 | Blott et al. |
| 9,050,398 B2 | 6/2015 | Armstrong et al. |
| 9,061,095 B2 | 6/2015 | Adie et al. |
| 9,180,231 B2 | 11/2015 | Greener |
| 9,220,822 B2 | 12/2015 | Hartwell |
| 9,408,755 B2 | 8/2016 | Larsson et al. |
| 9,421,132 B2 | 8/2016 | Dunn et al. |
| 9,655,807 B2 | 5/2017 | Locke et al. |
| 9,849,023 B2 | 12/2017 | Hall et al. |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0220660 A1 | 11/2003 | Kortenbach et al. |
| 2004/0010275 A1 | 1/2004 | Jacobs et al. |
| 2004/0054346 A1 | 3/2004 | Zhu et al. |
| 2004/0162512 A1 | 8/2004 | Liedtke et al. |
| 2004/0267312 A1 | 12/2004 | Kanner et al. |
| 2005/0119694 A1 | 6/2005 | Jacobs et al. |
| 2005/0142331 A1 | 6/2005 | Anderson et al. |
| 2005/0222613 A1 | 10/2005 | Ryan |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur et al. |
| 2006/0135921 A1 | 6/2006 | Wiercinski et al. |
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0032755 A1 | 2/2007 | Walsh |
| 2007/0052144 A1 | 3/2007 | Knirck et al. |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0108977 A1 | 5/2008 | Heaton et al. |
| 2008/0132821 A1 | 6/2008 | Propp et al. |
| 2008/0243096 A1 | 10/2008 | Svedman et al. |
| 2008/0275409 A1 | 11/2008 | Kane et al. |
| 2008/0287973 A1 | 11/2008 | Aster et al. |
| 2009/0005716 A1 | 1/2009 | Abuzaina et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0227938 A1 | 9/2009 | Fasching et al. |
| 2009/0227969 A1 | 9/2009 | Jaeb et al. |
| 2009/0246238 A1 | 10/2009 | Gorman et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262106 A1 | 10/2010 | Hartwell |
| 2010/0262126 A1 | 10/2010 | Hu et al. |
| 2010/0292717 A1 | 11/2010 | Petter-Puchner et al. |
| 2010/0312159 A1 | 12/2010 | Aali et al. |
| 2010/0318052 A1 | 12/2010 | Ha et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0130774 A1 | 6/2011 | Criscuolo et al. |
| 2011/0152800 A1 | 6/2011 | Eckstein et al. |
| 2011/0172760 A1 | 7/2011 | Anderson |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0236460 A1 | 9/2011 | Stopek et al. |
| 2011/0238095 A1 | 9/2011 | Browning |
| 2011/0264138 A1 | 10/2011 | Avelar et al. |
| 2011/0270301 A1 | 11/2011 | Cornet et al. |
| 2011/0282136 A1 | 11/2011 | Browning |
| 2011/0282309 A1* | 11/2011 | Adie ................ A61F 13/0209 604/319 |
| 2011/0305736 A1 | 12/2011 | Wieland et al. |
| 2012/0010637 A1 | 1/2012 | Stopek et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0059399 A1 | 3/2012 | Hoke et al. |
| 2012/0059412 A1 | 3/2012 | Fleischmann |
| 2012/0071841 A1 | 3/2012 | Bengtson |
| 2012/0121556 A1 | 5/2012 | Fraser et al. |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0197415 A1 | 8/2012 | Montanari et al. |
| 2012/0209226 A1 | 8/2012 | Simmons et al. |
| 2012/0209227 A1 | 8/2012 | Dunn |
| 2012/0253302 A1 | 10/2012 | Corley |
| 2012/0277773 A1 | 11/2012 | Sargeant et al. |
| 2013/0096518 A1 | 4/2013 | Hall et al. |
| 2013/0150813 A1 | 6/2013 | Gordon et al. |

(56) References Cited

U.S. PATENT DOCUMENTS

| | | |
|---|---|---|
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0310781 A1 | 11/2013 | Phillips et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blücher et al. |
| 2015/0159066 A1 | 6/2015 | Hartwell et al. |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth et al. |
| 2017/0143552 A1 | 5/2017 | Hartwell et al. |
| 2018/0221211 A1 | 8/2018 | Luckemeyer et al. |

FOREIGN PATENT DOCUMENTS

| | | | |
|---|---|---|---|
| CN | 101112326 A | | 1/2008 |
| CN | 101744688 A | | 6/2010 |
| CN | 102038575 A | | 5/2011 |
| CN | 103405846 A | | 11/2013 |
| CN | 203408163 U | | 1/2014 |
| DE | 2949920 A1 | | 3/1981 |
| DE | 3443101 A1 | | 5/1986 |
| EP | 0392640 A2 | | 10/1990 |
| EP | 0630629 A1 | | 12/1994 |
| EP | 1320342 A1 | | 6/2003 |
| EP | 2279016 A1 | | 2/2011 |
| EP | 2366721 A1 | | 9/2011 |
| EP | 2404626 A2 | | 1/2012 |
| EP | 2567717 A1 | | 3/2013 |
| EP | 2601984 A2 | | 6/2013 |
| GB | 2389794 A | | 12/2003 |
| GB | 2423019 A | | 8/2006 |
| GB | 2489947 A | | 10/2012 |
| GB | 2496310 A | | 5/2013 |
| JP | H0341952 A | | 2/1991 |
| JP | 2011521740 A | | 7/2011 |
| JP | 2014168573 A | | 9/2014 |
| KR | 101333344 B1 | * | 12/2005 |
| RU | 62504 U1 | | 4/2007 |
| SU | 1818103 A1 | | 5/1993 |
| WO | WO 02/05737 A1 | | 1/2002 |
| WO | WO 03/003948 A1 | | 1/2003 |
| WO | WO 2005/046761 A1 | | 5/2005 |
| WO | WO 2005/105174 A1 | | 11/2005 |
| WO | WO 2008/027449 A2 | | 3/2008 |
| WO | WO 2008/064502 A1 | | 6/2008 |
| WO | WO 2008/104609 A1 | | 9/2008 |
| WO | WO 2009/066106 | * | 11/2008 |
| WO | WO 2010/075180 | * | 12/2008 |
| WO | WO 2009/019495 A1 | | 2/2009 |
| WO | WO 2009/071926 A1 | | 6/2009 |
| WO | WO 2009/071933 A2 | | 6/2009 |
| WO | WO 2009/112062 A1 | | 9/2009 |
| WO | WO 2009/156709 A1 | | 12/2009 |
| WO | WO 2010/097570 A1 | | 9/2010 |
| WO | WO 2011/023384 A1 | | 3/2011 |
| WO | WO 2013/007973 | * | 6/2011 |
| WO | WO 2011/087871 A2 | | 7/2011 |
| WO | WO 2011/091169 A1 | | 7/2011 |
| WO | WO 2014/014922 | * | 2/2012 |
| WO | WO 2012/038727 A2 | | 3/2012 |
| WO | WO 2012/082716 A2 | | 6/2012 |
| WO | WO 2012/082876 A1 | | 6/2012 |
| WO | WO 2012/136707 A1 | | 10/2012 |
| WO | WO 2012/142473 A1 | | 10/2012 |
| WO | WO 2012/156655 A1 | | 11/2012 |
| WO | WO 2012/168678 A1 | | 12/2012 |
| WO | WO 2013/012381 A1 | | 1/2013 |
| WO | WO 2013/043258 A1 | | 3/2013 |
| WO | WO 2013/071243 A2 | | 5/2013 |
| WO | WO 2013/079947 A1 | | 6/2013 |
| WO | WO 2013/090810 A1 | | 6/2013 |
| WO | WO 2013/175309 A1 | | 11/2013 |
| WO | WO 2013/175310 A2 | | 11/2013 |
| WO | WO 2014/013348 A2 | | 1/2014 |
| WO | WO 2014/020440 A1 | | 2/2014 |
| WO | WO 2014/140578 A1 | | 9/2014 |
| WO | WO 2014/158526 A1 | | 10/2014 |
| WO | WO 2014/165275 A1 | | 10/2014 |
| WO | WO 2014/178945 A1 | | 11/2014 |
| WO | WO 2014/194786 A1 | | 12/2014 |
| WO | WO 2015/008054 A1 | | 1/2015 |
| WO | WO 2015/061352 A2 | | 4/2015 |
| WO | WO 2015/110409 A1 | | 7/2015 |
| WO | WO 2015/110410 A1 | | 7/2015 |
| WO | WO-2015109359 A1 | | 7/2015 |
| WO | WO-2015169637 A1 | | 11/2015 |

OTHER PUBLICATIONS

"Definition of Adhere," The Free Dictionary, accessed on Mar. 23, 2017 from http://www.thefreedictionary.com/adhere, 6 pages.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

International Preliminary Report on Patentability for Application No. PCT/EP2015/050963, dated Jul. 26, 2016, 8 pages.

International Search Report and Written Opinion for Application No. PCT/EP2015/050963, dated Apr. 20, 2015, 12 pages.

Kapischke M., et al., "Self-Fixating Mesh for the Lichtenstein Procedure-a Prestudy," Langenbecks Arch Surg, 2010, vol. 395, pp. 317-322.

"Definition of 3D Printer," American Heritage Dictionary of the English Language, Fifth Edition, accessed on Feb. 22, 2018 from URL: https://www.thefreedictionary.com, 2016, 1 page.

* cited by examiner

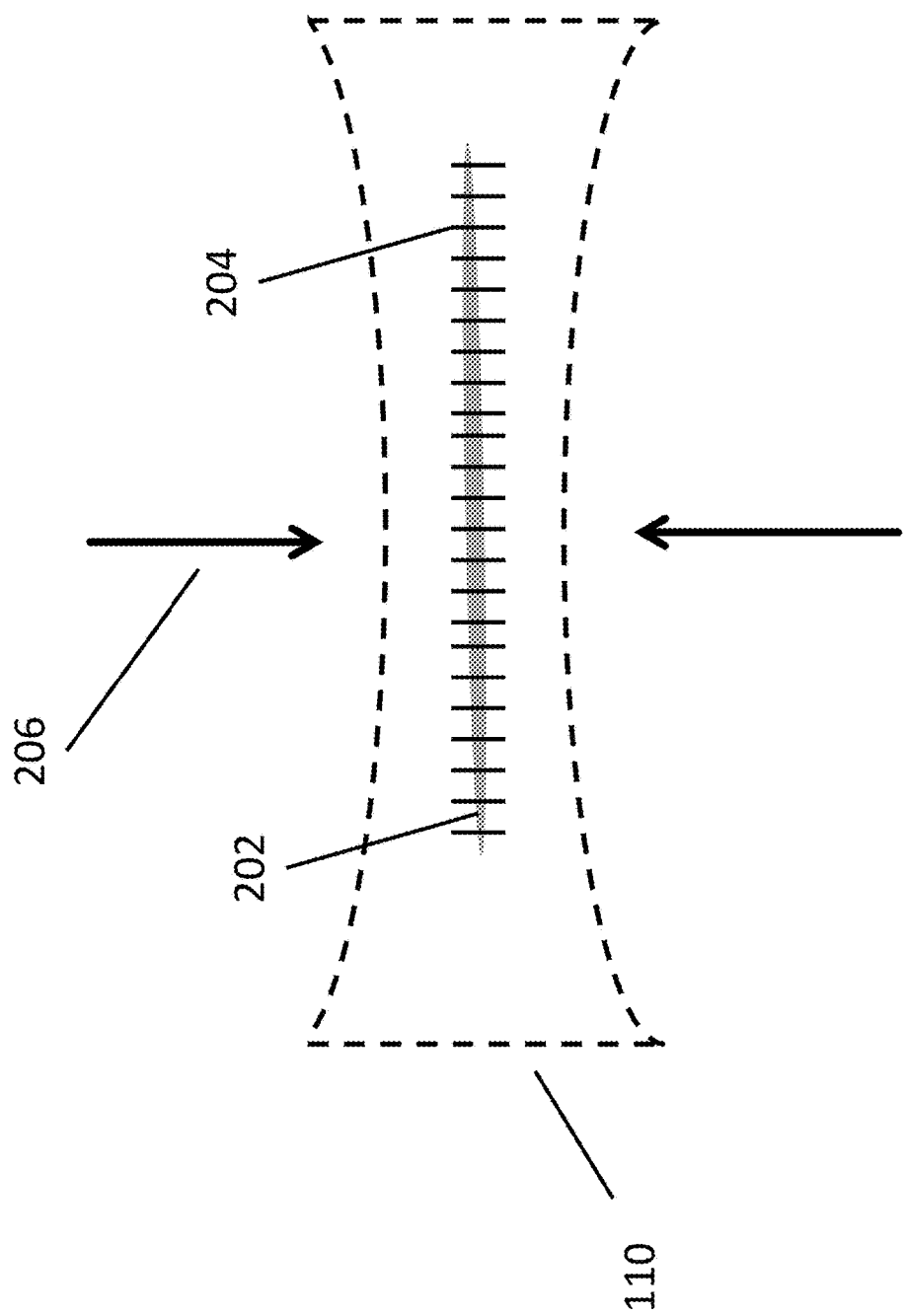

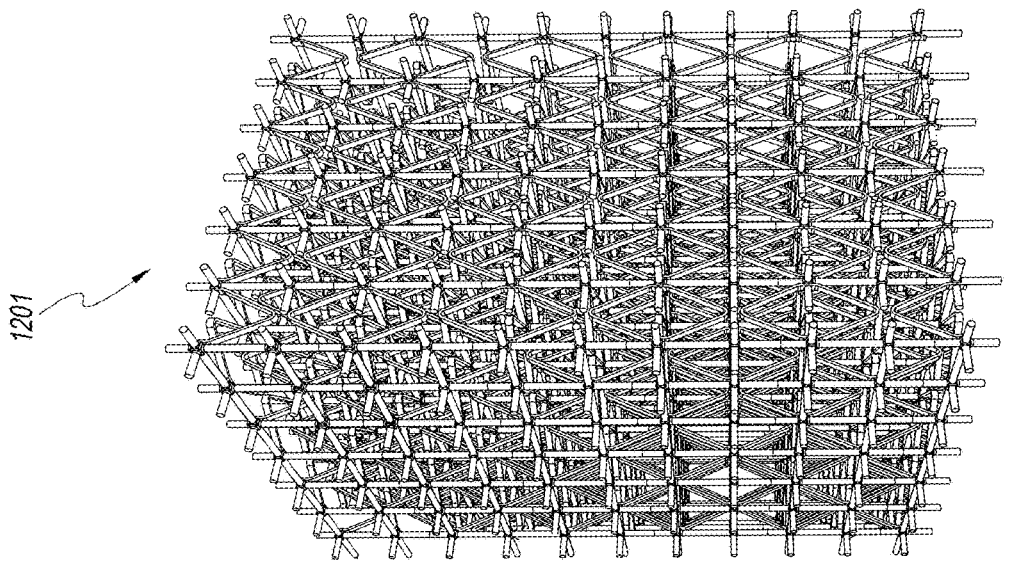
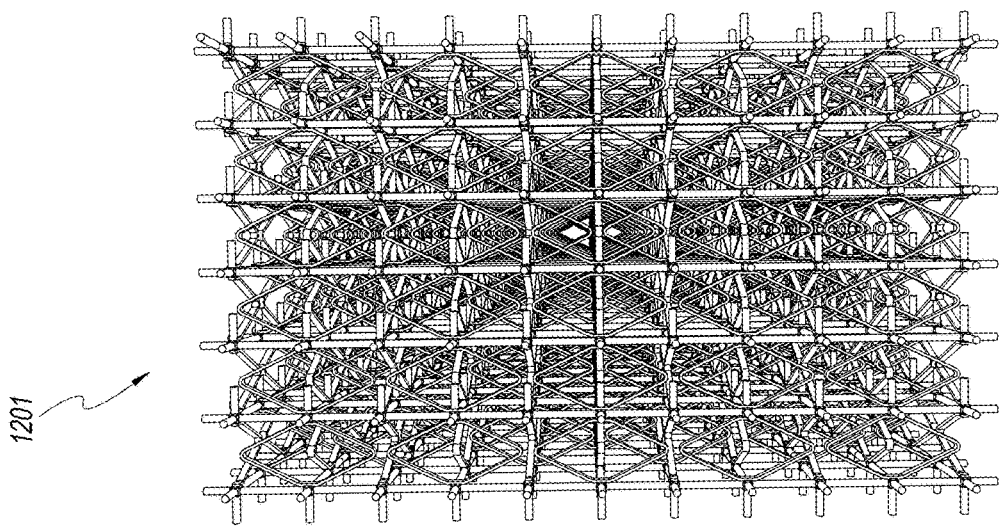
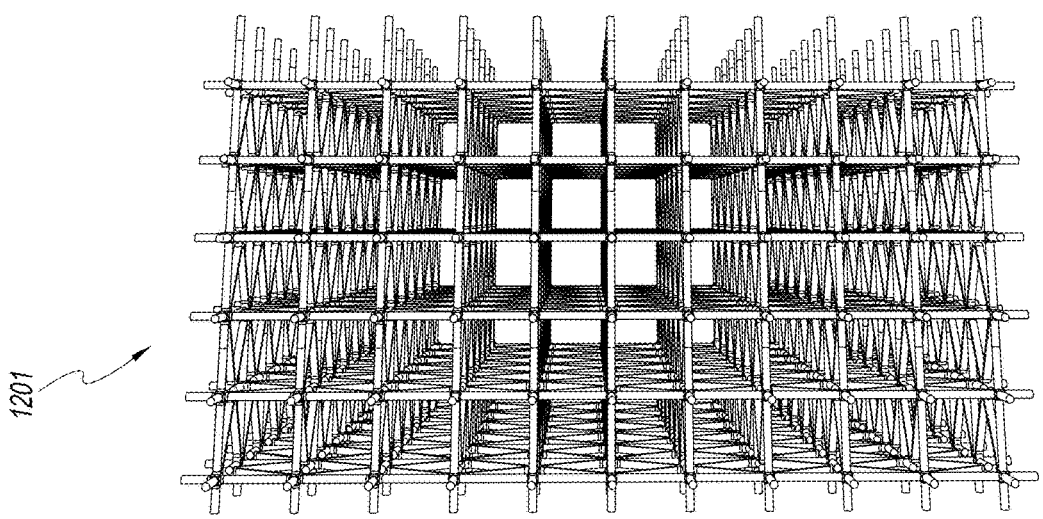
FIG. 5E

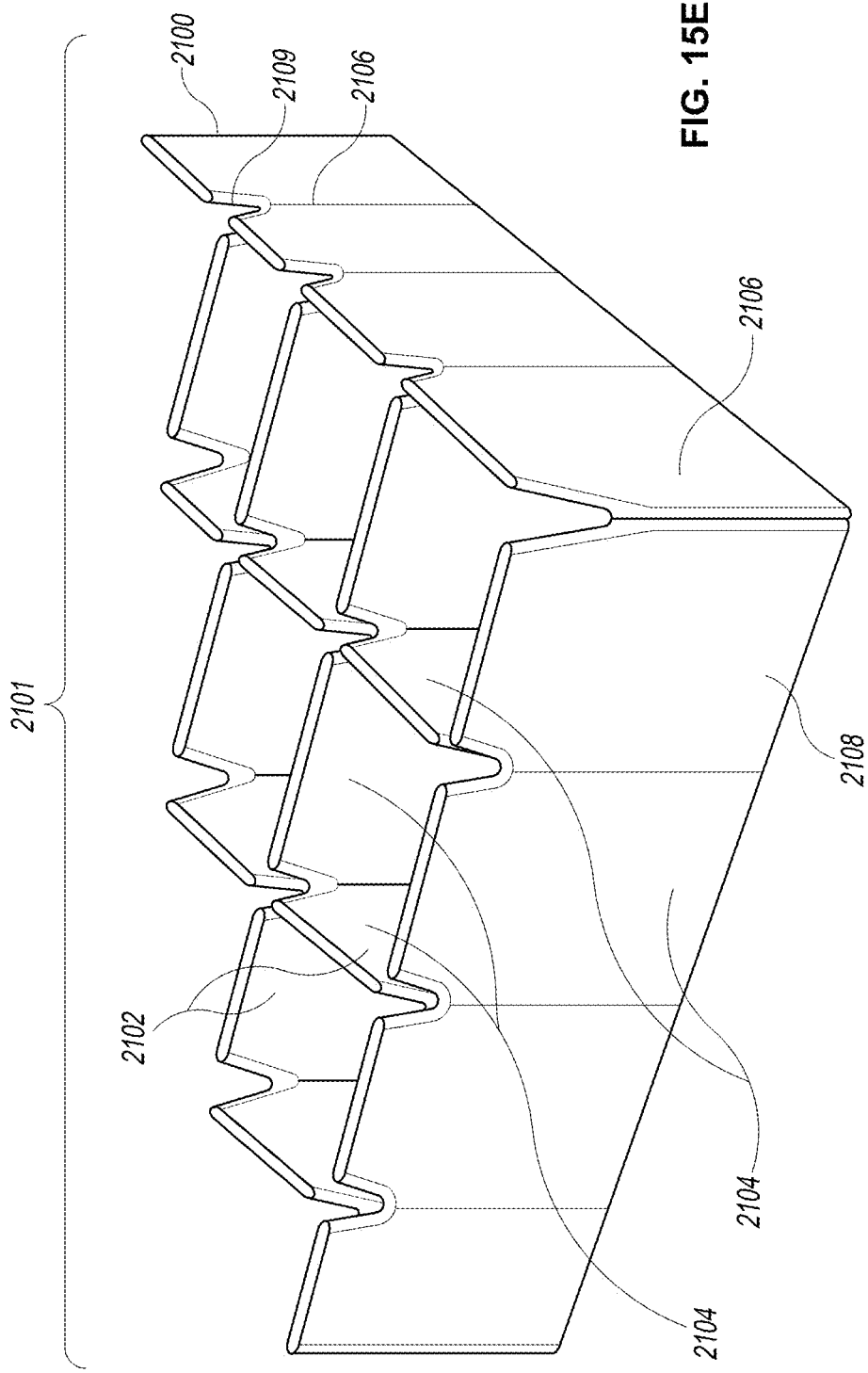

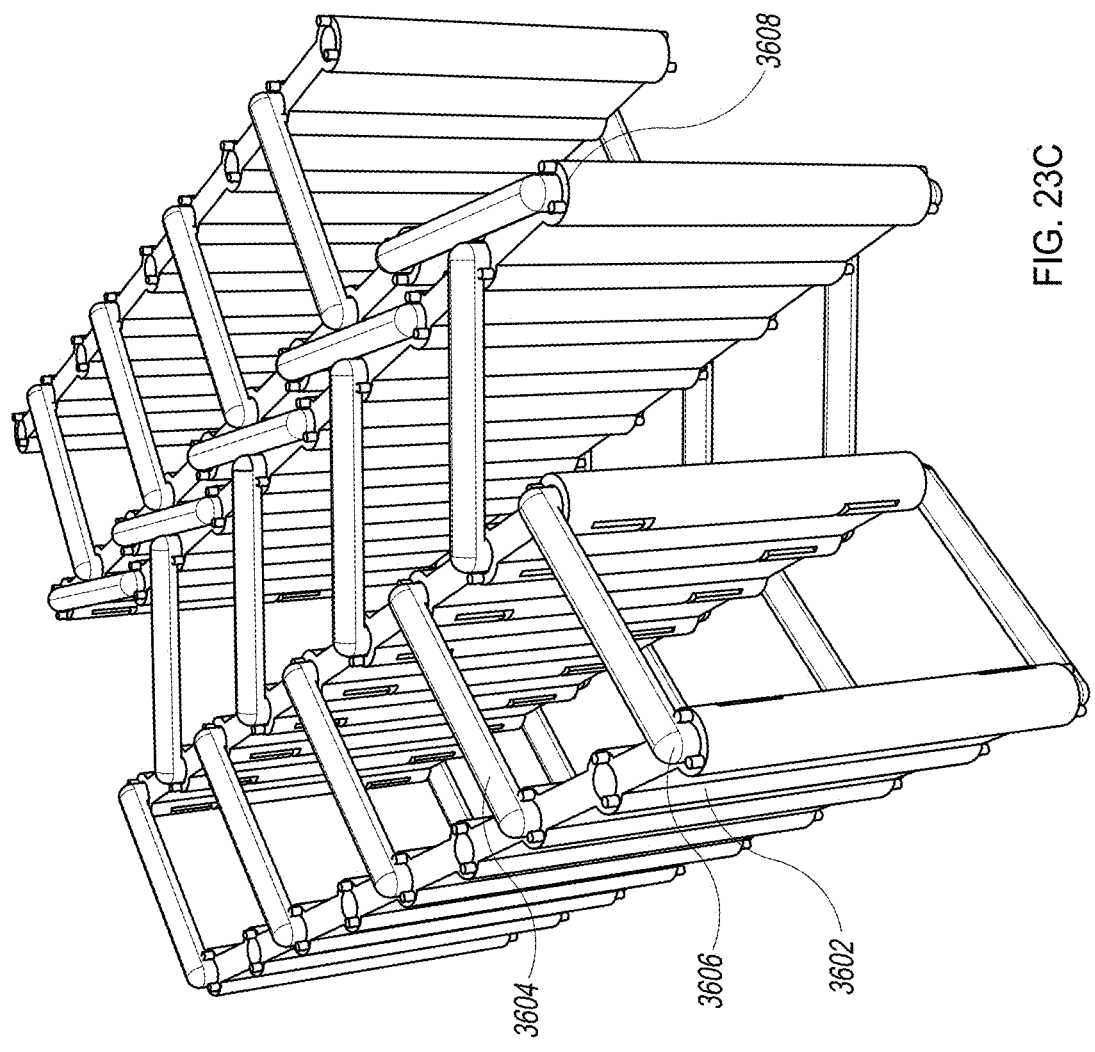

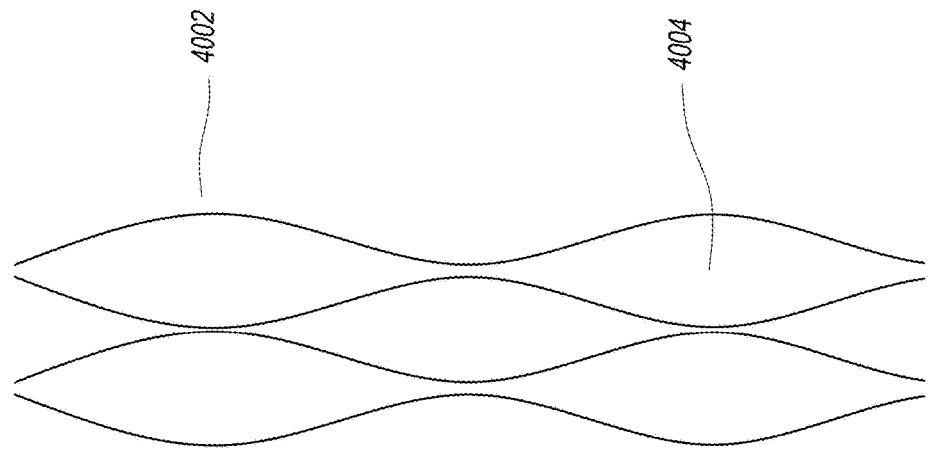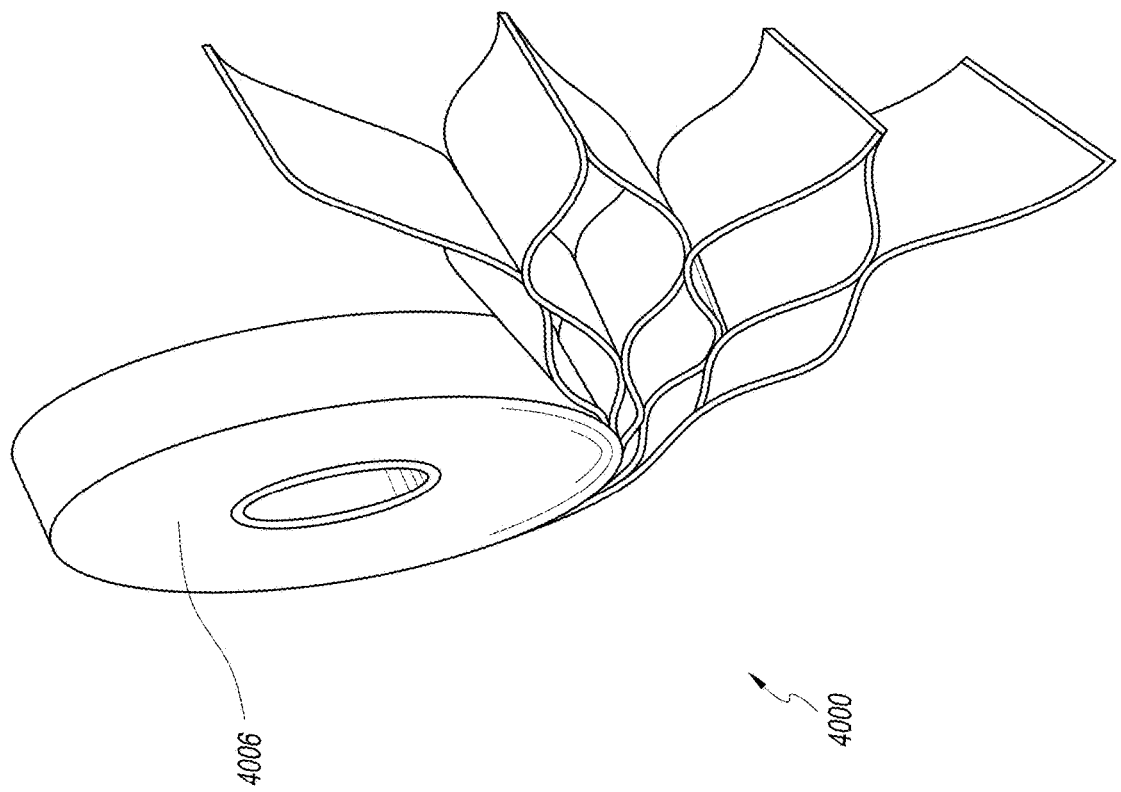
FIG. 27

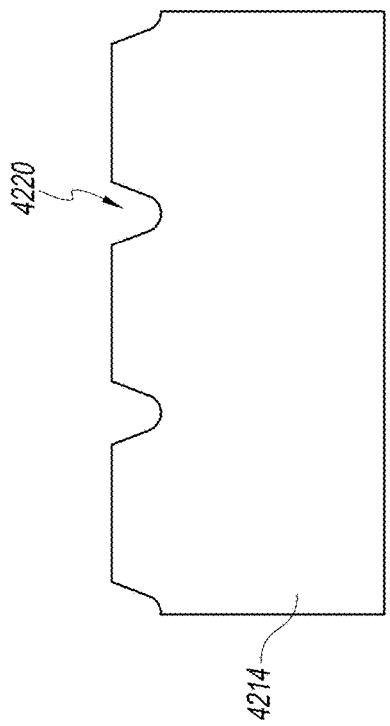
FIG. 29C
FIG. 29D
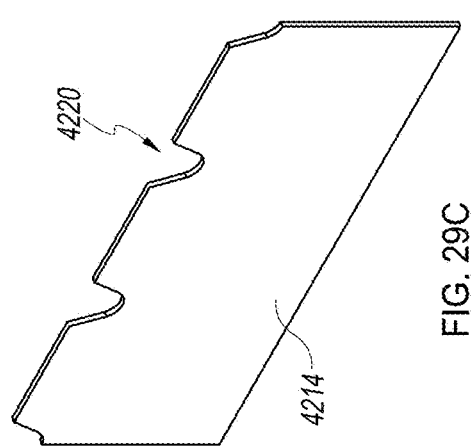
FIG. 29E
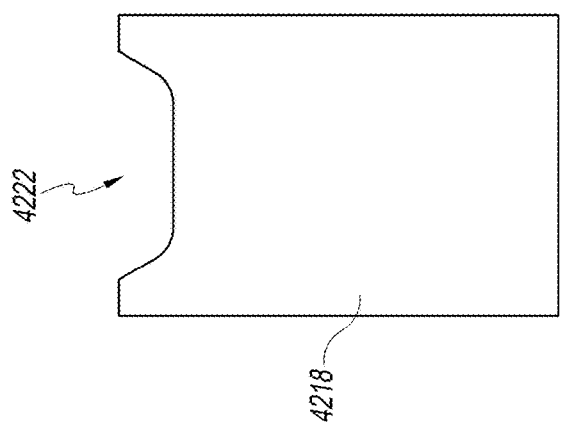
FIG. 29F

COLLAPSIBLE DRESSING FOR NEGATIVE PRESSURE WOUND TREATMENT

CROSS-REFERENCE TO RELATED APPLICATIONS

This application is a continuation of U.S. application Ser. No. 15/113,404, filed Jul. 21, 2016, which is a U.S. National Phase Application of PCT International Application Number PCT/EP2015/050963, filed on Jan. 20, 2015, designating the U.S., and published in English as WO 2015/110410 A1 on Jul. 30, 2015, which claims the benefit of U.S. Provisional Application No. 61/929,870, filed Jan. 21, 2014, and entitled COLLAPSIBLE DRESSING FOR NEGATIVE PRESSURE WOUND TREATMENT. The content of the aforementioned applications is hereby incorporated by reference in their entirety as if fully set forth herein. The benefit of priority to the foregoing applications is claimed under the appropriate legal basis, including, without limitation, under 35 U.S.C. § 119(e).

BACKGROUND OF THE INVENTION

Field of the Invention

Embodiments described herein relate to apparatuses, systems, and methods for the treatment of wounds, for example, by using dressings in combination with negative pressure wound therapy. Embodiments herein may be particularly useful for the treatment of incisional wounds.

Description of the Related Art

Negative pressure wound therapy has become a common therapy for the treatment of certain types of wounds, often improving the rate of healing while also removing exudates and other deleterious substances from the wound site. In some cases, negative pressure wound therapy is applied to incisional wounds, such as those resulting from surgical procedures. However, existing negative pressure wound treatment systems lack adequate mechanisms for applying closing force to the wound and/or supporting the sutures or other attachment means utilized to seal the incisional wound.

Additionally, prior art dressings for use with negative pressure have been difficult to apply, particularly around curved or non-flat body surfaces. Following application of negative pressure, wound exudate may soak into the dressing, which may be aesthetically unpleasing and potentially embarrassing in social situations.

SUMMARY OF THE INVENTION

Embodiments of the present invention relate to negative pressure wound closure and treatment devices, methods, and systems that facilitate closure and treatment of a wound. The devices, methods, and systems may be simultaneously used with negative pressure to remove wound fluids.

In some embodiments, a negative pressure wound treatment apparatus comprises:

a wound dressing comprising a backing layer and a stabilizing structure positioned below the backing layer, wherein the backing layer and the stabilizing structure are configured as a single unit for placement simultaneously over a wound, and wherein the stabilizing structure is configured for placement over skin surrounding the wound;

a port for communicating negative pressure to the wound dressing; and wherein the stabilizing structure is configured to collapse significantly more within a horizontal plane than within a vertical plane to apply a horizontal force to the skin surrounding the wound when the wound dressing is placed under negative pressure.

In certain embodiments, the wound dressing further comprises a wound contact layer, wherein the stabilizing structure is positioned between the backing layer and the wound contact layer.

In any of the embodiments above or described elsewhere in this specification, the wound dressing further comprises an acquisition distribution layer between the stabilizing structure and the backing layer.

In any of the embodiments above or described elsewhere in this specification, the wound dressing further comprises an absorbent layer between the stabilizing structure and the backing layer.

In any of the embodiments above or described elsewhere in this specification, the apparatus further comprises tissue anchors configured to attach the wound dressing to the skin surrounding the wound and/or to the stabilizing structure.

In any of the embodiments above or described elsewhere in this specification, the apparatus further comprises an adhesive configured to attach the wound dressing to the skin surrounding the wound.

In any of the embodiments above or described elsewhere in this specification, the wound dressing may be configured to relieve stress applied to sutures applied to the wound.

In any of the embodiments above or described elsewhere in this specification, the backing layer is transparent or translucent. In any of the embodiments above or described elsewhere in this specification, the wound dressing further comprises an obscuring layer between an absorbent layer and the backing layer. In any of the embodiments above or described elsewhere in this specification, the stabilizing structure may be less than 20% as thick as it is wide or long.

In some embodiments, a method of treating a wound with an apparatus as described herein this section or elsewhere in the specification comprises:

placing the wound dressing over the wound with the stabilizing structure positioned over the skin surrounding the wound;

applying negative pressure to the wound through the port; and wherein the stabilizing structure applies a horizontal force to the skin surrounding the wound when placed under negative pressure.

In certain embodiments, a negative pressure wound treatment apparatus may comprise:

a wound dressing comprising a backing layer, an absorbent layer, and a stabilizing structure positioned below the absorbent layer, wherein the backing layer, absorbent layer, and the stabilizing structure are configured as a single unit for placement simultaneously over a wound, and wherein the stabilizing structure is configured for placement over skin surrounding the wound;

wherein the absorbent layer comprises a plurality of through holes;

wherein the stabilizing structure is configured to collapse significantly more within a horizontal plane than within a vertical plane to apply a horizontal force to the skin surrounding the wound when the wound dressing is placed under negative pressure.

In particular embodiments, at least some of the plurality of through holes may be filled with a plug material to provide the absorbent layer with increased vertical rigidity. The plug material may be transparent. In embodiments, the absorbent layer is configured to collapse significantly more within a horizontal plane than within a vertical plane. Some embodiments may further comprise a wound contact layer beneath the stabilizing structure. In certain embodiments, the backing layer may be transparent. In some embodiments, plug material may be located within cells of the stabilizing structure.

Other non-limiting embodiments of wound closure and/or treatment devices, stabilizing structures and associated apparatuses are described below.

BRIEF DESCRIPTION OF THE DRAWINGS

Embodiments of the present disclosure will now be described, by way of example only, with reference to the accompanying drawings, in which:

FIGS. 3A-B illustrate embodiments of the application of a wound dressing to an incisional wound.

FIGS. 5A-E illustrate different views and photographs of embodiments of a stabilizing structure that may be used in a wound dressing.

FIGS. 15A-E are photographs of various embodiments of stabilizing structures comprising inserts disposed therein.

FIGS. 23A-G illustrate multiple views of an embodiment of a stabilizing structure.

FIG. 27 illustrates an embodiment of a stabilizing structure cut from a roll.

FIGS. 29A-F illustrate multiple views of an embodiment of a stabilizing structure.

DETAILED DESCRIPTION OF THE PREFERRED EMBODIMENTS

Figure 1:
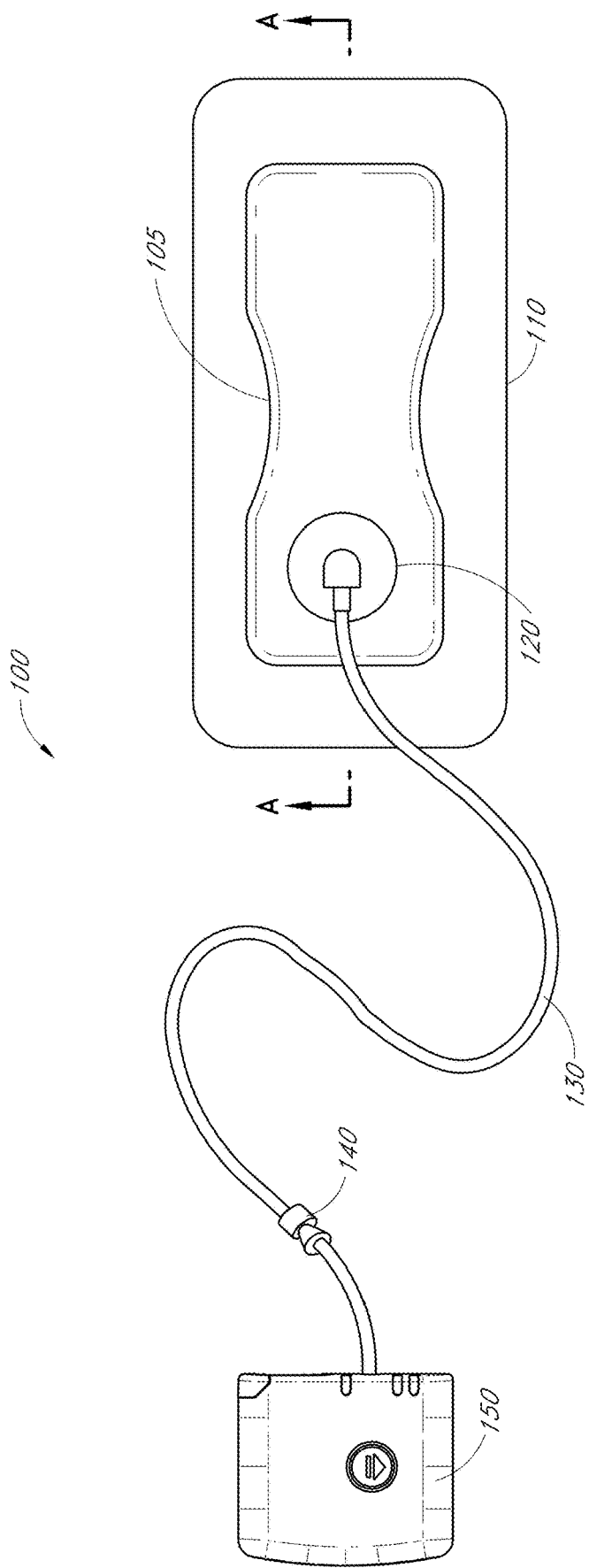
FIG. 1 illustrates an embodiment of a wound treatment system.

Embodiments disclosed herein relate to apparatuses and methods of treating a wound with reduced pressure, including pump and wound dressing components and apparatuses. Generally, the embodiments including the dressings described herein may be used in combination with a negative pressure system comprising a drape or wound cover placed over the filler. A vacuum source, such as a pump, may be connected to the cover, for example, through one or more tubes connected to an aperture or port made in or under the cover.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds, incisional wounds either as a result of surgery or other means, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). Unless stated otherwise, the term approximately is meant to represent a range of +/−10% of the stated value.

The negative pressure range for some embodiments of the present disclosure can be approximately −80 mmHg, or between about −10 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices and stabilizing structures described in this specification, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227. Further, any of the embodiments disclosed herein may be used without the application of reduced or negative pressure.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in U.S. Provisional Application Ser. No. 61/650,904, filed May 23, 2012, titled "APPARATUSES AND METHODS FOR NEGATIVE PRESSURE WOUND THERAPY," International Application No. PCT/IB2013/001469, filed May 22, 2013, titled "APPARATUSES AND METHODS FOR NEGATIVE PRESSURE WOUND THERAPY," U.S. Provisional Application Ser. No. 61/678,569, filed Aug. 1, 2012, titled "WOUND DRESSING AND METHOD OF TREATMENT," U.S. Provisional Application Ser. No. 61,753,374, filed Jan. 16, 2013, titled "WOUND DRESSING AND METHOD OF TREATMENT," U.S. Provisional Application Ser. No. 61/753,878, filed Jan. 17, 2013, titled "WOUND DRESSING AND METHOD OF TREATMENT," U.S. Provisional Application Ser. No. 61/785,054, filed Mar. 14, 2013, titled "WOUND DRESSING AND METHOD OF TREATMENT," and U.S. Provisional Application Ser. No. 61/823,298, filed May 14, 2013, titled "WOUND DRESSING AND METHOD OF TREATMENT," which are hereby incorporated by reference into this present application in their entireties. Embodiments of the wound dressings, wound treatment apparatuses and methods described herein may also be used in combination or in addition to those described in application Ser. No. 13/092,042, filed Apr. 21, 2011, published as US2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

Further embodiments of wound dressings may be found in PCT Application PCT/IB2013/002060, titled WOUND DRESSING AND METHOD OF TREATMENT, filed Jul. 31, 2013, and hereby incorporated by reference in its entirety. PCT Application PCT/IB2013/002060 is further appended to the present application as Appendix A. The various embodiments of dressings disclosed in Appendix A may be used in combination with any of the embodiments disclosed herein this section or elsewhere in the specification.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times or 10 times greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure wound treatment system 100 comprising a wound dressing 110 in combination with a pump 150. FIG. 1 depicts a representative wound dressing with a "waisted portion," however, many dressing embodiments have different shapes/sizes such as those disclosed herein this section or elsewhere in this specification, including Appendix A. The wound dressing 110 can be, without limitation, dressing embodiments or combinations of features of any number of wound dressing embodiments disclosed herein this section or elsewhere in this specification, including Appendix A. Here, the dressing 110 may be placed over a wound as described previously, and a conduit 130 may then be connected to the port 120, although in some embodiments the dressing 101 may be provided with at least a portion of the conduit 130 preattached to the port 120. Preferably, the dressing 110 is provided as a single article with all wound dressing elements (including optionally the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes. Embodiments of the dressing of FIG. 1 are further described with respect to FIGS. 35-36, which also provide additional details on the specific internal components of the dressing embodiment depicted in FIG. 1.

In some embodiments, fluid may be transported from the dressing 110 and stored in a fluid collection canister (not shown). Some embodiments, may call for fluid to be retained within the dressing such as within an absorbent material. The absorbent material may further comprise a superabsorbent polymer or a more conventional absorbent material such as cellulose.

Figure 2A:
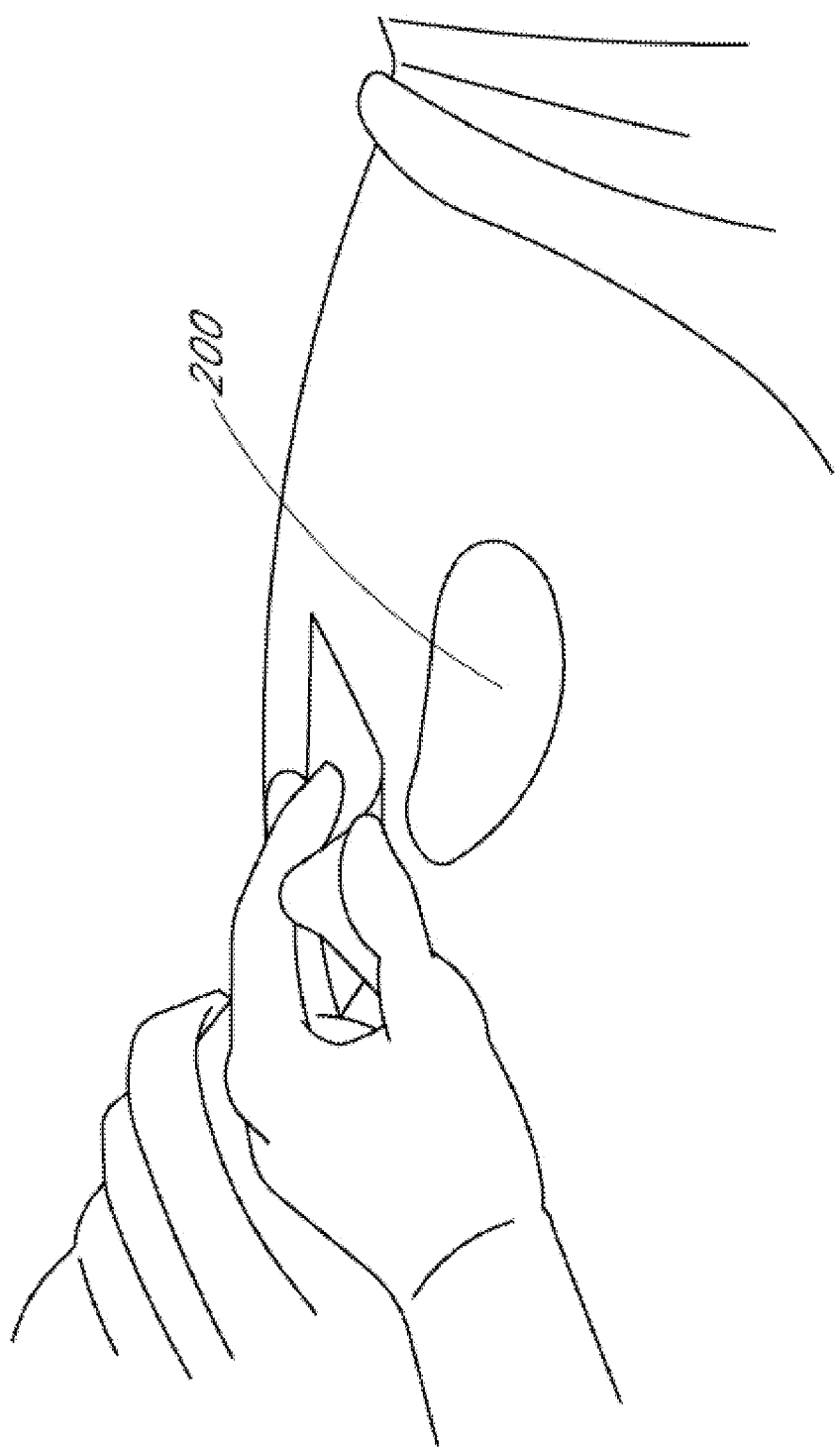
FIGS. 2A-E illustrate the use and application of an embodiment of a wound treatment system onto various wounds.
Figure 2B:
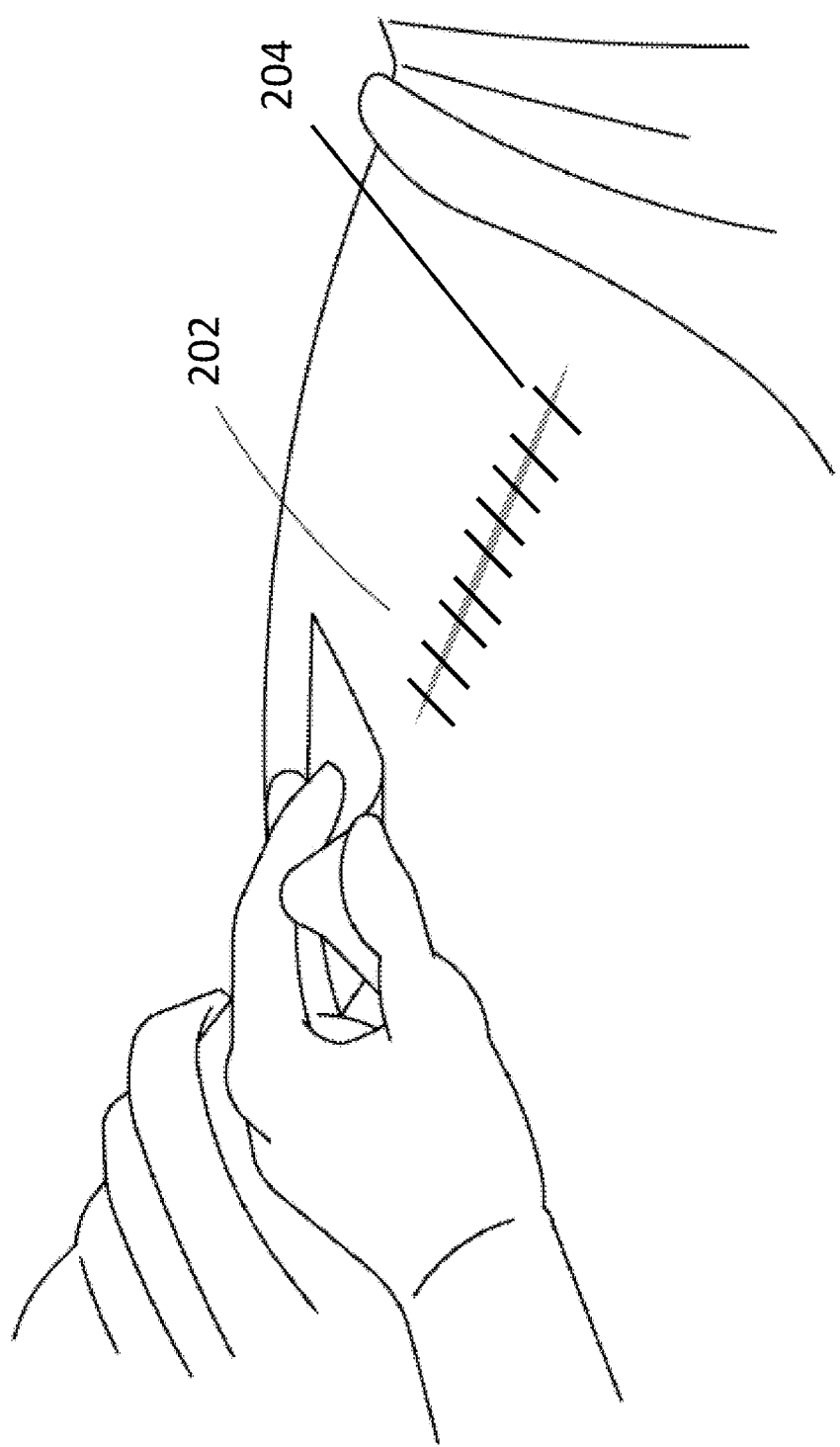
Figure 2C:
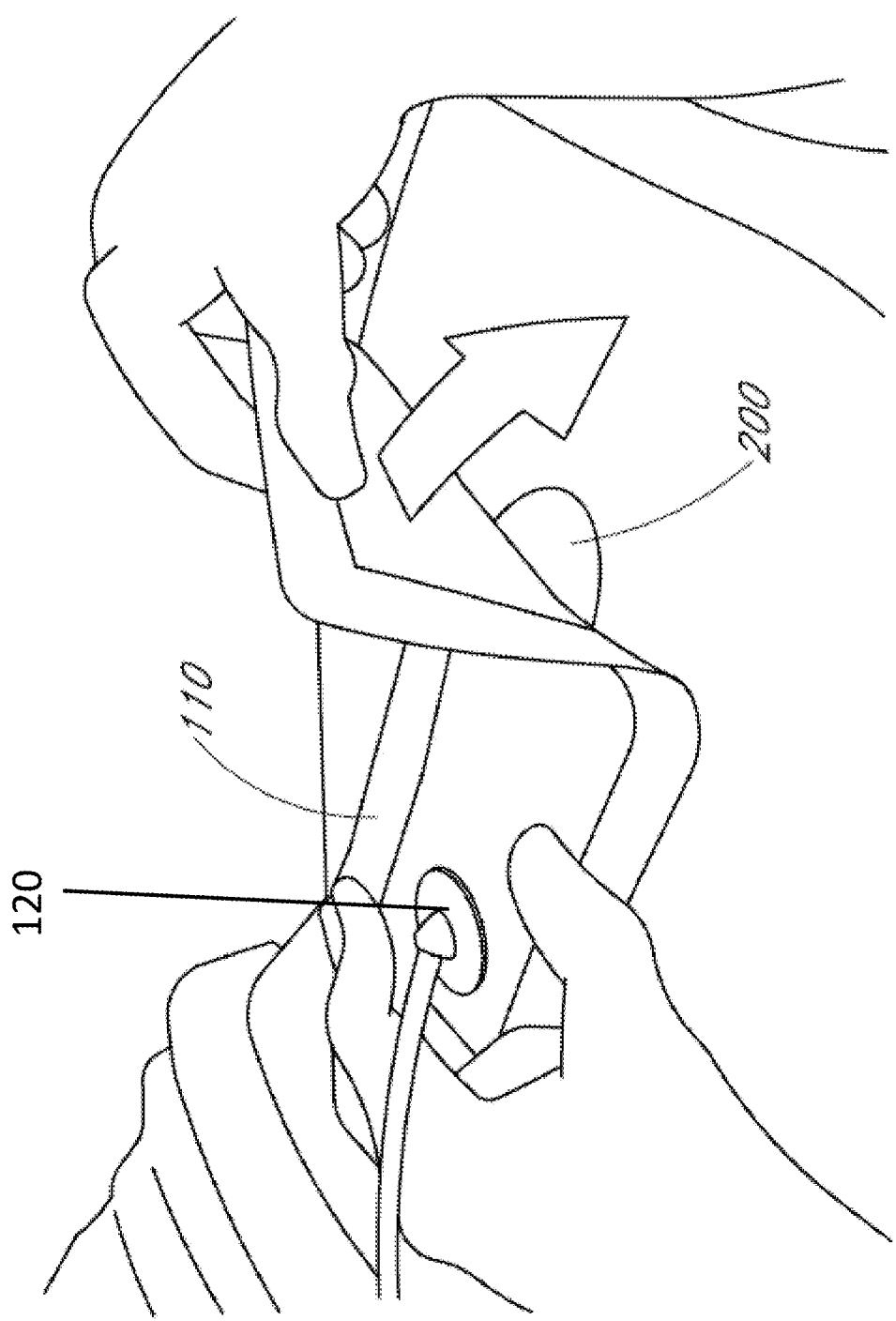
Figure 2D:
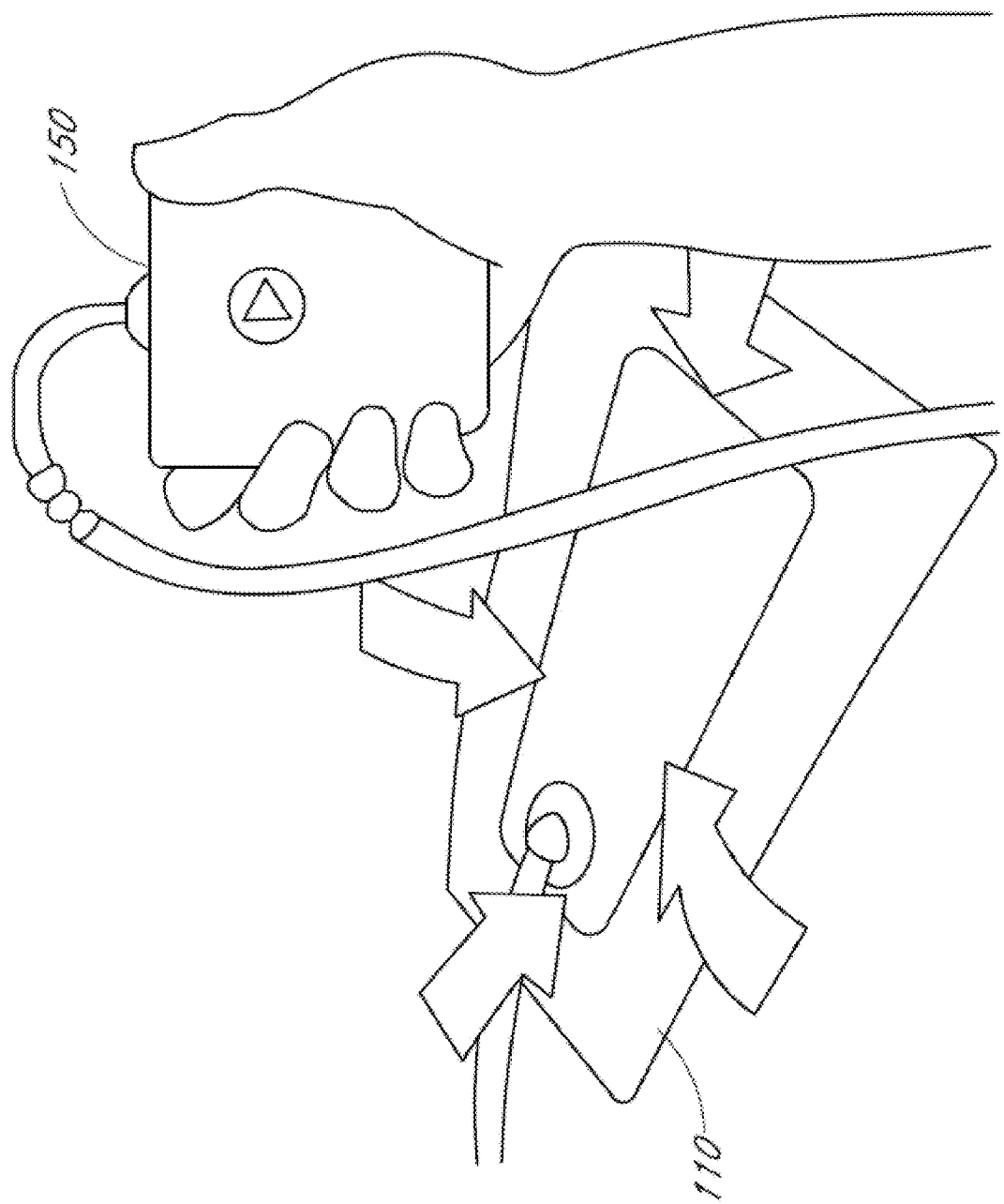
Figure 2E:
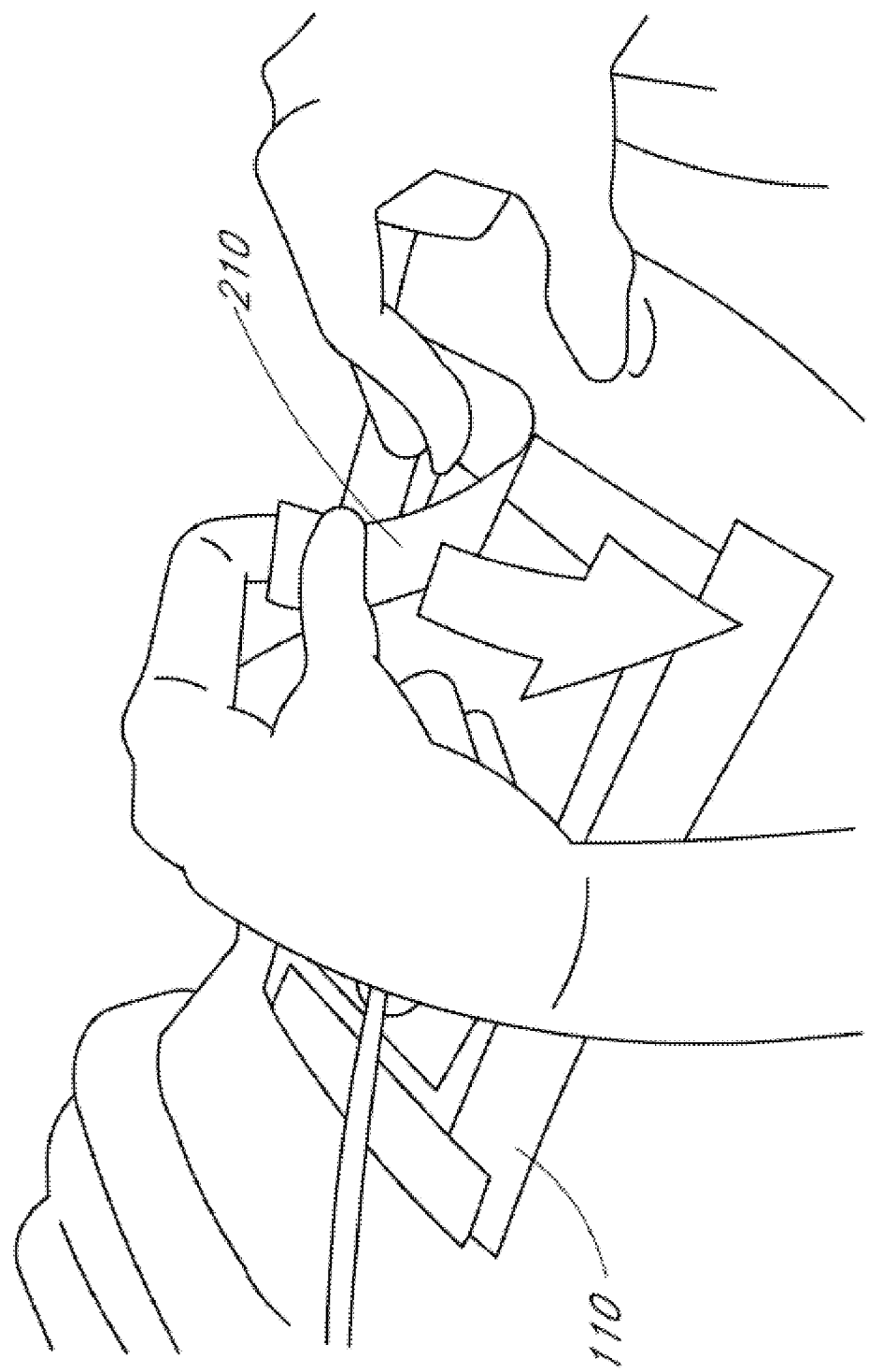

FIGS. 2A-E illustrate the use of an embodiment of a negative pressure wound treatment system used to treat a wound site on a patient. Further details regarding the internal components of embodiments of the dressings of FIG. 2C-E are described in FIGS. 35-36. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound. In embodiments, the wound may be any type of wound described herein this section or elsewhere in the specification.

FIG. 2B illustrates an incisional wound site 202 that may be irrigated and prepared as the wound site 200 described in relation to FIG. 2A. Typical incisional wounds are created by a scalpel or other means during surgery to allow a clinician access to the underlying tissues and organs. The incisional wound 202 may be closed, whereby the wound has been closed by sutures 204 or other means such as an adhesive, or the incisional wound may be open, wherein the wound has not yet been closed. As described above, throughout this specification reference is made to a wound and such a wound may be created by a variety of means including via incisional means. Thus, it will be understood by one skilled in the art, when the term "wound" is used in describing embodiments herein this section and elsewhere in the specification, the term "wound" encompasses incisional wounds such as those described in FIG. 2B.

After the skin surrounding the wound site 200 is dry, and with reference now to FIG. 2C, the wound dressing 110 may be positioned and placed over the wound site 200 or 202. Preferably, the wound dressing 110 is placed over and/or in contact with the wound site 200. In some embodiments, an adhesive layer is provided on the lower surface of the dressing 110, which may in some cases be protected by an optional release layer to be removed prior to placement of the wound dressing 110 over the wound site 200. Preferably, the dressing 110 is positioned such that the port 120 is in a raised position with respect to the remainder of the dressing 110 so as to avoid fluid pooling around the port. In some embodiments, the dressing 110 is positioned so that the port 120 is not directly overlying the wound, and is level with or at a higher point than the wound. To help ensure adequate sealing for negative pressure wound therapy, the edges of the dressing 110 are preferably smoothed over to avoid creases or folds. With reference now to FIG. 2D, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150. Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Turning to FIG. 2E, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

Figure 3B:
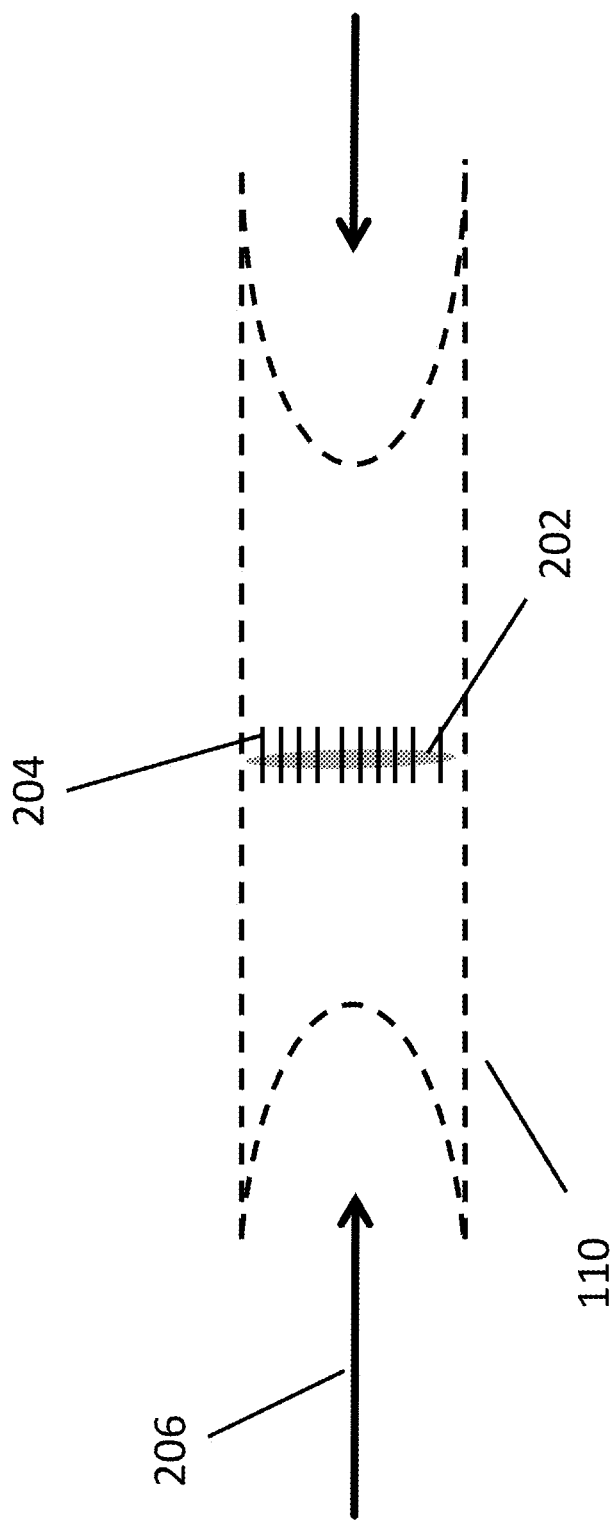

FIGS. 3A-B illustrate schematic embodiments of an outline of a wound dressing 110, similar to the dressing embodiments depicted in FIGS. 1-2E and 35-36, placed over an incisional wound 202 closed with sutures 204. As in FIGS. 1-2E, such a dressing may be connected to a source of negative pressure configured to apply negative pressure to a wound. In certain embodiments, the wound dressing 110 may collapse in a plane perpendicular to the vertical direction, thereby applying a horizontal force 206 to the incisional wound 202. In embodiments, the dressing 110 may collapse in any manner described herein this section or elsewhere in the specification, particularly as will be described in greater detail below in relation to FIGS. 4A-33C and FIGS. 35-36. For example, the dressing may collapse significantly more in the horizontal plane than in the vertical plane. By collapsing significantly more in the horizontal plane, the dressing may apply horizontal force to the wound while avoiding the potentially deleterious application of vertical forces.

As depicted in FIGS. 1-3B, in certain embodiments, the wound dressing may have a rectangular shape. When considered from a top down two-dimensional view, as in the schematic of FIGS. 3A-B, the wound dressing may collapse significantly more along the shorter dimension as depicted in FIG. 3A or can collapse significantly more along the longer dimension as depicted in FIG. 3B. By collapsing along the axis of the sutures 204, the dressing can both aid in closure of the wound by applying a closing force to the wound 206, and also serve to relieve tension on the sutures 204. In some embodiments, the dressings of FIGS. 3A-3B may also elongate in a perpendicular axis to the axis of closure.

In embodiments, the dressing may be adhered to the surface of the skin via any adhesion or attachment mechanism described herein this section or elsewhere in the specification. For example, the dressing may be adhered to the skin via an adhesive, such as cyanoacrylate adhesives. In some embodiments, the dressing may be adhered to the skin via tissue anchors, such as those described herein this section or in much greater detail elsewhere in the specification. Adherence of the dressing to the surrounding skin may allow the dressing to apply lateral closing forces to the wound by drawing the tissues surrounding the wound together, as described above.

Wound dressings such as wound dressing 110 described above and elsewhere in this specification may include as part of the wound dressing a wound closure device or stabilizing structure that facilitates closure of the skin surrounding the wound. For example, a wound dressing that comprises a backing layer may further comprise a wound closure device or stabilizing structure as described below, incorporated as a layer of the wound dressing and configured to be applied over the wound simultaneously with the backing layer. The inclusion of a wound closure device or stabilizing structure may facilitate the application of a horizontal force to skin surrounding the wound when the wound dressing is applied over the wound and adhered to skin surrounding the wound. The wound closure device or stabilizing structure, which may be positioned over skin surrounding the wound and adhered directly or indirectly thereto, may collapse under negative pressure more in a horizontal direction than in a vertical direction, thereby applying a horizontal force to the skin surrounding the wound.

Embodiments of various stabilizing structures and wound closure devices for use in a wound dressing will now be described. Any of these embodiments may be incorporated into the dressings described herein, as will be further described with respect to FIGS. 35-36 below. The stabilizing structures of FIGS. 4A-33C may be sized appropriately to fit within the footprint of the dressings of FIGS. 1-2E, or any of the dressing shapes/sizes disclosed herein this section or elsewhere in the specification. In alternative embodiments, any of the stabilizing structures described below need not be provided as a single unit simultaneously with other components of a wound dressing, but may be individually and separately applied over a wound, such as over the skin surround a wound. In such alternative embodiments, other wound dressing components, such as any of the layers described with respect to FIGS. 35-36, may be separately applied over the wound, and the stabilizing structure together with other wound dressing components form the wound dressing. Further embodiments of stabilizing structures and wound closure devices, as well as related methods of manufacture and use, are described throughout the specification and in the claims of International Application No. PCT/US2013/050619, filed Jul. 16, 2013, and International Application No. PCT/US2013/050698, filed Jul. 16, 2013, the entireties of both of which are hereby incorporated by reference.

Stabilizing Structures of FIGS. 4A-5E

FIGS. 4A-D illustrate different views of an embodiment of a stabilizing structure 1701. The stabilizing structure may be oriented in any direction when placed over a wound, but more preferably will be oriented to preferentially collapse in a horizontal plane. The stabilizing structure 1701 may be sized appropriately to fit within the footprint of a wound dressing, such that the structure shown in FIGS. 4A-4D may comprise just a portion of the stabilizing structure used in the wound dressing, or such that just a portion of the structure shown in FIGS. 4A-4D may be used in the wound dressing.

Here, the stabilizing structure 1701 comprises a first set of beams 1703 that are rigidly or semi-rigidly attached or bonded to a second set of intersecting beams 1705. These beams 1703, 1705 form a planar support structure 1702 that is preferably substantially rigid within a plane. The beams 1703, 1705 may meet at right angles to each other (although other configurations, e.g., honeycombs are possible). Two or more planar support structures 1702 may be joined together to form the stabilizing structure 1701, and each planar support structure 1702 is preferably separated from the other by spring elements 1711 and 1713, described in further detail below. The number of planar support structures 1702 used in the stabilizing structure may be tailored in relation to the size of the wound. For example, there may be 2, 3, 4, 5 or more planar support structures 1702 arranged parallel or substantially parallel to one another. The spring elements 1711, 1713 are preferably arranged so as to allow for compression of the stabilizing structure 1701 in one direction so as to bring the planar support structures 1702 closer together. In a preferred embodiment, the stabilizing structure 1701 may collapse to 40% or less of its original size, preferably 30% or less of its original size; more preferably, 20% or less of its original size; even more preferably, 10% or less of its original size. In some embodiments, the stabilizing structure 1701 may collapse to 5% or less of its original size.

The spring elements 1711, 1713 are preferably resiliently flexible and biased to be resiliently collapsible along a direction perpendicular to the plane defined by the planar support structure 1702. In some embodiments, the elements 1711, 1713 may be inelastic, and retain their shape when collapsed. In such embodiments, the spring elements or the stabilizing structure may be constructed with a ratchet mechanism that maintains the spring elements 1711, 1713 in their collapsed configuration.

Figure 4A:
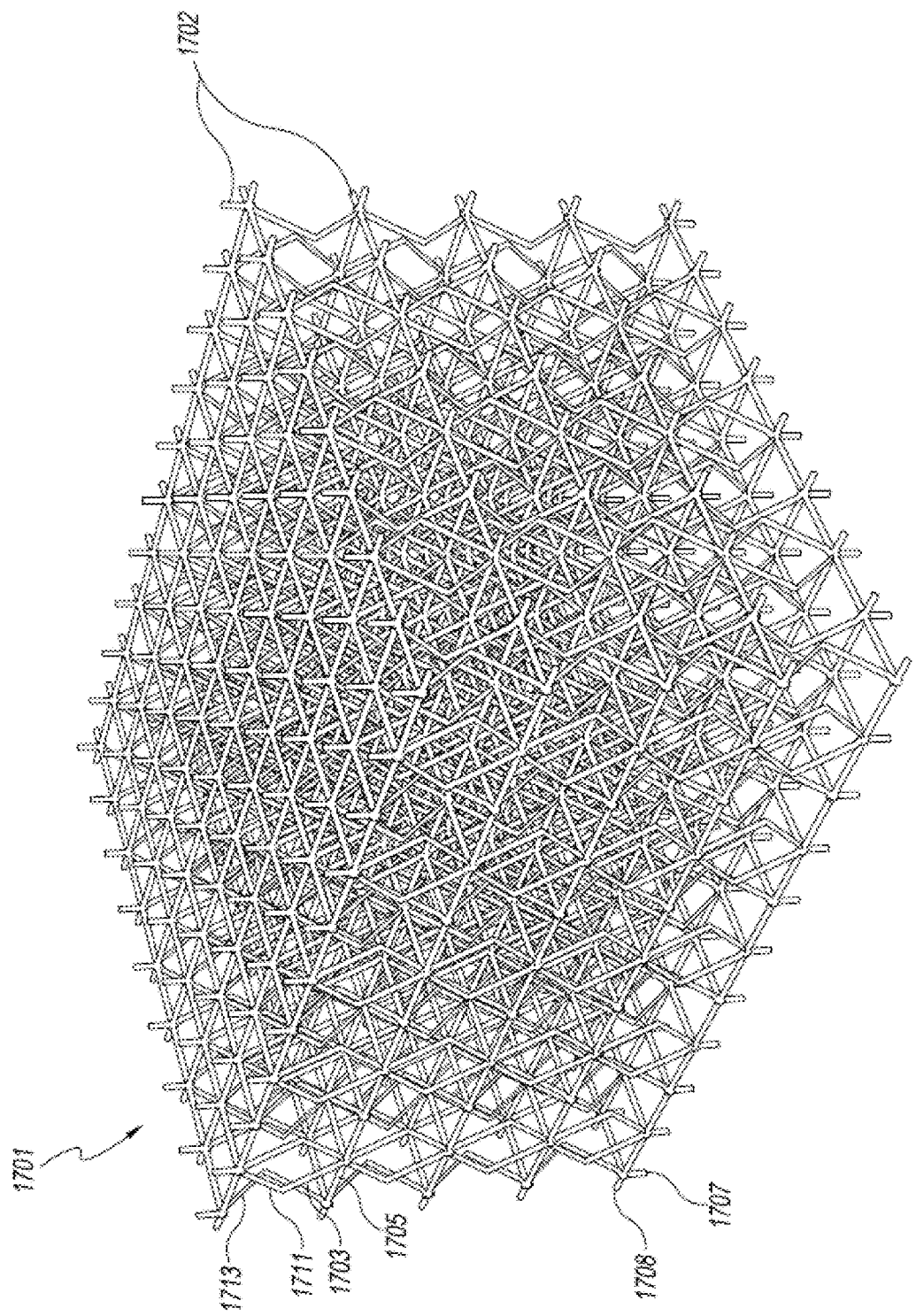
FIGS. 4A-D illustrate different views of embodiments of a stabilizing structure that may be used in a wound dressing.
Figure 4B:
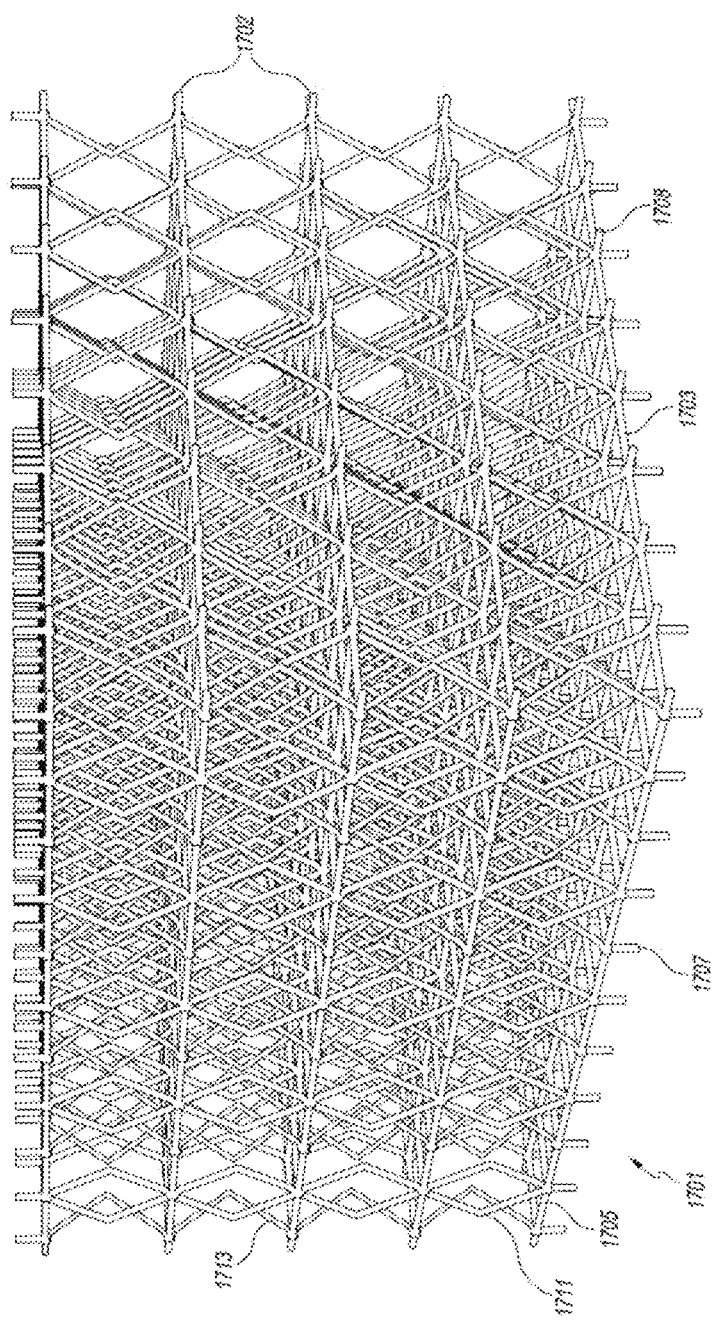
Figure 4C:
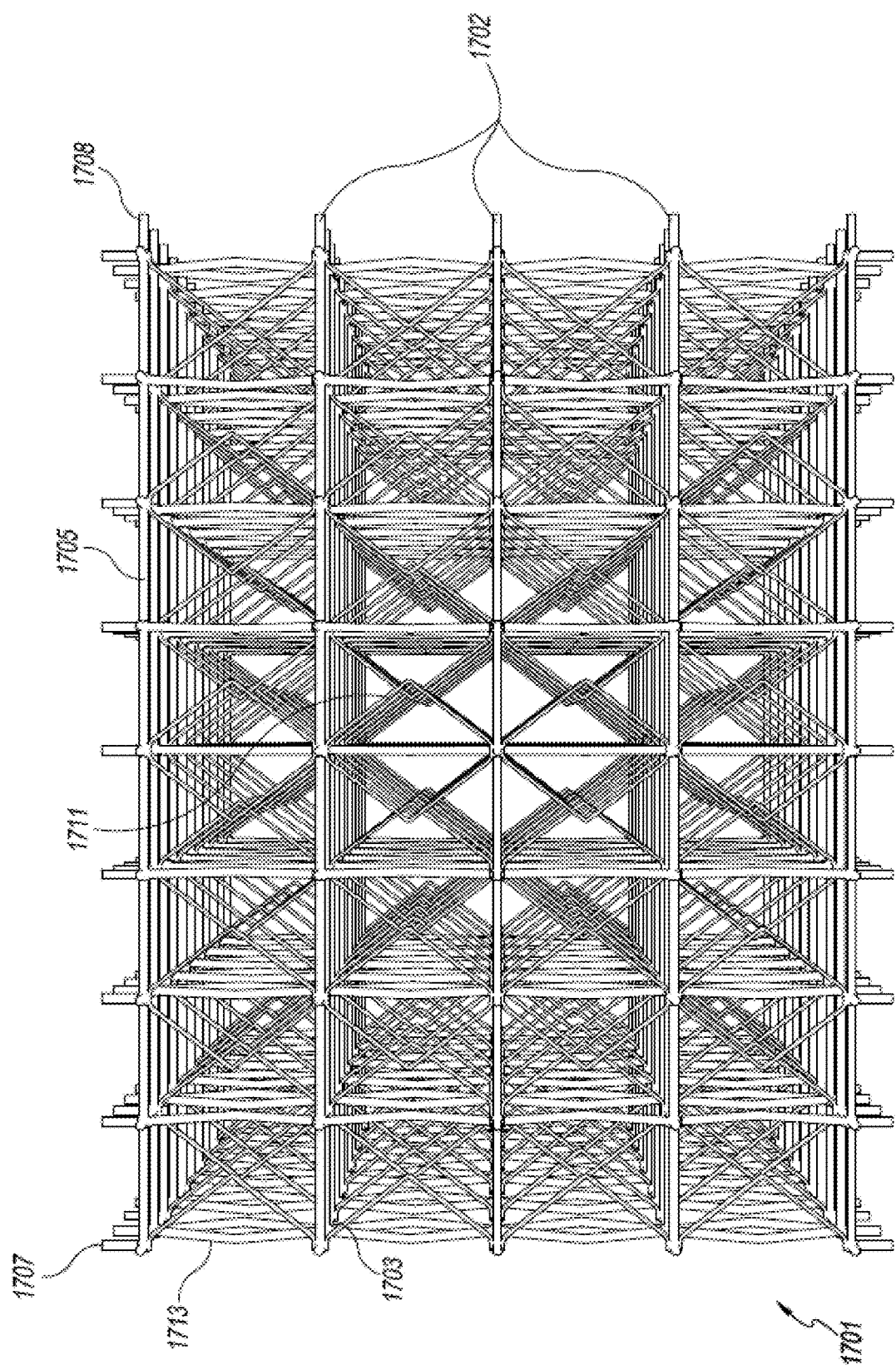
Figure 4D:
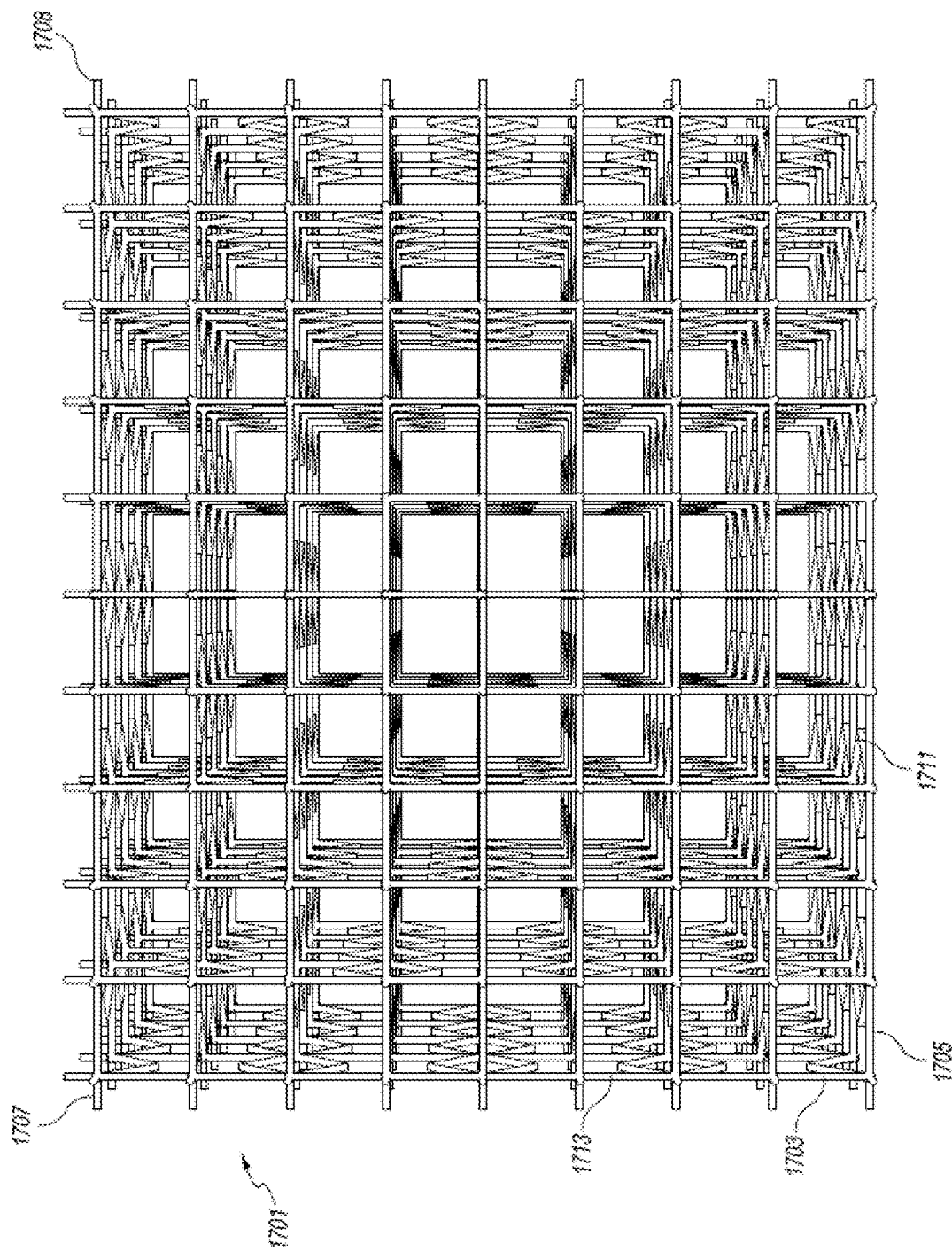
Figure 5A:
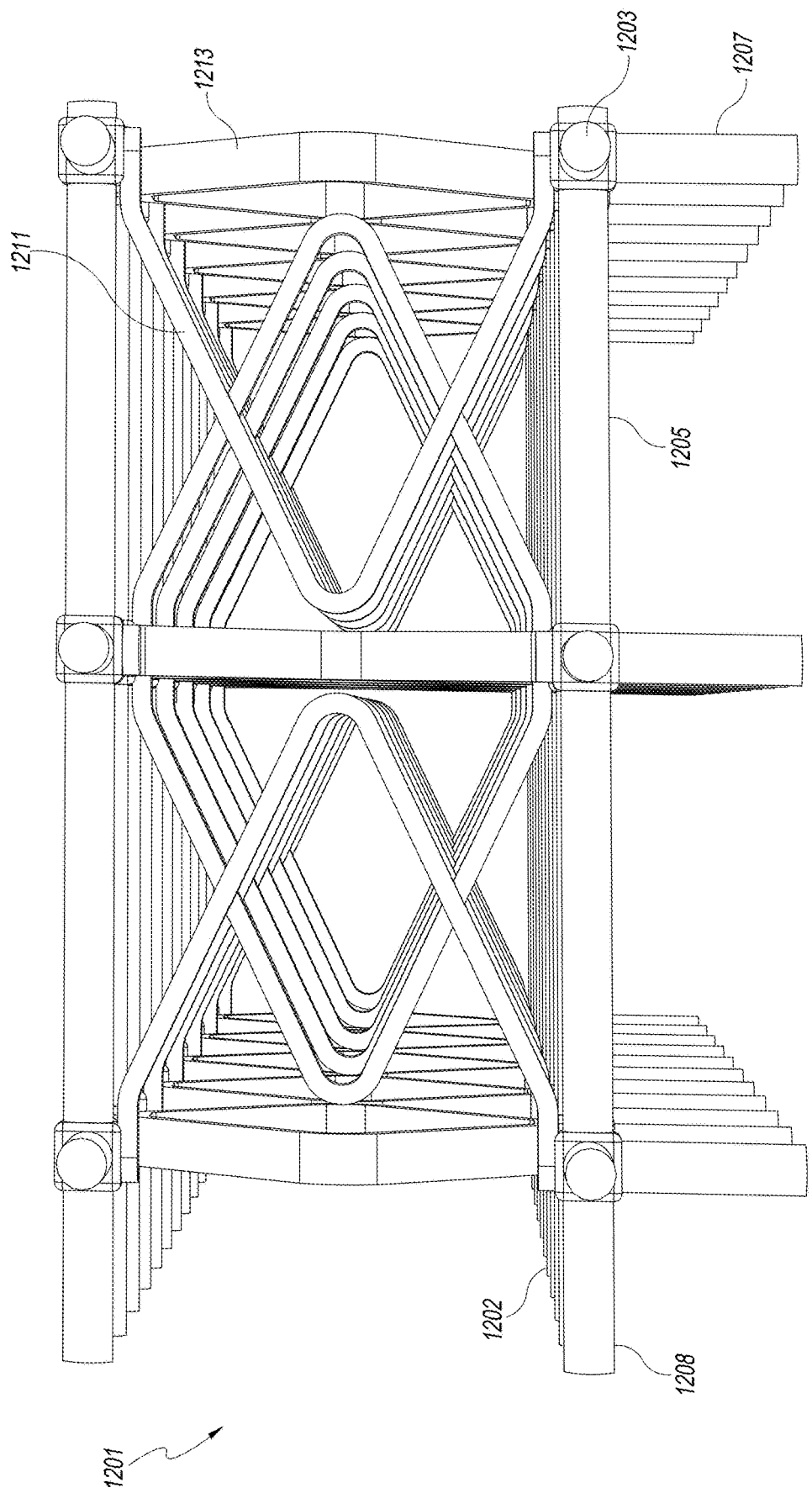
Figure 5B:
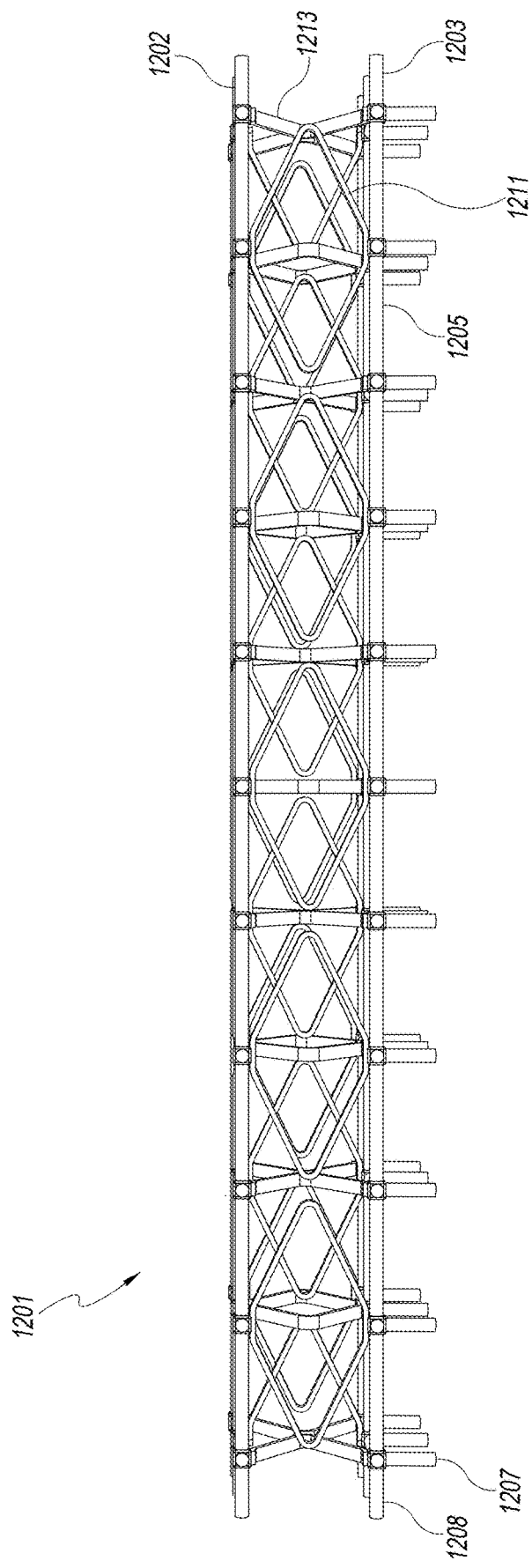
Figure 5C:
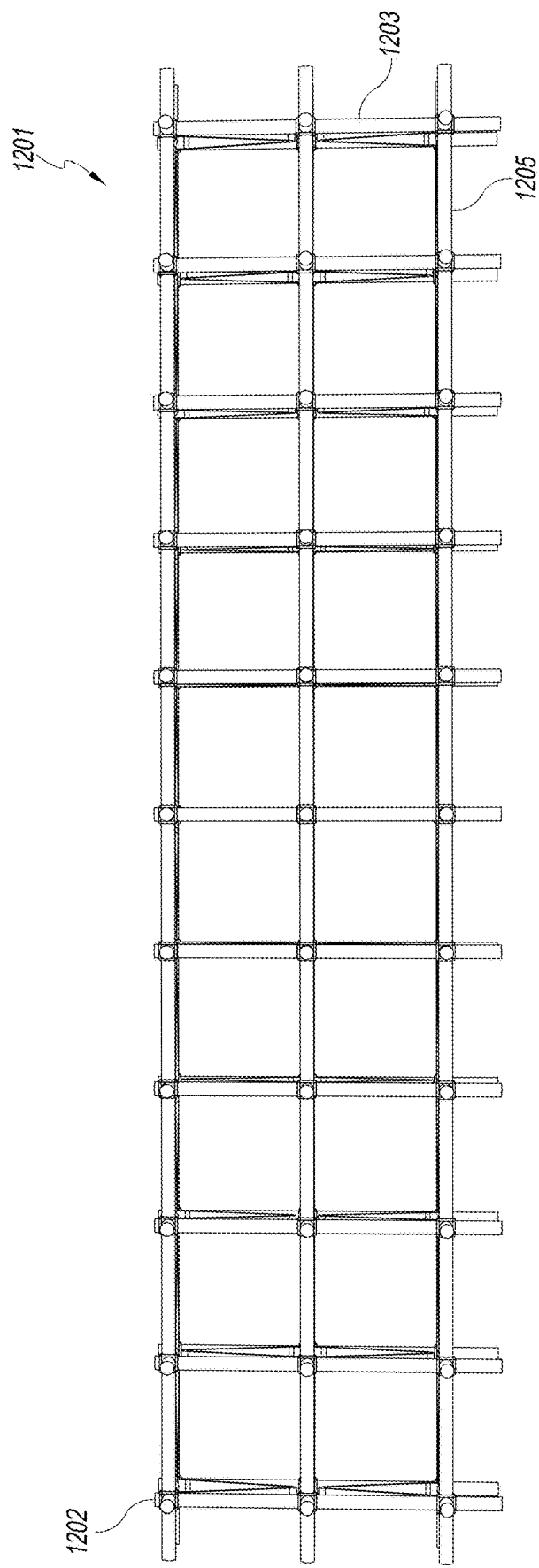
Figure 5D:
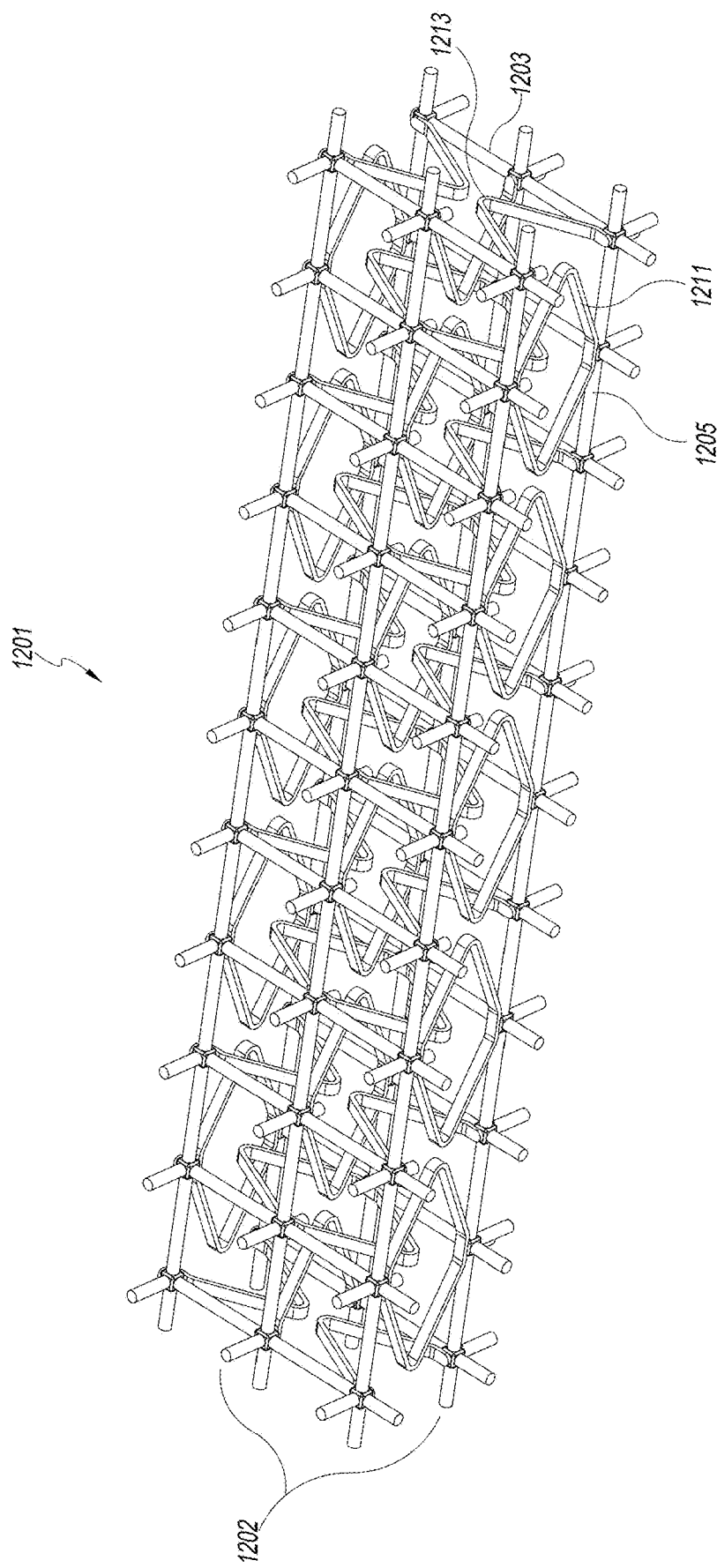

In a preferred embodiment, these spring elements 1711, 1713 may be V- or U-shaped. Each spring element may comprise two elongated portions that are bent relative to each other and form an obtuse angle (as shown in FIGS. 4A-C), or an acute angle (as shown in FIG. 5A). Spring elements 1711 preferably run in a plane parallel to beam 1705, and may be attached to either the beam 1703 or 1705. Similarly, spring elements 1713 preferably run in a plane parallel to beam 1703, and may be attached to either the beam 1703 or 1705. For both spring elements 1711, 1713, a preferred attachment point is at the junction between beams 1703 and 1705. Preferably, the spring elements 1711 are arranged in a first plurality of parallel planes, which run parallel to the direction of the beam 1705, and the spring elements 1713 are arranged in a second plurality of parallel planes which run parallel to the direction of the beam 1703. The spring elements 1711 located between two adjacent planar support structures 1702 may be arranged in a repeating pattern within the first plurality of parallel planes. The spring elements 1713 located between two adjacent planar support structures 1702 may be arranged in a repeating pattern within the second plurality of parallel planes. In one embodiment as illustrated in FIGS. 4A and 4C, adjacent spring elements 1711 and 1713 form a diamond shape. However, different patterns, arrangements and numbers of spring elements may be employed. In some embodiments, the spring elements 1711, 1713 may have a spring constant ranging between 10 and 30 N/m, more preferably between 15 and 25 N/m, and even more preferably 23 N/m. In some preferred embodiments, the force required to compress seven spring elements by 15 mm equals 250 g. In some embodiments, the force required to compress the same seven springs by the same distance ranges between 180 and 230 g. In some embodiments, there are a total of four spring elements 1711, 1713 per 10 cm³. Of course, one will recognize that factors such as the spring constants and/or number of springs may be tailored to the particular tissue type and wound closure desired, and that higher or lower spring constants or numbers of springs may be used.

Standoffs 1707 and 1708 may be provided at the edges or along the outer faces of the structure 1701, and which may be configured to contact the skin surrounding a wound. In some embodiments, the standoffs 1707, 1708 may be extensions of the beams 1703, 1705, or may be provided separately. In some embodiments, the standoffs 1707, 1708 may be provided with hook or anchor elements configured to anchor tissue, such as the tissues of the skin, placed into contact with them. Additionally or alternatively, hook or anchor elements attached to the structure 1701 may be provided separately from or instead of the standoffs 1707, 1708. Preferably, the hook or anchor elements are configured so as to be have a release force (once engaged into tissue) that causes no or minimal pain to the patient while permitting sufficient pulling force to be applied thereto so as to allow for wound closure. FIGS. 5A-E illustrate different views of embodiments of a stabilizing structure 1201. This embodiment is similar in some respects and in function to the embodiment described above in relation to FIGS. 4A-D, and share similar elements. The structure comprises beams 1203 and 1205 that form a planar support structure 1202 separated by spring elements 1211 and 1213. Standoffs 1207 and 1208 may also be provided. Here, however, the spring elements 1211 and 1213 are thicker and have portions that are bent relative to each other at acute angles. Additionally, compared to FIGS. 4A-D, the structure 1201 has a greater volume and greater number of spring elements 1211, 1213. As illustrated best in FIG. 5D, the spring elements 1211 form a repeating diamond pattern within a first plurality of parallel planes, with the diamond location being staggered between adjacent parallel planes. A corresponding pattern is employed for spring elements 1213 with a second plurality of parallel planes. A similar configuration may be seen in FIGS. 4A-4D.

Stabilizing Structures of FIGS. 6A-14 and 25

Figure 6A:
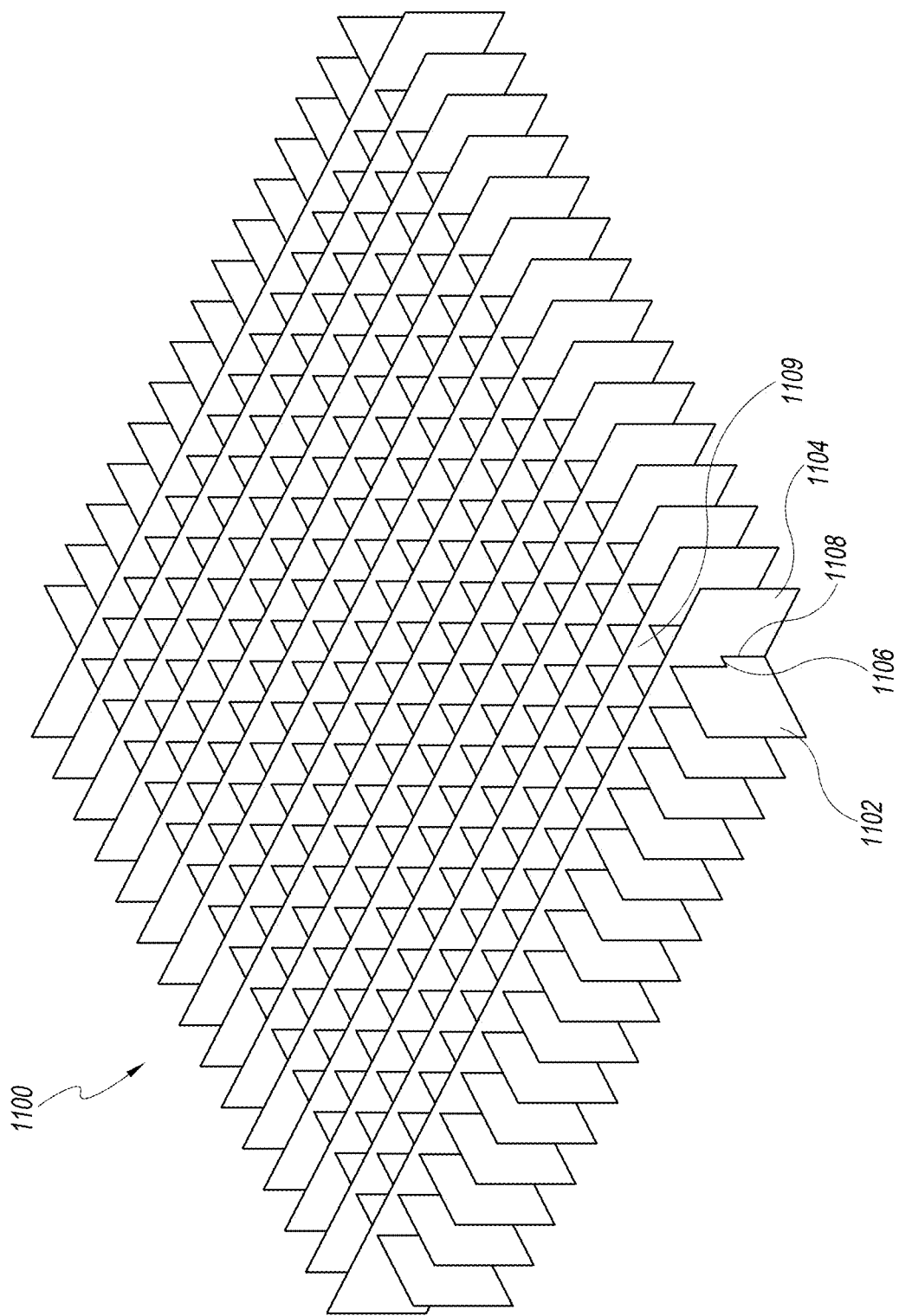
FIGS. 6A-D illustrate additional embodiments of a stabilizing structure.

FIGS. 6A-E illustrate additional embodiments of a stabilizing structure 1100. FIG. 6A shows a perspective view of an embodiment of a stabilizing structure 1100. Here, the stabilizing structure 1100 is preferably comprised of two or more interlocking strips (described below in more detail with relation to FIG. 6B) that extend in directions approximately perpendicular to each other when in a substantially uncollapsed configuration. The stabilizing structure is preferably configured to collapse in one direction or along a first plane while remaining relatively rigid and collapse-resistant in a direction perpendicular to the first direction or plane.

Figure 6B:
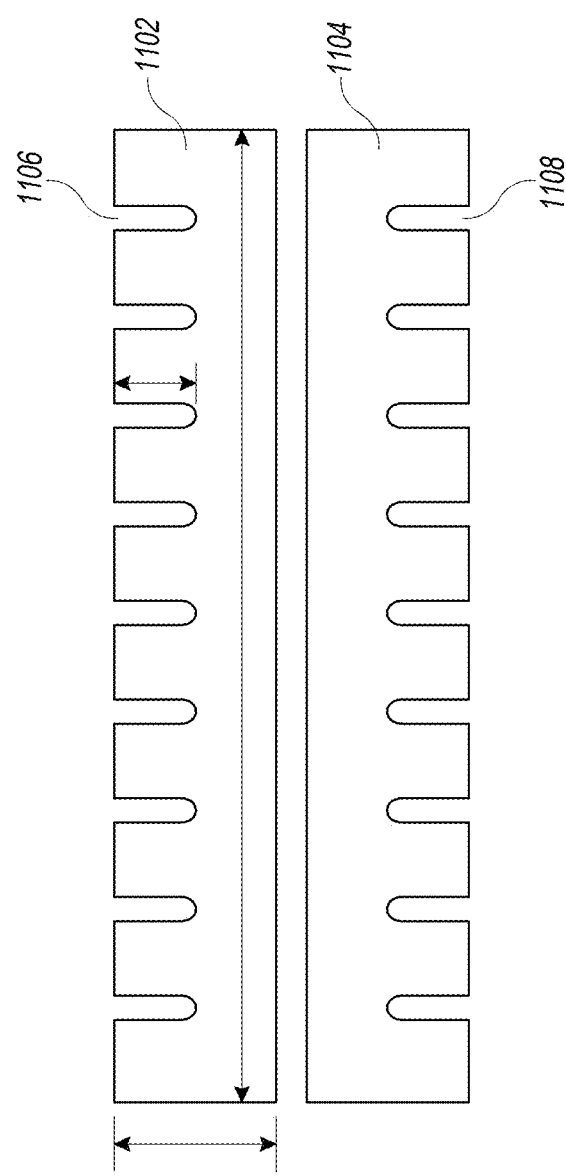

FIG. 6B illustrates side views of a bottom strip 1102 and a top strip 1104 that may be used to make a stabilizing structure 1100 such as the embodiment illustrated in FIG. 6A. Each of the top and bottom strips 1102, 1104 are preferably configured to movably interlock with each other, for example via matching notches 1106 and 1108. One or more notches 1106 may be provided on a top side of bottom strip 1102, and similarly, one or more notches 1108 may be provided on a bottom side of top strip 1104. When assembled together, the one or more top and bottom strips 1102, 1104 may be positioned so that the notches 1106, 1108 line up. Preferably, the top and bottom strips 1102, 1104 are positioned at substantially perpendicular angles to each other, thereby permitting the notches 1106, 1108 to slot together so as to create a movably interlocking structure. Typically, the number of notches 1106 on the bottom strip 1102 will equal the number of top strips 1108 that will form the stabilizing structure 1100, and vice versa. The notches 1106, 1108 are preferably shaped with a width that permits the strips 1102, 1104 to move from approximately perpendicular angles to angles far from perpendicular (i.e., close to parallel) to each other, thus permitting the stabilizing structure 1100 to articulate and collapse along one direction or plane.

In a preferred embodiment, the strips 1102, 1104 are constructed from a rigid or semi-rigid material, such as a polymer. Examples of suitable polymers include polyethylene, polypropylene, polyurethane, polyvinyl chloride, polystyrene, polyacrylate, polymethyl methacrylate, PEEK, silicone, polyurethane, polycarbonate, composites and laminates, or combinations thereof. In some embodiments, the material may include compressed or "felted" reticulated foam. Of course, other materials, such as cardboard or metal may be used. Preferably, the materials may be at least partially porous so as to permit fluid to flow through the material. Further, such properties may aid in distributing negative pressure through the device and to the wound, and may aid in removing fluid from the wound dressing. Such materials may include, for example, low density polypropylene, foamed material, or sintered material. The material used does not necessarily need to be strong along the length of the strips 1102, 1104, but should preferably be able to withstand pressure applied to a top or bottom edge. Preferably, the material is capable of withstanding the pressure from atmospheric pressure exerted on a drape when up to 200 mmHg negative pressure is applied to the wound. In some embodiments, the material can withstand a force of 5 psi applied to a top or bottom edge.

In a preferred embodiment, each strip 1102, 1104 measures 180 mm long by 30 mm high. The thickness of the strips 1102, 1104 may range, for example, between 1.50 to 2.40 mm, although the thickness will be selected at least partly based on the ability of the material to withstand pressure being applied along its edge. The thickness is preferably balanced between keeping the material thin enough to minimize the compressed thickness of the stabilizing structure 1000, while keeping the material thick enough to avoid causing excessive localized pressure upon the wound bed. The notches 1106, 1108 may measure approximately 15 mm in height, and may be spaced apart from other notches by 18 mm. Although the notches 1106, 1108 are shown with rounded bottoms, these may also be cut with squared-off or triangular bottoms. In some embodiments, the rounded edges reduce stresses onto the strips 1102, 1104 so as to prevent fracture and crack propagation, and may also increase the springiness of the stabilizing structure 1100.

It will be understood that the interlocking strips 1102, 1104 may not necessarily need to be joined together via notches. Hinges or other devices could be used to provide the articulation or movable interlocking ability illustrated above. In some embodiments, hinges may be constructed from thinner areas of the same material used to construct the strips 1102, 1104, and are configured to flex or bend to a predetermined position. The stabilizing structure 1100 could also be molded as a single piece such that the interlocking strips 1102, 1104 form a single unit.

Returning to FIG. 6A, the perspective view illustrates an example of a stabilizing structure 1100 configuration with multiple interlocking top and bottom strips 1102, 1104 movably interlocked via multiple notches 1106, 1108. The intersections of two top strips 1102 and two bottom strips 1104 form a quadrilateral-shaped boundary space 1109. When the top and bottom strips 1102, 1104 are at perpendicular angles to each other, the space 1109 will be square or rectangular. However, as the stabilizing structure 1100 collapses along a direction or plane, the space 1109 will become more diamond- or parallelogram-shaped. The stabilizing structure 1100 will preferably comprise multiple spaces 1109, which form cells defined by the walls of the top and bottom strips and with openings on top and bottom ends.

Figure 6C:
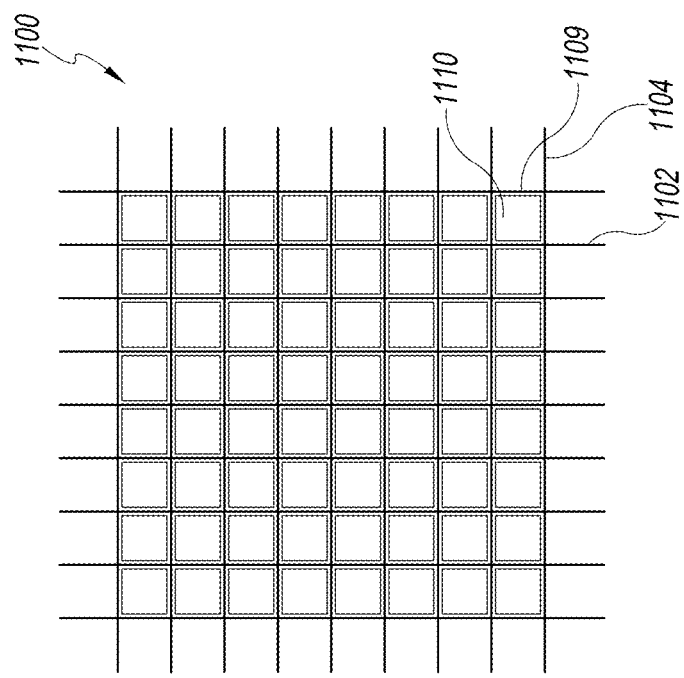

FIG. 6C illustrates a top view of an embodiment of the stabilizing structure 1100 where a porous material 1110 has been placed into the quadrilateral-shaped boundary space 1109. Here, the porous material 1110 used is preferably soft and conformable so as to be able to adapt to the any change in the configuration of the stabilizing structure 1100 if it collapses. Preferably, the porous material is a foam, such as a polyurethane foam. This porous wound filler material may be cast around the stabilizing structure 1100 so as to completely encapsulate it. When used, the resulting stabilizing structure 1100 may be cut to size so as to fit into a wound. Such porous material 1110 may be used to aid in the fluid transmission or wicking of fluid from within a wound, and may also, when in contact with the wound (e.g., when used in negative pressure wound therapy), aid in the healing of the wound.

Figure 6D:
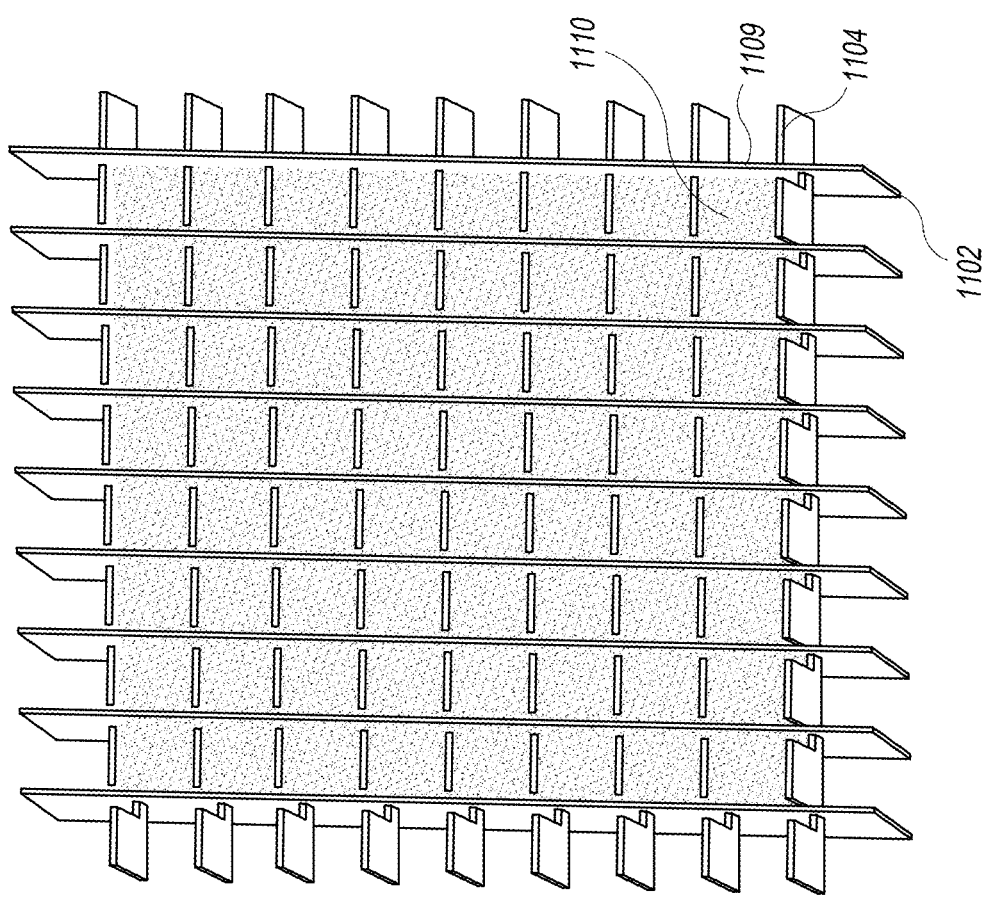

FIG. 6D illustrates a perspective illustration of an embodiment of the stabilizing structure 1100 with a porous wound filler material 1110 inserted into the spaces 1109. In some embodiments, additional porous material may also be used to encapsulate or surround the structure 1100. For example, a sock or wrap may be fitted around the structure 1100, and may for example be constructed from foam or gauze. When the stabilizing structure 1100 is incorporated as part of a wound dressing placed over skin surrounding a wound, the structure may be oriented to coincide with landmarks on the skin or the shape of the opening or incision in the skin.

Advantageously for some types of wounds, the stabilizing structure of FIG. 6A may elongate in a direction perpendicular to the primary direction of closure, but still within the horizontal plane. Such elongation can be beneficial to wound healing as the physiology of the wound may dictate that it should lengthen as it closes.

In use, the stabilizing structure 1100 may be placed over a wound such that the upward facing portion of the structure 1100 is substantially rigid and resists collapse in the vertical direction once negative pressure is applied to the wound (e.g., once covered by a drape as described previously). A porous material such as foam may be placed around, into, and/or so as to surround or encapsulate the stabilizing structure 1100. As negative pressure is applied, the structure 1100 will then preferably collapse in the plane perpendicular to the vertical direction, aiding in wound closure.

Figure 7A:
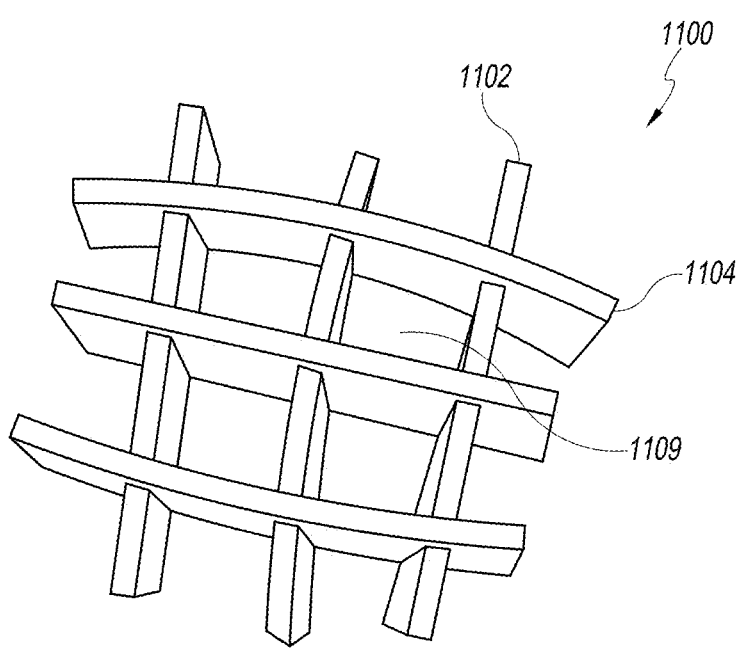
FIGS. 7A-C illustrate an embodiment of a stabilizing structure manufactured from felted foam.
Figure 7B:
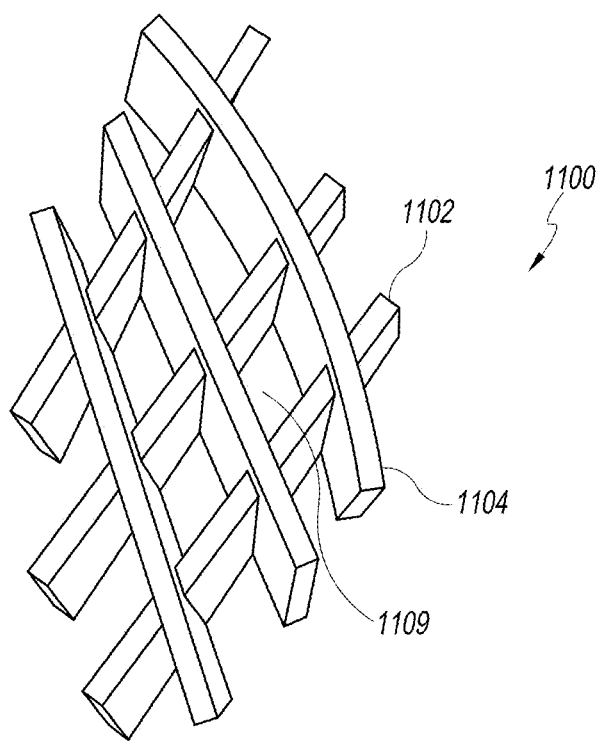
Figure 7C:
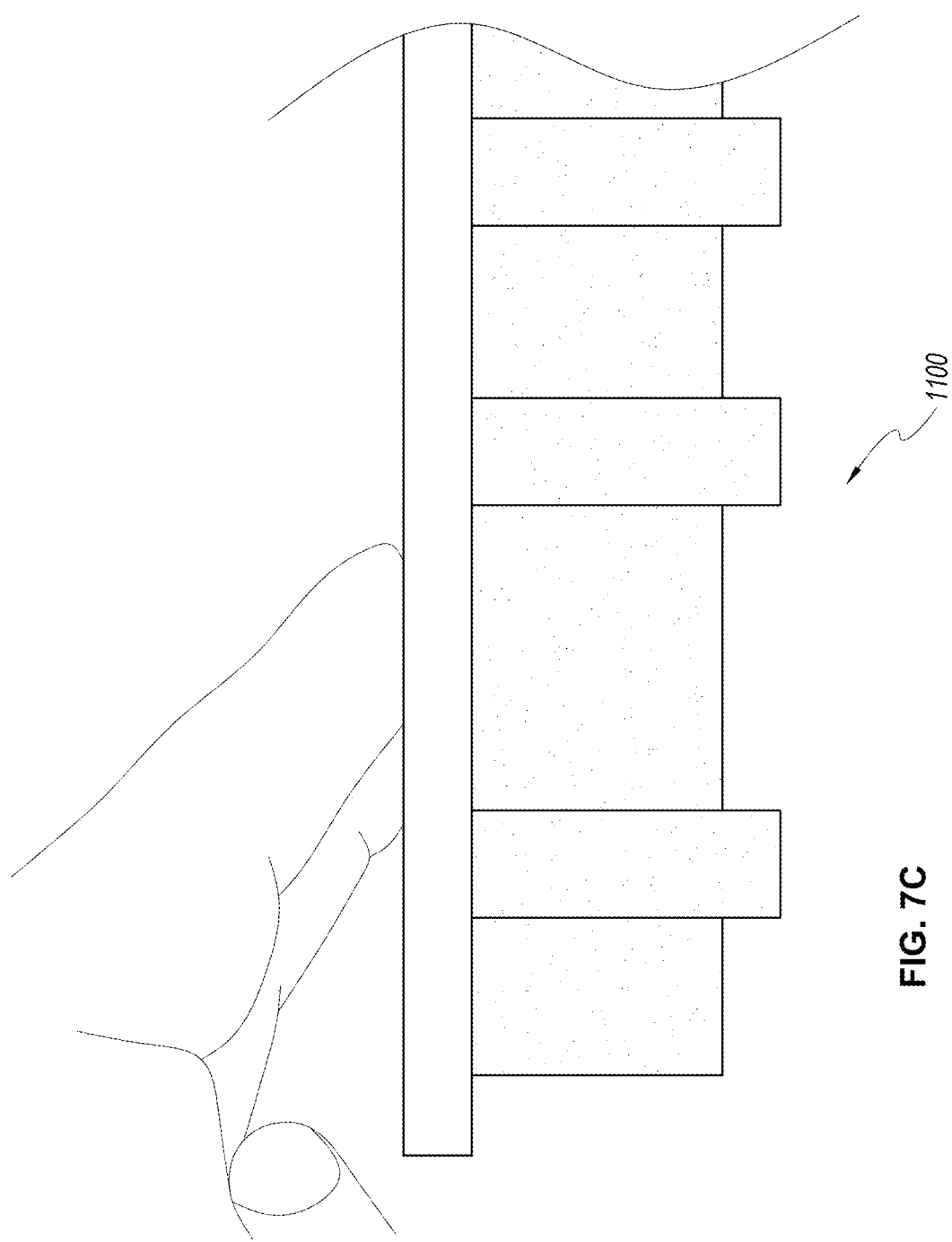

FIGS. 7A-C illustrate embodiments of a stabilizing structure 1100 similar to that described above in relation to FIGS. 6A-E. Here, the stabilizing structure 1100 is constructed from interlocking strips constructed from felted foam. The physical relationship between and the mechanism for the interlocking top and bottom strips 1102 and 1104 are substantially similar to what was discussed previously above, and will not be repeated here. Felted foam, however, is foam (e.g., polyurethane foam) that has been heated and compressed. After this procedure, the foam will be stiffer and less compressible, while still remaining porous. Such a material may be advantageously used in a stabilizing structure 1100, as the material may be compressible in a plane defined by the top and bottom strips 1102, 1104, as shown in FIG. 7B. However, the material is substantially rigid in the vertical direction, as illustrated in FIG. 7C, where a weight has been placed over the foam without substantial buckling. Here, the foam can support approximately 6 kg of weight, and embodiments of the device have been measured to support at least 3 psi of applied pressure without collapse. Further, while such material is substantially rigid, the porous nature of the material permits negative pressure to be transmitted to the wound and for wound exudate to be removed.

Figure 8A:
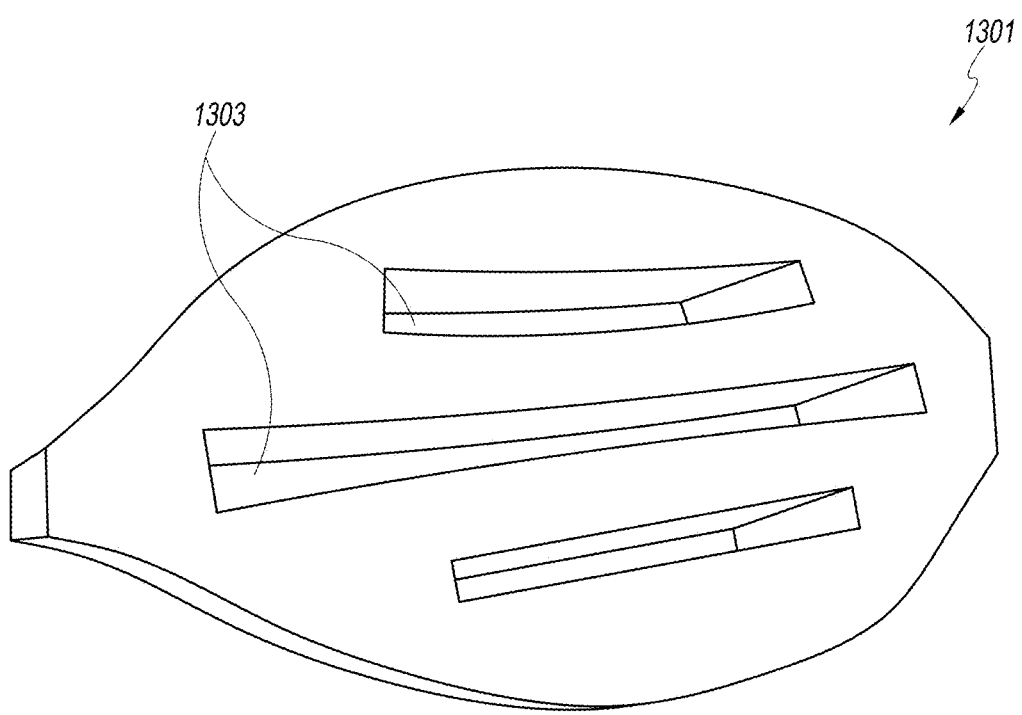
FIGS. 8A-B are photographs of further embodiments of stabilizing structures comprising a porous wound filler material.
Figure 8B:
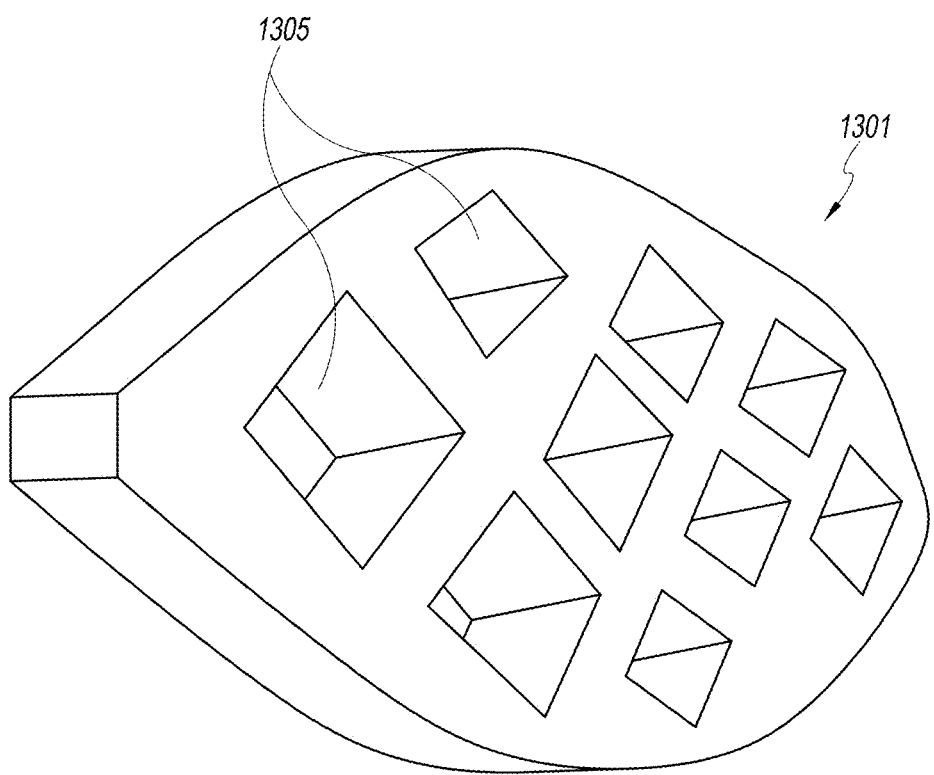

FIGS. 8A-B are photographs of further embodiments of stabilizing structures. FIG. 8A illustrates an embodiment of a stabilizing structure 1301 that preferentially collapses along one direction. Here, the stabilizing structure 1301 comprises a porous material (e.g., foam) into which one or more slots 1303 have been cut. These slots 1303 preferably extend longitudinally through the thickness of the stabilizing structure 1301. Accordingly, the empty space will permit the stabilizing structure to preferentially collapse in a direction when a force is applied in a direction perpendicular to the slots 1303. Because the empty space is easier to compress than the remainder of the foam, the width and thickness of the foam will preferably not (or minimally) compress compared to the resulting compression perpendicular to the length of the stabilizing structure 1301.

As illustrated in FIG. 8B, the stabilizing structure 1301 may also be provided with holes or cells 1305 in other configurations, such as diamond-shaped holes forming a lattice. This configuration permits compression along the length and width of the stabilizing structure due to the compressible holes 1305, while the comparatively more rigid thickness of the foam resists compression to a greater extent.

In some embodiments, stabilizing structures similar to those illustrated above in FIGS. 6A-E may be constructed as a single unit, for example by molding, rather than from multiple parts. As with the previously-described embodiments, the stabilizing structures are configured to form an array of one or more cells defined by one or more walls and forming a plane, with each cell having a top and bottom end with an opening extending through the top and bottom ends in a direction perpendicular to the plane. In some embodiments, the stabilizing structures may have cells that are square, diamond, oblong, oval, lozenge, and/or parallelepiped, and non-limiting examples of the same are illustratedelsewhere in the specification. While some embodiments may have cells that are all the same shape, the cells may also be tailored to be larger, smaller, or differently-shaped than other cells in the structure. The shape and size of the cells may be tailored to the desired characteristics (e.g., resilience and ease of collapse) for optimal wound closure and healing.

Construction of a single unit stabilizing structure may be advantageous in terms of ease of use and cost. For example, single unit stabilizing structures may be trimmed as necessary to fit onto a wound site. The material used is preferably biocompatible, and even more preferably nonadherent to the wound site. Suitable materials are preferably chosen to be soft while remaining sufficiently strong to resist collapse in a vertical direction, and may include polymers, such as polyethylene, polypropylene, polyurethane, silicone (including siloxanes), ethyl vinyl acetate, and copolymers and blends thereof. The hardness of the material may affect the thickness of the resulting stabilizing structure, and may be selected based upon the desired thickness of the stabilizing structure components (including hinges and other joints thereof) and the ability of the stabilizing structure to resist collapse, e.g., due to the atmospheric pressure acting upon a drape placed over the stabilizing structure. Suitable durometer hardnesses of materials used range from about 30 shore to 120 shore (as measured on the Shore durometer type A scale), preferably from about 40 shore to 60 shore, and even more preferably about 42 shore. Generally, the material chosen is preferably softer (while still satisfactorily meeting other material requirements), as harder materials may provide reduced levels of closure as the hardness increases.

Figure 9A:
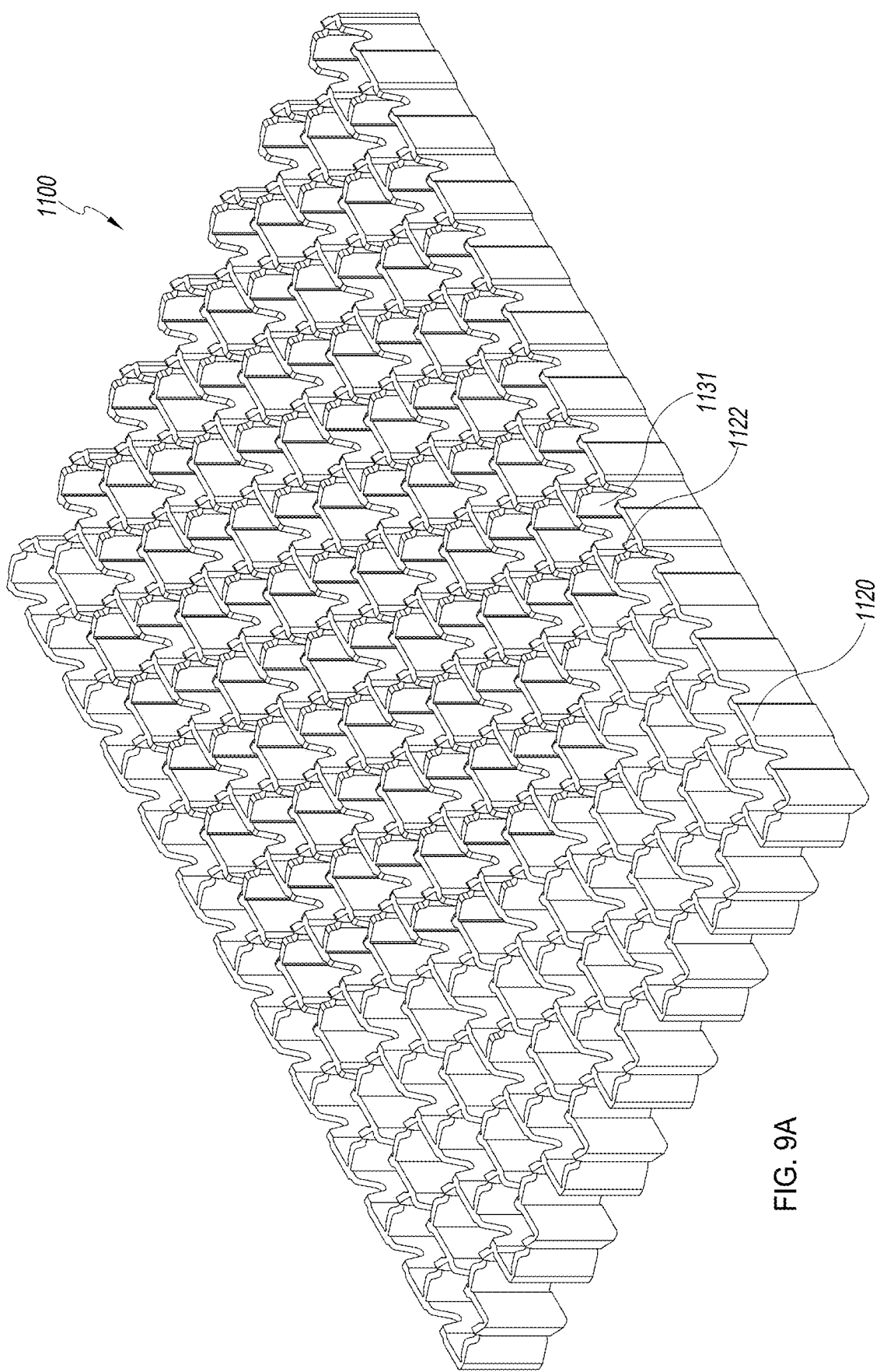
FIGS. 9A-B, 10, 11, 12, 13, and 14 illustrate additional embodiments of a stabilizing structure.
Figure 9B:
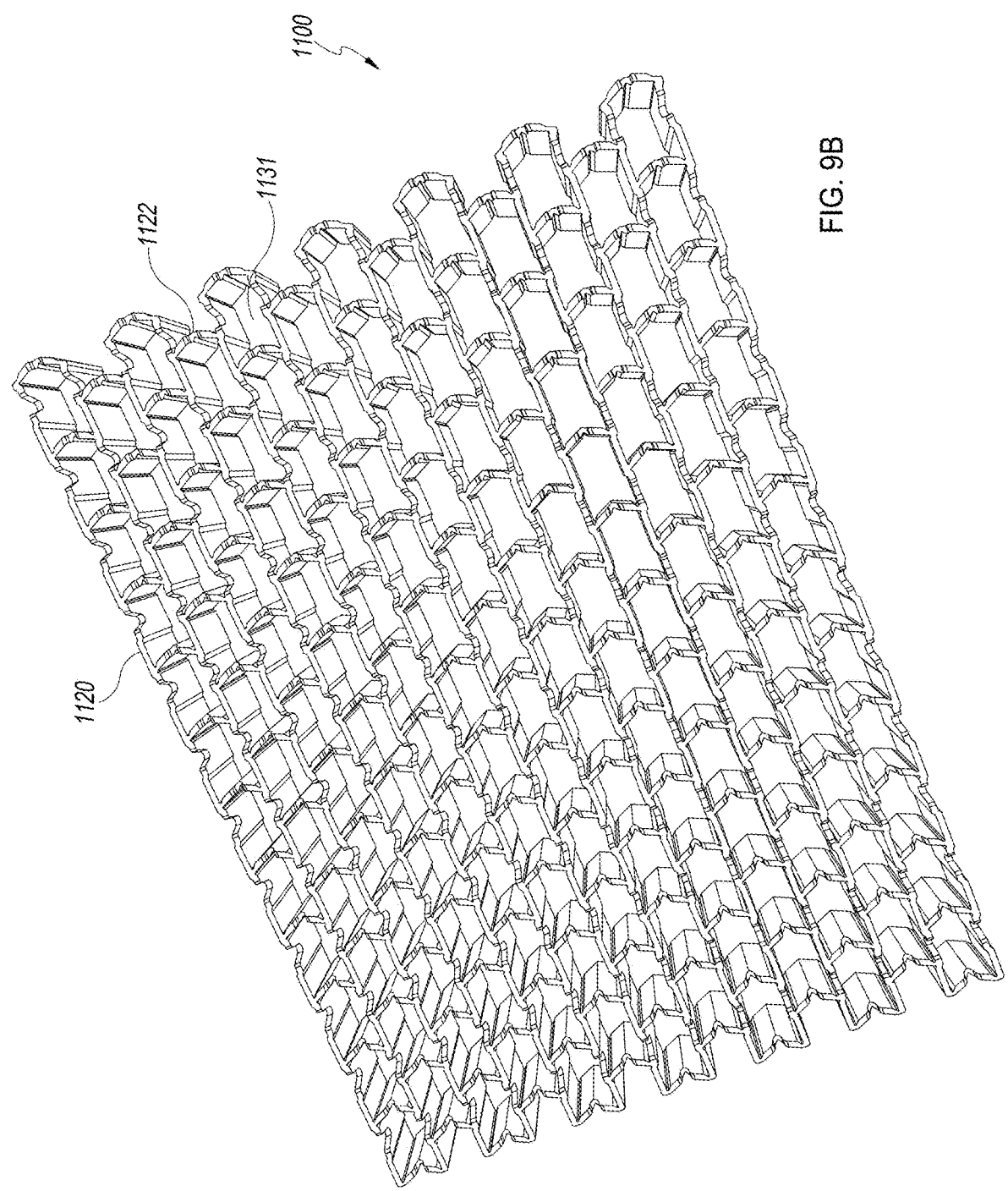

FIGS. 9A-B illustrate an embodiment of a stabilizing structure 1100 configured to preferentially collapse in only one horizontal direction while remaining substantially rigid or uncollapsed when force is applied in a vertical direction. Preferably, the stabilizing structure 1100 is constructed as a single unit as illustrated so as to form one or more cells 1131. Here, two or more longitudinal strips 1120 (which form the walls of the cells) may have relatively straight configurations, and are connected together via one or more collapsible cross strips 1122. It will be appreciated that in a single unit embodiment, the strips are merely portions of the same material that may have been formed together to form the entire single unit structure. The collapsible cross strips 1122 may be angled or indented so as to make them more likely to collapse in a direction generally parallel to their length. In this embodiment illustrated in this section or elsewhere in this specification, the collapsible cross strip 1122 is more likely to collapse at the apex of the angled portion and at the junctions to the longitudinal strips 1120 when a force is applied in a direction approximately parallel to the general length of the collapsible cross strip 1122. In some embodiments, the collapsible cross strip is configured to fold into a portion (which may be thinner) of the longitudinal cross strip 1120.

In some configurations, one or both of the longitudinal strips 1120 and/or collapsible cross strips 1122 may comprise one or more notches positioned along a length thereof. These notches promote fluid transfer across the structure, and aid in distributing negative pressure. In some embodiments, notches may be used in conjunction with a porous material so as to enhance fluid transfer. In relation to the longitudinal strips 1120, the collapsible cross strips 1122 may be positioned alternately along the length of the longitudinal strips 1120, as best illustrated in FIG. 9B, to form a configuration somewhat analogous to a "stretcher bond" used in bricklaying. Of course, other configurations are possible. Further, although this embodiment is illustrated as being formed as a single unit, those of skill in the art will recognize that this embodiment (and the others described below) may be constructed from multiple pieces joined or connected together.

Figure 10:
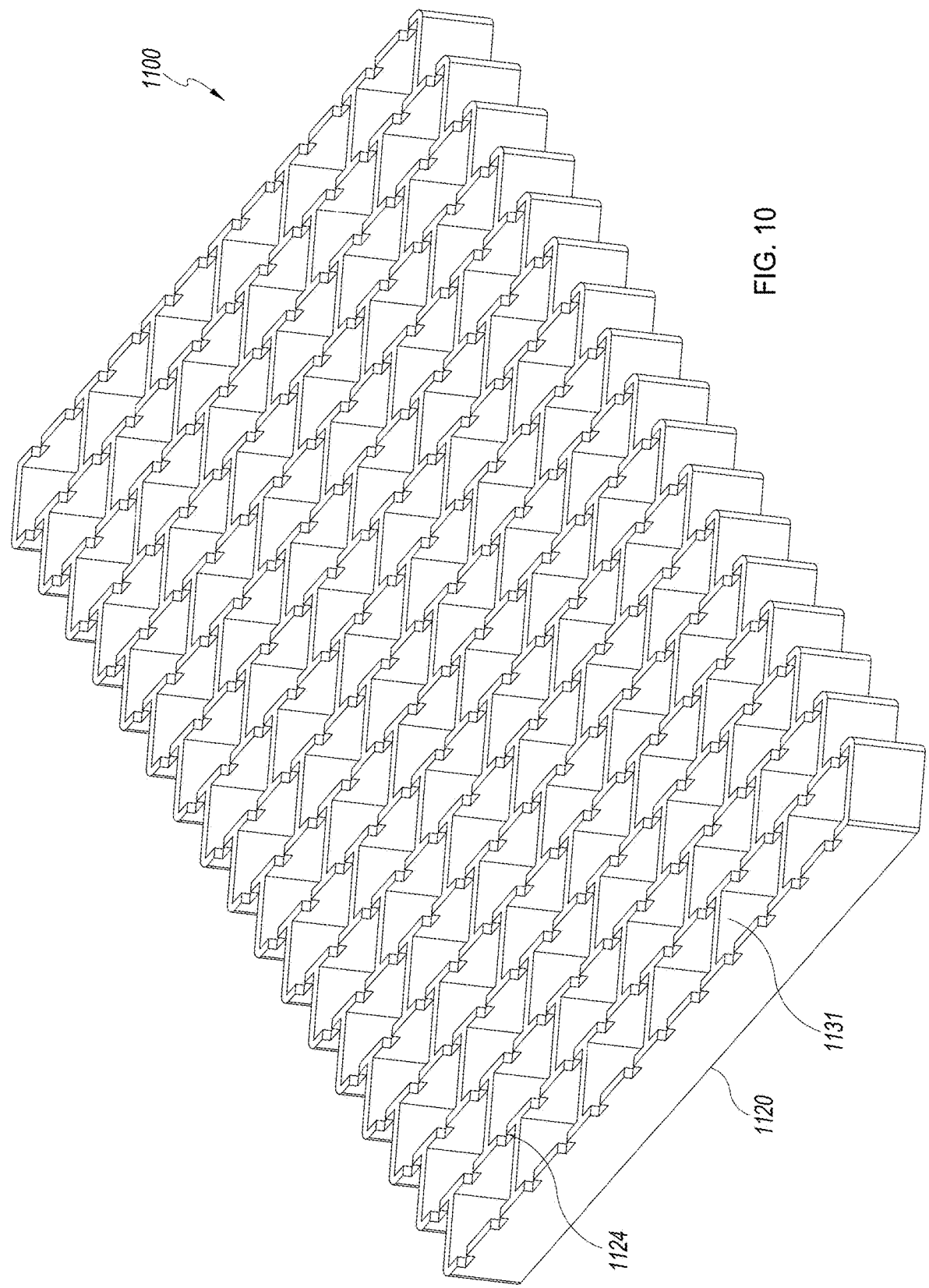

FIG. 10 illustrates another embodiment of a stabilizing structure 1100, here comprising two or more longitudinal strips 1120 attached to each other via one or more angled cross strips 1124 so as to form cells 1131. As with the embodiment illustratedelsewhere in the specification, the stabilizing structure 1100 is configured to collapse when pushed in a direction perpendicular to the length of the longitudinal strips 1120, while remaining substantially rigid or uncollapsed when force is applied in a vertical direction. The angled cross strips 1124 are preferably attached to the longitudinal strips 1120 so as to form a non-perpendicular angle so as to promote collapse of the stabilizing structure 1100 in the direction perpendicular to the length of the longitudinal strips 1120. As with FIGS. 9A-B, one or more notches may be formed on either or both of the longitudinal strips 1120 and/or angled cross strips 1124.

Figure 11:
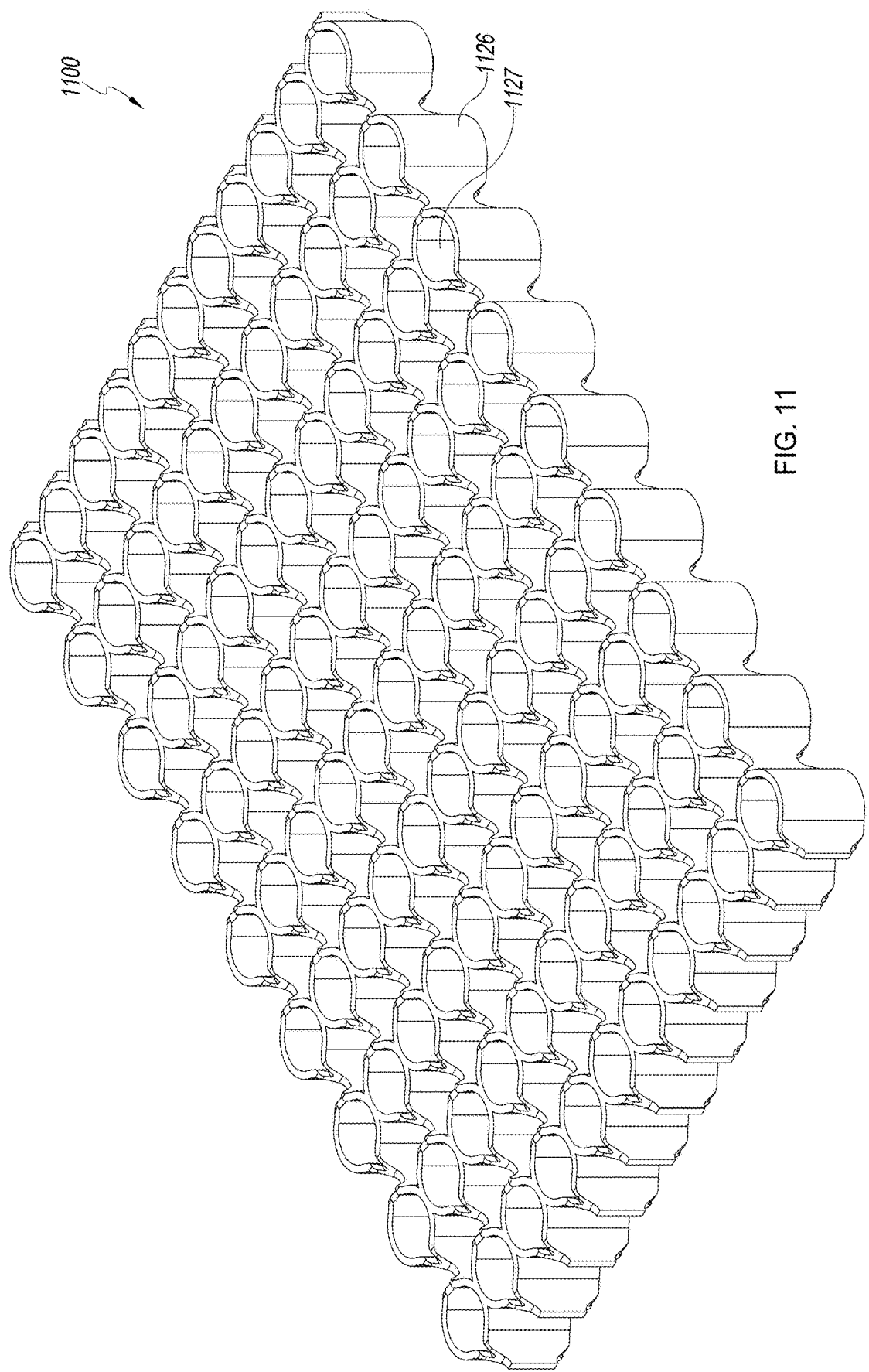

FIG. 11 illustrates a single unit stabilizing structure 1100 comprising one or more pairs of curved longitudinal strips 1126. Each individual longitudinal strip 1126 may be formed as a "wavy" strip (when seen from a vertical orientation) that, when joined face-to-face, form a one or more circular or ovoid cells 1127. As with the other stabilizing structures illustrated in this section or elsewhere in this specification, this structure 1100 is configured to preferably collapse along a horizontal plane or direction while remaining substantially rigid or uncollapsed when force is applied in a vertical direction. Although the structure 1100 is illustrated here as being formed from a single unit, the structure may be constructed from two or more curved longitudinal strips 1126 welded or attached together at the points shown. As with several other embodiments described in this section or elsewhere in this specification, one or more notches may be made onto the walls so as to aid in fluid transfer across and through the structure 1100.

Figure 12:
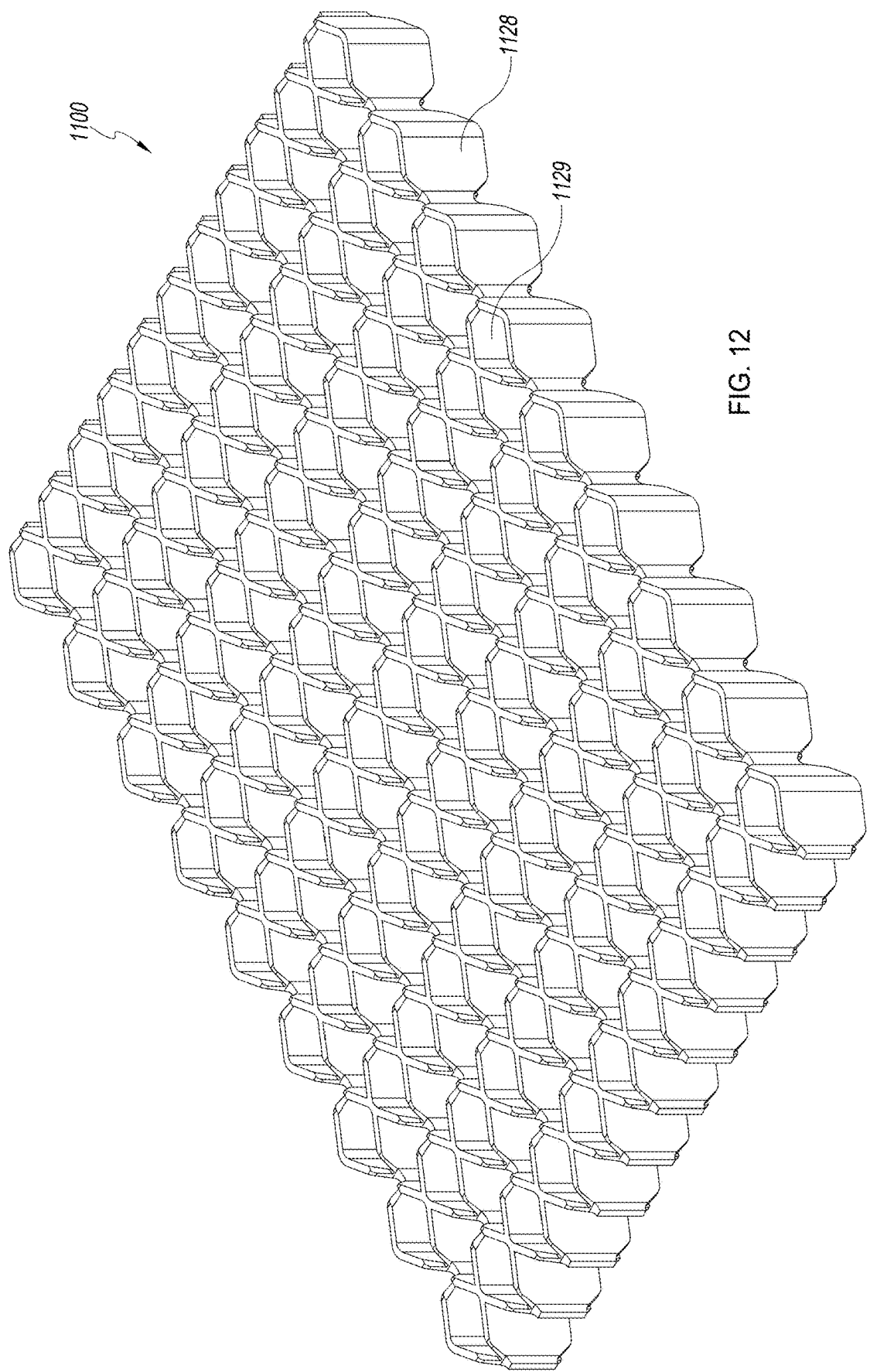

FIG. 12 illustrates a stabilizing structure 1100 similar to the one illustrated in FIG. 11. Here, however, zigzag longitudinal strips 1128 are joined to form diamond-shaped (rather than circular or ovoid) cells 1129. It will be of course appreciated that this embodiment may also be manufactured using substantially straight strips in a style similar to the embodiments illustrated in FIGS. 6A-D.

Figure 13:
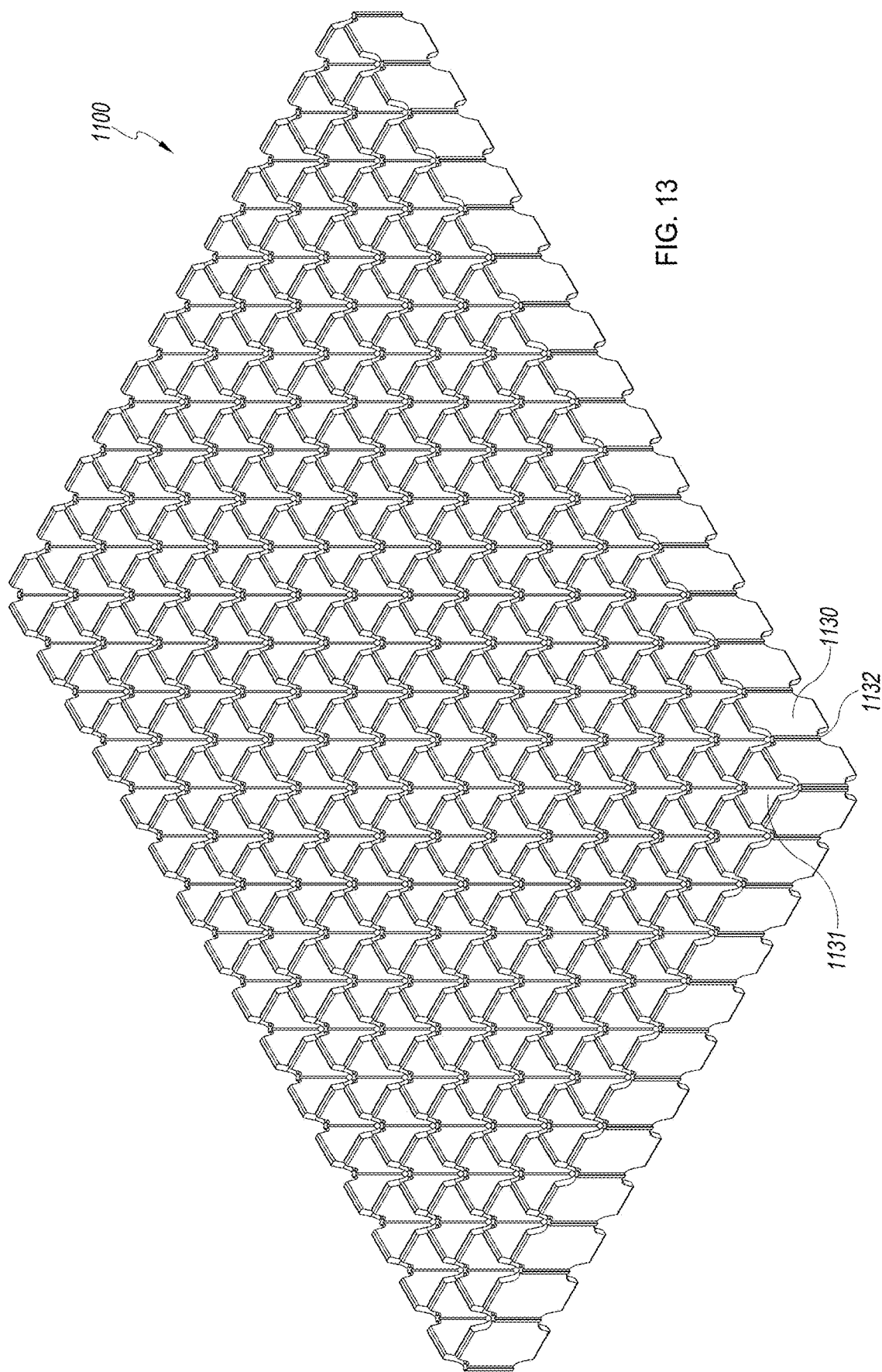

FIG. 13 illustrates a stabilizing structure 1100 comprising vertical segments 1130 joined together at approximately perpendicular angles so as to form quadrilateral or square cells 1131. Preferably, the vertical segments 1130 are of a square or rectangular shape, with tapers 1132 that join the segments together in a movable and flexible configuration. As with the other embodiments described in this section or elsewhere in this specification, this stabilizing structure 1100 may be manufactured as a single unit, and is preferably configured to collapse in a horizontal plane or direction while remaining substantially uncollapsed in a vertical direction.

Figure 14:
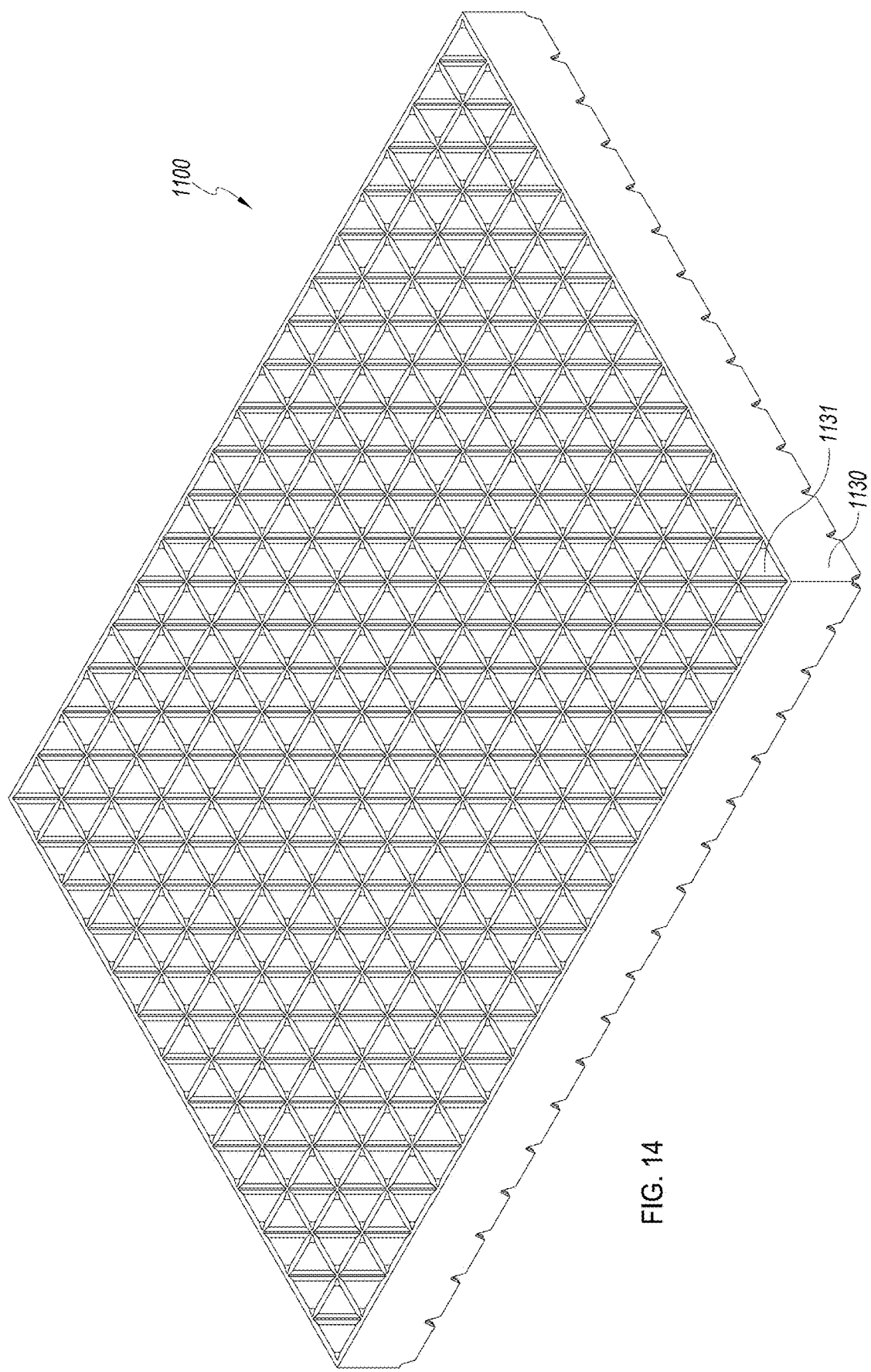

FIG. 14 illustrates another stabilizing structure 1100 similar to the embodiment illustrated above in FIG. 13. The vertical segments 1130 are preferably joined together so as to form one or more quadrilateral or square cells 1131. Here, however, the vertical segments 1130 do not comprise a tapered portion 1132. However, one or more notches may be present on the underside (wound-facing side) of the structure 1100, and which function as described in preceding embodiments. Although this embodiment may be manufactured from multiple vertical segments 1130, it is preferably molded as a single unit.

In some embodiments, the stabilizing structures described in this section or elsewhere in this specification may be entirely molded from a single type of material, such as a plastic. In other embodiments, the stabilizing structures described in this section or elsewhere in this specification may be constructed via an overmolding process whereby the more rigid portions of the structure are molded first and the hinges or flexible portions are molded second. In further embodiments of the stabilizing structure described in this section or elsewhere in this specification, a soft polymer could be molded over the entire structure to soften the feel of the device. In other embodiments, the soft polymer could be molded only over the bottom portion of the stabilizing device, while in some embodiments the softer polymer can be molded over the top and/or the sides of the device. In some embodiments, the soft polymer could be molded over particular edges of the stabilizing structure, such as those on the bottom, sides, and/or top. In certain embodiments, the soft polymer could be molded over any side or combination of sides of the stabilizing device. The soft polymer may act like a softened rim surrounding the hard edges of the stabilizing structure.

Figure 25:
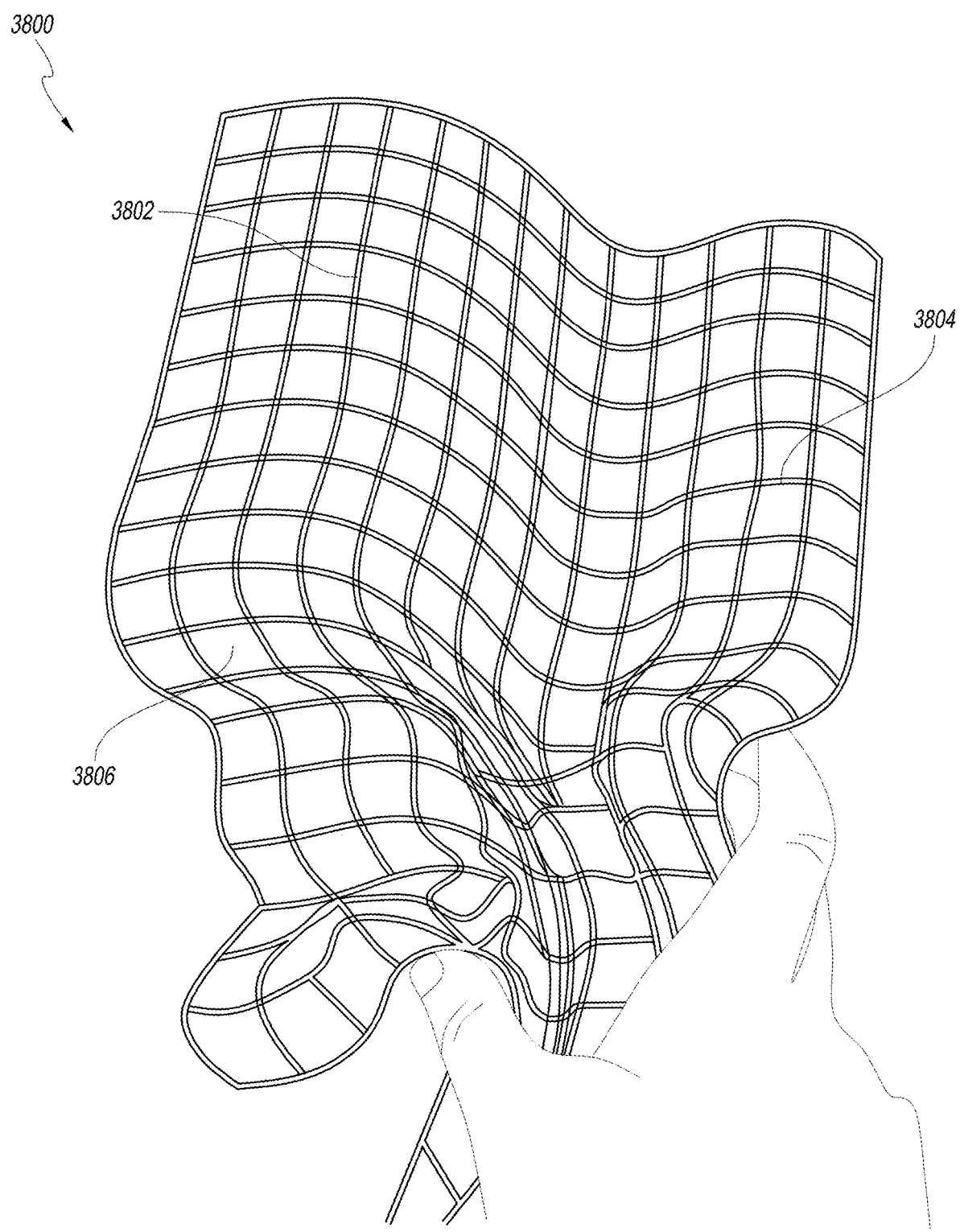
FIG. 25 illustrates an embodiment of a fully flexible stabilizing structure.

FIG. 25 illustrates an embodiment of a stabilizing structure 3800 similar to the structures described above. In this embodiment, the longitudinal strips 3802 and cross strips 3804 are formed from a single piece of material and form rows of flexible cells 3806 that are configured to collapse in a horizontal plane. Because each of the longitudinal and cross strips are formed from the same flexible material, applying a lateral force to the structure causes the cells to collapse generally independently of each other. In other words, the collapse of one or more cells in a row does not necessarily cause the collapse of other cells in the same row.

Stabilizing Structures of FIGS. 15A-21B

Figure 15A:
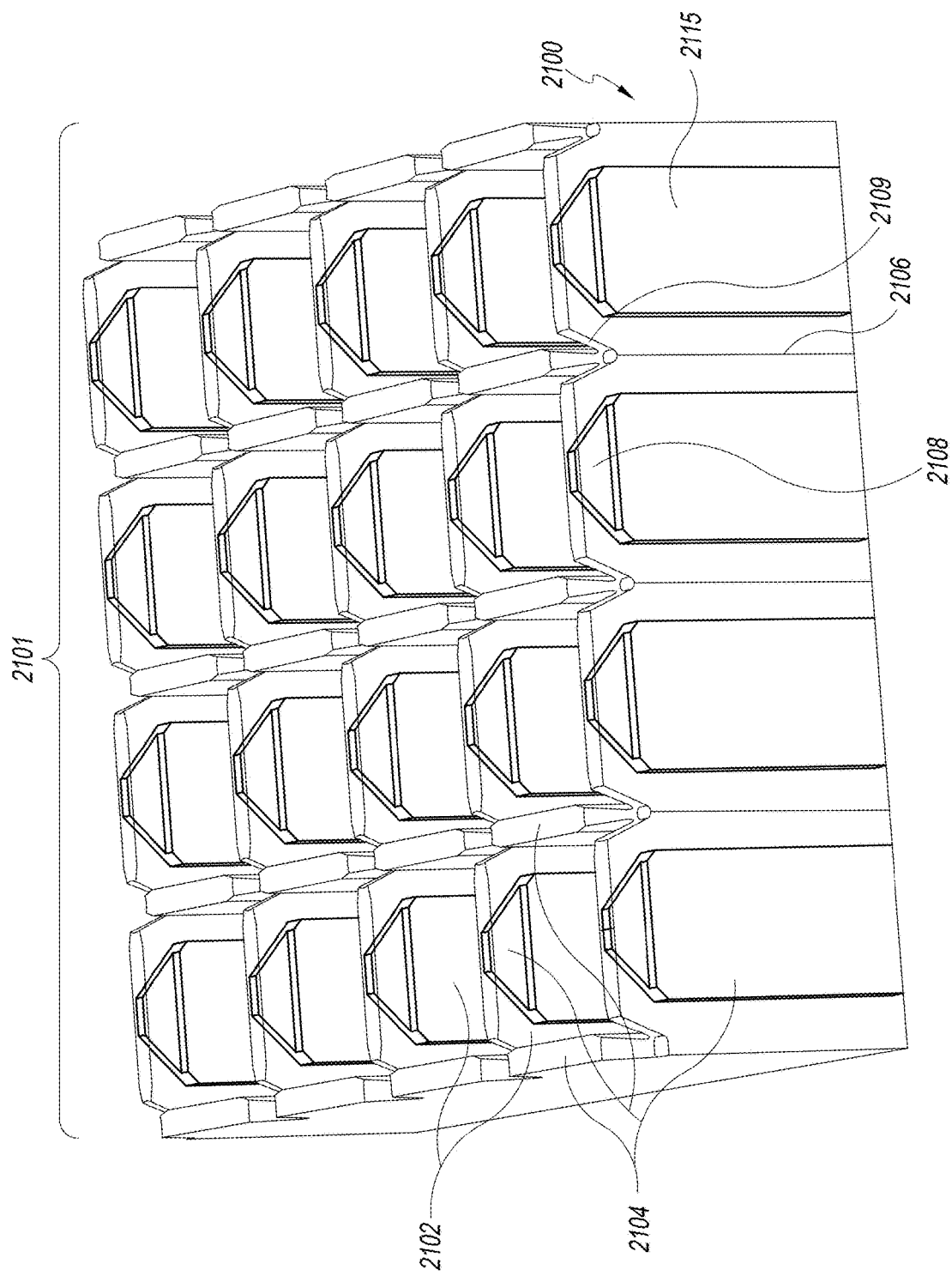

FIG. 15A is a photograph of an embodiment of a stabilizing structure 2100 that may be placed over a wound and incorporated into a wound dressing. Here, the device comprises a plurality of cells 2102 provided side-by-side in a generally planar configuration. Preferably, the stabilizing structure 2100 is configured to collapse in a direction along a plane 2101 defined by the width of the device, without significantly collapsing in a direction perpendicular to the plane 2101. That is, when viewed in the figure, the stabilizing structure 2100 will collapse in the horizontal direction, but will not compress in the vertical direction. In some embodiments, the stabilizing structure collapses in conjunction with the movement of tissue. Here, the cells 2102 are preferably open at both ends in a direction perpendicular to the plane 2101.

Each of the cells 2102 is preferably formed with four walls 2104, each wall 2104 being joined to the next by a flexible joint 2106. The joints 2106 are preferably designed so as to be more flexible than the walls 2104, and promote collapse of the stabilizing structure 2100 in the direction of the plane. Of course, it will be understood that other configurations are possible, and in some embodiments each cell 2102 may be defined by less than or greater than four walls 2104, for example five walls or six walls, thus forming pentagonal or hexagonal cells. The cells 2102 may not necessarily be symmetric, and can form rectangular, diamond, rhomboidal, trapezoidal, parallelepiped, oblong, oval, lozenge and other such shapes in addition to the square-walled embodiment illustrated in this section or elsewhere in this specification.

One or more of the walls 2104 defining the one or more cells 2102 may further comprise an insert 2115 disposed therein, and described in greater detail below in FIGS. 16A-F. Preferably, the insert 2115 will be constructed from a material more rigid than the material used to construct the remainder of the wall 2104. Some suitable materials may include metals such as titanium, stainless steel, and largely inert alloys (such as monel and hastelloy), and/or polymers such as polyurethane, silicone, rubber, isoprene, polyethylene, polypropylene, nylon, polyacrylate, polycarbonate, and PEEK. Some embodiments may also comprise composite materials, including resin-reinforced fiber composites where the resin may be, for example, various types of epoxies. Suitable fibers may include glass, carbon, carbon nanotubes, graphene, and aramids (e.g., Kevlar). Preferably, the material chosen for the insert 2115 is not only sufficiently rigid, but also able to adhere to the material used in the wall 2104. For example, the insert material is preferably able to adhere to softer polymers such as silicones or polyurethanes used in the wall 2104. The more rigid materials used in the insert 2115 may provide for additional collapse resistance in the direction perpendicular to the plane for the stabilizing structure 2100.

In some embodiments, one or more notches 2109 may be provided between multiple walls 2104, and which may further aid in permitting the flexible joints 2106 to move. Without wishing to be bound by theory, the notches 2109 may also aid in distributing negative pressure and transmitting fluid throughout the stabilizing structure 2100 when negative pressure is applied, for example in a clinical care setting. Some embodiments may also comprises holes in the walls 2104 or joints 2106, or be constructed from porous materials.

Preferably, a cavity 2108 is provided within each wall 2104 for the insert 2110 to be disposed therein. The walls 2104 may be molded around each insert 2115. An insert 2115 may also be inserted into the cavity 2108 after the wall 2104 is manufactured. While the embodiment illustrated here and in the subsequent images shows a single insert 2115 in each wall 2104, some embodiments may be provided with one or more inserts 2115 disposed therein.

Figure 15B:
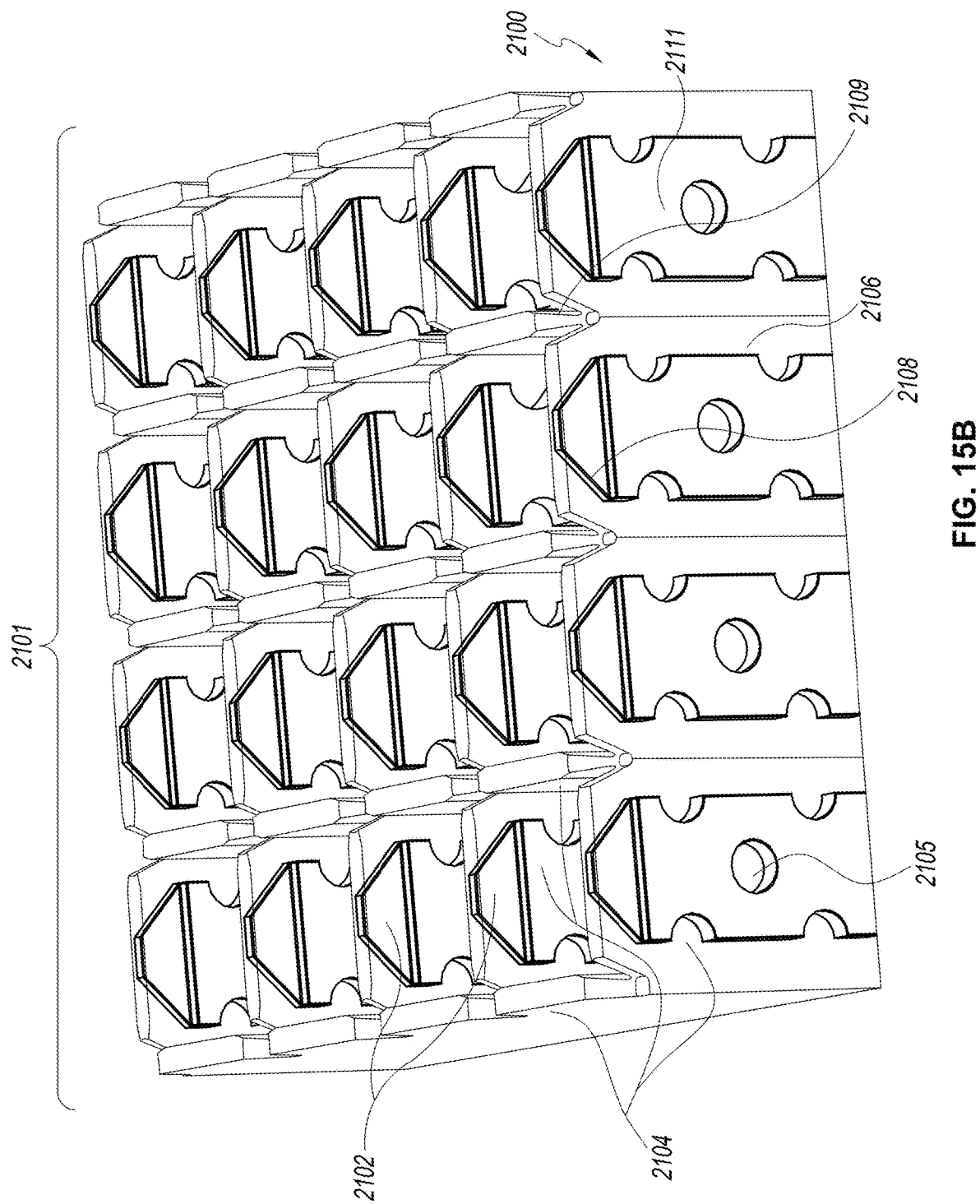

FIG. 15B illustrates an embodiment of a stabilizing structure 2100 with many similar features to FIG. 15A. Here, an insert 2111 comprises structural differences compared to the insert 2110, and is discussed in more detail below in relation to FIG. 15E. When inserted or placed within the cavity 2108, one or more of the walls 2104 may comprise a hole 2105 communicating through at least one aperture in the insert 2111. In addition to any notches 2109, the one or more holes 2105 may permit additional displacement of wound exudate and distribution of negative pressure within the stabilizing structure 2100.

Figure 15C:
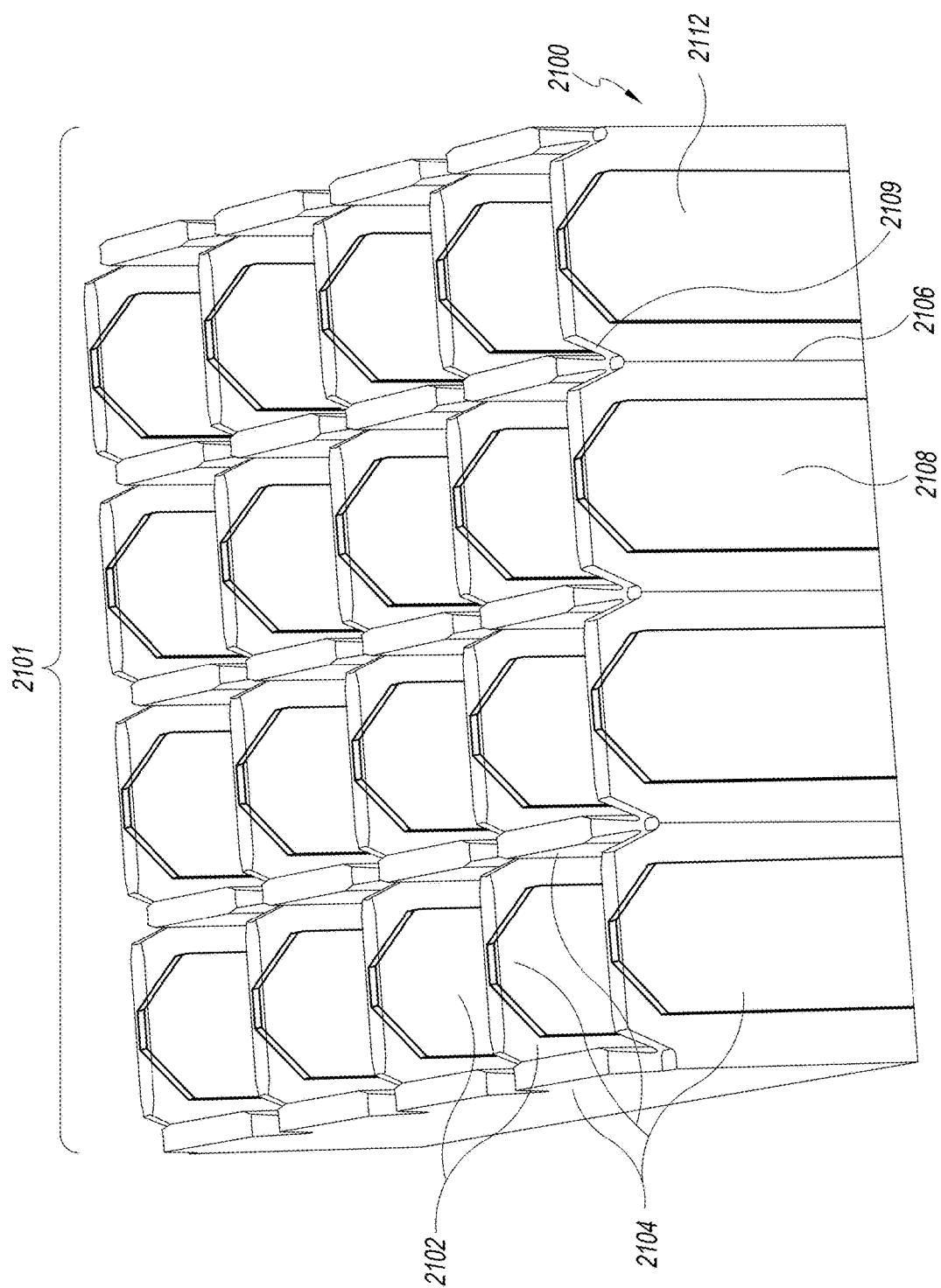

FIG. 15C illustrates an embodiment of a stabilizing structure 2100 with similar features as the other embodiments described previously. In this embodiment, the stabilizing structure 2100 comprises an insert 2112 described in greater detail below in FIG. 16F.

Figure 15D:
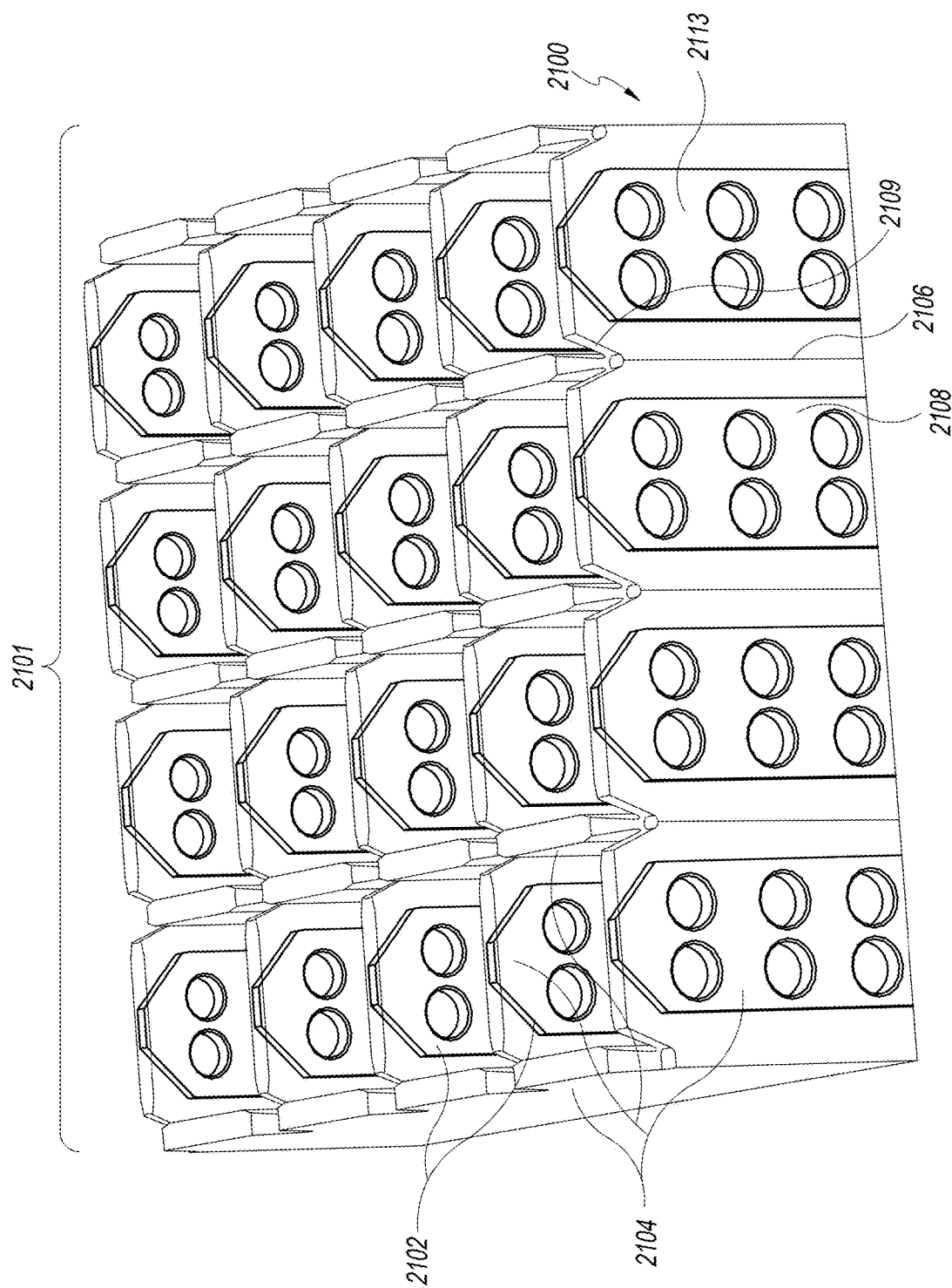

Similarly, FIG. 15D illustrates an embodiment of a stabilizing structure 2100 comprising an insert 2113 described in greater detail below in FIG. 16D. FIG. 15E illustrates an embodiment of a stabilizing structure 2100 comprising an insert 2114 described in greater detail in relation to FIG. 16A.

In the preceding embodiments of stabilizing structures 2100 comprising various inserts 2110, 2111, 2112, 2113, 2114, and 2115, it will of course be understood that embodiments of the stabilizing structure 2100 does not need to contain only one type of insert. Likewise, each cell 2102 or wall 2104 may comprise one or more different types of inserts, or no inserts at all. Varying the different inserts and other properties of the cells 2102 and walls 2104 may thus permit the stabilizing structure 2100 to be tailored to the appropriate wound type so as to effect optimal wound closure and/or treatment.

FIGS. 16A-F illustrate examples of different inserts that may be used as part of a stabilizing structure 2100. Preferably, these inserts may be placed, molded into, or formed as part of a wall 2104 in a stabilizing structure 2100 (e.g., of the types illustrated above in FIG. 15A-E). Various modifications may be made, as described below, that may improve or alter characteristics of the inserts.

Figure 16D:
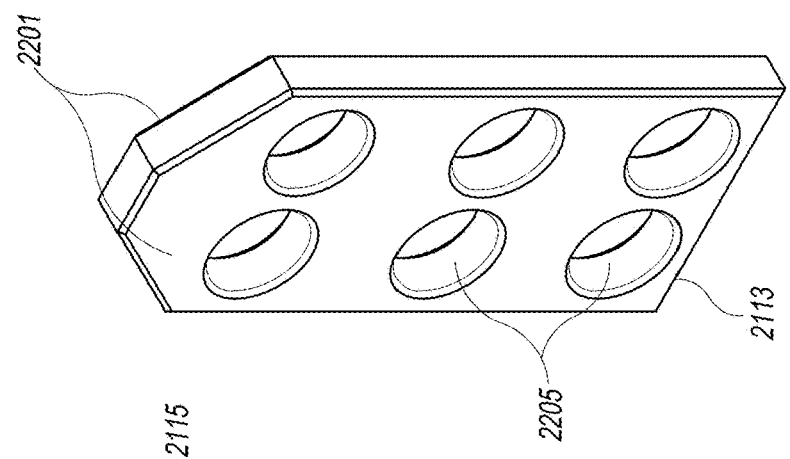
FIGS. 16A-F illustrate various embodiments of inserts that may be used in stabilizing structures.
Figure 16C:
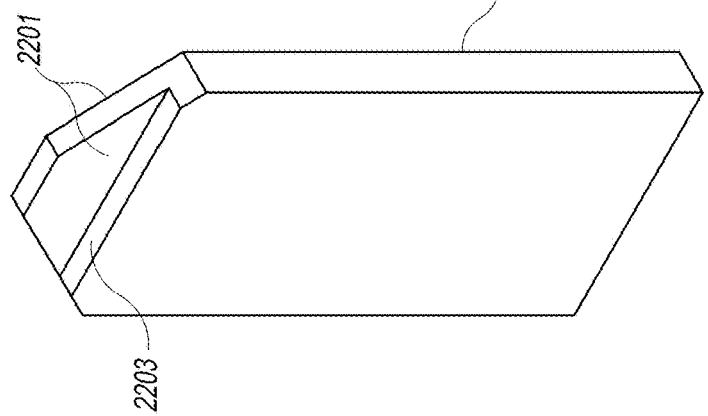
Figure 16B:
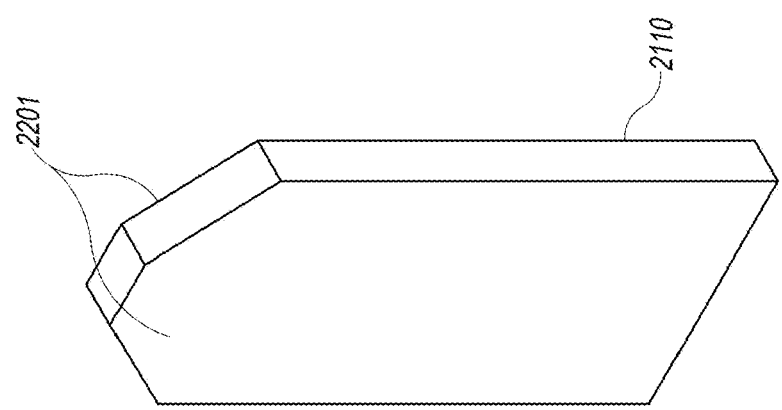
Figure 16A:
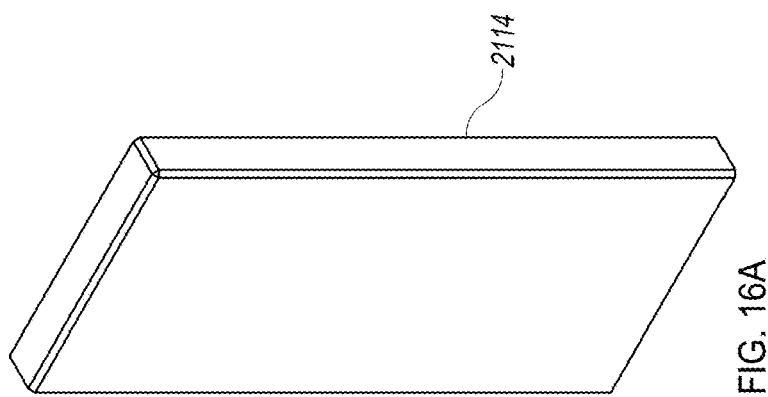

Turning now to FIG. 16A, the embodiment of the insert 2114 illustrated here is approximately rectangular in shape, and is adapted to be inserted or formed into one or more of the walls 2104 of an embodiment of the stabilizing structure 2100. In some embodiments, one or more of the inserts 2114 may have a height greater than the width, and the wall 2104 may have a height of at least about 1 mm, at least about 5 mm, at least about 10 mm, at least about 15 mm, at least about 20 mm, at least about 25 mm, at least about 30 mm, at least about 35 mm, at least about 40 mm, at least about 50 mm, at least about 75 mm, at least about 100 mm, at least about 150 mm, at least about 200 mm, at least about 250 mm, at least about 300 mm, at least about 350 mm, at least about 400 mm, or more than 400 mm, particularly in extremely obese patients. Preferably, in average patients, the heights may range from about 10 mm to 40 mm. These measurements may apply to any stabilizing structure described in this section or elsewhere in this specification.

In some embodiments of any stabilizing structure described in this section or elsewhere in this specification, the width may be between about 1 mm to 30 mm, 2 mm to 25 mm, 4 mm to 20 mm, 6 mm to 18 mm, 8 mm to 16 mm, or 10 mm to 14 mm, preferably about 10.8 mm. These measurements may apply to any stabilizing structure described in this section or elsewhere in this specification.

The insert 2114 is preferably thin but with enough structural strength to resist collapse, and in some embodiments of any stabilizing structure described in this section or elsewhere in this specification, the thickness may be at least about 0.01 mm to 10 mm, 0.2 mm to 8 mm, 0.4 mm to 6 mm, 0.5 mm to 4 mm, 0.75 mm to 3 mm, or 1-2 mm. These measurements may apply to any stabilizing structure described in this section or elsewhere in this specification.

In some embodiments of any stabilizing structure described in this section or elsewhere in this specification, multiple discrete stabilizing structures may be stacked on top of one another to form a larger stabilizing structure, to extend the height of the device to any of the dimensions described in this section or elsewhere in this specification (including the dimensions provided for the inserts above). The stacking of multiple stabilizing structures may allow the clinician to have further flexibility in their treatment strategies.

FIG. 16B illustrates an embodiment of the insert 2110 with a generally rectangular configuration, but provided with two notches 2201 cut diagonally across a top end of the insert 2100. The notches 2201 may facilitate clearance of the insert 2100 from any notches 2109 that may be provided in the walls 2104. Further, the notches 2201 may also aid in the insertion of the insert 2100 into the cavity 2108 of the wall 2104. The notches 2201 may also be helpful in conjunction with the notches 2109 in further defining a channel or other opening for fluid to be transmitted or transferred between and through each cell 2102. The notches 2201 may also aid in ensuring that the entire stabilizing structure is able to more easily collapse.

FIG. 16C illustrates an embodiment of an insert 2115 provided with two notches 2201 as well as a horizontal lip 2203. The horizontal lip 2203 may aid in inserting the insert 2115 into the cavity 2108 of the wall 2104, or may aid in fixing the wall 2104 around the insert 2115 when the wall is molded around it. The horizontal lip 2203 may be beneficial in effectively reducing the bulk of the insert at one end of the wall 2104, and in conjunction with a softer material used in the wall 2104, may thereby increase comfort due to the correspondingly greater amount of wall material. In some embodiments, the horizontal lip 2203 and/or notches 2201 may be present on both ends of the insert 2115 or other inserts described in this section or elsewhere in this specification. In some embodiments, the horizontal lip 2203 is approximately half the thickness of the overall insert 2115. For example, the insert 2115 may be between 0.5 mm and 4 mm in thickness, preferably 2 mm. If the insert 2115 measures 2 mm in thickness, the thickness of horizontal lip 2203 may be 1 mm.

FIG. 16D illustrates an embodiment of the insert 2113, and which is similar to the embodiment used in the stabilizing structure 2100 illustrated in FIG. 15D. This insert 2113 may comprise one or more apertures 2205, which in some embodiments may communicate with one or more holes 2105 that may be formed through one or more walls 2104. In some embodiments, the apertures 2205 are arranged in a 2×3 pattern illustrated here, although other arrangements are possible. Notches 2201 may also be present.

Figure 16F:
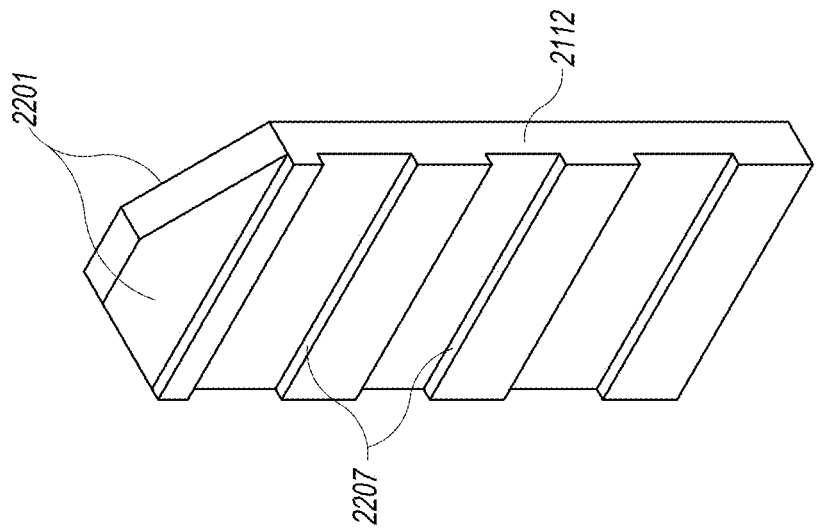
Figure 16E:
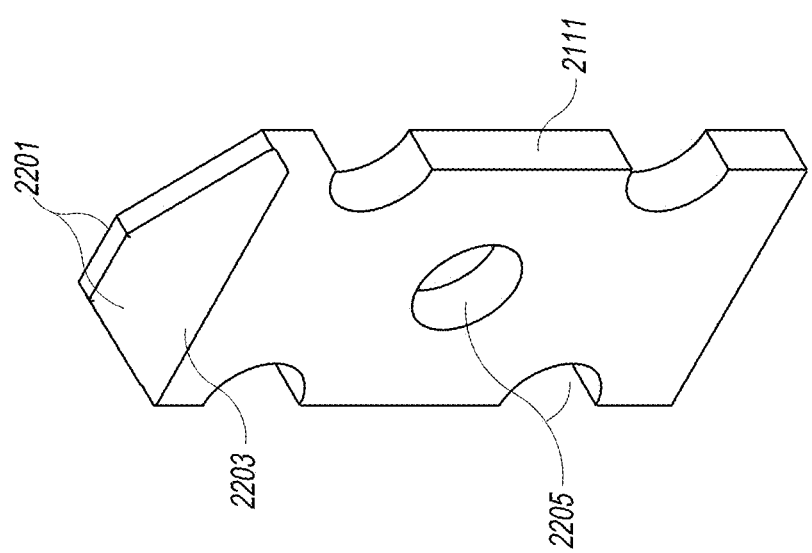

FIG. 16E illustrates an embodiment of the insert 2111, which is similar to the embodiment used in the stabilizing structure 2100 illustrated in FIG. 15B. The insert 2111 preferably comprises two notches 2201. A horizontal lip 2203 may also be provided. Preferably, one or more apertures 2205 may be formed therein. In some embodiments, one or more of the apertures 2205 may extend to the edge of the insert 2111 as illustrated. In some embodiments, the apertures 2205 may be configured to have four apertures arranged around a central aperture, although other configurations are of course possible. In some embodiments, the reduced amount of insert material at the locations of the apertures may be advantageous to provide a greater amount of softer wall material at a hinge point, where this may consequently increase flexibility. In a preferred embodiment, the insert 2111 has a height of 25 mm and a width of 10.8 mm, with a thickness of 2 mm. The first set of apertures may be centered approximately 5 mm from the bottom edge of the insert 2111, the central aperture may then be centered approximately 11 mm from the bottom, and the top set of apertures may be centered 17 mm from the bottom.

FIG. 16F illustrates an embodiment of the insert 2112, which shares some similarities to the embodiment used in the stabilizing structure 2100 illustrated above in FIG. 15C. The insert 2112 preferably may comprise one or more channels 2207 formed therein. Preferably, the one or more channels 2207 are disposed in a horizontal configuration across the width of the insert 2112. While the insert 2112 is preferably configured, like several other embodiments described in this section or elsewhere in this specification, to remain substantially uncompressed in the vertical direction, the inclusion of one or more horizontal channels 2207 may aid in providing additional rigidity in the direction of the plane defined by the cells 2102. In such a case, the rigidity of the one or more walls 2104 may be enhanced, and may thus control the compression of the stabilizing structure 2100 such that any collapse or bending occurs substantially only at the one or more joints 2106.

FIGS. 17A-F illustrate an embodiment of a stabilizing structure 3001 configured to be applied over a wound and may be incorporated into a wound dressing. The stabilizing structure 3001 preferably comprises at least one top strip 3002 extending in a first direction (e.g., along an x axis) and at least one bottom strip 3004 extending in a second direction (e.g., along a y axis perpendicular to the x axis), these being preferably arranged into an array comprising multiple strips 3002, 3004. The strips 3002, 3004 are preferably connected together in a movably interlocking configuration, which preferably comprises an interlock mechanism 3006. The strips 3002, 3004 are preferably arranged in an un-collapsed configuration wherein the strips 3002 and 3004 are disposed at angles approximately perpendicular to each other. This arrangement forms a first plane that the stabilizing structure 3001 preferably adopts. Preferably, the stabilizing structure 3001 is more rigid in the direction perpendicular to the plane (i.e., in the vertical direction or along a z axis), and thereby substantially resists compression or deformation in that direction.

Figure 17A:
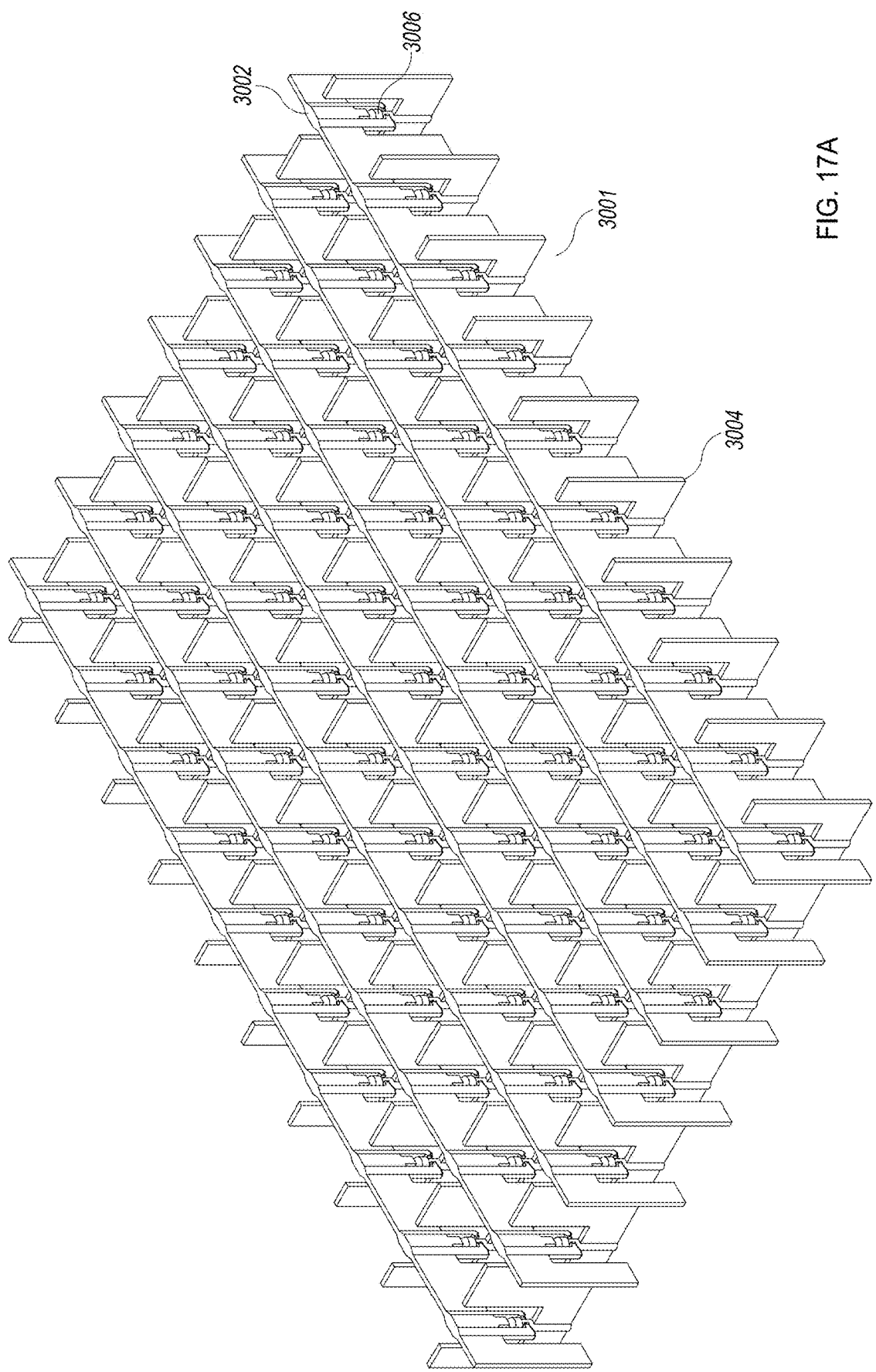
FIGS. 17A-F illustrate multiple views of an embodiment of a stabilizing structure.
Figure 17B:
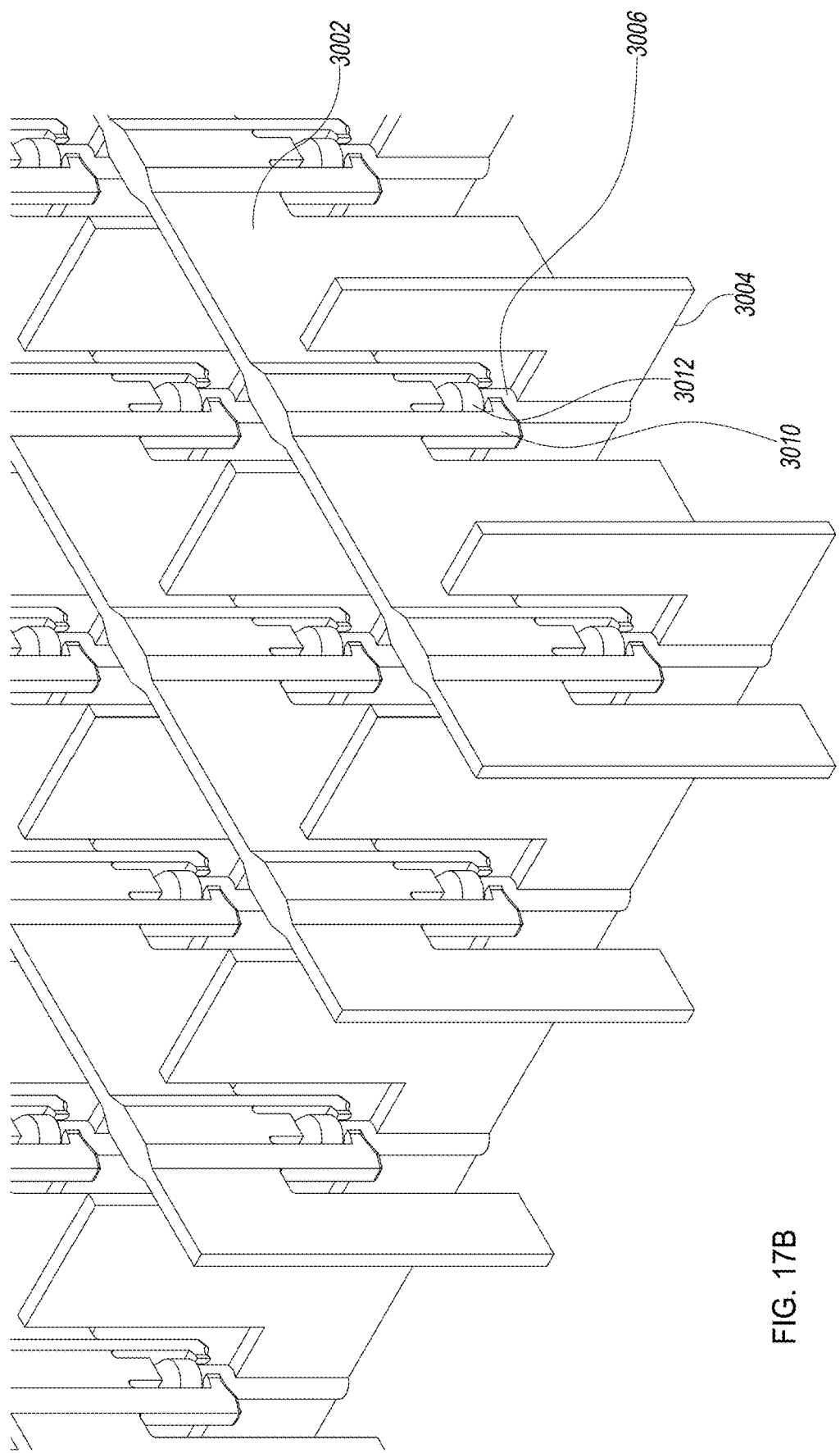
Figure 17C:
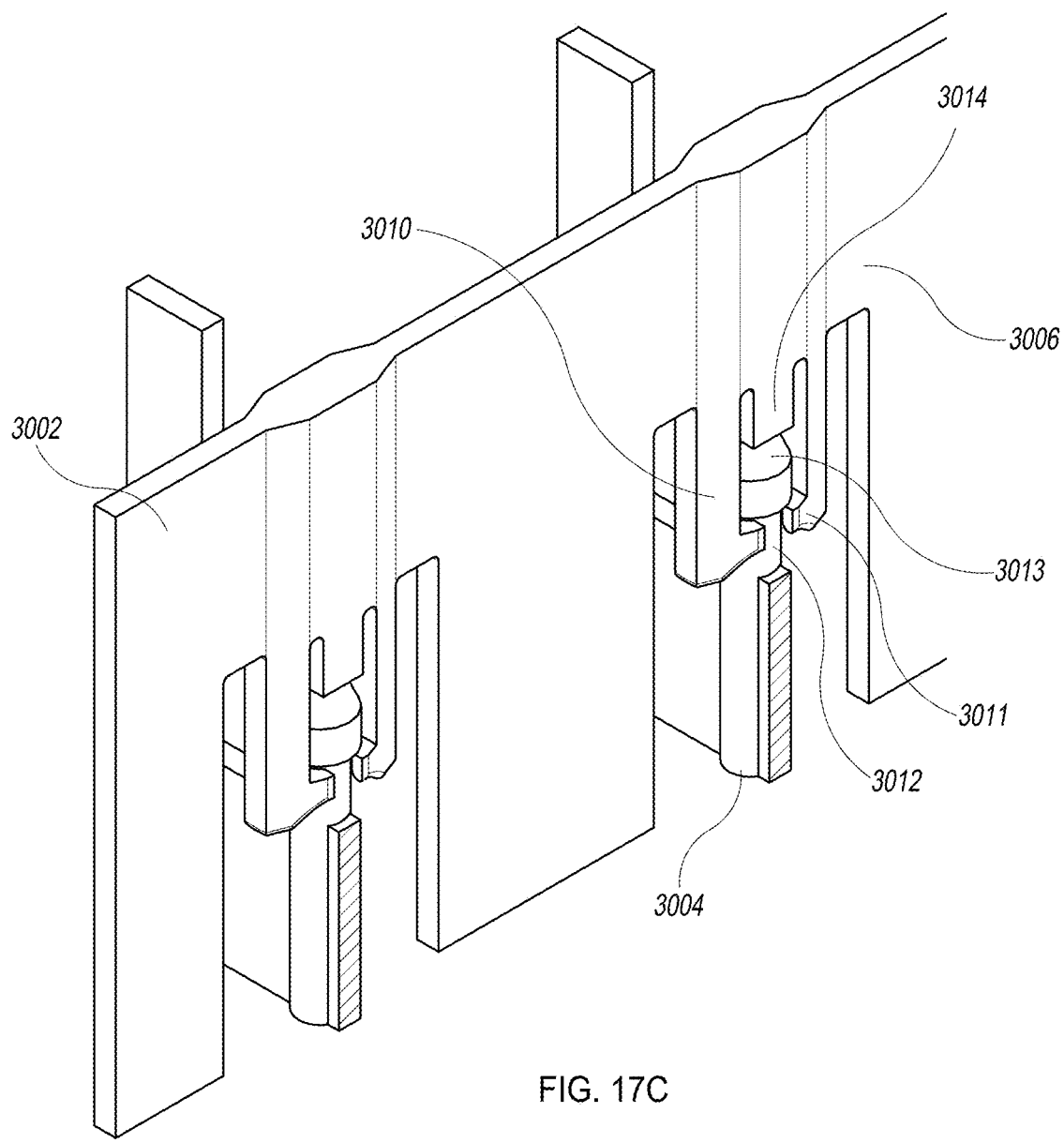
Figure 17D:
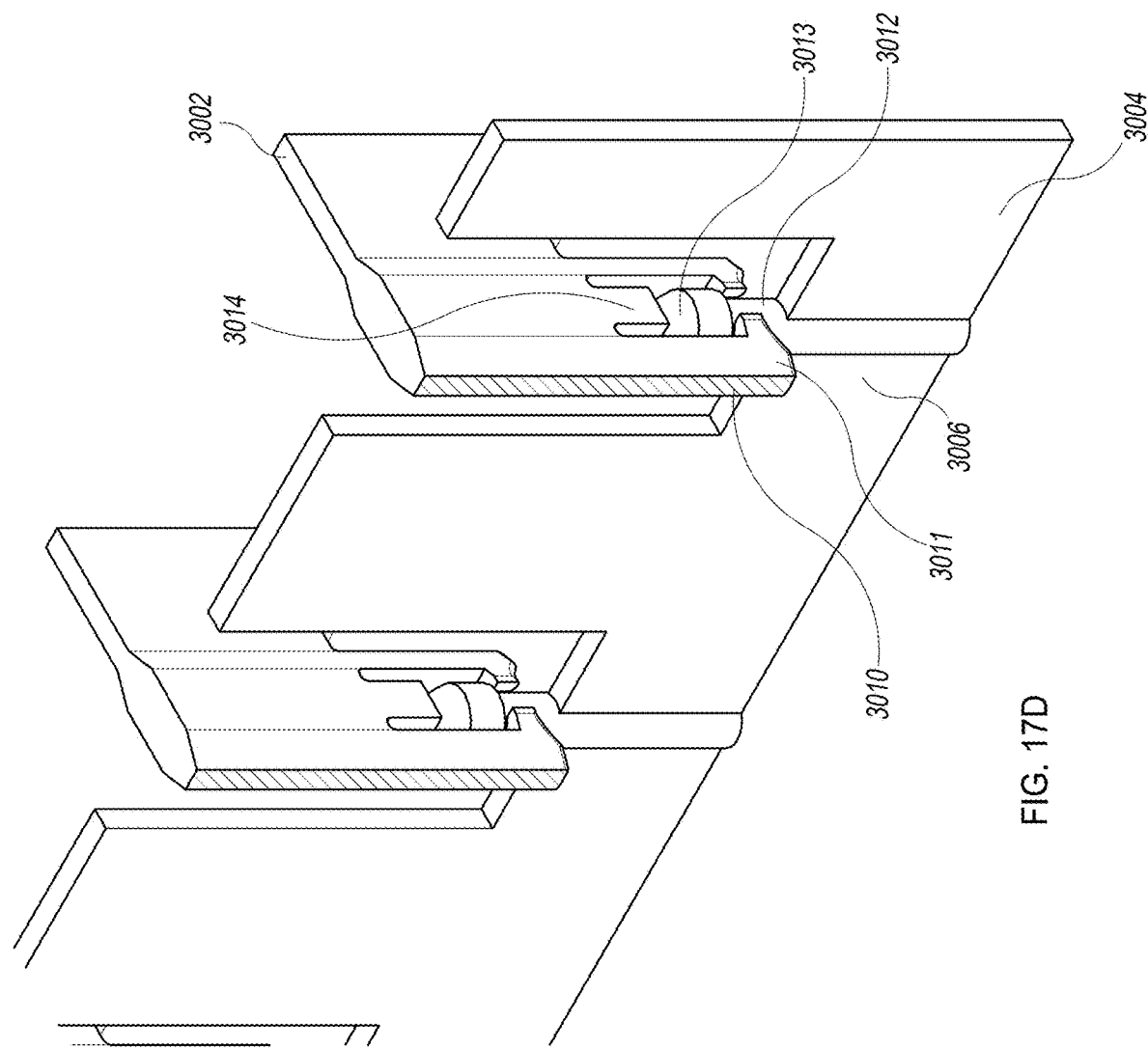
Figure 17E:
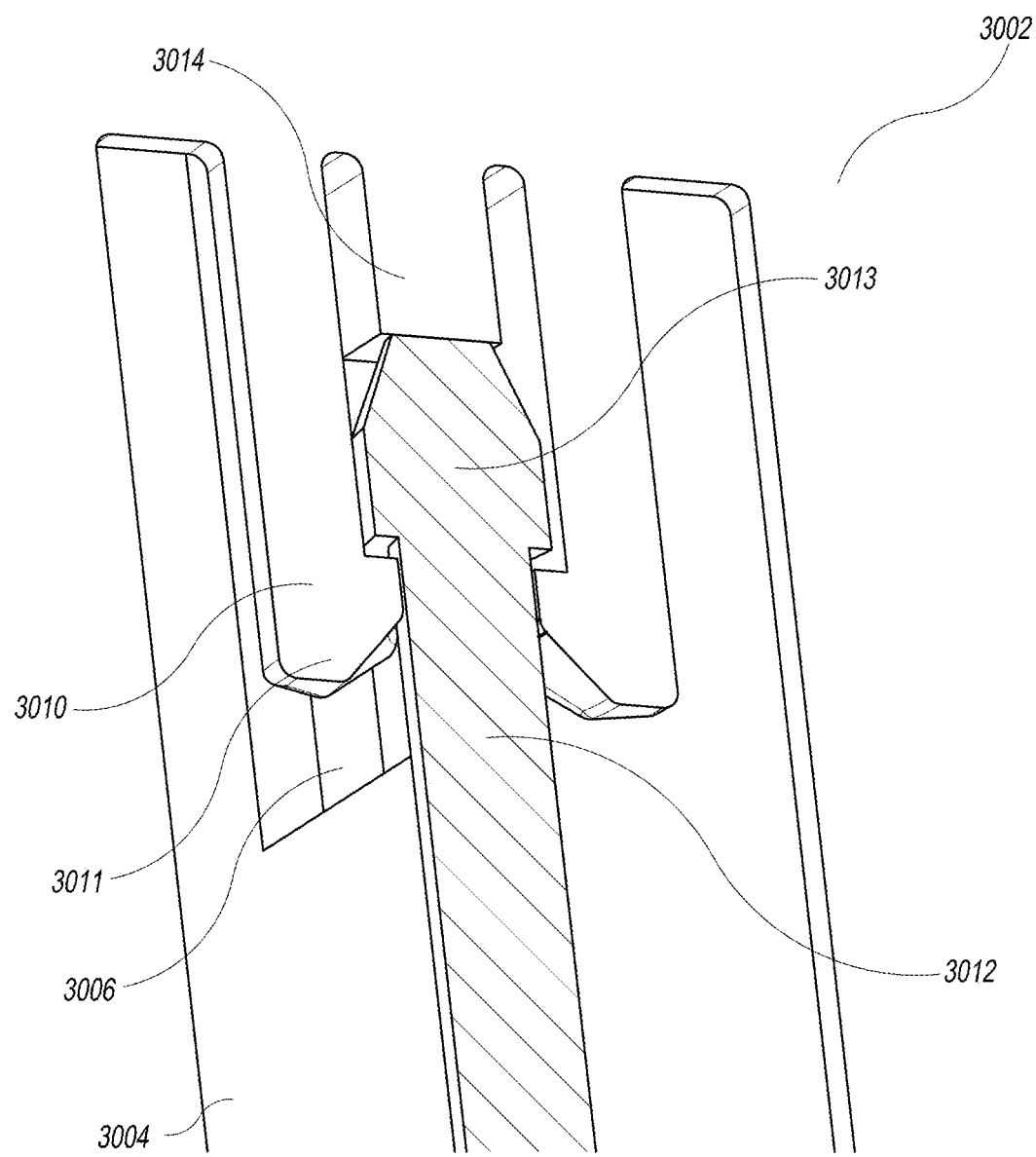
Figure 17F:
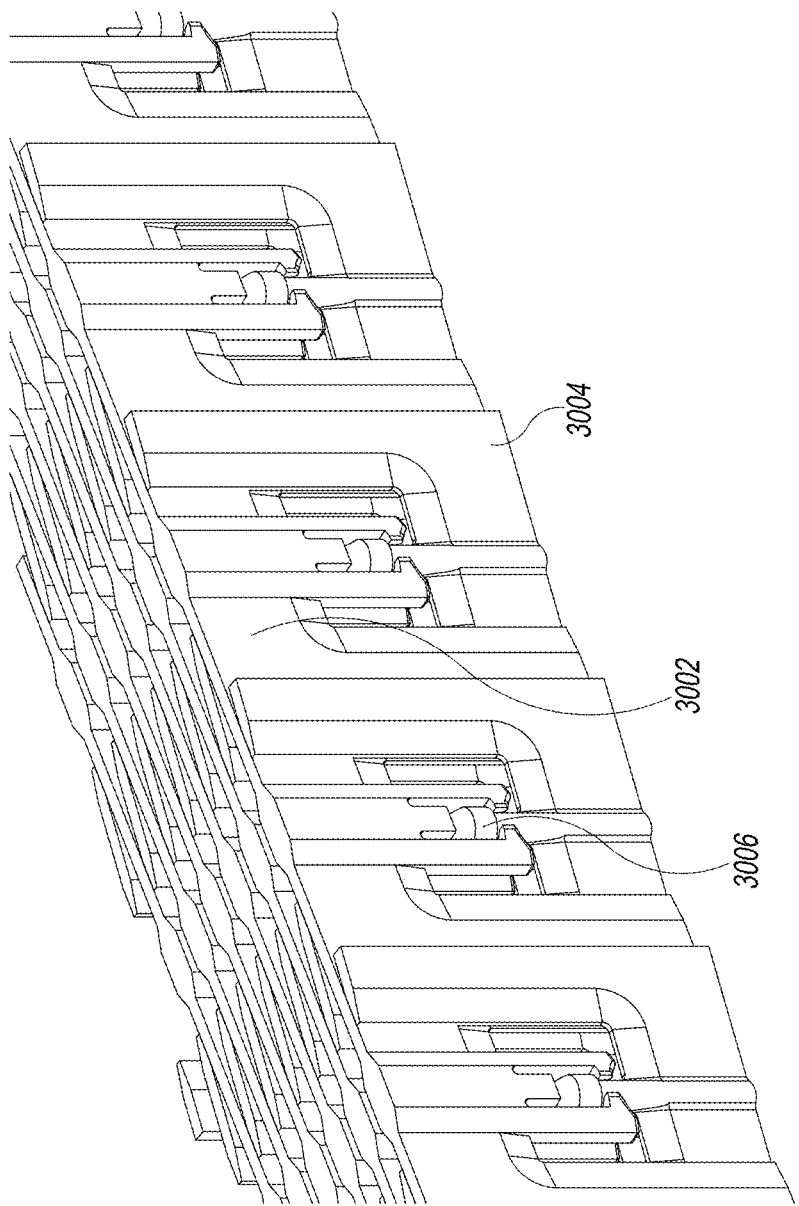

To aid in the closure of a wound, the stabilizing structure 3001 is preferably movable from the substantially un-collapsed configuration to a collapsed configuration, as illustrated in FIG. 17F. This may be beneficial for wound closure and healing, as described previously. In use, negative pressure may apply a closing force across the margins of the wound that the stabilizing structure 3001 is inserted into. As the structure 3001 is preferably configured to be substantially rigid in the vertical direction (i.e., perpendicular to the plane defined by the structure 3001), pressure resulting from atmospheric pressure exerted onto the structure 3001 via the drape is focused substantially downward rather than outward, such that the wound margins are no longer pushed outward as in conventional negative pressure dressings.

Preferably, the structure 3001 adopts a smaller area in the first plane as a result of moving to the compressed configuration. In some embodiments, the stabilizing structures described in this section or elsewhere in this specification are able to reduce their captured volume when in a collapsed configuration (i.e., the volume change between an uncompressed and compressed stabilizing structure) by at least 10%, preferably at least 15%, and even more preferably at least 25%.

FIGS. 17C-E illustrate close-ups of the interlock mechanism 3006. It is to be noted that although reference may be made to various parts of the interlock mechanism 3006 being present on either the top strip 3002 or bottom strip 3004, this description should not be considered as limiting in terms of orientation, and the same interlock mechanism 3006 may be constructed with the top or bottom strips 3002, 3004 reversed.

In a preferred embodiment, the interlock mechanism 3006 preferably comprises two clasps 3010 extending downward from the top strip 3002. Preferably, the clasps 3010 are parallel to each other so as to be on opposite sides of a projection 3012 extending upward from the bottom strip 3004. The clasps 3010 preferably comprise a lip or hook 3011 that may secure themselves under an end 3013 located at the distal end of the projection 3012. In a preferred configuration, the enlarged end 3013 is arranged such that all or a portion of the lip 3011 engages with the enlarged end 3013. The combination of the lip 3011 and enlarged end 3012 may aid in preventing the top strip 3002 from disengaging in a vertical direction away from the bottom strip 3004. In some embodiments, the projection 3012 may abut on the bottom edge of the top strip 3002. In some embodiments, however, and as illustrated here, a stabilizing post 3014 may be present to locate the distal side of the projection 3012 and enlarged end 3013.

FIGS. 18A-D illustrate an embodiment of a stabilizing structure 3201 assembled in a similar manner to the embodiment illustrated above in FIGS. 17A-F. Here, the interlock mechanism 3006 comprises four clasps 3010 surrounding the projection 3012 and the enlarged end 3013 of the projection 3012. Preferably, the clasps 3010 are arranged in a mutually orthogonal configuration, although different orientations are contemplated as well. It will be understood that any number of clasps 3010 may be used to secure the projection 3012, for example three or five clasps 3010.

Figure 18A:
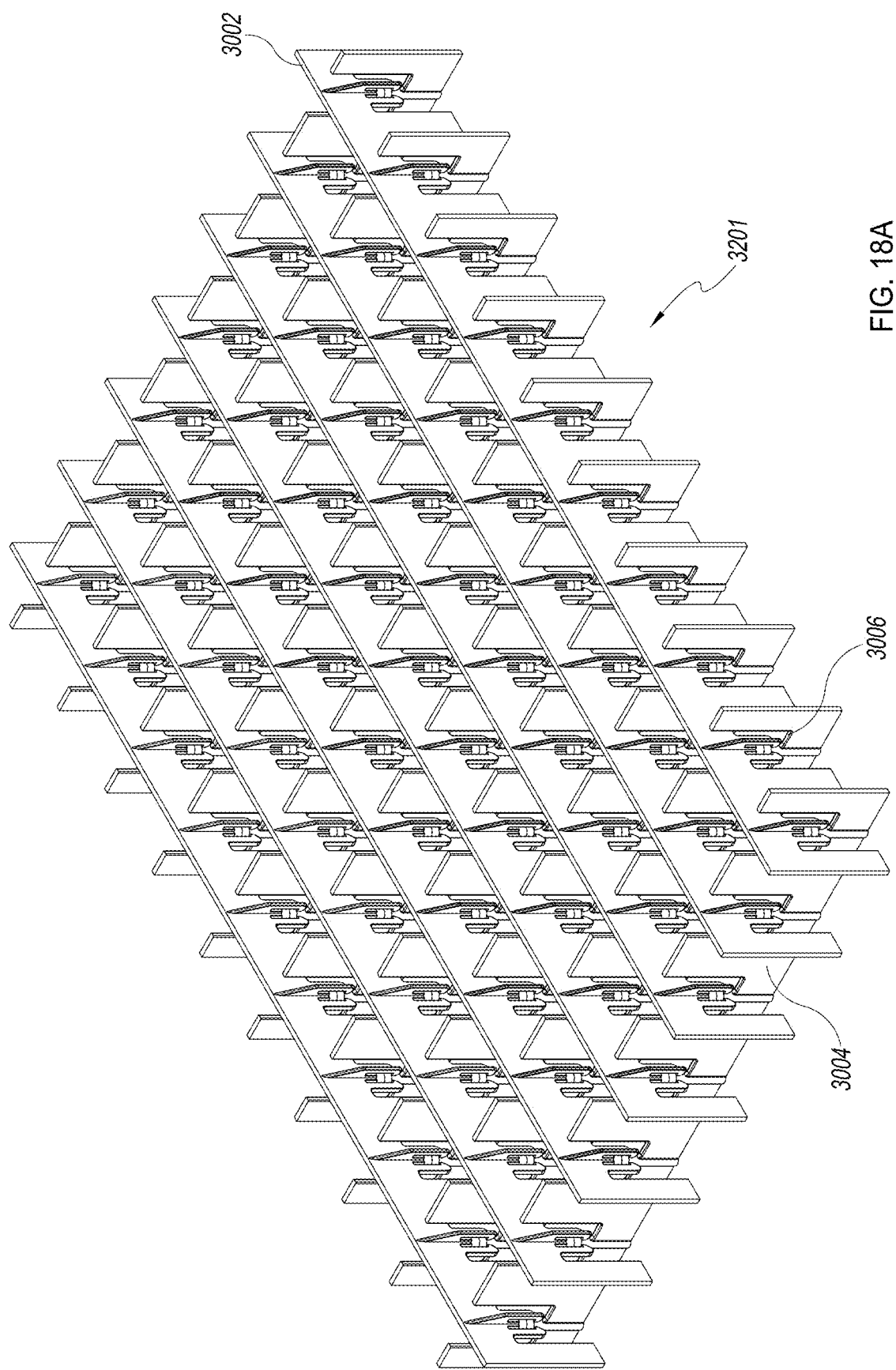
FIGS. 18A-D illustrate multiple views of an embodiment of a stabilizing structure.
Figure 18B:
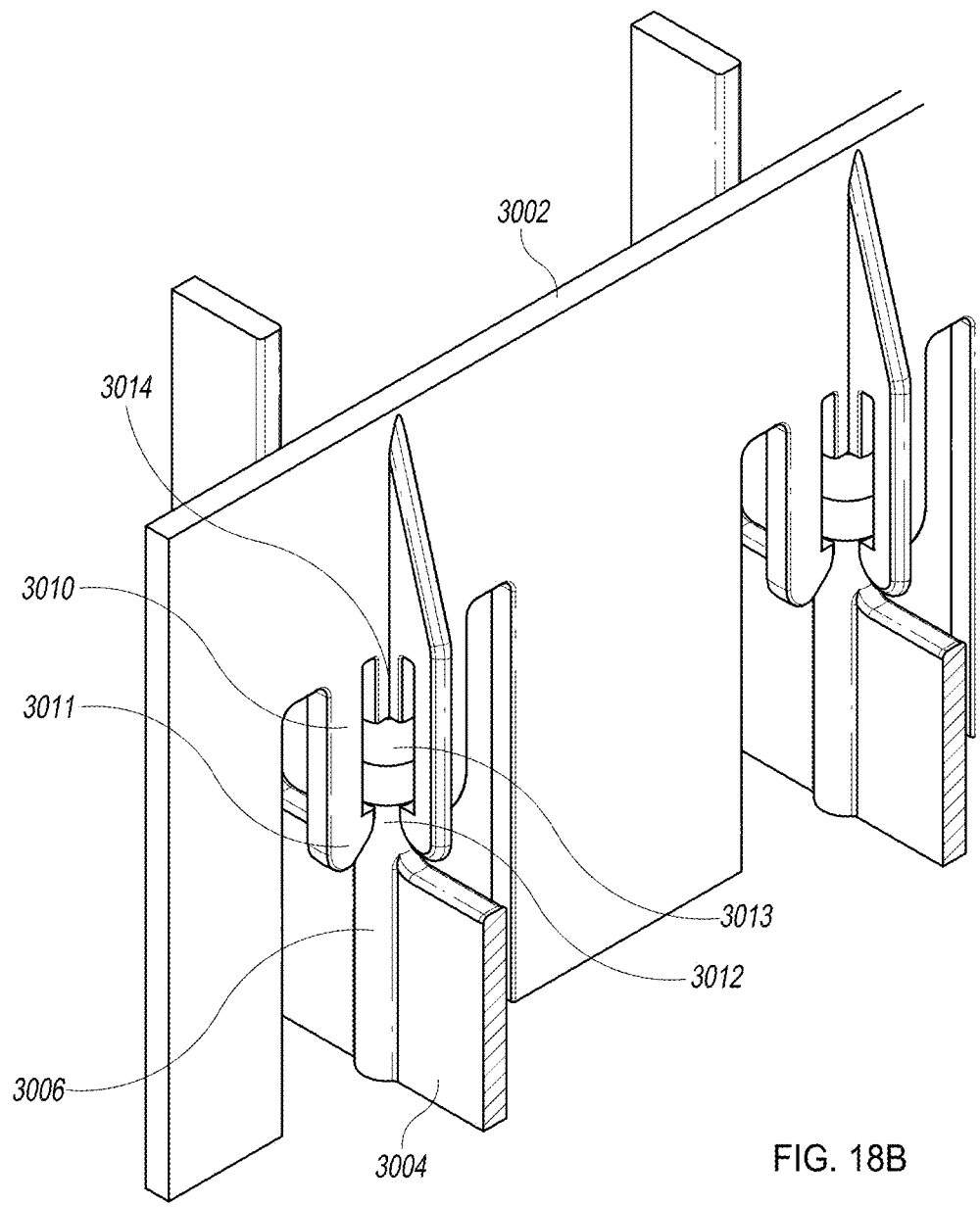
Figure 18C:
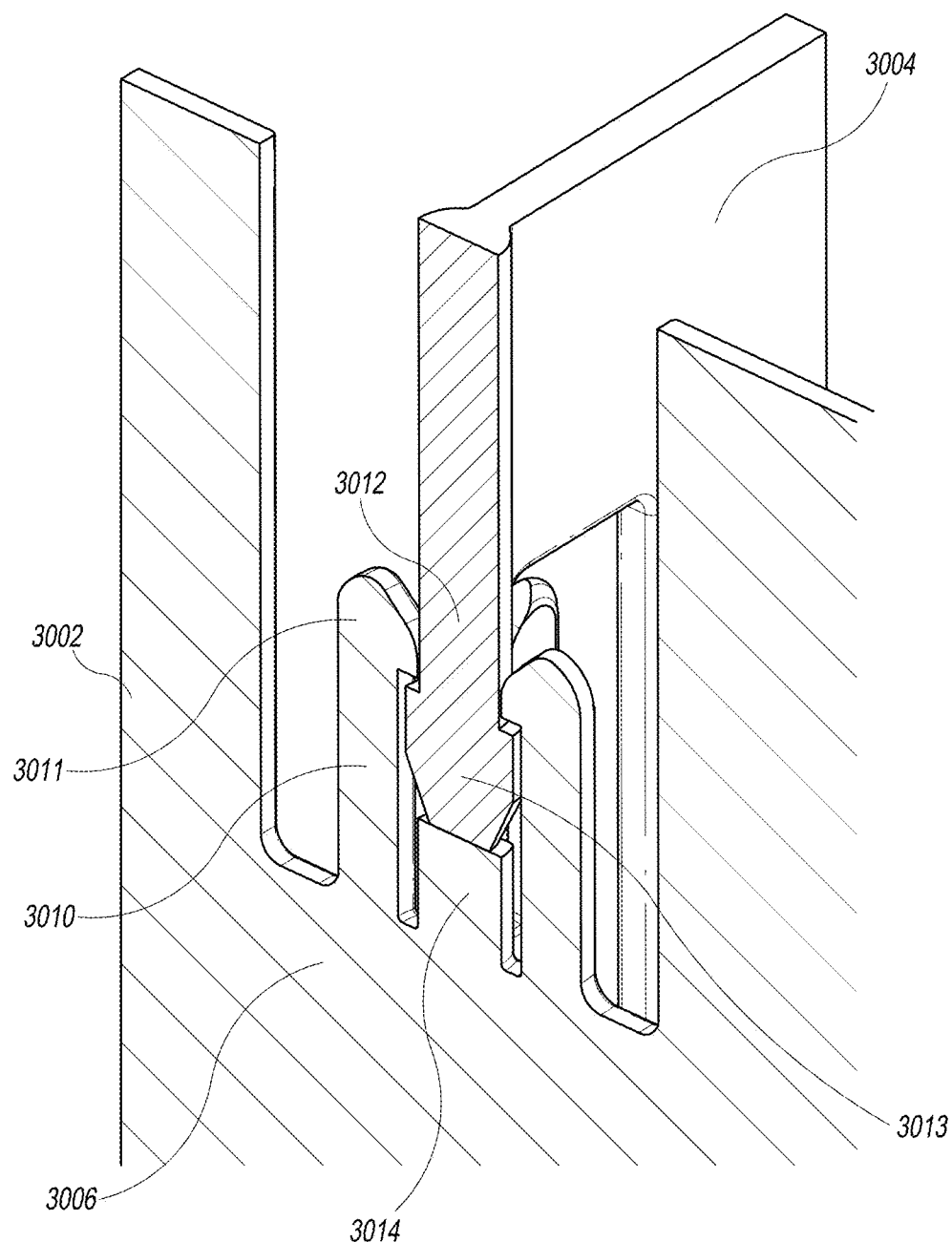
Figure 18D:
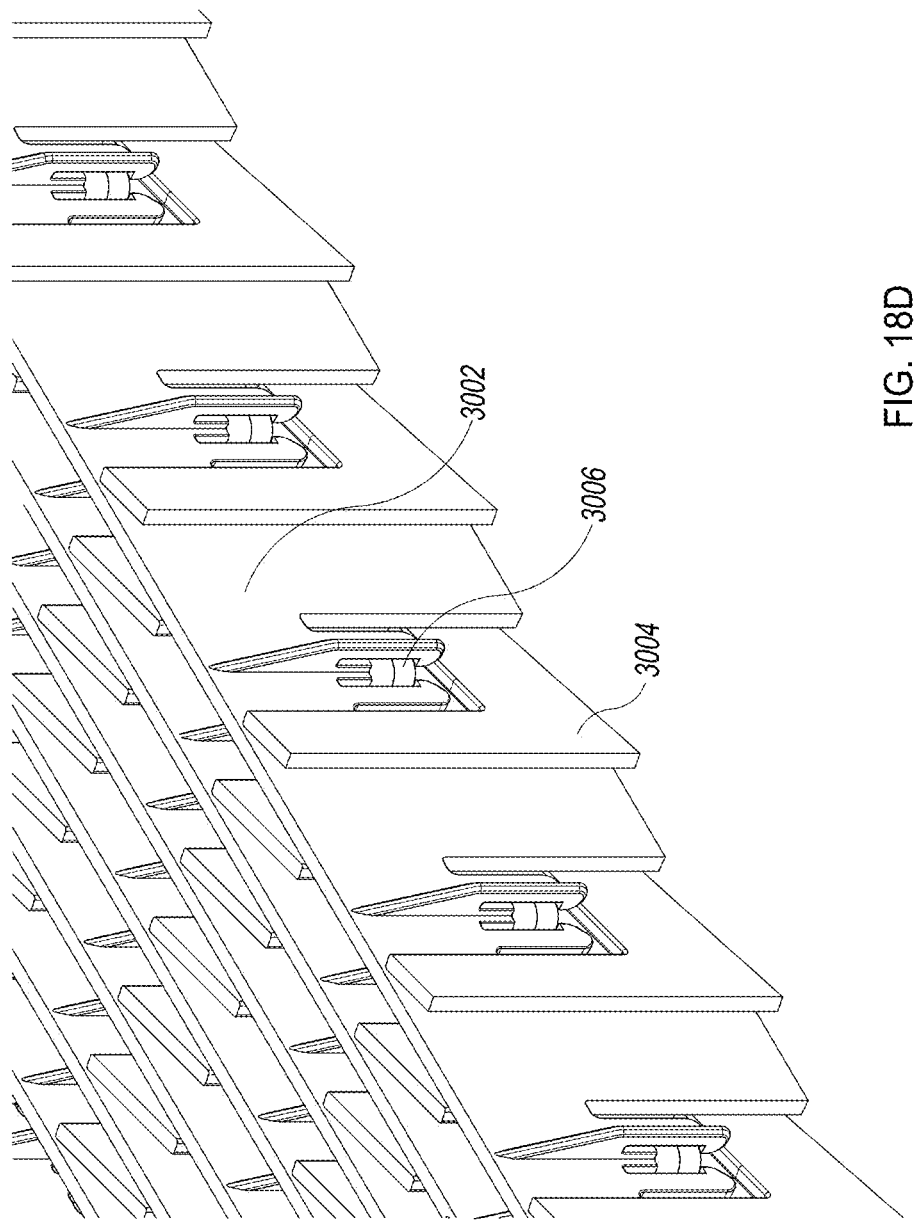

It will be noted that due to the addition of additional clasps 3010 in comparison to the embodiment illustrated in FIGS. 17A-F, the embodiment illustrated here will have a compressed configuration that is slightly larger, as illustrated in FIG. 18D. This may be useful in some situations; for example, some wounds may require a more gradual closure of the wound margins, and the embodiment described here may be well adapted for this purpose.

FIGS. 19A-E illustrate an embodiment of a stabilizing structure 3301 comprising an interlock mechanism 3006 arranged in a tubular conformation. In this embodiment, a cup-shaped member 3020 is preferably configured to receive the enlarged end 3013 of the projection 3012. The projection 3012 may extend vertically from the top strip 3002. The cup-shaped member 3020 is preferably cylindrical or tubular in shape, and may extend vertically from the bottom strip 3004, although it will be understood that the cup-shaped member 3020 and projection 3012 may be located on opposite strips.

Preferably, one or more slits 3021 are formed into the cup-shaped member 3020 so as to permit some "give" to permit the projection 3012 to be received into the cup-shaped member. A lip or hook 3022 may also aid in securing the enlarged end 3013 of the projection 3012. A stabilizing post 3014 may also be present to prevent the projection 3012 from extending too deeply into the cup-shaped member 3020.

Figure 19A:
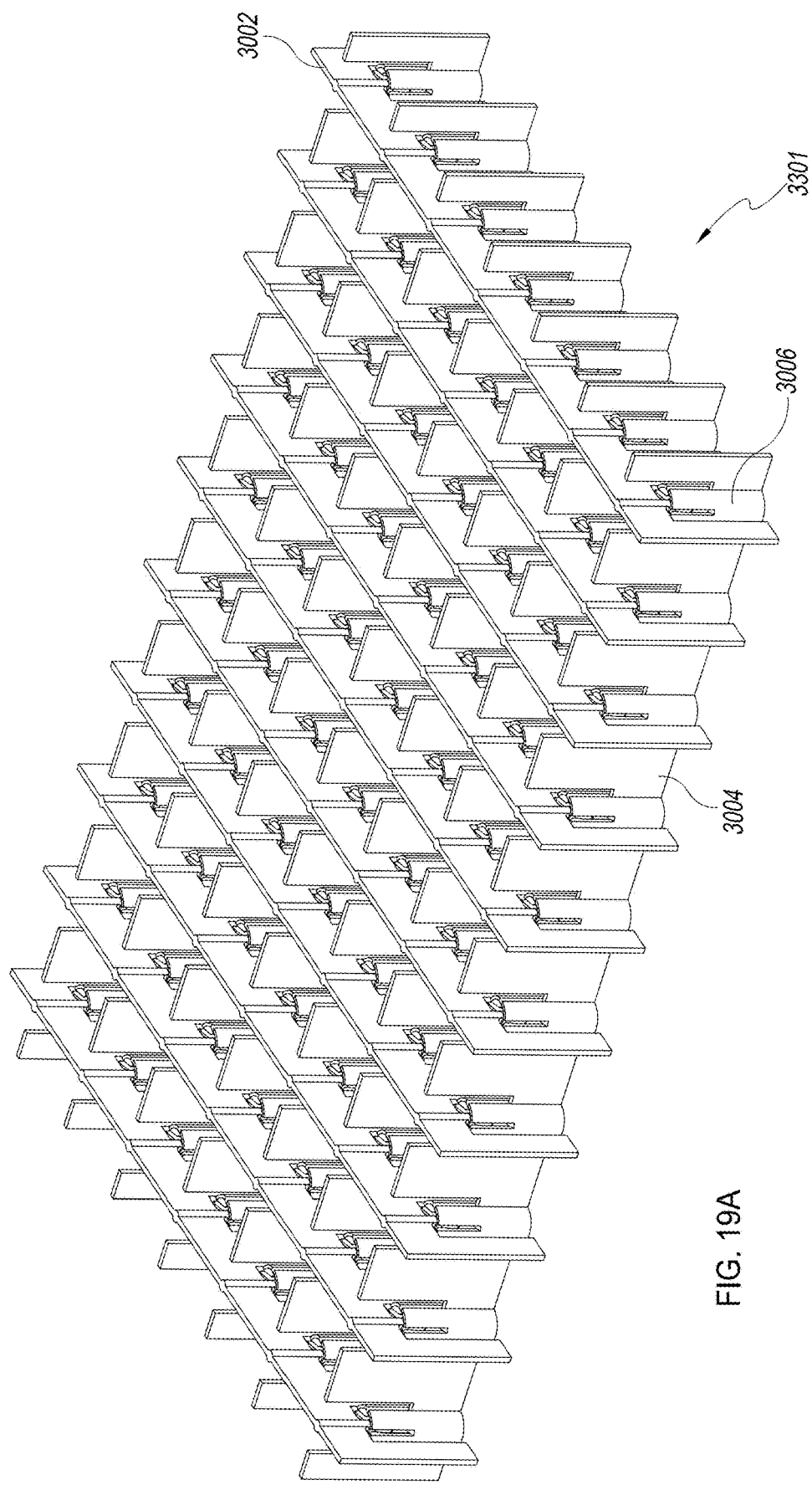
FIGS. 19A-E illustrate multiple views of an embodiment of a stabilizing structure.
Figure 19B:
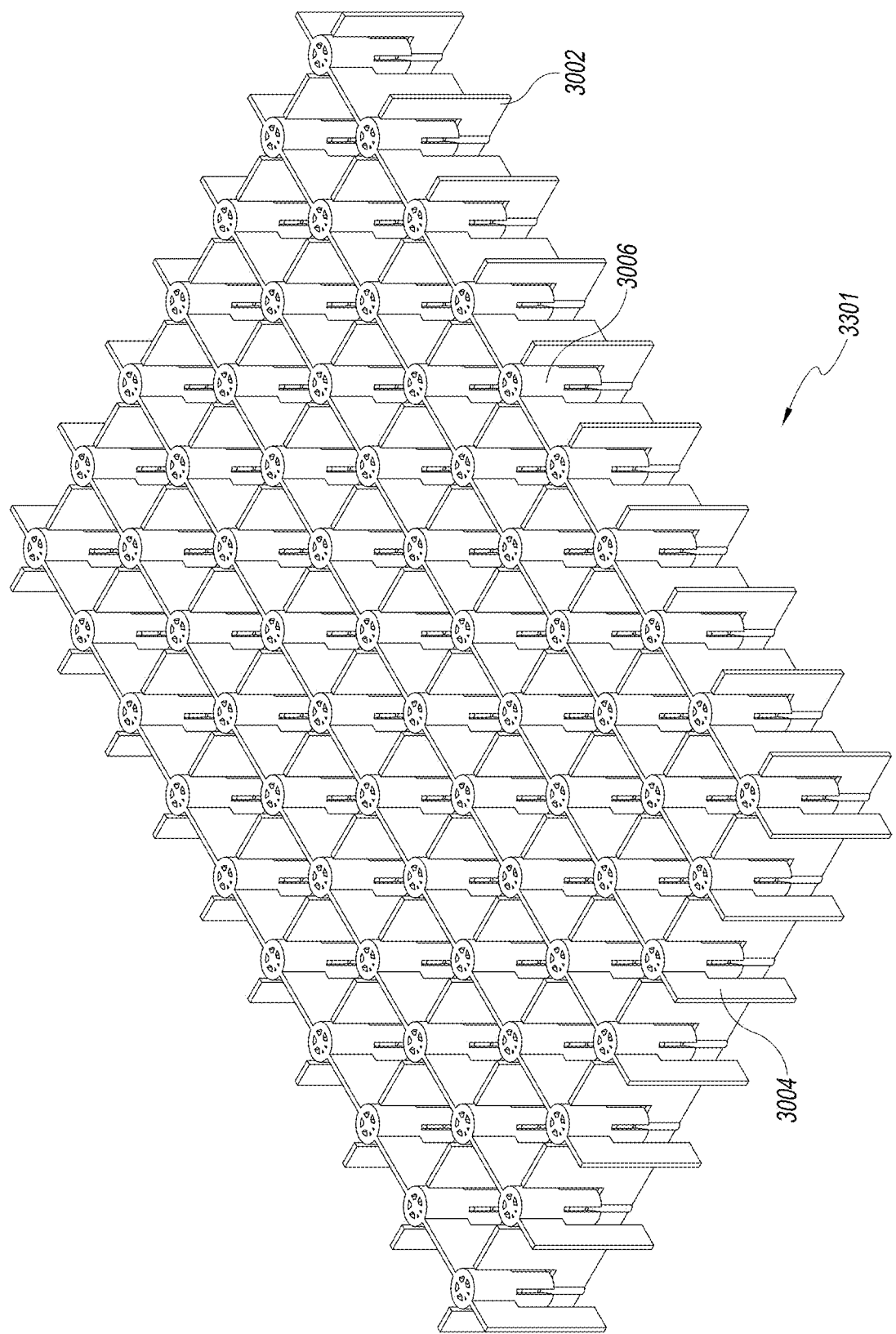
Figure 19C:
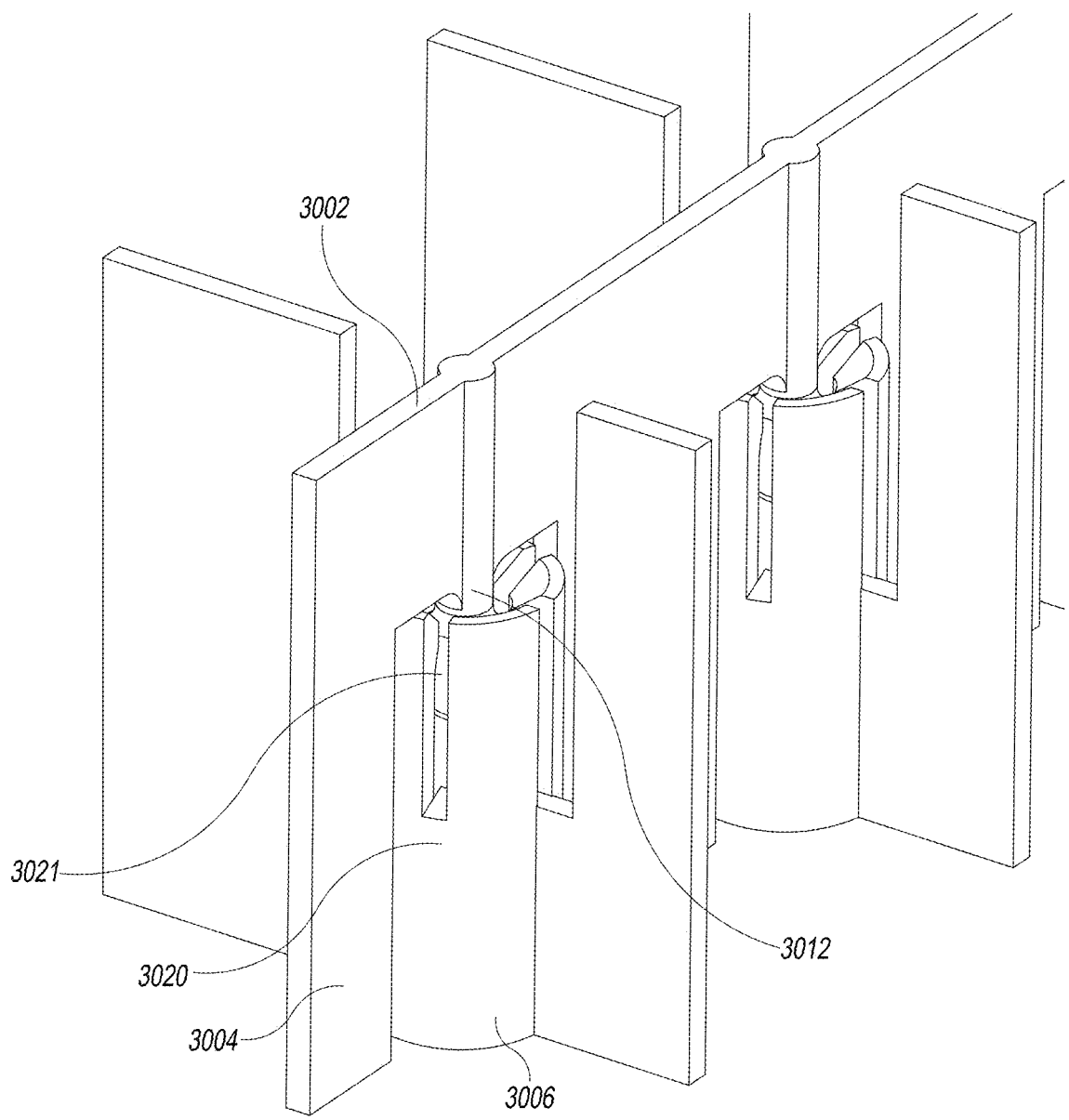
Figure 19D:
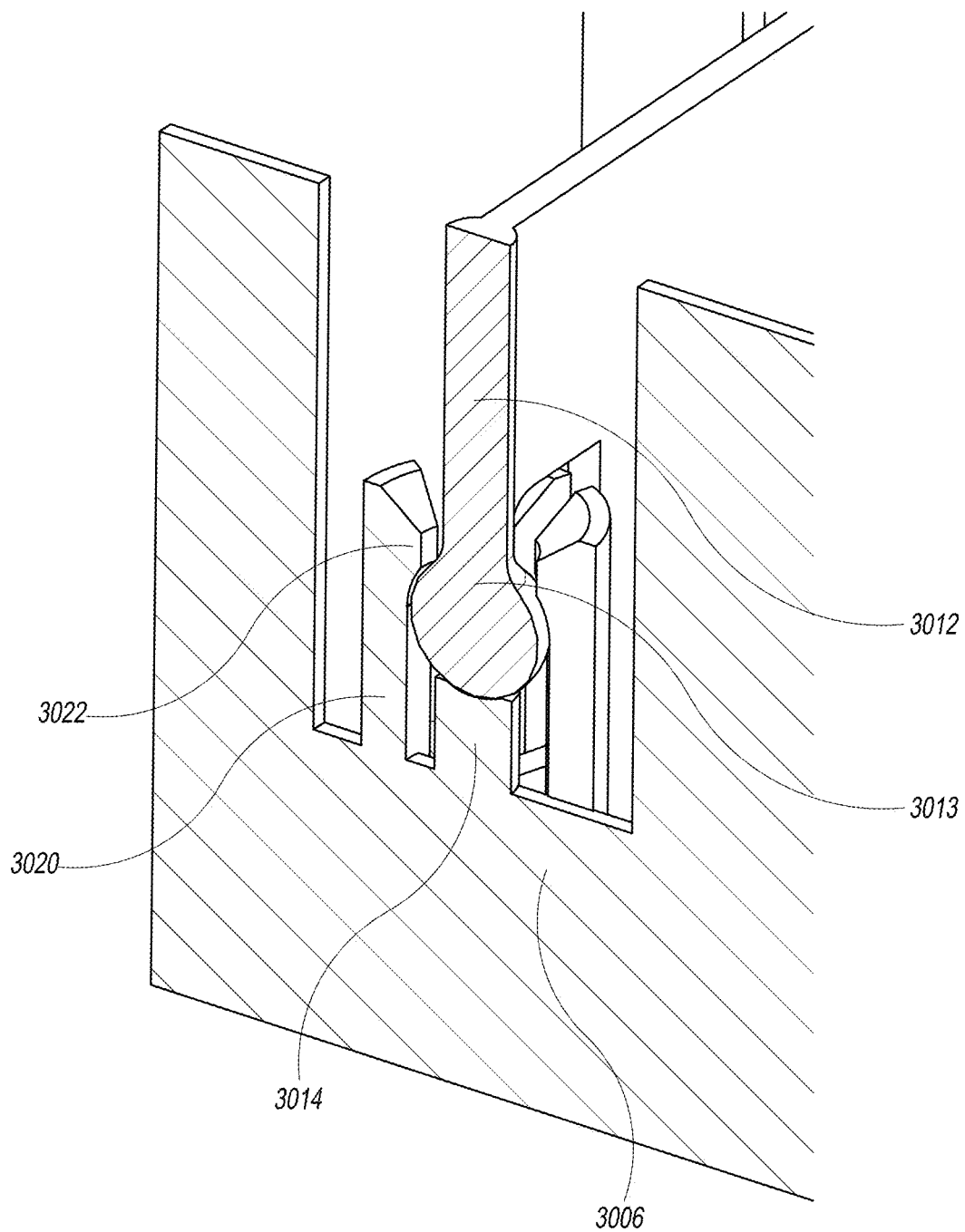
Figure 19E:
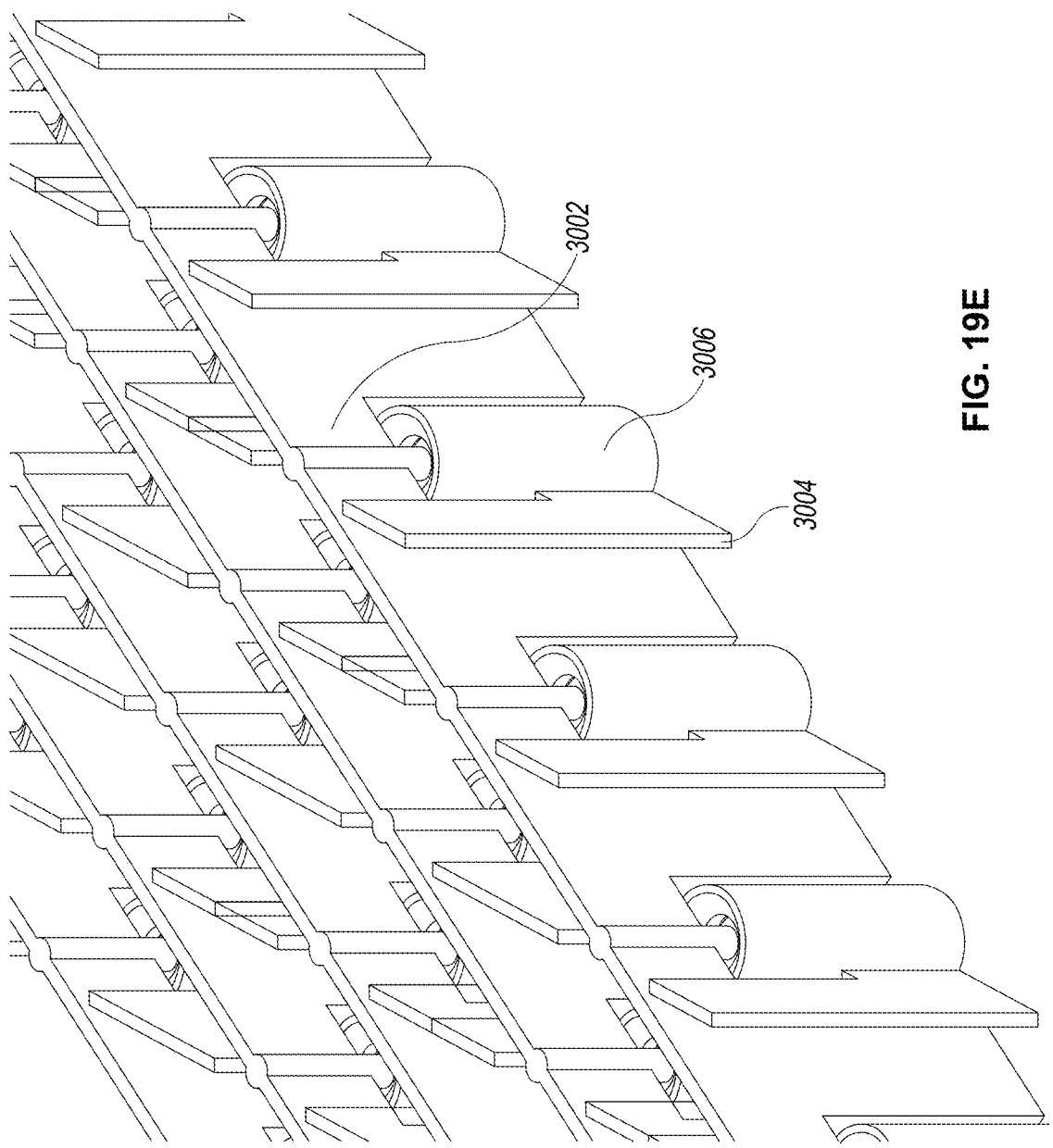

FIG. 19E illustrates a compressed view of an embodiment of the stabilizing structure 3301. Compared to FIG. 17F, this embodiment has a slightly larger compressed configuration.

Figure 20:
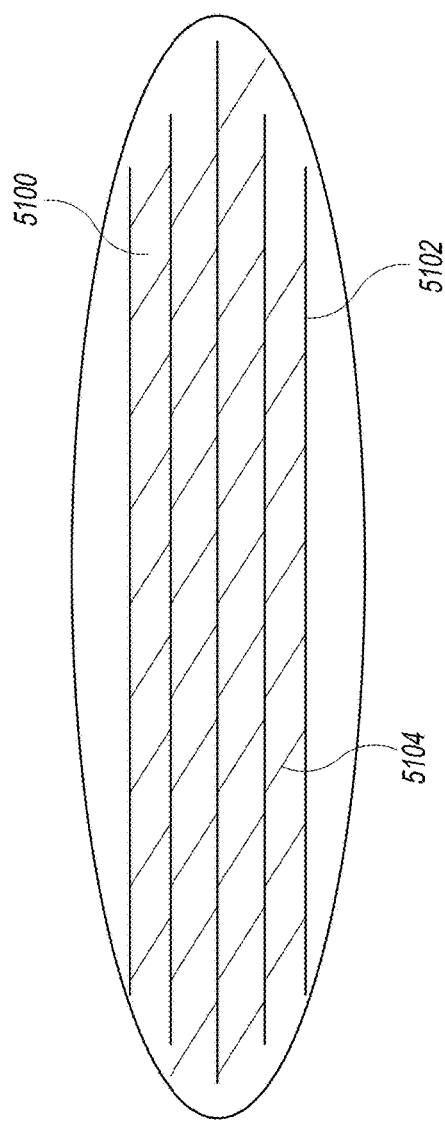
FIG. 20 schematically illustrates an embodiment of a stabilizing structure.

FIG. 20 schematically illustrates an embodiment of a stabilizing structure 5100 configured to be placed over a wound and that may be incorporated into a wound dressing. Preferably, the stabilizing structure 5100 preferably comprises at least one, and more preferably at least two, long strips 5102 whose longitudinal length may be oriented along a longitudinal axis of a wound, or along a direction along which closure is sought. Each of the one or more long strips 5102 are preferably substantially rigid and extend substantially along the entire length of a wound. In a preferred embodiment, the long strip 5102 is continuous and does not have any breaks or hinges along its length. This is in contrast to certain other embodiments described above.

One or more struts 5104 are preferably attached at one or more points to the long strip 5102. Preferably, these struts 5104 are movably attached, for example via a hinge-like attachment or flexible joint, such that these may collapse in a direction perpendicular to a longitudinal length defined by the length of the one or more long strips 5102. In some embodiments, the struts 5104 may be angled at a non-perpendicular angle with respect to the long strip 5102 so as to collapse more readily. In embodiments comprising two or more long strips 5102, the struts 3404 may be hinged between two parallel long strips 5102.

It will be recognized that while these struts 5104 may be configured to collapse along a direction perpendicular to the longitudinal length of the one or more long strips 5102, the struts 5104 are preferably rigid in a vertical direction (i.e., in the direction extending upward from a plane defined by the wound). As such, a combination of the struts 5104 and the long strips 5102 may thus form a stabilizing structure 5100 that is substantially rigid in a vertical direction while being collapsible in a horizontal direction perpendicular to the longitudinal axis of the long strips 5102 (i.e., in the plane of the wound or the skin surrounding the wound).

Figure 21B:
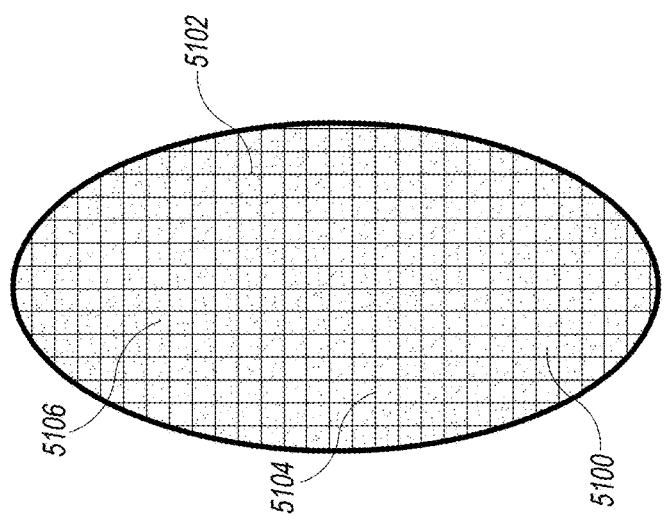
FIG. 21B illustrates a top view of an embodiment of an oval shaped stabilizing structure with foam.
Figure 21A:
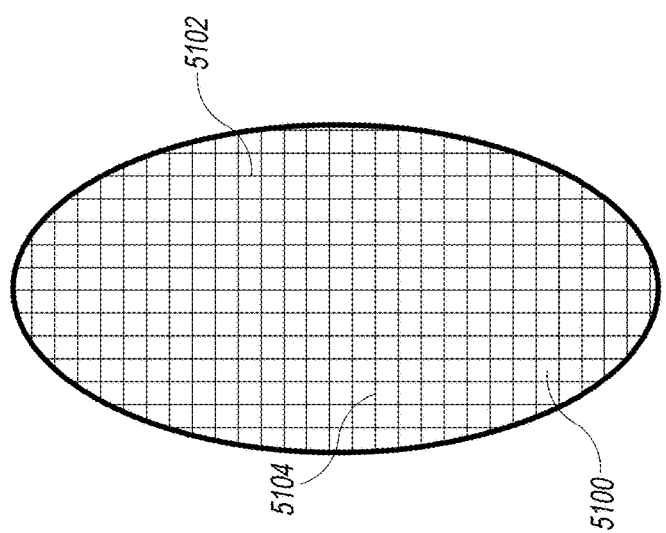
FIG. 21A illustrates a top view of an embodiment of an oval shaped stabilizing structure.

FIG. 21A illustrates a top view of an embodiment of stabilizing structure 5100 cut into an oval shape. Preferably, the stabilizing structure 5100 comprises a plurality of elongate strips 5102 whose longitudinal length may be oriented along a longitudinal axis of a wound, or along a direction along which closure is sought. Each of the plurality of elongate strips 5102 is preferably substantially rigid and may extend substantially along the entire length of a wound. A plurality of intervening members are positioned between adjacent elongate strips 5102. These intervening members may be struts 5404 as described with respect to FIG. 20, preferably attached at one or more points to the elongate strips 5402. The intervening members may also be portions of elongate strips such as described with respect to FIGS. 18A-19E above, extending perpendicular or at an angle to elongate strips 5102. The stabilizing structure of FIG. 21A may also comprise the embodiments described with respect to FIGS. 15A-16F.

FIG. 21B illustrates a top view of an embodiment of an oval shaped stabilizing structure 5100 placed over a wound. This embodiment may have the same configuration as described above with respect to FIG. 21A. Additionally, foam 5106 can be inserted between and around the stabilizing structure.

Stabilizing Structures of FIGS. 22A-24 and 26-27

In some embodiments, the collapse of a stabilizing structure as described herein this section or elsewhere in the specification can occur slowly, thereby applying increasing longitudinal tension over a long period of time. In certain embodiments, the collapse and lengthening of the structure can occur immediately upon application of negative pressure. In further embodiments, the collapse can occur at any rate.

Figure 22A:
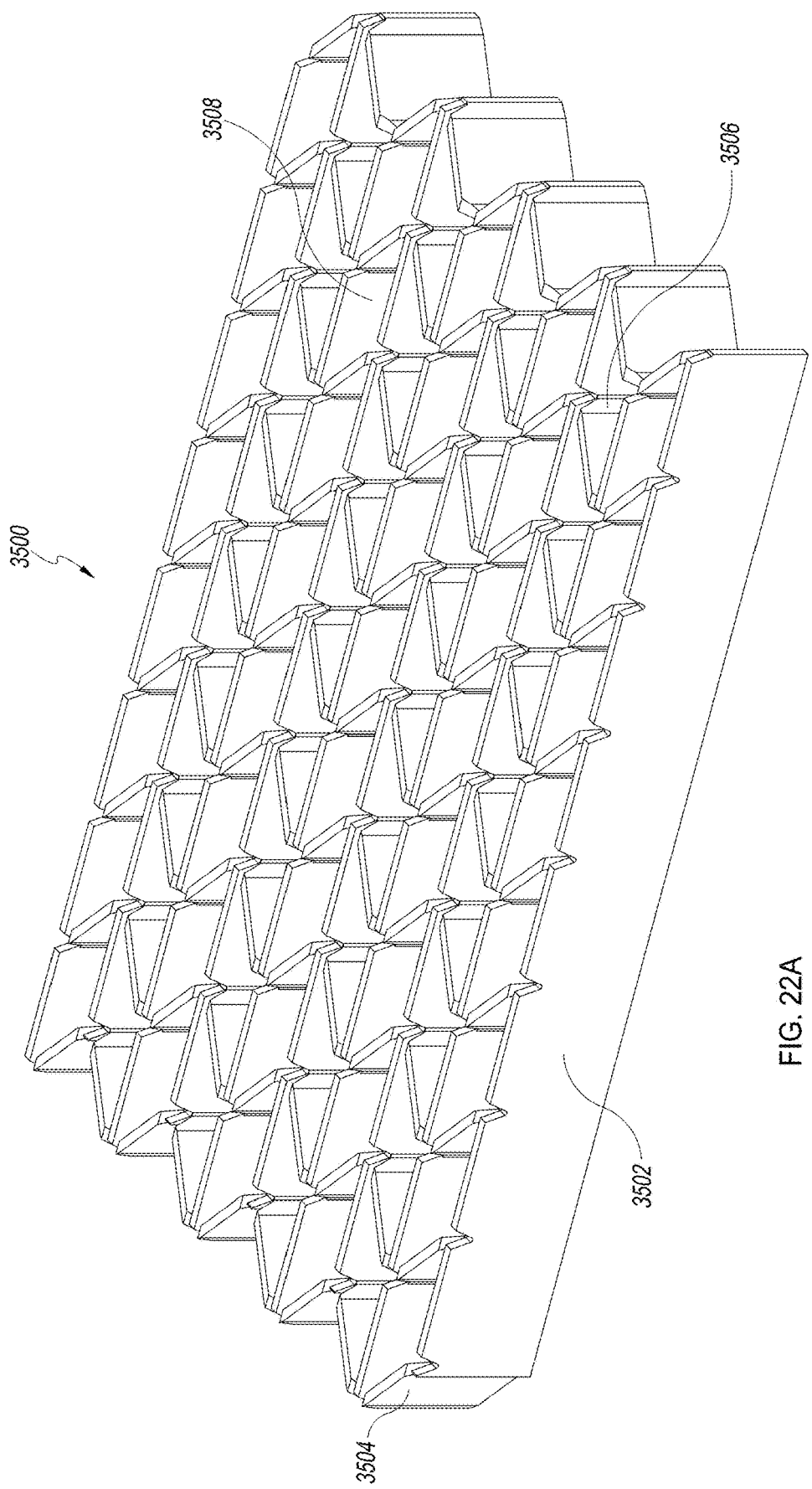
FIGS. 22A-C illustrate multiple views of an embodiment of a stabilizing structure.
Figure 22B:
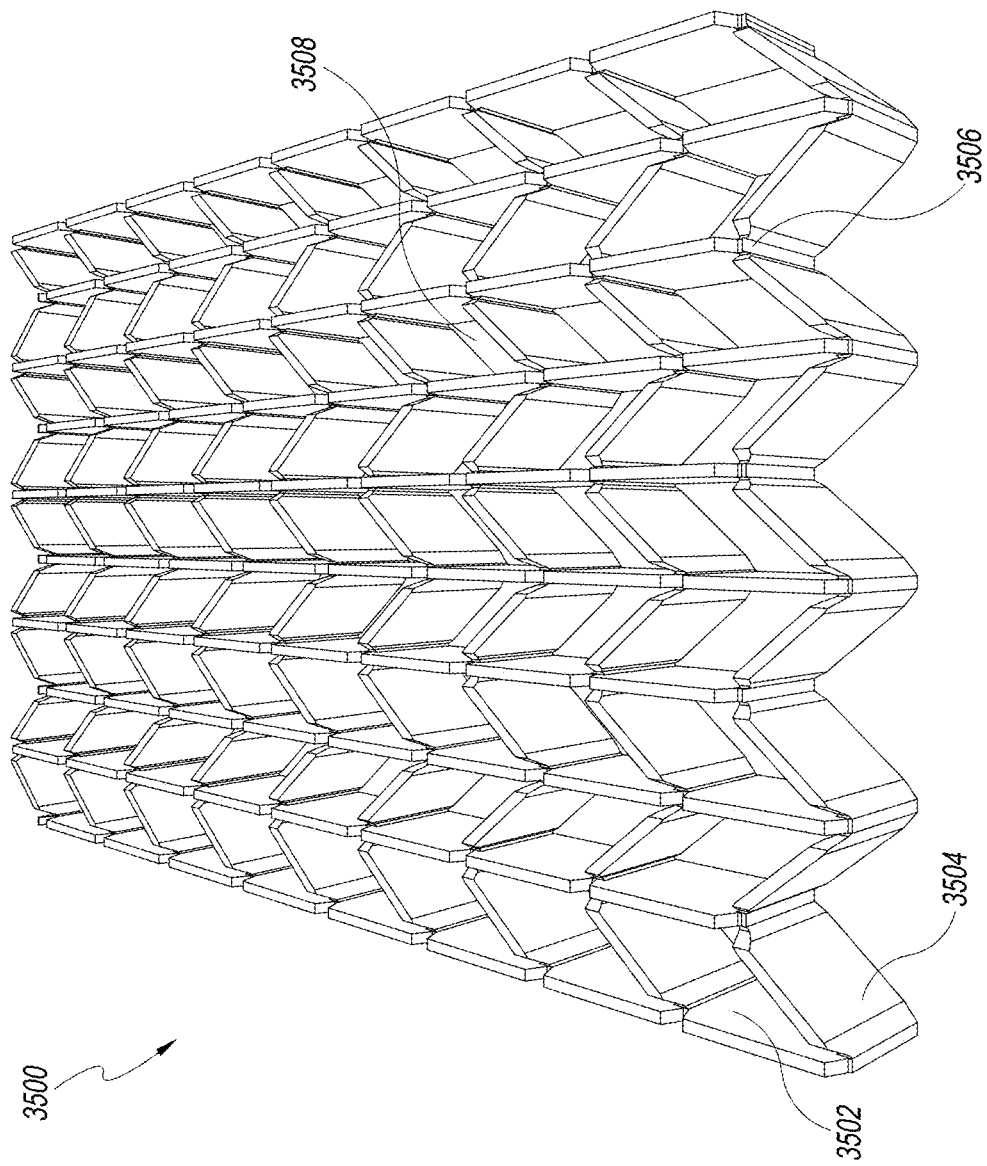
Figure 22C:
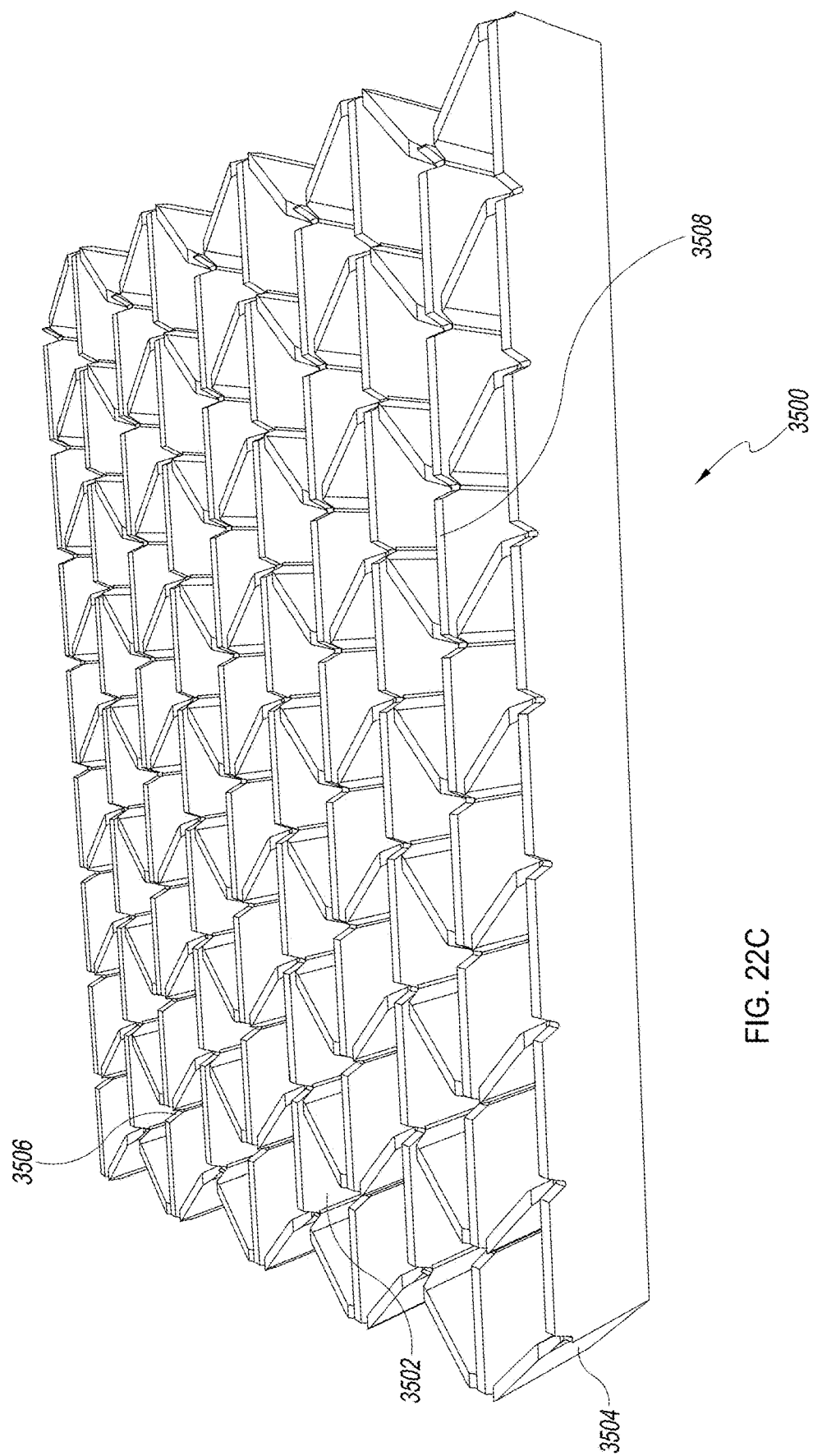

FIGS. 22A-C illustrate another embodiment of a stabilizing structure 3500. The stabilizing structure 3500 comprises a plurality of elongate strips 3502 arranged in parallel, and whose longitudinal length can be aligned with the longitudinal axis of a wound. The stabilizing structure further comprises a plurality of intervening members 3504 connected to the elongate strips 3502 by a plurality of joints 3506. As illustrated, the plurality of intervening members 3504 between adjacent elongate strips 3502 define a row of cells 3508 between each pair of adjacent elongate strips.

In some embodiments, the elongate strips 3502 are rigid. In certain embodiments, the elongate strips 3502 are semi-rigid. In particular embodiments, the elongate strips 3502 are flexible. In some embodiments, the elongate strips 3502 are compressible. As illustrated in FIGS. 22A-22C, one embodiment comprises a plurality of strips that are rigid in a vertical dimension but also are flexible and capable of bending along their length.

In some embodiments, the intervening members 3504 are rigid. In certain embodiments the intervening members 3504 are semi-rigid. In particular embodiments, the intervening members are flexible and/or compressible. As illustrated in FIG. 22A-22C, one embodiment comprises intervening members in the form of panels equally spaced apart between adjacent strips, to define a plurality of similar-shaped (e.g., diamond-shaped) cells. In other embodiments, the intervening members need not be equally spaced. The intervening members may be attached to the strips by joints 3506 in the form of a hinge (e.g., a living hinge or a more flexible piece of material between the strips and the intervening members).

In some embodiments, the plurality of intervening members 3504 are configured to pivot relative to the elongate strips 3502 and to collapse so as to allow the elongate strips to collapse relative to one another and come closer together. In some embodiments, the joints 3506 are configured to pivot and collapse in only one direction. In certain embodiments, the joints 3506 are configured to pivot and collapse in both directions, comprising a full 180 degrees of rotation relative to the elongate strips 3502. In certain embodiments, when the joints pivot, they pivot completely so as to rest the intervening members 3504 against the elongate strips 3502. In some embodiments, the joints do not pivot completely and the intervening members do not come to rest against the elongate strips 3502.

Preferentially, in certain embodiments, by controlling the direction in which the pivoting occurs, the collapsed length of the stabilizing structure 3500 can be controlled. In particular embodiments, because of the rigidity of the elongate strips, the cells 3508 in a row between adjacent elongate strips are configured to collapse together as the adjacent elongate strips 3502 collapse relative to one another. In some embodiments, one or more rows of cells 3508 between adjacent strips 3502 are configured to collapse in a first direction, and one or more rows of cells between adjacent strips 3502 are configured to collapse in a second direction opposite the first direction. As illustrated in FIGS. 22A-22C, the orientation of cells in adjacent rows alternates so that cells of a first row collapse in a first direction, and cells of a next row collapse in an opposite second direction. Joints 3506 may be configured so that joints 3506 in adjacent rows collapse in different directions.

By configuring the joints 3506 and/or cells of the stabilizing structure to pivot and collapse in preferred directions, the length of the collapsed structure can be modified. The embodiment shown in FIGS. 22A-22C will have a shorter collapsed length than a structure where all the rows of cells 3508 are configured to collapse in the same direction. Thus, the collapsed length of the structure can be controlled depending on the orientation of the cells and the direction in which the intervening members collapse between adjacent rows.

In FIGS. 22A-22C, the intervening members 3504 in adjacent rows are generally aligned so that the intervening members connect to the elongate strips at approximately the same location on opposite sides of the strip and share the same joint 3506 location. In other embodiments, the intervening members 3504 between a first elongate strip 3502 and a second elongate strip 3502 are offset relative to intervening members 3504 between the second 3502 and a third adjacent strip 3502. In these embodiments, the intervening members 3504 are staggered such that they do not share the same joint 3506 location.

As shown in FIGS. 22A-22C, the enclosed cell 3508 formed by two intervening members and two sections of the elongate strips is a quadrilateral. In some preferred embodiments, the enclosed shape can be a square, rectangle, diamond, oblong, oval, and/or parallelepiped. In some embodiments, the enclosed shape is a rhomboid. In certain embodiments the enclosed shape is a trapezoid.

In certain preferred embodiments, the joint 3506 may be configured to limit the range of motion of the intervening member 3504, and may be used to prevent the intervening members 3504 from becoming fully perpendicular to the adjacent strips. Thus, the joint may be configured to pre-set the intervening members 3504 in a partially collapsed position. For example, a lip or other portion of material at the joint may be used to limit the angular motion of the intervening members. The lip or other portion of material may also prevent the joint from collapsing completely flat. In some embodiments, the joint may be configured to prevent the intervening members from rotating in 180 degrees along the plane formed by the strips.

In some embodiments, when the stabilizing structure 3500 is placed over a wound, the elongate strips 3502 are positioned generally parallel to the lateral edges of the wound. Preferably, the stabilizing structure is configured such that the elongate strips are positioned parallel to the longitudinal axis of the wound. The strips may also bend along their length and bow outwardly. The stabilizing structure may be cut to an appropriate size. In other embodiments, the elongate strips 3502 are positioned perpendicular to the edge of the wound, or may not be oriented along any edge of the wound.

In the embodiments of FIGS. 22A-22C, as well as in other embodiments of stabilizing structures described in this section or elsewhere in this specification, the strips can be constructed from a material selected from the group consisting of silicone, polyurethane rigid plastics, semi-rigid plastics, flexible plastic materials, composite materials, biocompatible materials and foam. In some embodiments, the intervening members can be constructed from a material selected from the group consisting of silicone, polyurethane, rigid plastics, semi-rigid plastics, flexible plastic materials, composite materials, biocompatible materials and foam. In some embodiments, the stabilizing structure is surrounded by absorbent materials. In certain embodiments the stabilizing structure is surrounded by non-absorbent materials. In some embodiments the material surrounding the stabilizing structure is foam. In particular embodiments, the spaces between the intervening members 3504 and the elongate strips 3502 are filled with foam.

Figure 23A:
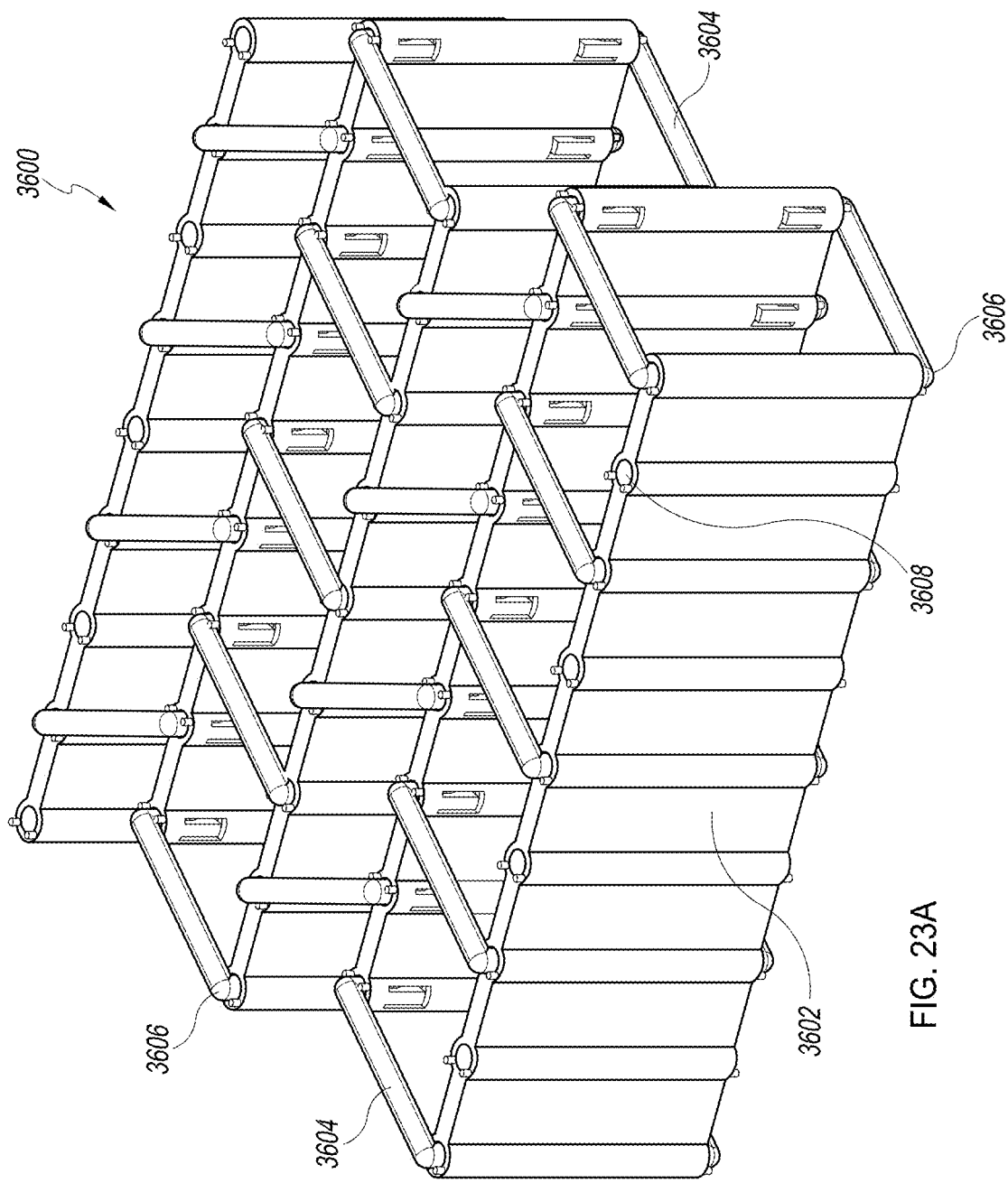

FIGS. 23A-G illustrate an embodiment of a stabilizing structure 3600 that is similar to the ones described above in relation to FIGS. 22A-C. As illustrated in FIG. 23A, in some embodiments, the stabilizing structure 3600 comprises a plurality of elongate strips 3602 connected by a plurality of intervening members 3604 at a plurality of joints 3606. As illustrated in FIGS. 23A-G, the plurality of intervening members comprise a plurality of bars 3604 connecting adjacent elongate strips and connected to the elongate strips at upper and lower joint locations. The plurality of joints in one embodiment comprise a plurality of pins 3606 connected to the bars and received in upper and lower vertical openings in the strips 3602. Other types of joints are also contemplated, including ball joints. The bars are preferably equally spaced within a row between adjacent elongate strips, and may be offset or staggered in an adjacent row, such that in an adjacent row, the bars connect to the elongate strip at a location between the bars of the first row. In other embodiments, the intervening member can comprise a wire or other elongate structure configured to extend between adjacent elongate strips.

Figure 23B:
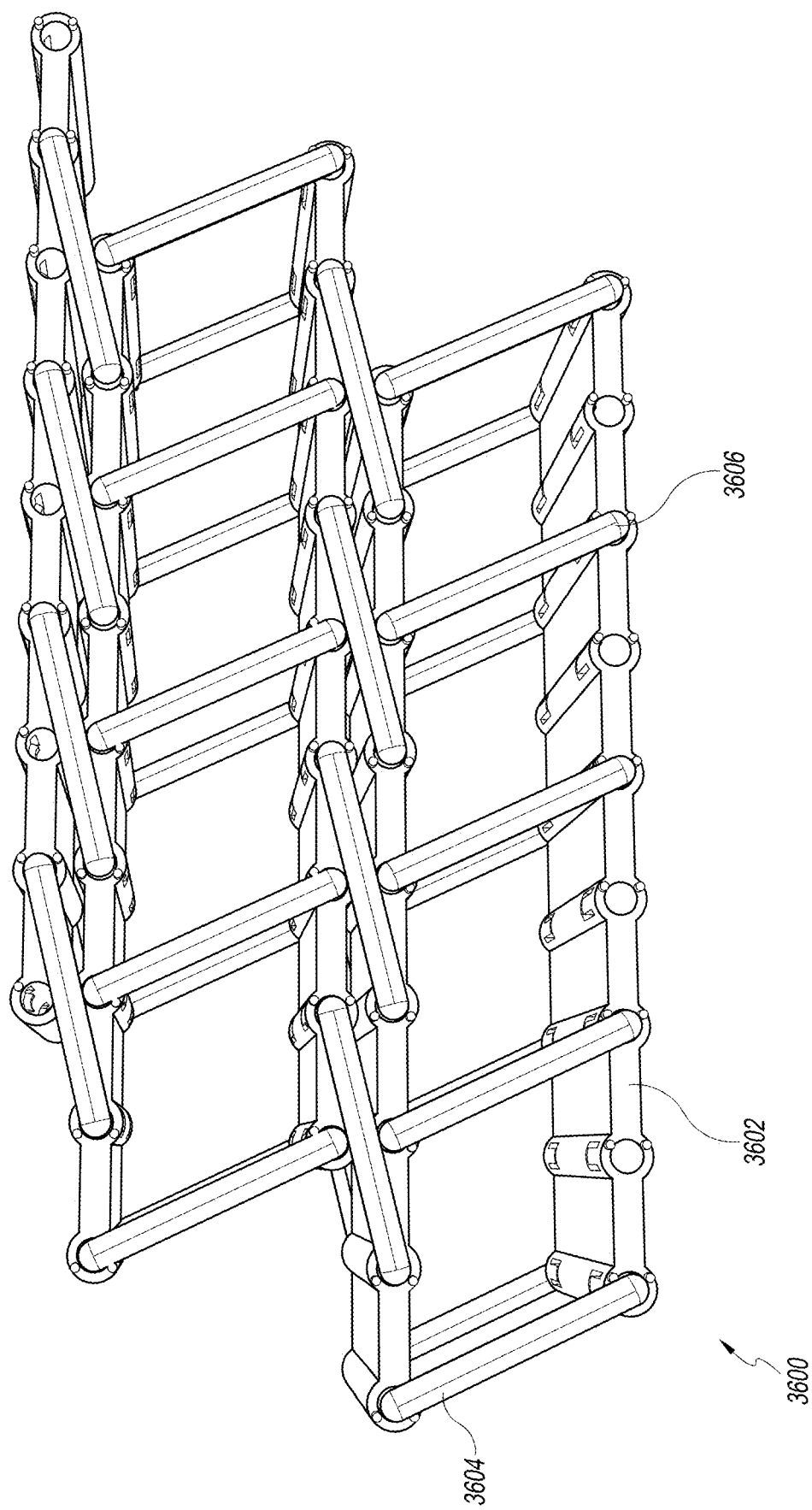
Figure 23D:
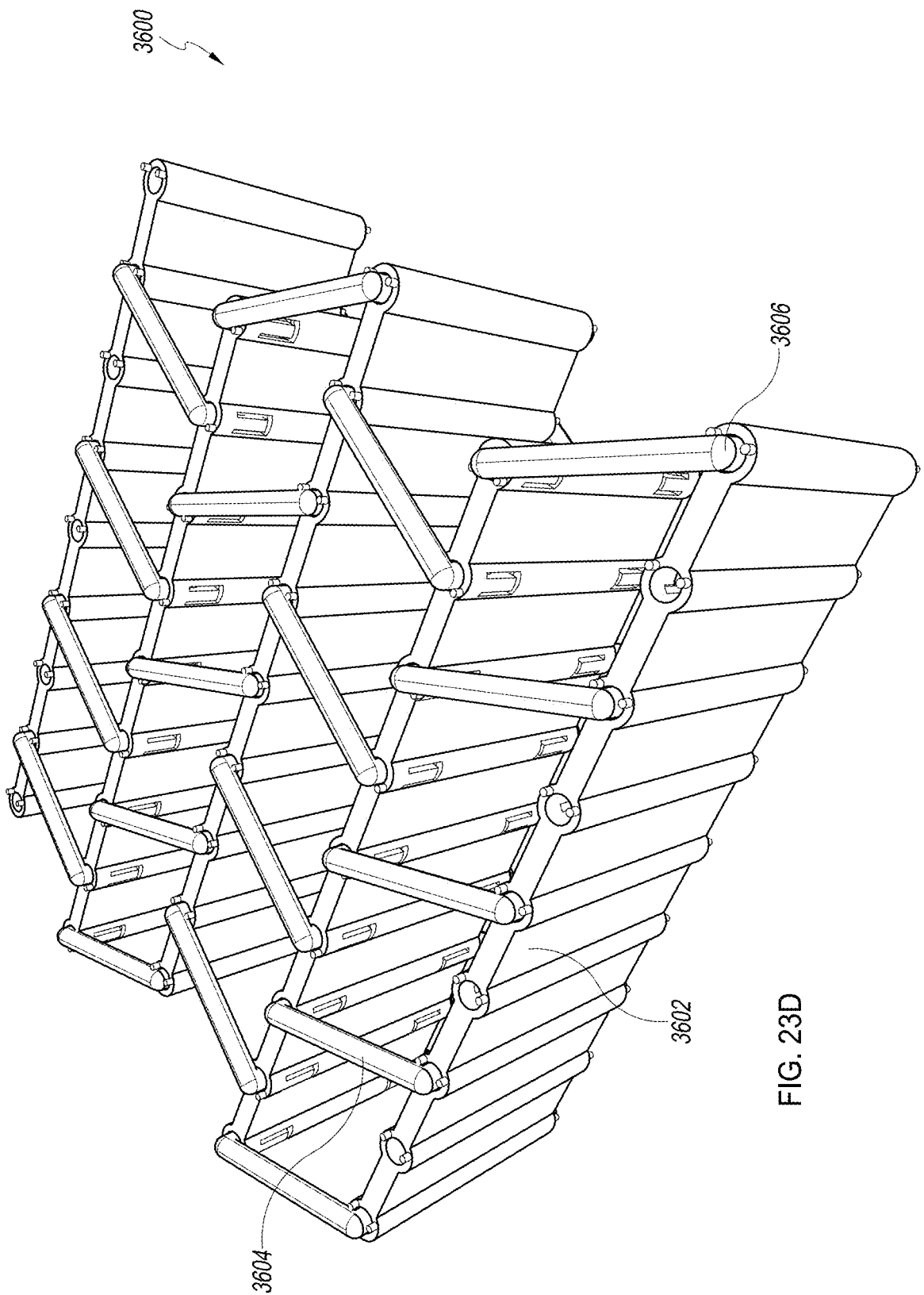

Preferably, as illustrated in the top view of FIG. 23B and the front view of FIG. 23C, in certain embodiments the pins cause the bars to protrude above the vertical top and the vertical bottom of the elongate strips 3602. In other embodiments, the bars 3604 may be connected to the elongate strips so that they are located flush with the vertical top and vertical bottom of the elongate strips 3602. In further other embodiments, the bars 3604 may be connected so that they are located below the vertical top of the elongate strips 3602 and above the vertical bottom of the elongate strip.

As illustrated in FIGS. 23A and 23C, the joints 3606 can preferably comprise a plurality of stops 3608 configured to limit the rotation of the bars relative to the strips. The stops may protrude vertically from the strips to limit the movement of the bars. For example, these stops may be used to prevent the bars from becoming fully perpendicular with respect to the adjacent strips, and may be used to provide a preferential direction of collapse to adjacent rows. As shown in FIG. 23A, a first row may have bars angled in a first direction, and a second row may have bars angled in a second direction. In some embodiments, there are two stops per bar on a given strip, to restrict motion in two directions. In other embodiments, there is one stop or three or more stops per bar on a given strip.

Figure 23E:
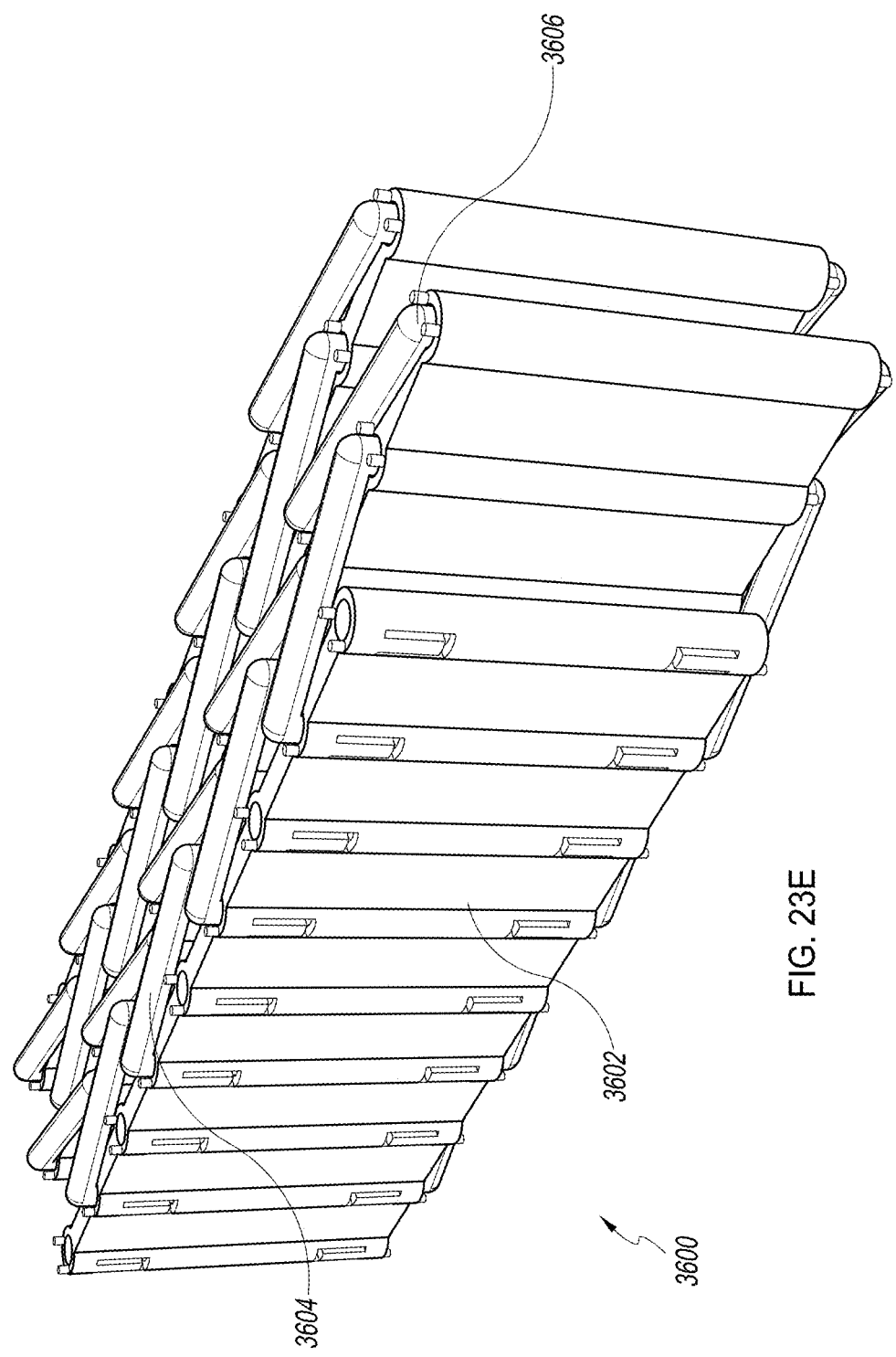
Figure 23F:
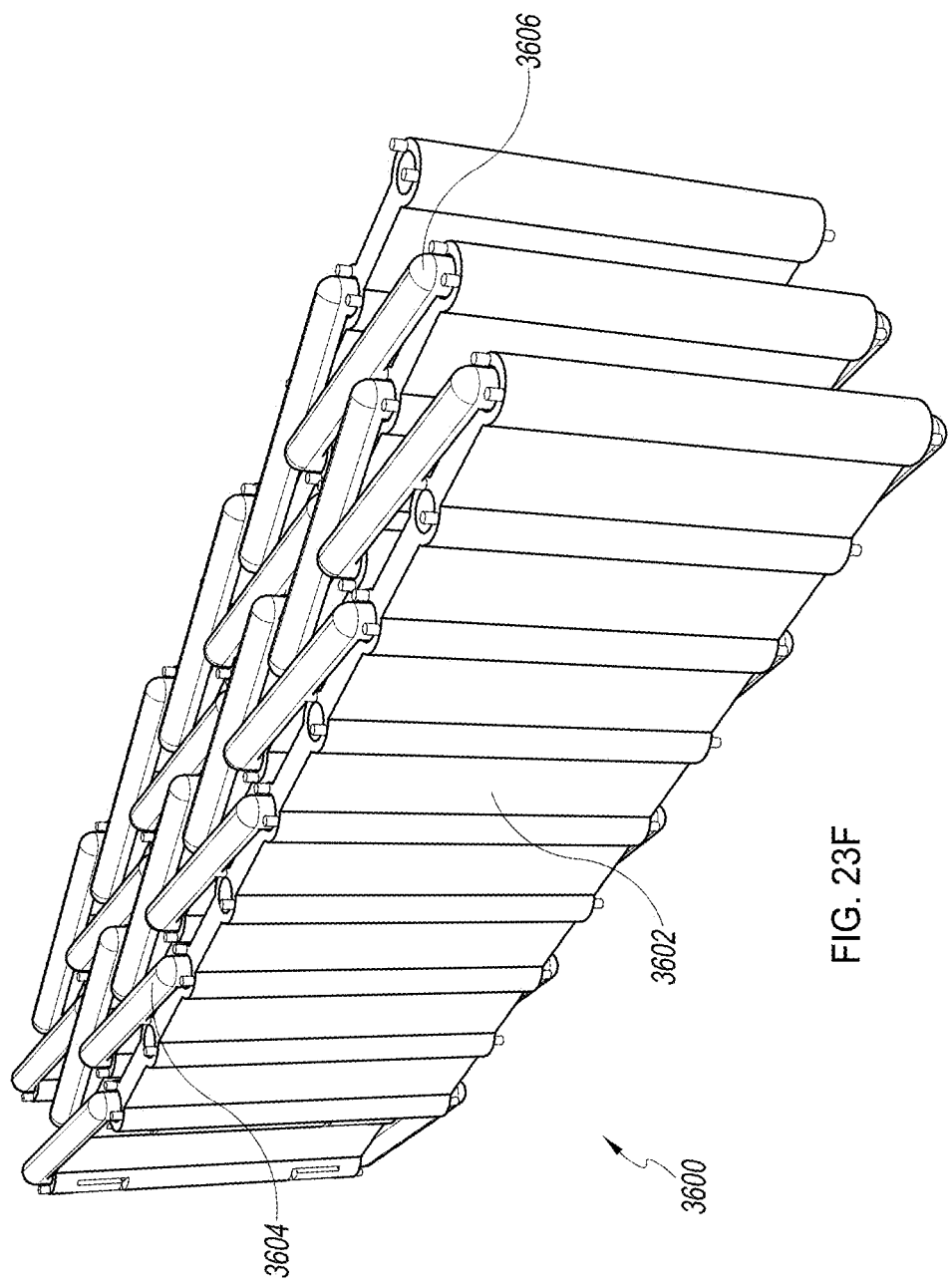
Figure 23G:
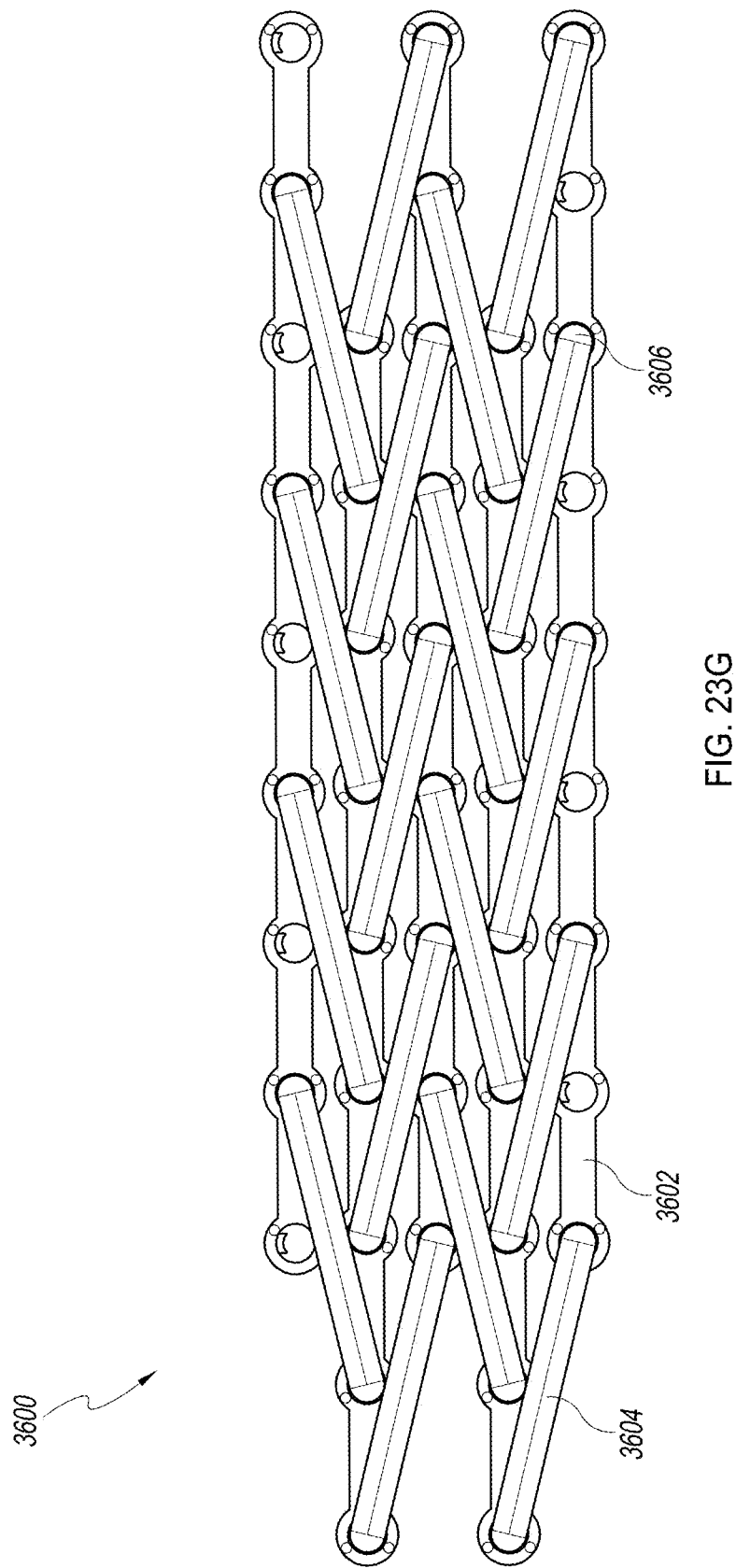

FIGS. 23E-G illustrate the stabilizing structure 3600 in a collapsed configuration. Similar to the structures of FIGS. 23A-C and FIG. 23B, the structure 3600 may be positioned to collapse in a direction perpendicular to the longitudinal axis of the wound. As described above, the stabilizing structure may be surrounded by or filled with absorbent material such as foam. In one embodiment, because the vertical space between the upper and lower bars of the structure 3600 are open (as best shown in FIG. 23C), elongate blocks of foam or other compressible material may be placed in between adjacent strips to provide a desired compressibility as the structure collapses.

Figure 24:
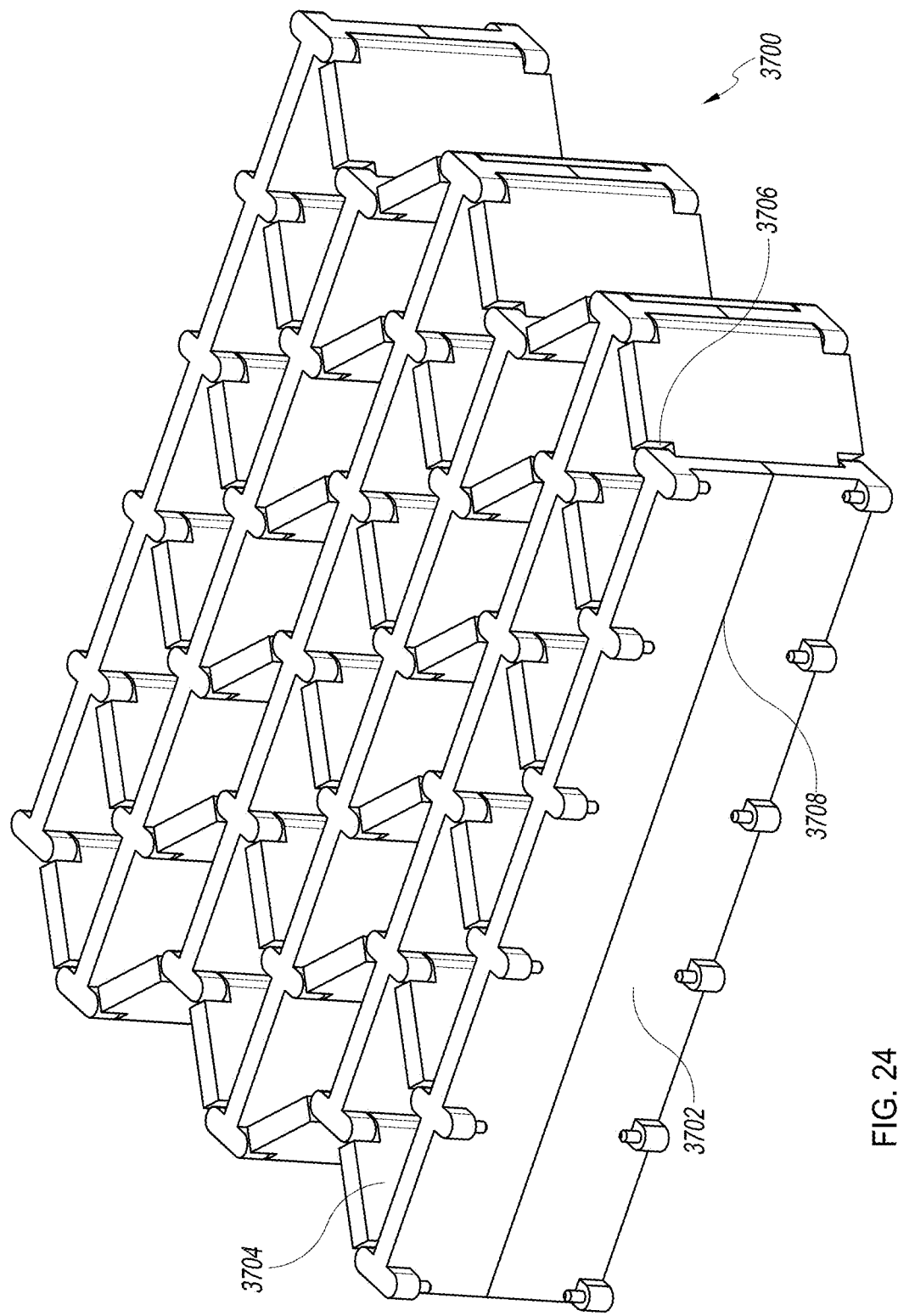
FIG. 24 illustrates one embodiment of a hinged stabilizing structure for closing a wound.

FIG. 24 illustrates an embodiment of a stabilizing structure 3700 that is similar to the structures described above in relation to FIGS. 22A-C and FIGS. 23A-G. In certain embodiments, the stabilizing structure 3700 can collapse in any manner described above. The elongate strip 3702 as illustrated is formed in two halves, and can be separated along line 3708. The intervening members 3704 can be in the form of panels as described above. The joints 3706 on the upper half of an elongate strip may comprise pins located on opposite sides of the strip extending downward from the top of the upper half of the strip. The joints 3706 on the lower half of an elongate strip may comprise pins located on opposite sides of the strip extending upward from the bottom of the lower half of the strip. These pins may engage vertical openings located at the four corners of the intervening member 3704. As the upper and lower halves are brought together, the pins may engage the openings in the panels. The upper and lower halves may be secured by any number of mechanisms, such as with adhesive and mechanical connections.

In the FIG. 24 embodiment, with the ability to separate the two halves of 3702 along line 3708, intervening members 3704 may be easily removed or replaced. In some embodiments, only some of the intervening members 3704 are removed. In certain embodiments, alternating intervening members 3704 are removed. In certain preferred embodiments, intervening members are removed in a preferential manner so as to allow the stabilizing structure 3700 to collapse in a controlled manner most appropriate for a particular wound. For example, the joints 3706 may have variable levels of resistance to rotation, thus allowing for control over the collapse of the structure by adding or removing the intervening members 3704. Additionally, stops such as those described in relation to FIG. 31A, could be incorporated into the structure or any other structure described in this section or elsewhere in this specification to further control collapse. In some embodiments, the intervening members are replaced or removed to maximize the collapsed length of the structure 3700. In certain embodiments, intervening members are replaced or removed to minimize the collapsed length of structure 3700. In some embodiments, intervening members are replaced or removed to attain a desired length for the collapsed structure.

Figure 26:
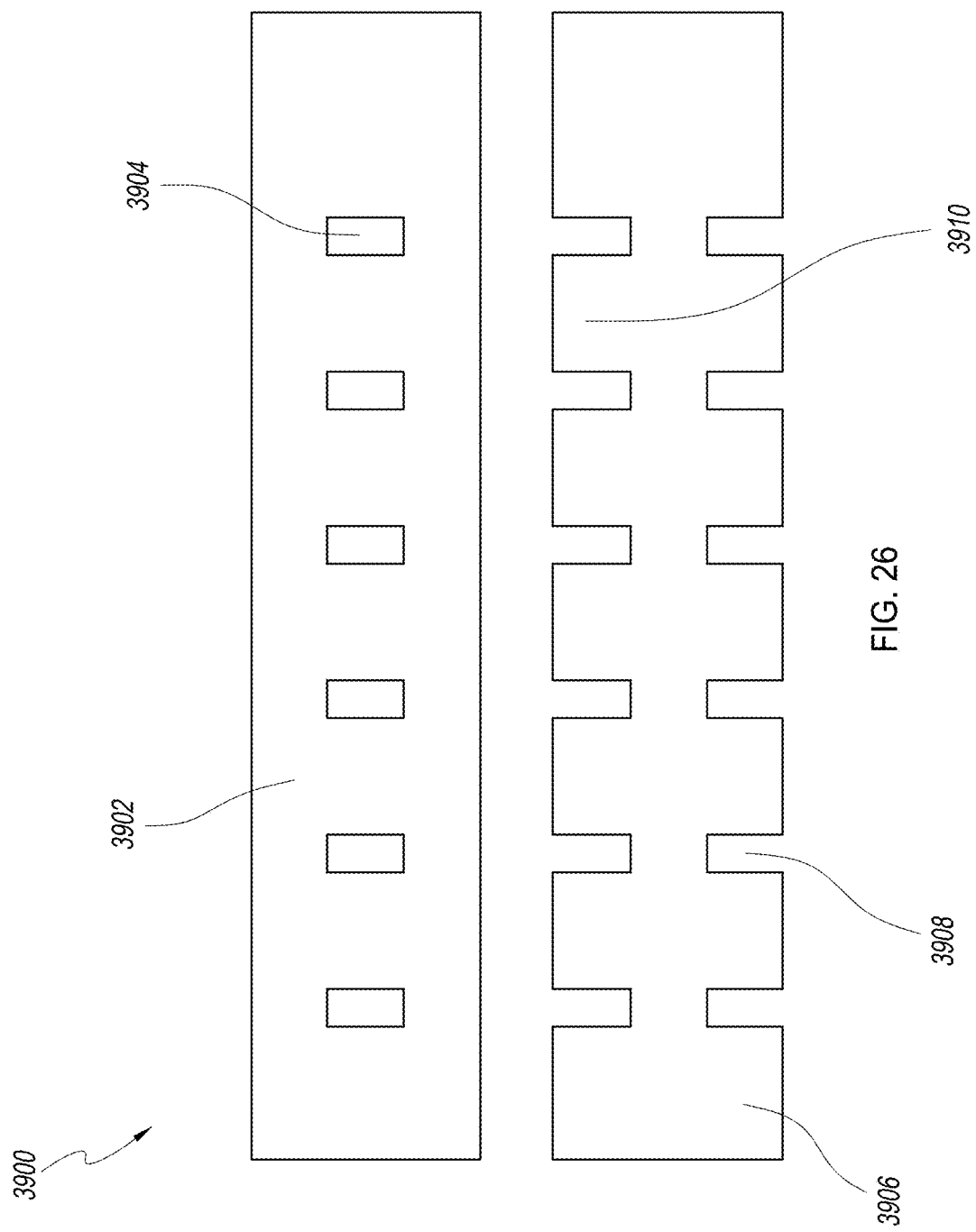
FIG. 26 illustrates one embodiment of a stabilizing structure for a wound.

FIG. 26 illustrates another embodiment of elongate strips 3900 that may be used to form a stabilizing structure. The first strip 3902 illustrated in the upper portion of FIG. 26 may be an elongate strip having a plurality of spaced apart openings 3904 extending along a central axis of the strip. The second strip 3906 illustrated in the lower portion of FIG. 26 may have a plurality of spaced apart notches 3908 extending from the upper and lower edges of the second strip and separate by a middle portion. A plurality of the first strips 3902 and a plurality of the second strips 3906 can be assembled into a stabilizing structure similar to what is shown in FIGS. 6A, 6C and 6D, wherein the plurality of first strips 3902 are arranged in parallel to each other, and the plurality of second strips 3906 are arranged in parallel to each other. The plurality of first 3902 and second strips 3906 engage one another by the middle portions 3910 of the second strips positioned through the openings 3904 in the first strips, to place the plurality of first strips at an angle to the plurality of second strips. This structure is configured to collapse in a horizontal plane while remaining rigid in the vertical plane.

FIG. 27 illustrates an embodiment of a stabilizing structure 4000 similar to the embodiment of FIG. 11 described above. A plurality of longitudinal strips 4002 can be provided each in the form of a wavy strip that, when joined face-to-face, form one or more circular or ovoid cells 4004. The entire structure can be collapsed into a substantially flat configuration, and can be contained within a roll 4006. To use the stabilizing structure, a portion of the structure can be unrolled and cut at a desired length. Preferably, as the stabilizing structure is unrolled it expands to its natural, deployed configuration. It will be appreciated that other embodiments of the stabilizing structure, and not just embodiments using the wavy strips of FIG. 11, may be assembled into a rolled configuration.

Figure 28:
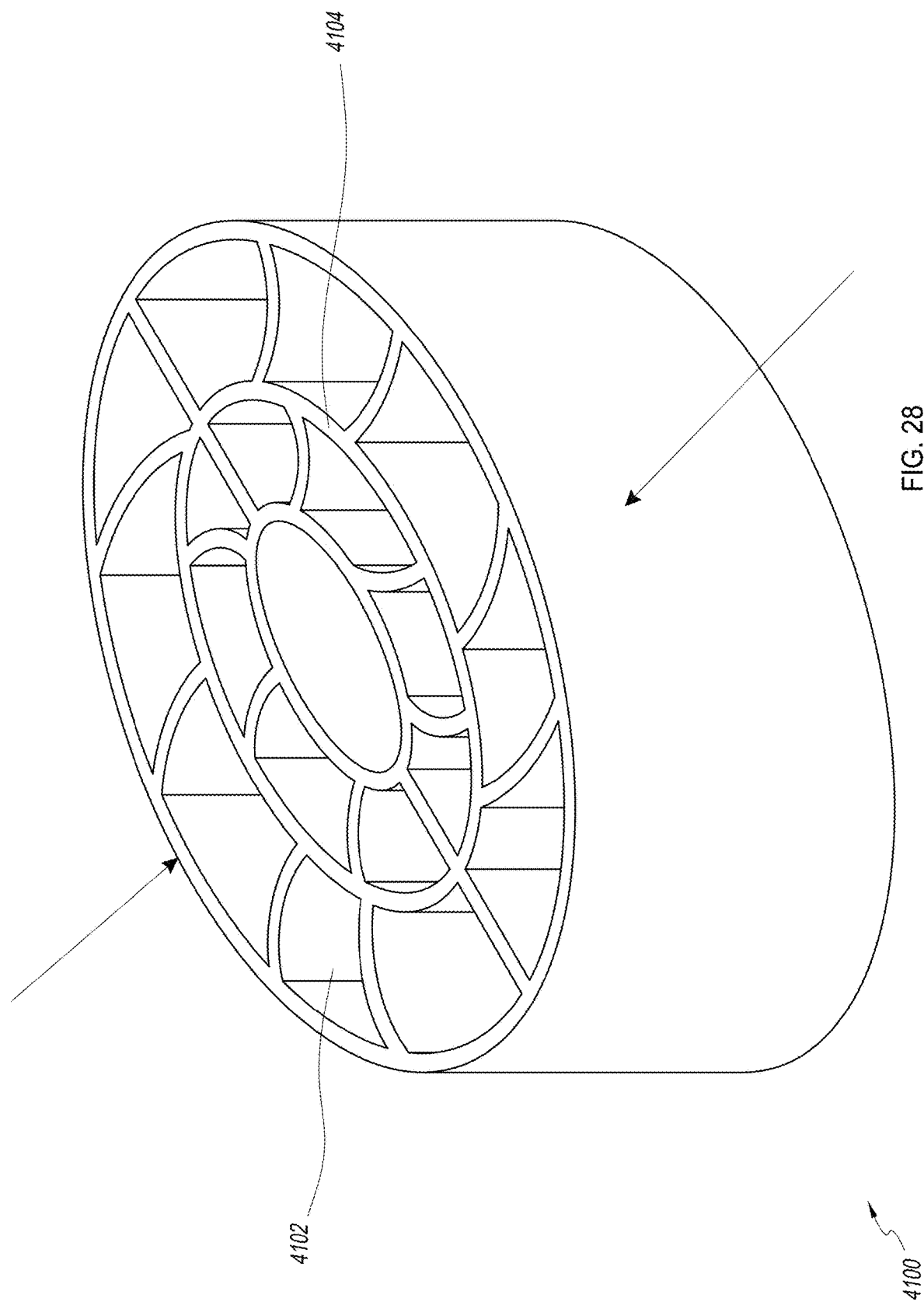
FIG. 28 illustrates an embodiment of a stabilizing structure having an oval shape.

FIG. 28 illustrates another embodiment of a stabilizing structure. In this embodiment, the stabilizing structure 4100 has an elongate, preferably oval shape, wherein cells 4102 within the oval shape have a plurality of cells arranged in a plurality of concentric rings 4104. In the embodiment illustrated, a central oval cell is surrounded by two oval-shaped rings. Other embodiments can include more than two oval-shaped rings.

Figure 29A:
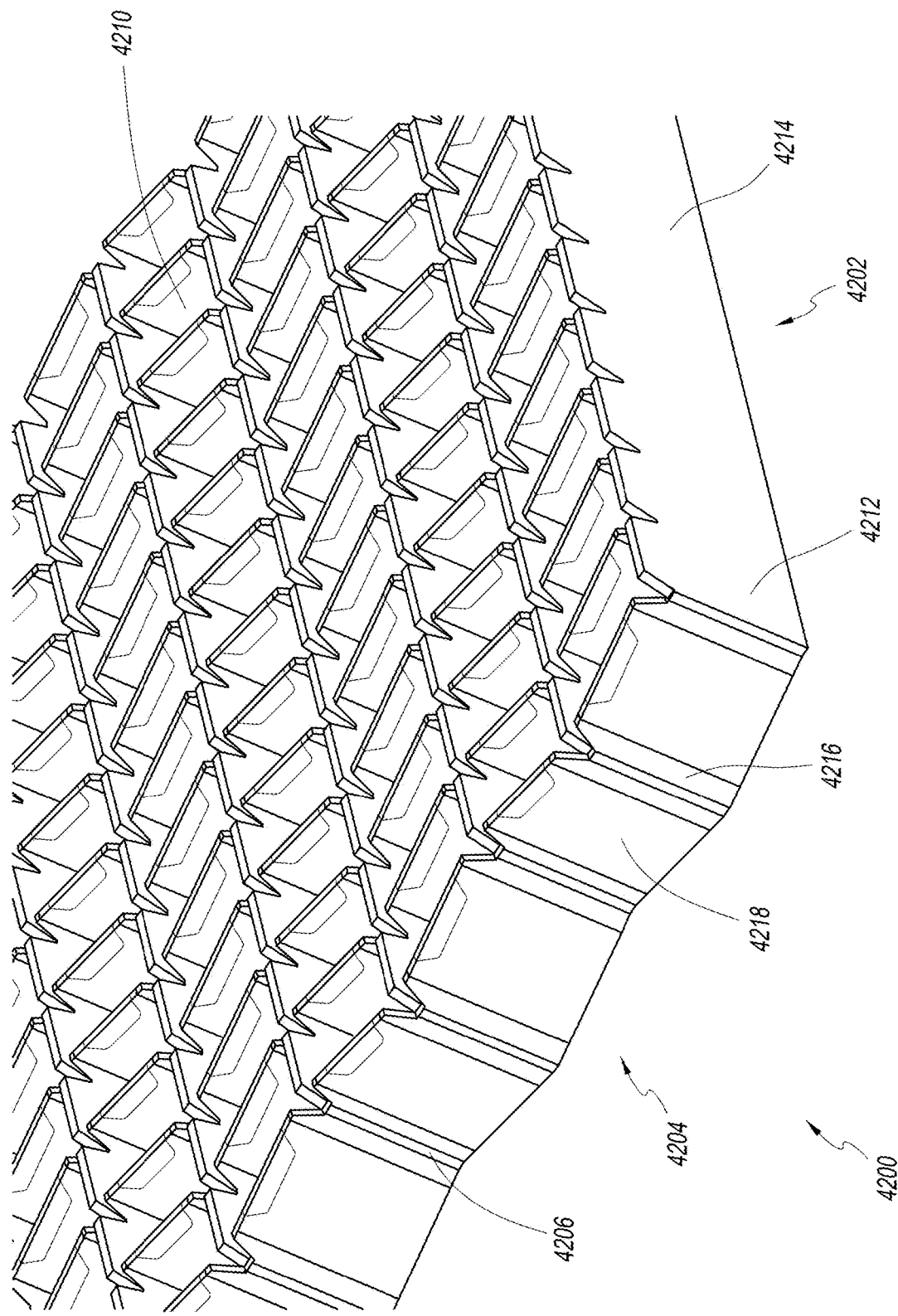
Figure 32A:
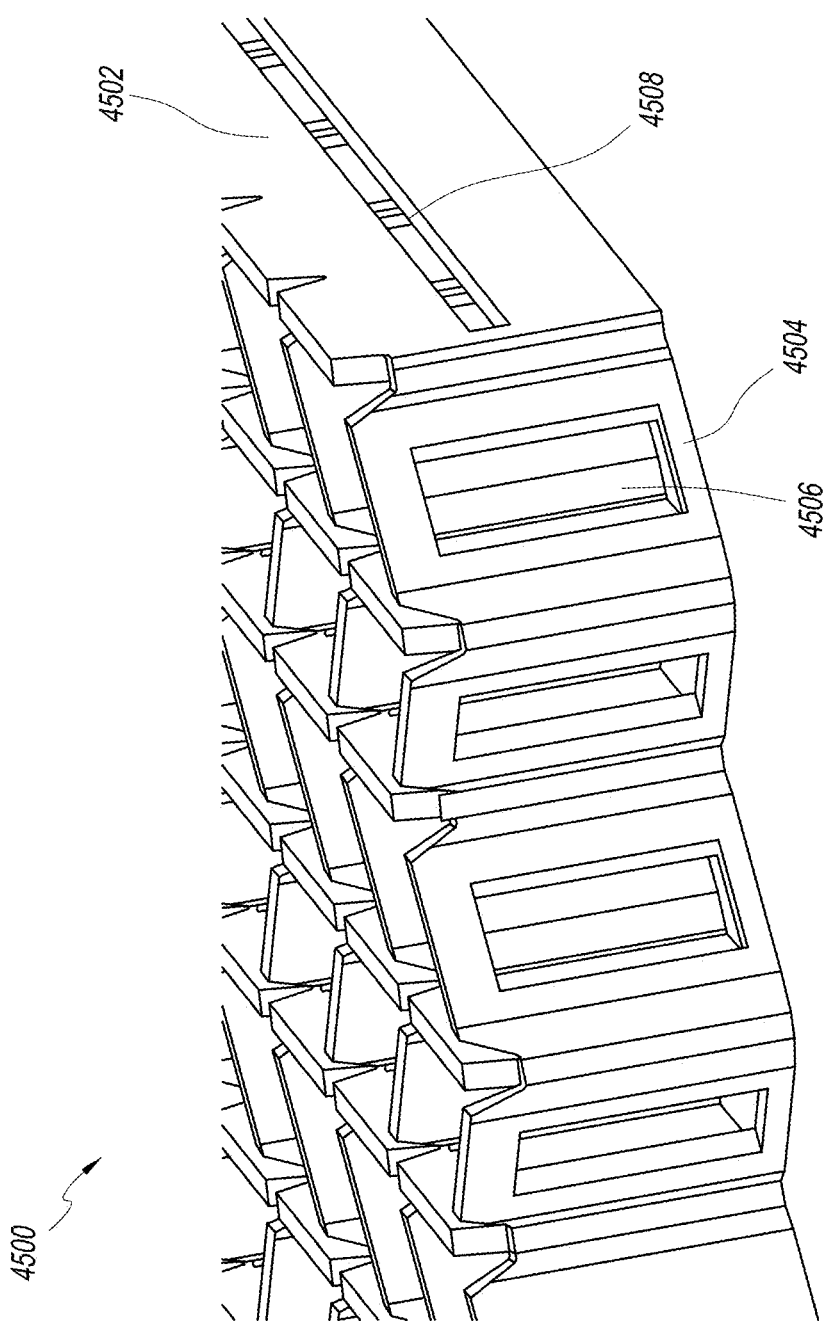
FIGS. 32A-B illustrate multiple embodiments of a stabilizing structure comprising windows.
Figure 32B:
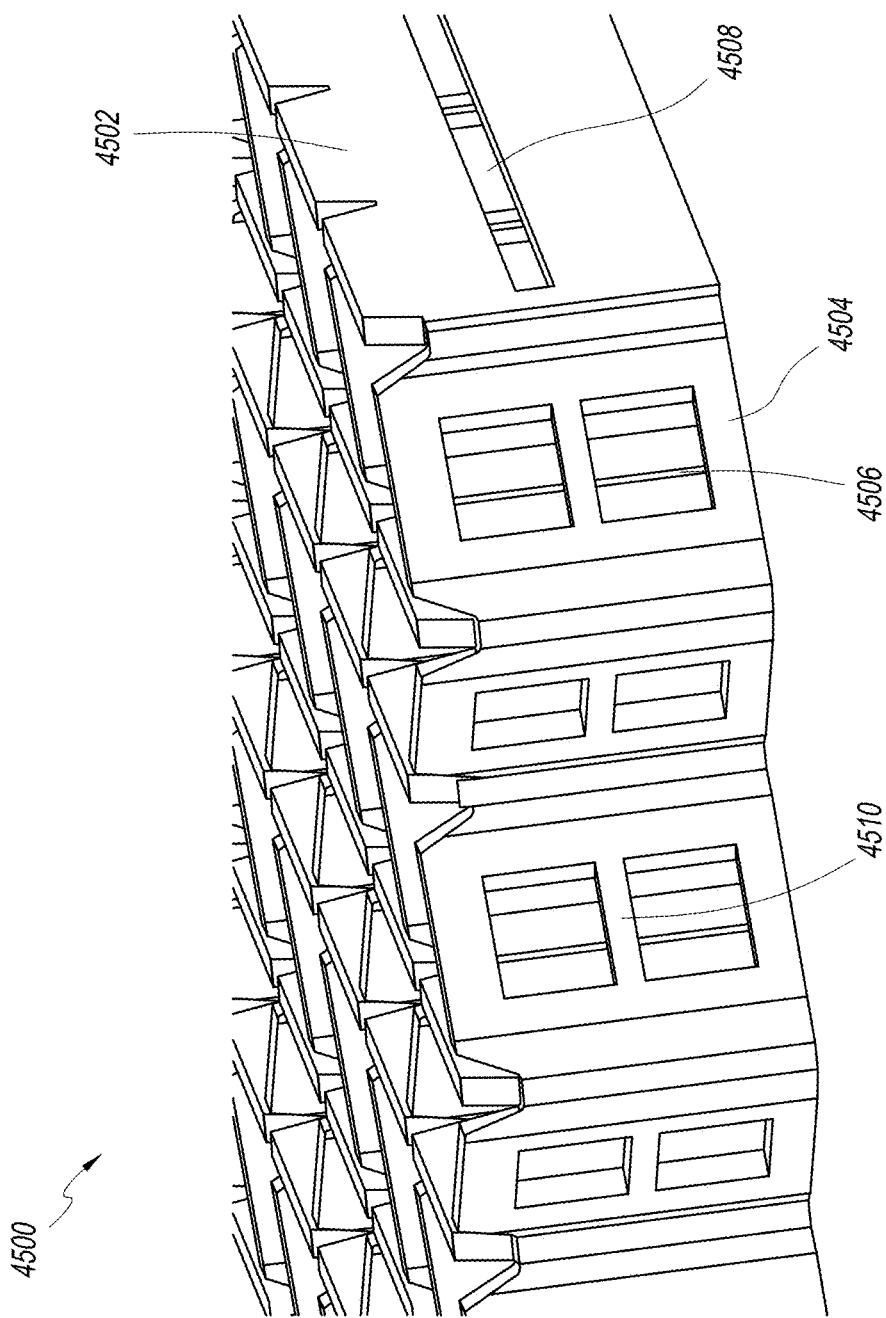

Stabilizing Structures of FIGS. 29A-32B45

FIGS. 29A-F illustrate embodiments of a stabilizing structure 4200 that are similar to the embodiments described above in relation to FIGS. 22A-25. The stabilizing structure may comprise a plurality of elongate strips 4202 arranged in parallel, whose longitudinal length can be aligned with the longitudinal axis when placed over a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time.

In some embodiments, the stabilizing structures described in this section or elsewhere in this specification can placed over a wound for a period of time and then removed or replaced with another stabilizing structure. The stabilizing structure may be individually removed and replaced, or a wound dressing incorporated the stabilizing structure may be removed and replaced. For example, a stabilizing structure could be placed over a wound for a period of time, promoting closure of the wound by applying force to draw the edges closer together. After a period of time has passed, the stabilizing structure can be replaced by a stabilizing structure of a different size or collapsibility, for example a stabilizing structure of a smaller size or decreased density. This process could be repeated over and over. In some embodiments, the stabilizing structure is configured to remain over the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate.

In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 29B:
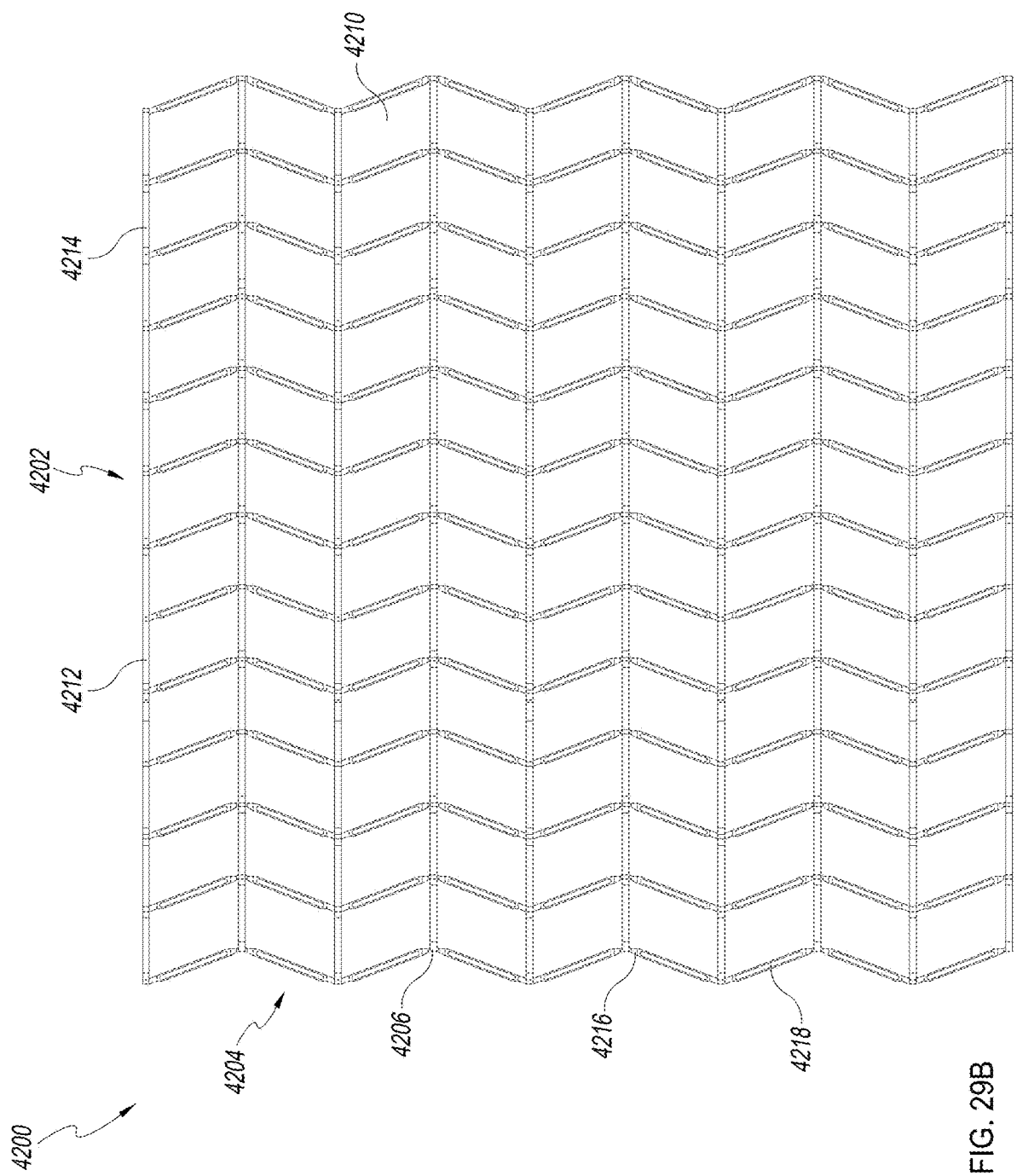
Figure 30A:
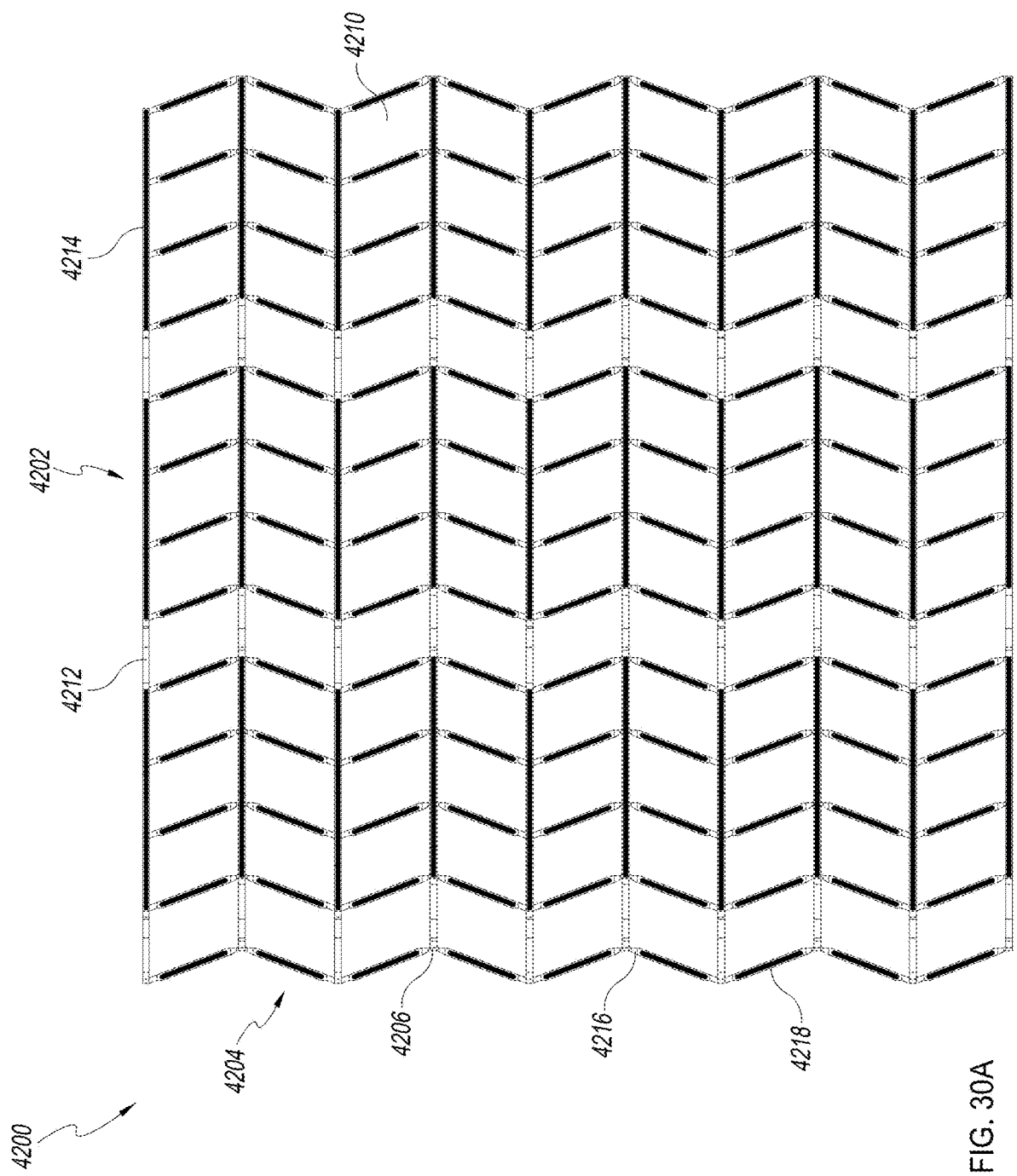
FIGS. 30A-D illustrate multiple views of an embodiment of a stabilizing structure comprising openings for fluid passage.
Figure 30B:
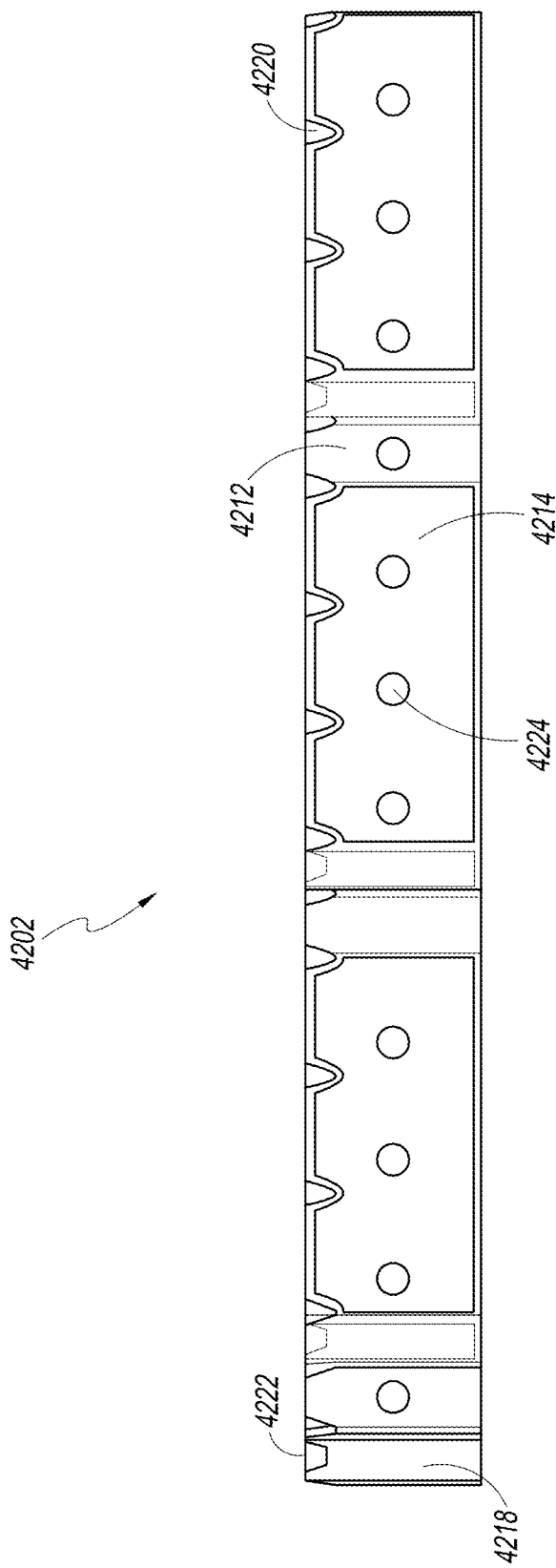
Figure 30D:
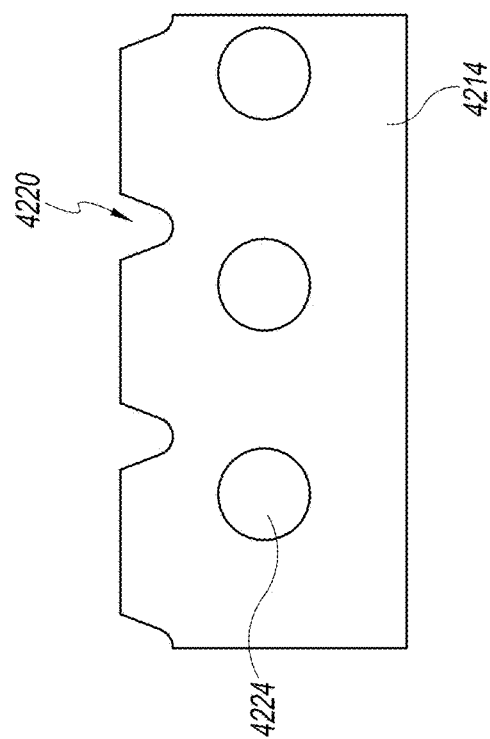
Figure 30C:
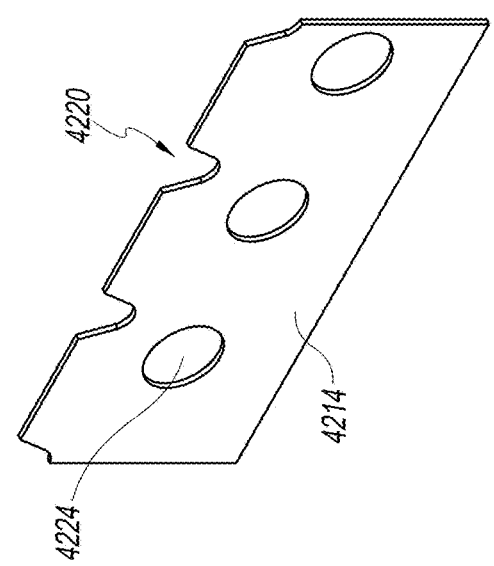

As illustrated in the perspective view of FIG. 29A and the top view of FIG. 29B, the intersection of the intervening members 4204 and the elongate strips 4202 may define a plurality of cells 4210. In certain embodiments, the cells 4210 may be of any of the shapes and sizes described in this section or elsewhere in this specification, such as those described in relation to FIGS. 22A-22C. For instance, a cell may be in the shape of a square, a diamond, an oblong, an oval, and/or a parallelepiped.

The joints 4206 are configured to allow the intervening members 4204 to collapse, similar to the joints described in FIGS. 22A-C and FIG. 24. The joints 4206 can be configured to allow the intervening members to collapse in any manner as described in this section or elsewhere in this specification in relation to other embodiments, such as those described in relation to FIGS. 22A-C. For example, the joints 4206 may be configured to allow or preferentially cause a first row of intervening members 4204 to collapse in one direction, while allowing or preferentially causing an adjacent row to collapse in another direction.

The elongate strips 4202 may comprise alternating flexing segments 4212 and supporting segments 4214. In a preferred embodiment, the flexing segments 4212 can be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 29A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material).

The elongate strips 4202 may be manufactured from a female mold that may further encompass the entire stabilizing structure 4200. The supporting segments 4214 can be inserted into the female mold, followed by an injection of a flexible polymer such as silicone and/or polyurethane to encase the supporting segments 4214 within the flexible polymer frame. The supporting segments 4214 can be inserted into the mold in any desired manner or quantity, allowing for many potential variations of the stabilizing device.

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure 4200. In such embodiments, the elongate strips 4202 may form pockets that are open from one side (e.g., from the top) to allow insertion and removal of the supporting segments 4214.

FIGS. 29C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 29C-D or any other similar shape.

The intervening members 4204 in some embodiments may comprise a first material 4216 with an embedded insert 4218 made of a more rigid material. One embodiment of the embedded insert is illustrated in FIGS. 29E-F. In certain embodiments, the insert 4218 is placed within a female mold and a flexible polymer such as silicone and/or polyurethane is injected around the insert to entomb the insert 4218 within a flexible polymer frame. The inserts 4218 can be inserted into the mold in any desired manner or quantity, allowing for many potential variations of the stabilizing device. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 29E illustrates a front view of insert 4218, while FIG. 29F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 29A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 29C-D, the sections may be detached along perforations or lines in the elongate strips corresponding to the notches 4220.

In some embodiments, the inserts 4218 may be entombed within first material 4216 in a variable number of intervening members 4204 to control the shape and collapse of the stabilizing structure 4200. In other embodiments, the inserts 4218 may be inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the stabilizing structure in a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 29A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

As described above and applicable to all stabilizing structures or wound closure devices described in this section or elsewhere in the specification, a soft polymer could be molded over the entire stabilizing structure 4200 to soften the feel of the device, thereby protecting the skin, organs and/or other tissues. In other embodiments, the soft polymer could be molded only over the bottom portion of the stabilizing device 4200, while in some embodiments the softer polymer can be molded over the top and/or the sides of the device. In some embodiments, the soft polymer could be molded over particular edges of the stabilizing structure 4200, such as those on the bottom, sides, and/or top. In certain embodiments, the soft polymer could be molded over any side or combination of sides of the stabilizing structure 4200. The soft polymer may act like a softened rim surrounding the hard edges of the stabilizing structure 4200.

FIGS. 30A-D illustrate multiple views of another embodiment of the stabilizing structure 4200, similar to the stabilizing structures depicted in FIGS. 22A-C and 29A-E. As in the stabilizing structure embodiment depicted in FIGS. 29A-F, the stabilizing structure 4200 comprises elongate strips 4202 and intervening members 4204. The elongate strips 4202 may comprise openings 4224 configured to allow the passage of fluid through the elongate strips 4202. To construct the openings, holes or other shapes may be punched directly through the elongate strips 4202. In the embodiment illustrated and as further shown in FIGS. 30C and 30D, the elongate strips 4202 further comprise more rigid inserts 4214 as described above. In such embodiments, the openings 4224 may be punched through the rigid inserts 4214 in locations of the strip where the inserts are located, as well as through flexing segments 4212 where the inserts are not located. The openings can be configured to evenly distribute fluid throughout the stabilizing device and/or direct fluid flow along a particular passage or direction. In other embodiments, the intervening members comprise openings, similar to the openings described in relation to the elongate strips.

Figure 31A:
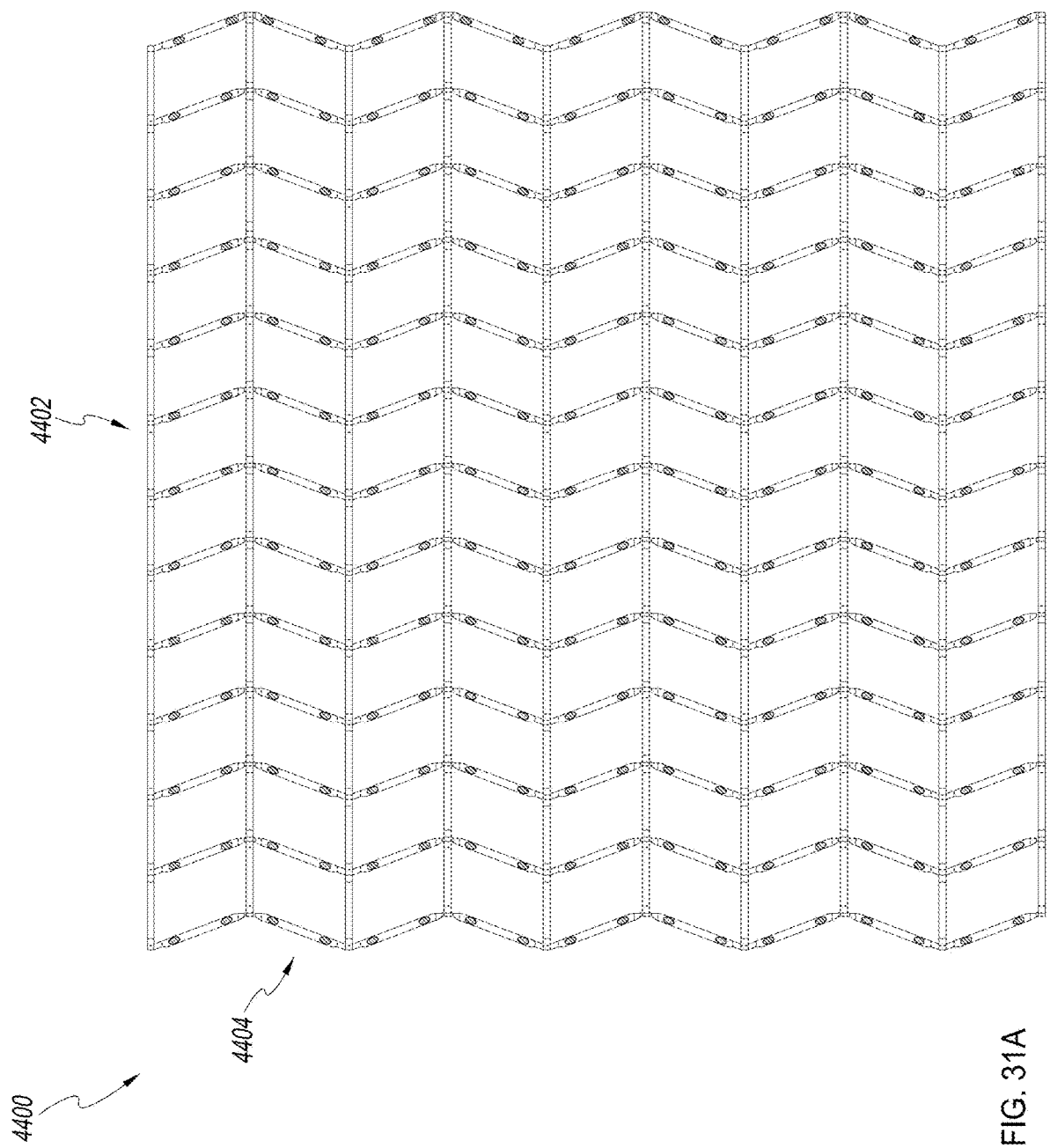
FIGS. 31A-C illustrate multiple embodiments of a stabilizing structure.
Figure 31B:
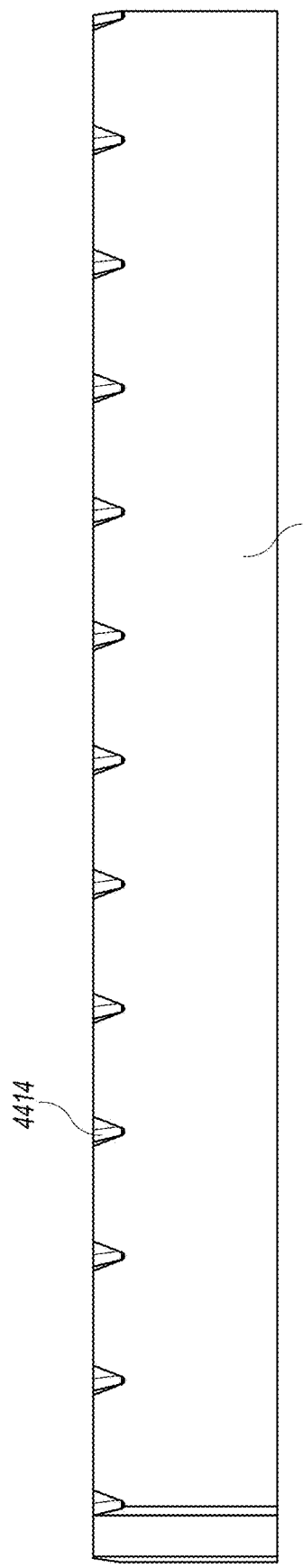
Figure 31C:
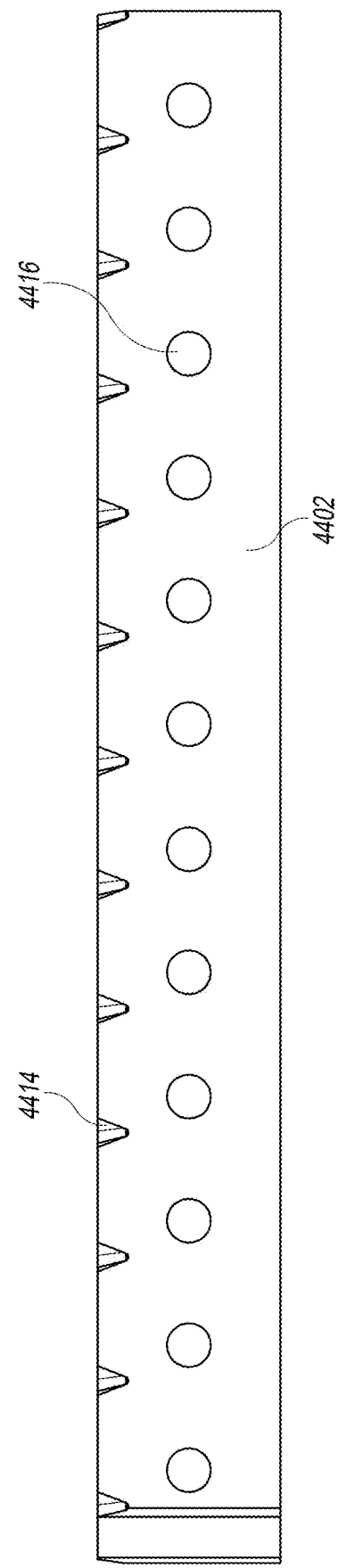

FIGS. 31A-B illustrate embodiments of a stabilizing structure 4400, with functional and structural elements similar to the embodiments of the stabilizing structure depicted in FIGS. 29A-F. Similar to the other stabilizing structures described previously, the stabilizing structure 4400 comprises elongate strips 4402 and intervening members 4404. The elongate strip 4402 may be a single unitary strip with no differing flexing segments or support segments and further comprise notches 4414. In certain embodiments, the elongate strip 4402 can be comprised entirely of rigid or semi-rigid materials such as polyvinyl chloride. In other embodiments, the elongate strip 4402 may be comprised entirely of flexible or semi-flexible material such as silicone and/or polyurethane. Similar to the embodiments described in FIGS. 29A-F, stabilizing structure 4400 may collapse in any manner described in this section or elsewhere in this specification within any timescale described in this section or elsewhere in this specification. FIG. 31C depicts an embodiment of stabilizing structure 4400 wherein the elongate strips 4402 comprise notches 4414 and openings 4416 to allow the passage of fluid.

FIGS. 32A-B illustrate embodiments of stabilizing structure 4500 that are similar to the stabilizing structures described above in relation to FIGS. 24A-27. Stabilizing structure 4500 comprises elongate strips 4502 and intervening members 4504. Intervening members 4504 can further comprise windows 4506, configured to allow the passage of fluid. In some embodiments, all intervening members 4504 may comprise windows 4506, however in other embodiments only the horizontally outermost intervening members 4504 comprise windows 4506, while the inner intervening members are similar to other embodiments described in this section or elsewhere in this specification.

In certain embodiments, at least about 5% of the intervening members comprise windows, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the intervening members.

The elongate strip 4502 may further comprise a gap 4508, configured to allow the passage of fluid. The gap may extend nearly the entire length of the elongate strips 4502 or extend only a portion of the length of the elongate strip 4502.

FIG. 32B illustrates an embodiment of a stabilizing structure 4500, where the windows 4506 further comprise bars 4510. In certain embodiments, at least about 5% of the windows comprise bars, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the windows.

Figure 33A:
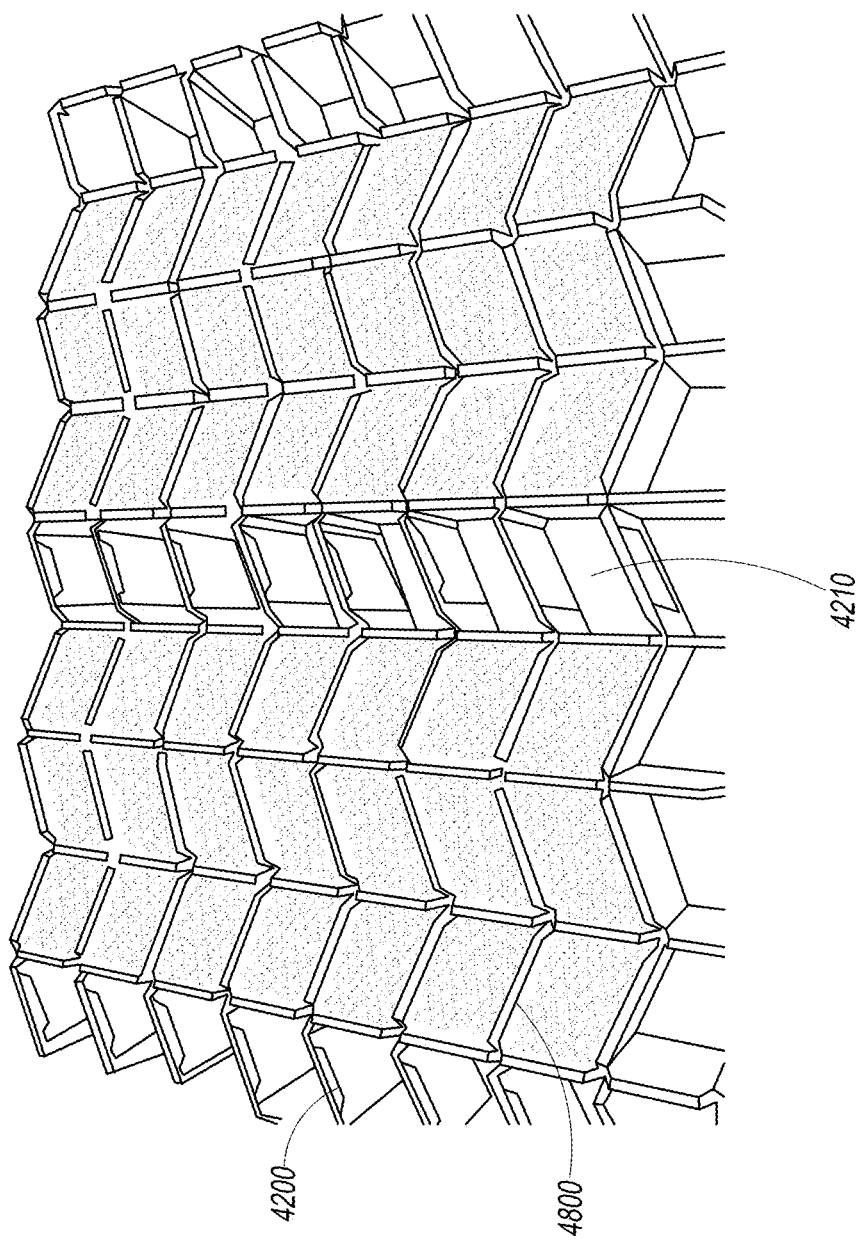
FIGS. 33A-C are photographs of various embodiments of a stabilizing structure comprising foam inserts.
Figure 33B:
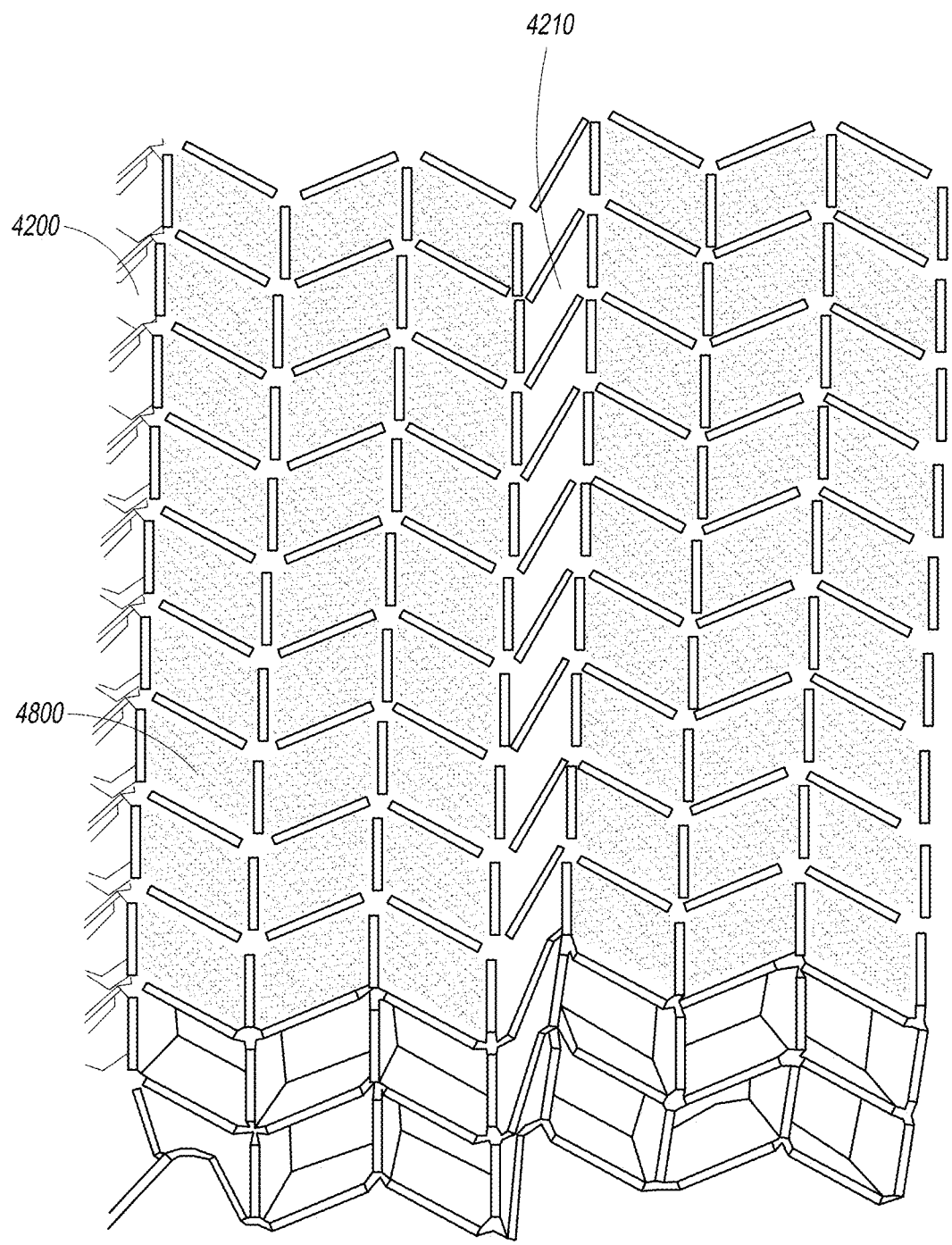
Figure 33C:
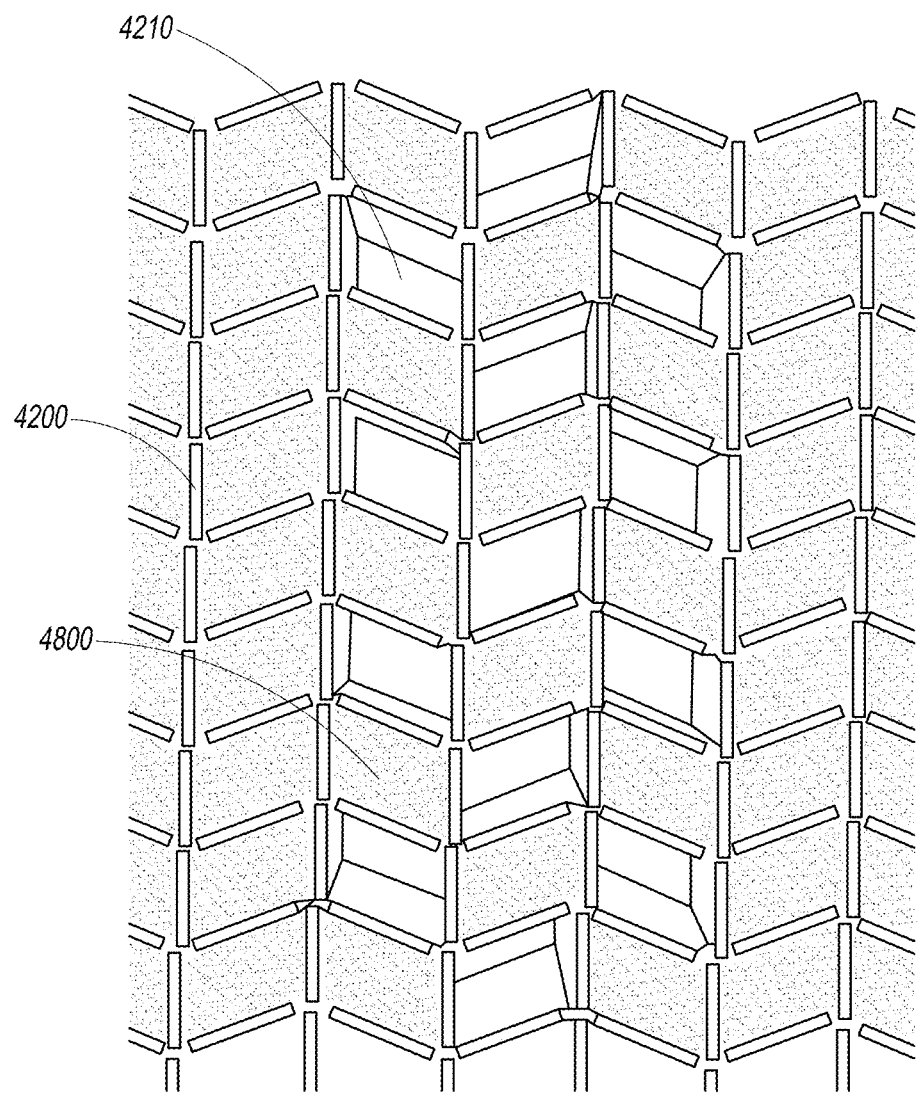

FIGS. 33A-C are photographs of embodiments of stabilizing structure 4200, similar to those embodiments of a stabilizing structure described in relation to FIGS. 29A-32B, further comprising foam inserts 4800. The inserts 4800 may be constructed from any material described in this section or elsewhere in this specification, including flexible foams, semi-flexible foams, semi-rigid foams, and rigid foams and other porous or compressible materials. The stiffness of the foam inserts 4800 can be used to control the collapse of stabilizing structure 4200. For example, stiffer foams may impede the collapse of the stabilizing structure 4200, while flexible foams may allow the stabilizing structure to collapse more quickly and easily. Varying the flexibility/stiffness of the foams allows the structure to collapse at any rate as described in this section or elsewhere in this specification. In some embodiments, the overall density of the stabilizing structure and/or wound closure device may be altered by increasing or reducing the amount of foam within the structure 4200. By reducing the overall density, the structure will be more readily collapsible. Thus, the use of a lower density structure with less foam may allow for greater wound closure as such a structure is more readily collapsible. Conversely, the use of a higher density structure with more foam may be less collapsible. In other embodiments, the foam inserts only comprise a portion of the individual cells 4210.

In some embodiments, the foams may be configured to degrade or dissolve over time, thereby allowing foam inserts to prop the stabilizing structure open initially, before later degrading or dissolving in a controlled manner to control the rate of collapse of the stabilizing structure. In further embodiments, the foam inserts may be impregnated with biologically active materials that may promote wound healing. For example, the biologically active materials may be anti-inflammatory molecules, growth factors, or anti-microbials.

FIG. 33A is a photographic perspective view of the stabilizing structure 4200 in an open state whereby the cells 4210 that do not contain foam are not collapsed. FIG. 33B is a photographic of the top of stabilizing structure 4200 wherein the cells 4210 are in a collapsed state. FIG. 33C is a photograph of a top view of the stabilizing structure 4200 wherein some of the rows have alternating cells filled with foam inserts 4800 or without foam inserts 4210. In some embodiments, the foam inserts can be inserted into at least about 5% of the cells, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of cells.

Foam or other porous material may surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement over the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

Figure 34A:
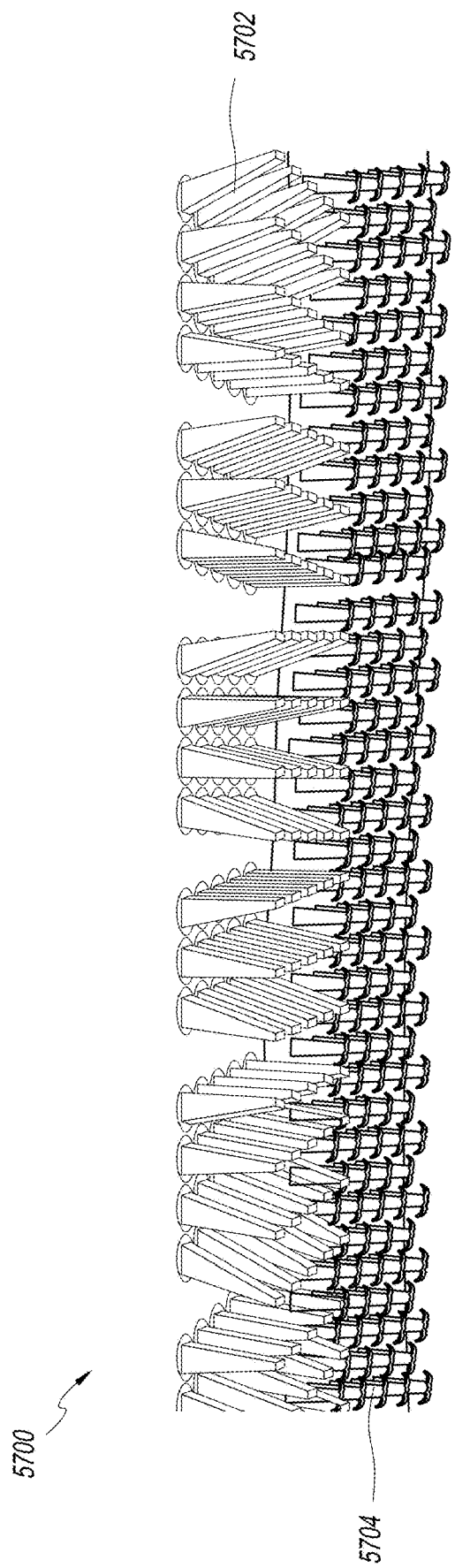
FIG. 34A-B are photographs of various embodiments of tissue anchors.
Figure 34B:
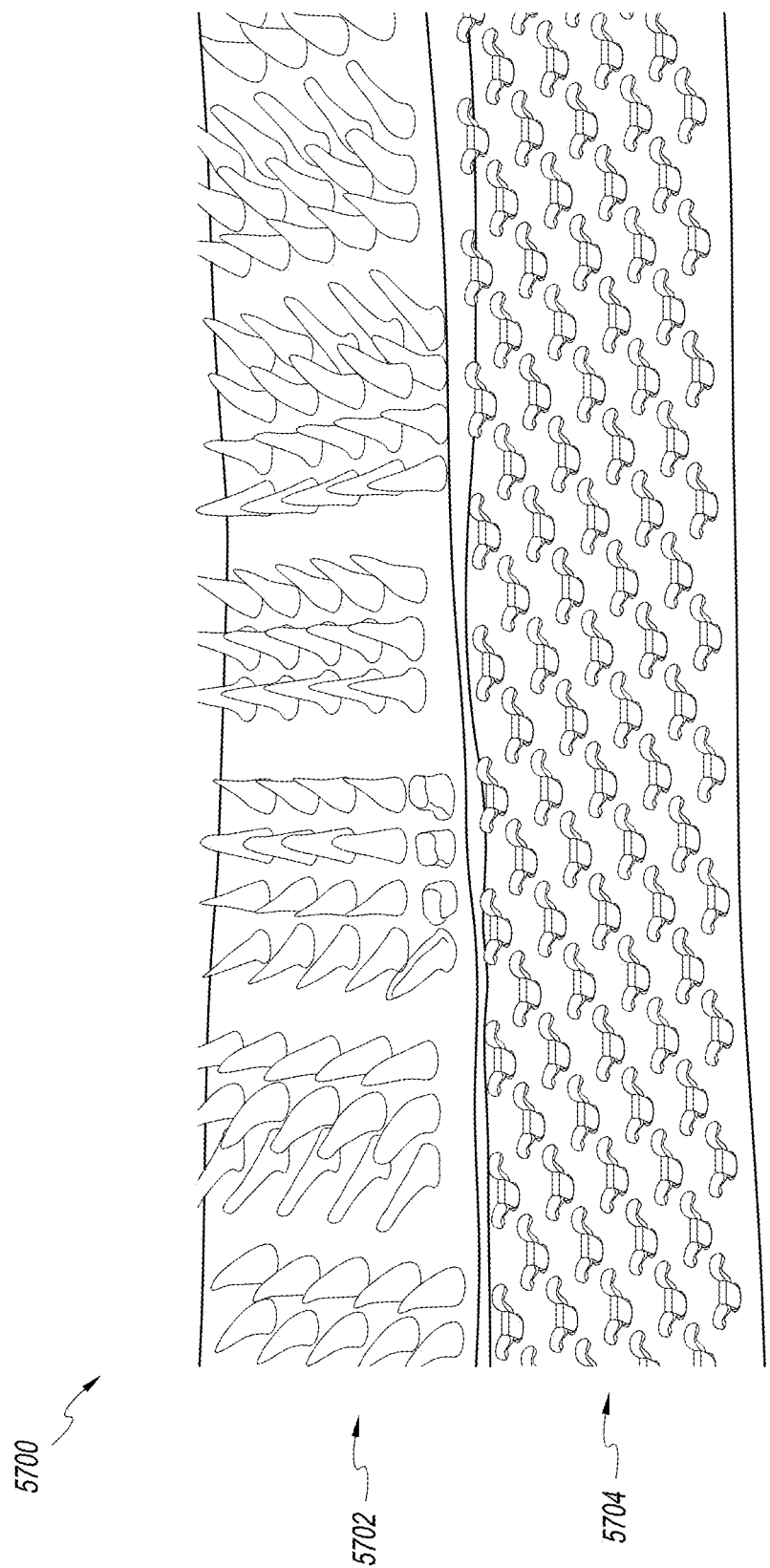

The Tissue Anchors of FIGS. 34A-B

FIGS. 34A-B are photographs of embodiments of an anchoring layer 5700 comprising two types of tissue anchors 5702 and 5704. One or more anchoring layers or anchors as described herein may be provided on any suitable surface of any of the stabilizing structure described herein to promote adherence to tissue. For example, one or more anchoring layers or anchors may be provided on a skin facing surface of the stabilizing structure. In certain embodiments, tissue anchors 5702, 5704 may comprise anchors such as those produced by Velcro industries, various barbs and/or various hooks. Anchors such as those described in relation to FIGS. 34A-B or elsewhere in this specification may be used to grip or penetrate various tissues, such as the tissues of the skin. Further, the structure of the anchors can have various forms depending on the tissue they are intended to penetration and grip. For example, longer anchors can be used for loosely bound tissues such as fat or connective tissue, while shorter anchors can be used for denser tissues such as muscle. Depending upon the shape of the anchor, shorter anchors may be more desirable for softer, fatty tissue, while longer anchors are utilized for denser tissues. Anchors with more rigid stems can be utilized to penetrate denser tissues.

In some embodiments, anchors can have bilateral prongs that tend to collapse upon insertion in tissue and yet expand when pulled in an opposite direction such that a certain pulling force can be applied to tissue. The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms. Further examples of suitable tissue anchors may include the hook and loop configuration of Velcro, barbs, hooks, spikes, pegs, arrowheads, or any suitable shape. Similar to anchors, some surfaces may serve to grip tissue, such as the tissues of the skin. For example, textured surfaces, such as roughened sandpaper-like surfaces, or nano-textured surfaces that may facilitate tissue adhesion.

In embodiments, the anchors 5702, 5704 may be suitable to grip or adhere to the skin. The anchors may penetrate the outer layers of the skin, such as the stratum corneum and adhere. The anchors may have various lengths for optimal penetration of the skin or gripping of other tissues. For example, the length of the anchors may be at most about 0.01 mm, at most about 0.1 mm, at most about 0.2 mm, at most about 0.5 mm, at most about 1 mm, at most about 2 mm, at most about 3 mm, at most about 5 mm, at most about 10 mm, at most about 20 mm, at most about 30 mm, at most about 40 mm, at most about 50 mm, at most about 75 mm, at most about 100 mm, or more than 100 mm.

In some embodiments, the use of surface anchors can be used in combination with a surgical adhesive, providing a much stronger bond than the adhesive alone, and providing temporary adhesion while the adhesive sets. In some embodiments, the surgical adhesive can be added to the anchors themselves. In certain embodiments, the surgical adhesive may simply be applied between the anchors to coat at least a portion of the anchoring layer. In further embodiments, the anchors may be replaced with a surgical adhesive, and the surgical adhesive may act to anchor a device to the surrounding wound.

In certain embodiments, the anchors may be constructed from a variety of materials, including any materials disclosed elsewhere in the specification, such as: synthetic or natural polymers, metals, ceramics, or other suitable materials. The anchors may be constructed from biodegradable materials such as biodegradable synthetic or natural polymers. Non-limiting examples of biodegradable synthetic polymers include: polyesters such as polylactic acid or polyglycolic acid, polyanhydrides, and linear polymers with biodegradable linkages. Further, the anchors may be constructed of biodegradable biological materials, such as autografts, allografts, and/or xenografts. In certain embodiments, the anchors may be constructed from any material described herein this section or elsewhere in the specification. For example, the anchors may be constructed from various polymers, such as silicone, or from metals such as stainless steel, aluminum alloys, or titanium alloys.

Figure 35:
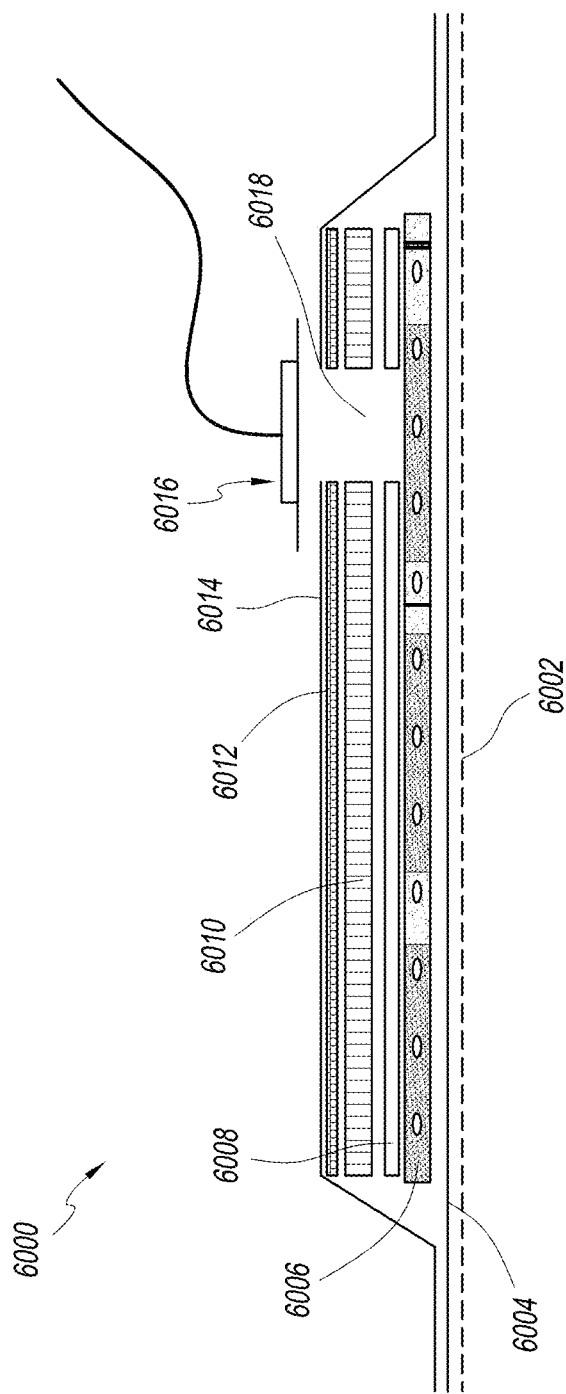
FIG. 35 is an illustration of an embodiment of a wound dressing comprising a stabilizing structure.
Figure 36:
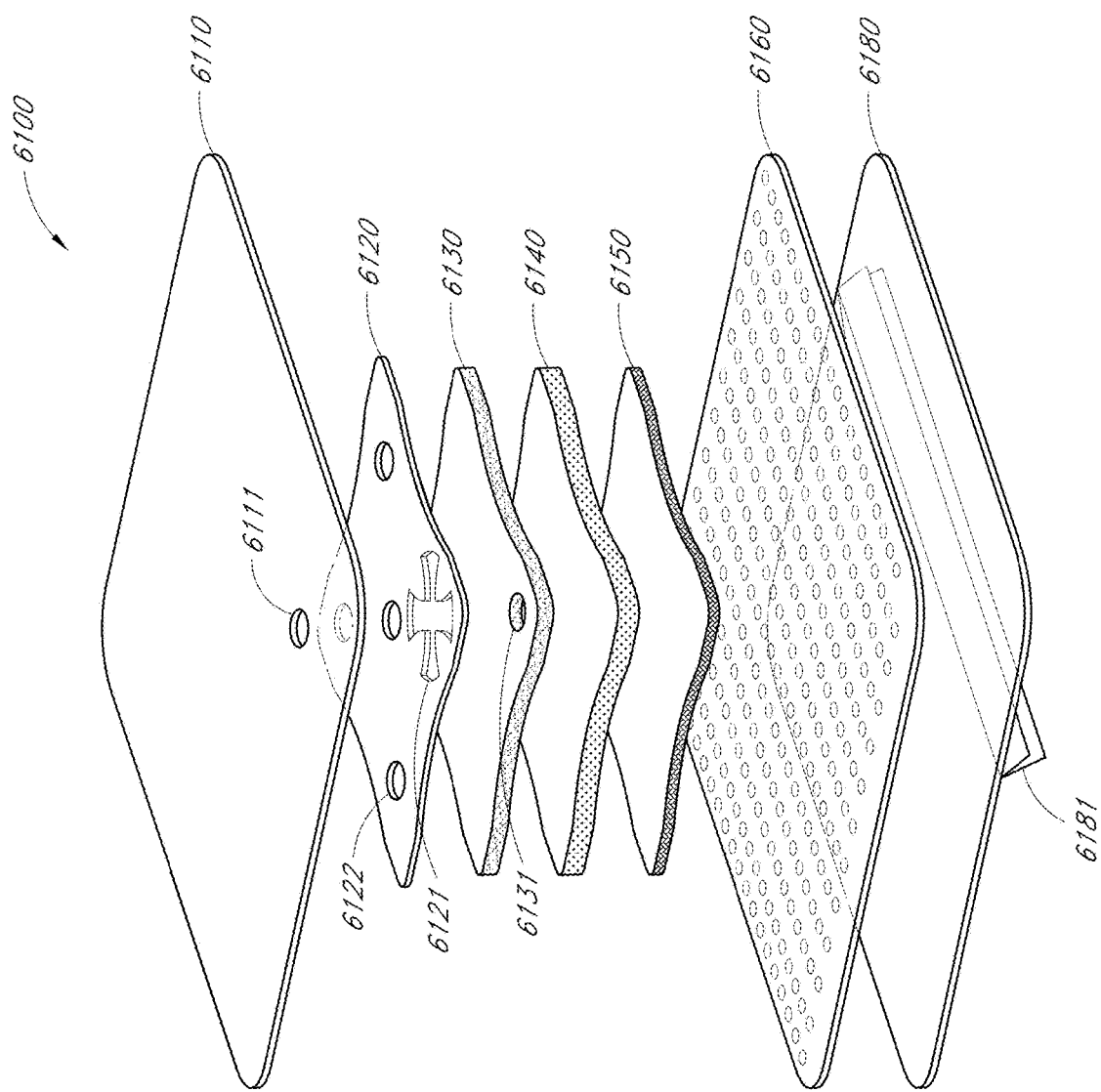
FIG. 36 is an illustration of an exploded view of an embodiment of a wound dressing comprising a stabilizing structure.
Figure 37:
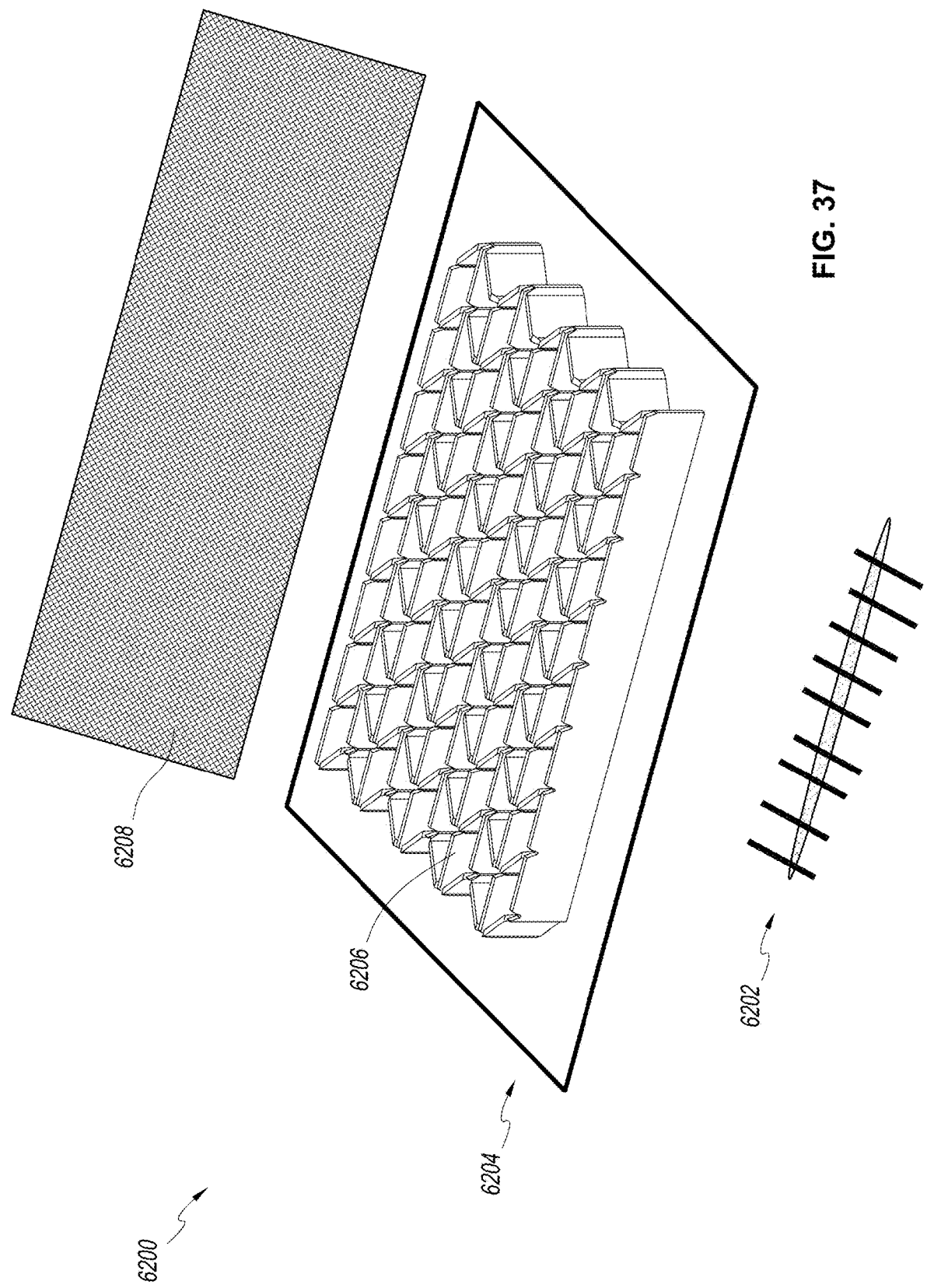
FIG. 37 is an illustration of an embodiment of a stabilizing structure in combination with a drape and wound contact layer.

The Wound Dressings and Systems of FIGS. 35-37

FIG. 35 illustrates a cross-sectional view of a dressing 6000 for use in negative pressure wound therapy, similar to the dressings described in relation to FIGS. 1-3B. Although this figure illustrates a dressing having one particular shape, the construction of the layers can be applied to any of the embodiments described herein this section or elsewhere in the specification. As will be described in greater detail herein this section or elsewhere in the specification, in particular embodiments the various components of dressing may be optional. For example, the dressing may contain all of the layers and components described herein this section or elsewhere in the specification, or the dressing may only contain some of the layers.

In some embodiments, the dressing 6000 comprises a release layer 6002, a wound contact layer 6004, a stabilizing structure 6006, an acquisition distribution layer (ADL) 6008, an absorbent layer 6010, an obscuring layer 6012, and a backing layer 6014. The dressing 6000 may be connected to a port 6016, described in greater detail in Appendix A. At least the wound contact layer 6004, stabilizing structure 6006, absorbent layer 6010, obscuring layer 6012, and backing layer 6014 may have properties described in greater detail in Appendix A, as well as or instead of the properties described herein this section.

In certain embodiments, the wound contact layer 6004, absorbent layer 6010, obscuring layer 6012, ADL layer

6008, and/or backing layer may be optional and can be incorporated or not incorporated into the dressing in any combination. As described in relation to FIGS. 1-2E, the dressing may be applied as a single unit comprising any of these optional elements and other elements such as the stabilizing structure. In certain embodiments and as described previously with respect to FIG. 1, the wound dressings of FIGS. 35-36 may be provided as a single article with all selected optional wound dressing elements or combination of elements, pre-attached and integrated into a single unit. In embodiments and as described in more detail later in relation to FIG. 37, most of the optional elements can be removed and the stabilizing structure can be placed directly over a closed wound and covered with a drape or backing layer.

It should be understood by one skilled in the art that the shape of the dressings depicted in FIGS. 1-3B, 35 and 36 is non-limiting. In other embodiments, the dressing may have a square shape, a lobed shape, an oval shape, a rounded shape, a diamond shape, a sacral shape, or any other suitable shape as may be desired for the treatment of a wound. Further details regarding embodiments of dressings with different shapes may be found in Appendix A.

It should be further understood by one skilled in the art that the design of the port and various layers of the dressings depicted in FIGS. 1-3B and 35A-B is non-limiting. In embodiments, the various layers of the dressing may be constructed from different materials, have different designs, or be attached to one another in various manners. Further, the dressings depicted in FIGS. 1-3B and 35A-B may additionally comprise further layers, structures, and functions. Additional details on the many possible embodiments of the dressings may be found in Appendix A.

Returning to FIG. 35, in certain embodiments, the stabilizing structure 6006 is similar to the stabilizing structures described in relation to FIGS. 4A-33C. As with the stabilizing structures described previously, the stabilizing structure 6006 is configured to collapse in any manner described herein this section or elsewhere in the specification. Further, the stabilizing structure 6006 may be constructed from any material or be of any design described herein this section or elsewhere in the specification, particularly as relates to the stabilizing structures of FIGS. 4A-33C. The stabilizing structure 6006 may be of any shape or size described herein this section or elsewhere in the specification, however in some embodiments the height of the stabilizing structure is at most 1 mm, 3 mm, 5 mm, 10 mm, 15 mm, 20 mm, 25 mm, 30 mm, 40 mm, 50 mm, or more than 50 mm. An outer perimeter of the stabilizing structure 6006 may be smaller or larger than the outer perimeter of the dressing layer positioned above, for example the ADL 6010 and/or absorbent layer 6010. In some embodiments, the entire outer perimeter of the stabilizing structure 6006 may be spaced inward from the outer perimeter of the overlying layer by 5 mm, or approximately 5 mm, or 2 mm to 8 mm, or approximately 2 mm to approximately 8 mm.

In certain embodiments, the collapsibility of the stabilizing structure allows the dressing 6000 to collapse in any manner described herein this section or elsewhere in the specification. As described previously in relation to FIGS. 3A-B, the dressing may collapse along different axes. As described previously, the dressing may collapse on various timescales. In embodiments, the dressing may only partially collapse for example, a dimension of the dressing may be reduced by at least about 5%, 10%, 25%, 50%, 75%, or more.

In particular embodiments, the stabilizing layer may further comprise tissue anchors such as those described in relation to FIGS. 34A-B. In certain embodiments, the tissue anchors are only attached to discrete portions of the stabilizing structure as needed. For example, the tissue anchors may cover at most about 5%, at most about 10%, at most about 20%, at most about 30%, at most about 50%, at most about 75%, and at most about 100% of the outside of the stabilizing structure. As described above, the tissue anchors may be particularly suited for attachment to the skin. In some embodiments, the tissue anchors may be substituted or supplemented by an adhesive, such as those described herein this section or elsewhere in the specification.

In some embodiments, the tissue anchors may be located on the wound contact layer 6004 and/or the backing layer 6014. For example, the tissue anchors may cover at most about 5%, at most about 10%, at most about 20%, at most about 30%, at most about 50%, at most about 75%, and at most about 100% of the wound contact layer and/or the backing layer.

By positioning the tissue anchors directly on the stabilizing structure 6006, the stabilizing structure can attach directly to the skin, thus allowing for the transmittal of closure force from the stabilizing structure directly to the skin and wound. In particular embodiments, the tissue anchors attached to the stabilizing structure penetrate through the wound contact layer into the skin. In some embodiments of the dressing, the wound contact layer is removed, thus allowing the tissue anchors or adhesives of the stabilizing structure to directly interact with the surrounding skin. Some embodiments may call for the tissue anchors to be positioned along the two edges of the dressing running parallel to the incision to relieve tension in the tissue around the incision. Further examples of tissue anchors and stabilizing structures may be found in PCT Patent Application PCT/US2014/061627, filed Oct. 21, 2014, entitled NEGATIVE PRESSURE WOUND CLOSURE DEVICE, the entirety of which is hereby incorporated by reference.

Returning to FIG. 35, the dressing 6000 may optionally comprise a wound contact layer 6004 for sealing the dressing 6000 to the healthy skin of a patient surrounding a wound area. The wound contact layer may comprise three layers: a polyurethane film layer, a lower adhesive layer and an upper adhesive layer. The upper adhesive layer may assist in maintaining the integrity of the dressing 6000, and the lower adhesive layer may be employed for sealing the dressing 6000 to the healthy skin of a patient around a wound site. The lower adhesive layer may also be employed to seal the dressing 6000 to the tissue anchors. The polyurethane film layer can be perforated. Some embodiments of the polyurethane film layer and upper and lower adhesive layers may be perforated together after the adhesive layers have been applied to the polyurethane film. Pressure sensitive adhesives, such as silicone, hot melt, hydrocolloid or acrylic based adhesives or other such adhesives, may be formed on both sides or optionally on a selected single side of the wound contact layer. In certain embodiments, the upper adhesive layer may comprise an acrylic pressure sensitive adhesive, and the lower adhesive layer may comprise a silicone pressure sensitive adhesive. Alternatively, the wound contact layer 6004 may not be provided with adhesive.

In some embodiments, the wound contact layer 6004 may be transparent or translucent. The film layer of the wound contact layer 6004 may define a perimeter with a rectangular or a square shape. A release layer 6002 may be removably attached to the underside of the wound contact layer 6004, for example covering the lower adhesive layer, and may be peeled off using flaps. Some embodiments of the release layer 6002 may have a plurality of flaps extending along the length of the layer 6002.

In alternative embodiments, a transmission layer (not shown) may be included in the dressing. The transmission layer may be in multiple locations, such as: below the stabilizing structure, between the stabilizing structure and the wound contact layer, above the stabilizing structure, between the stabilizing structure and the acquisition distribution layer, or between any other component layers of the dressing. Some embodiments of the transmission layer may be formed of a material having a three dimensional structure. For example, a knitted or woven spacer fabric (such as Baltex 7970 weft knitted polyester) or a non-woven fabric can be used. In some embodiments, the transmission layer can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 6000 where the absorbent layer 6010 helps lock the liquid away or itself wicks the liquid onwards towards the cover layer 6014 where it can be transpired. Other materials can be utilized, and examples of such materials are described in U.S. Patent Pub. No. 2011/0282309, hereby incorporated by reference and made part of this disclosure. However, the transmission layer is optional and more details regarding the transmission layer can be found in Appendix A.

Some embodiments may comprise a wicking or acquisition distribution layer (ADL) 6008 to horizontally wick fluid such as wound exudate as it is absorbed upward through the layers of the dressing 6000. Lateral wicking of fluid may allow maximum distribution of the fluid through the absorbent layer 6010 and may enable the absorbent layer 6010 to reach its full holding capacity. This may advantageously increase moisture vapor permeation and efficient delivery of negative pressure to the wound site. Some embodiments of the ADL 6008 may comprise viscose, polyester, polypropylene, cellulose, or a combination of some or all of these, and the material may be needle-punched. Some embodiments of the ADL 6008 may comprise polyethylene in the range of 40-150 grams per square meter (gsm). In some embodiments, the ADL 3440 may have a thickness of 1.2 mm or about 1.2 mm, or may have a thickness in the range of 0.5 mm to 3.0 mm, or about 0.5 mm to about 3.0 mm.

In certain embodiments, the ADL 6008 or any suitable wicking layer may penetrate the cells of the stabilizing structure to wick fluid away from the wound. The cells may be partially or fully penetrated by the ADL 6008 or suitable wicking layer depending upon the density and/or compressibility of the ADL 6008 or suitable wicking layer. In some embodiments, the cells may contain both superabsorber and an ADL 6008 or suitable wicking layer.

As described above, the dressing 6000 may comprise an absorbent or superabsorbent layer 6010. The absorbent layer can be manufactured from ALLEVYN™ foam, Freudenberg 114-224-4 and/or Chem-Posite™ 11C-450, or any other suitable material. Alternatively, the layer may be formed from gauze. In some embodiments, the absorbent layer 6010 can be a layer of non-woven cellulose fibers having superabsorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In some embodiments, the absorbent layer 6010 may have a thickness of 1.7 mm or about 1.7 mm, or may have a thickness in the range of 0.5 mm to 3.0 mm, or about 0.5 mm to about 3.0 mm.

For example, some embodiments of the absorbent layer 6010 may comprise a layered construction of an upper layer of non-woven cellulose fibers, superabsorbent particles (SAP), and a lower layer of cellulose fibers with 40-80% SAP. In some embodiments, the absorbent layer 6010 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc., more than 15 times its own weight or more than 20 times its own weight. Preferably, the material is capable of absorbing more than 30 times its own weight of 0.9% W/W saline, etc. The absorbent layer 6010 can have one or more through holes 6018 located so as to underlie the suction port.

Some embodiments of the present disclosure may employ a masking or obscuring layer 6012 to help reduce the unsightly appearance of a dressing 6000 during use due to the absorption of wound exudate. The obscuring layer 6012 may be a colored portion of the absorbent material, or may be a separate layer that covers the absorbent material. The obscuring layer 6012 may be one of a variety of colors such as blue, orange, yellow, green, or any color suitable for masking the presence of wound exudate in the dressing 6000. For example, a blue obscuring layer 6012 may be a shade of blue similar to the shade of blue commonly used for the material of medical gowns, scrubs, and drapes. Some embodiments of the obscuring layer 6012 may comprise polypropylene spunbond material. Further, some embodiments of the obscuring layer 6012 may comprise a hydrophobic additive or coating. Other embodiments may comprise a thin fibrous sheet of 60, 70, or 80 gsm. In some embodiments, the obscuring layer 6012 may have a thickness of 0.045 mm or about 0.045 mm, or may have a thickness in the range of 0.02 mm to 0.5 mm, or about 0.02 mm to about 0.5 mm.

FIG. 36 depicts an exploded view of an embodiment of a dressing similar to the dressing embodiment of FIG. 35, comprising a backing layer 6110, an obscuring layer 6120, an absorbent layer 6130, an ADL 6140, a stabilizing structure 6150, and a wound contact layer 6160. Here, the dressing 6100 is square shaped rather than rectangular.

However, as described previously, the dressing may take many shapes and many dressing embodiments are described in more detail in Appendix A. In addition to the components described below, embodiment illustrates the release layer 6180, flap(s) 6181, and through hole 6131.

The obscuring layer 6120 may comprise at least one viewing window 6122 configured to allow a visual determination of the saturation level of the absorbent layer. The at least one viewing window 6122 may comprise at least one aperture made through the obscuring layer. The at least one viewing window 6122 may comprise at least one uncolored region of the obscuring layer. Some embodiments of the obscuring layer may comprise a plurality of viewing windows or an array of viewing windows.

The masking capabilities of the obscuring layer 6120 should preferably only be partial, to allow clinicians to access the information they require by observing the spread of exudate across the dressing surface. The partial masking nature of the obscuring layer 6120 enables a skilled clinician to perceive a different color caused by exudate, blood, by-products etc. in the dressing allowing for a visual assessment and monitoring of the extent of spread across the dressing. However, since the change in color of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

The obscuring layer 6120 can have one or more through holes located so as to underlie the suction port. Some embodiments may have a maltese cross 6121 or other shaped cutout underlying the suction port, wherein the diameter of the maltese cross 6121 is greater than the diameter of the port. This may allow a clinician to easily asses the amount of wound exudate absorbed into the layers beneath the port. The obscuring layer 6120 may have an outer perimeter that is larger than the dressing layer or layers provided beneath it, for example the absorbent layer 6130, ADL 6140 and/or stabilizing structure 6150. In some embodiments, the entire outer perimeter of the obscuring layer 6120 is spaced 1 mm, or approximately 1 mm, or 0.5 mm to 3 mm, or approximately 0.5 to approximately 3 mm, beyond the dressing layer or layers provided beneath it. The larger perimeter of the obscuring layer 6120 may ensure that the underlying layers are adequately covered for visual obscuring of wound exudate. Further details and experiments relating to the obscuring layer may be found in Appendix A.

The dressing 6100 may also comprise a backing layer, or cover layer 6110 extending across the width of the wound dressing. The cover layer 6110 may be gas impermeable but moisture vapor permeable. Some embodiments may employ a polyurethane film (for example, Elastollan SP9109) or any other suitable material. For example, certain embodiments may comprise translucent or transparent 30gsm EU33 film. The cover layer 6110 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer 6110 can have an orifice 6111 located so as to underlie the suction port. The orifice 6111 may allow transmission of negative pressure through the cover layer 6110 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

Regarding the relative thicknesses of the layers of the dressing 6100, in some embodiments the wound contact layer 6160 may be flat and the top film layer 6110 may be contoured over the inner layers of the dressing 6100. The stabilizing structure 6150 may be half as thick as the ADL 6140 in some embodiments. In further embodiments, the stabilizing structure 6150 may be as thick or thicker than the ADL layer 6140. For example, the stabilizing structure may be at least about 1.5 times as thick, 2 times as thick, 3 times as thick, 5 times as thick, or 10 times as thick or more. In some embodiments, the absorbent layer 6130 may be about 1.5 times thicker than the stabilizing structure 6150. The obscuring layer 6120 may be about half the thickness of the spacer layer 6150.

In some embodiments, the length or width of the stabilizing structure 6150 may be greater that the thickness. For example, the stabilizing structure 6150 may have a thickness that is at most about: 10% of the length or width, 20% of the length or width, 30% of the length or width, 40% of the length or width, 50% of the length or width, or more than 50%. In some embodiments, the relative dimensions of the stabilizing structure 6150 may the same as the relative dimensions of the stabilizing structure embodiments described elsewhere in the specification.

FIG. 37 depicts an embodiment of system 6200 for the treatment of an incisional wound 6202 comprising a wound contact layer 6204 such as those described herein this section or elsewhere in the specification, a stabilizing structure 6206 such as those described herein this section or elsewhere in the specification, and a drape 6208 such as those described herein this section or elsewhere in the specification. This system may further comprise a source of negative pressure (not shown) in fluid communication with the wound. As is described elsewhere in the specification, tissue anchors such as those described in relation to FIGS. 34A-B or adhesives may be used to adhere the stabilizing structure 6206 to the skin surrounding the incisional wound 6202.

In some embodiments, gauze (not shown) may be placed under the stabilizing structure 6206 to prevent the formation of granulation tissue. Further, gauze may be substituted for the foam and/or absorbent layers described herein this section or elsewhere in the specification. In some contexts, gauze may advantageously reduce the formation of granulation tissue when used in combination with stabilizing structures such as those described herein this section or elsewhere in the specification, particularly in relation to FIGS. 1-3B and FIGS. 35-37.

Figure 38:
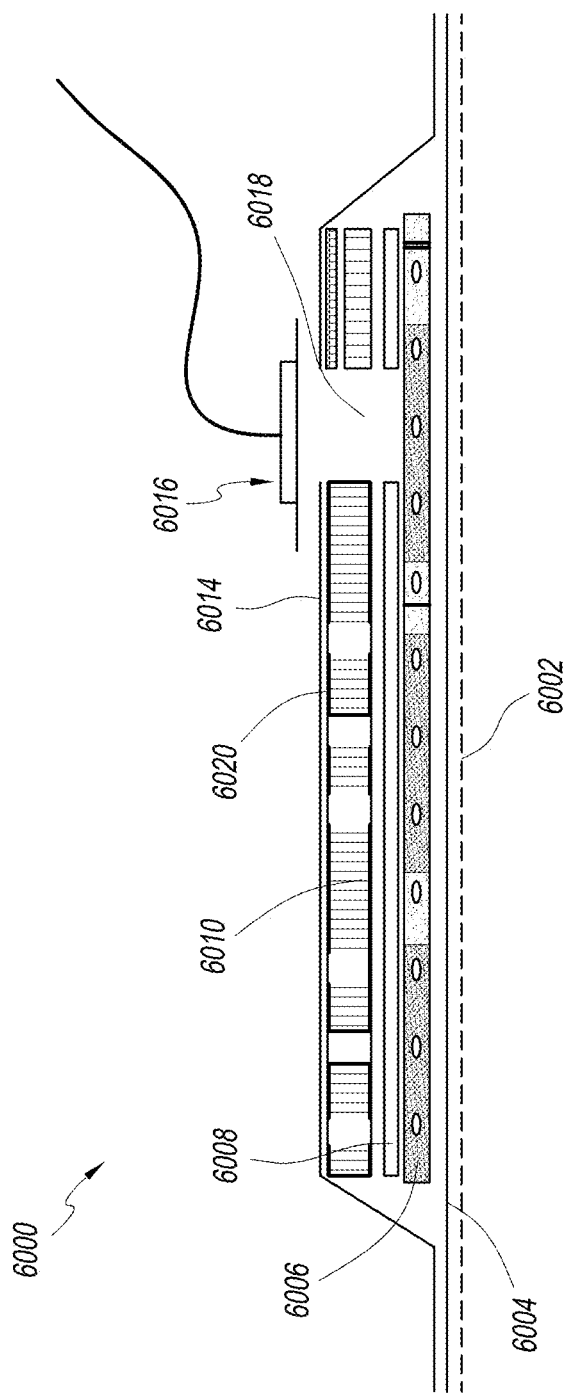
FIG. 38 is an illustration of an embodiment of a wound dressing comprising an absorbent layer with through holes.

FIG. 38 depicts an embodiment of a dressing 7000, similar to the embodiment 6000 depicted in FIG. 35 and described elsewhere in the specification. Similar to the dressing of FIG. 35, the stabilizing structure 6006 may be under the absorbent layer 6010 and beneath an optional acquisition distribution layer 6008, the absorbent layer optionally comprising superabsorbent material. The dressing 7000 may or may not have a masking layer, potentially allowing for direct viewing of and through the absorbent layer. The absorbent layer 6010 may comprise multiple through holes 6020 that pass through the layer. Further examples of through-holes may be found in U.S. Application No. 62/013,989, filed Jun. 18, 2014, entitled WOUND DRESSING AND METHOD OF TREATMENT, and U.S. Application No. 62/085,774, filed Dec. 1, 2014, entitled WOUND DRESSING AND METHOD OF TREATMENT. The aforementioned applications are hereby incorporated by reference in their entireties.

In some embodiments, some or all of through holes 6020 may comprise (that is, be plugged or filled using) a plug material, for example a soft, transparent and optionally hydrophobic material (e.g. silicone). The plug material is preferably made of a more rigid material than that of the absorbent layer. The plug material can provide the benefit of preventing lateral swelling of super absorbent particles in the absorbent layer 6010, which can cause the particles to spill out of the absorbent layer 6010 material at the cut edges, thereby filling (at least partially) the through holes 6020. The transparency of the plug material provides visibility through to the wound bed. As a result of the hydrophobic nature of some embodiments of the plug material, the through holes 6020 will remain transparent throughout wear time as colored wound exudate and other substances should not be drawn into the plug material because it is hydrophobic. In embodiments comprising an obscuring layer with viewing windows (not shown in FIG. 38, but described elsewhere in the specification), the viewing windows may be aligned with the through holes through the absorbent layer to allow for visualization through the dressing. As a further example, the though holes may be aligned with the cells of the stabilizing structure 6006, allowing for viewing all the way down into the wound, if the ADL is transparent or not included. In certain embodiments, the ADL may comprise through holes that align with the through holes in the absorbent layer. However, such alignment may not be necessary as the stabilizing structures described herein this section and elsewhere in the specification do not substantially obscure viewing in the vertical direction. In certain embodiments the cells of the stabilizing structure may optionally also be filled or partially filled with the plug material.

As described above, some examples of the plug material are non-absorbent, so they do not fill with exudate. In certain embodiments, larger through holes can be provided in dressing embodiments that utilize the plug material compared to dressing embodiments without plug material. In some embodiments, when plugs are provided in through holes 6020 of the absorbent layer 6010 and optionally in the cells of the stabilizing structure 6006, the cells of the stabilizing structure 6006 may be the same shape and dimension as the through holes 6020 or vice-versa. In other embodiments, when plugs are provided in through holes 6020 of the absorbent layer 6010, no stabilizing structure 6006 is provided.

The through holes 6020 in the absorbent layer 6010 may form a repeating pattern across the area of the absorbent layer 6010 with the exception of the area of the absorbent layer 6010 including the larger through hole 6018 for the port 6016. The repeating pattern may be in the form of a grid or array of through holes 6020 though other patterns may be used. In some embodiments, the through holes 6020 in the absorbent layer 6010 may be spaced apart by 10 mm (or about 10 mm) or less. In certain embodiments, the through holes may be spaced apart by at least about 0.5 mm, 1 mm, 2 mm, 4 mm, 5 mm, 10 mm, 15 mm, 20 mm, 30 mm, 40 mm, 50 mm, 75 mm, or more than 75 mm. In embodiments, the diameter of the through holds may be at most about 0.05 mm, 0.1 mm, 0.2 mm, 0.5 mm, 1 mm, 2 mm, 3 mm, 4 mm, 5 mm, 10 mm, 15 mm, 20 mm, 30 mm or more than 30 mm. In embodiments, the through hole 6018 underlying the port 6016 may be separate from the repeating pattern of through holes 6020 in the absorbent layer and larger than the through holes 6020, however in some embodiments the repeating pattern of through holes 6020 can continue across the entire area (or substantially all of the area) of the absorbent layer 6010 and the port can be placed over a selected one of the through holes in the array, or over a selected group of adjacent through holes in the array.

The through holes 6020 can be cut or formed in some embodiments by punching, die cutting, or laser cutting the sheet materials used to form the absorbent layer 6010. However, the creation of apertures, for example by hole-punching, has the disadvantages of resulting in the generation of waste and also the mechanical weakening of the material. By forming through slits in a material, these slits being capable of expanding to form apertures on extension of the material, increased visibility of the wound can be achieved without significant material waste. In this manner, it is also possible to achieve extension of the slit to form a circular hole without mechanically weakening the material. Examples of such lattice cutting techniques are disclosed in International Patent Publication No. PCT/US2007/079529, filed Sep. 26, 2007, titled "LATTICE DRESSING," the entirety of which is hereby incorporated by reference. In some embodiments separate plug material portions can be provided to the through holes in various layers (here, absorbent layer 6010), for example as the holes are punched or cut in the layer. In some embodiments, the layers may be stacked and hole punched or cut together and accordingly a single portion of plug material can be provided extending through the holes of multiple layers. In certain embodiments, as described previously, the through holes of the absorbent layer may be filled with a plug material. The plug material may be more rigid than the surrounding absorbent material (e.g. silicone material), thereby creating "pillars" of plug material within the absorbent layer. Due to the hydrophobicity and rigidity of the pillars, while under negative pressure the pillars may maintain their vertical stiffness while the absorbent layer compresses horizontally. Therefore, the absorbent layer will demonstrate anisotropic collapse, similar to the anisotropic collapse experienced by the stabilizing structures described throughout the specification. During collapse, the absorbent layer will compress horizontally while maintaining vertical rigidity, thereby causing the pillars to be drawn closer to one another. In certain embodiments, the absorbent layer may be constructed from a less dense non-woven material, thereby allowing for greater collapse in the absorbent layer. In other embodiments, the absorbent layer may be constructed from more dense materials, thereby reducing the amount of horizontal compression.

Figure 39:
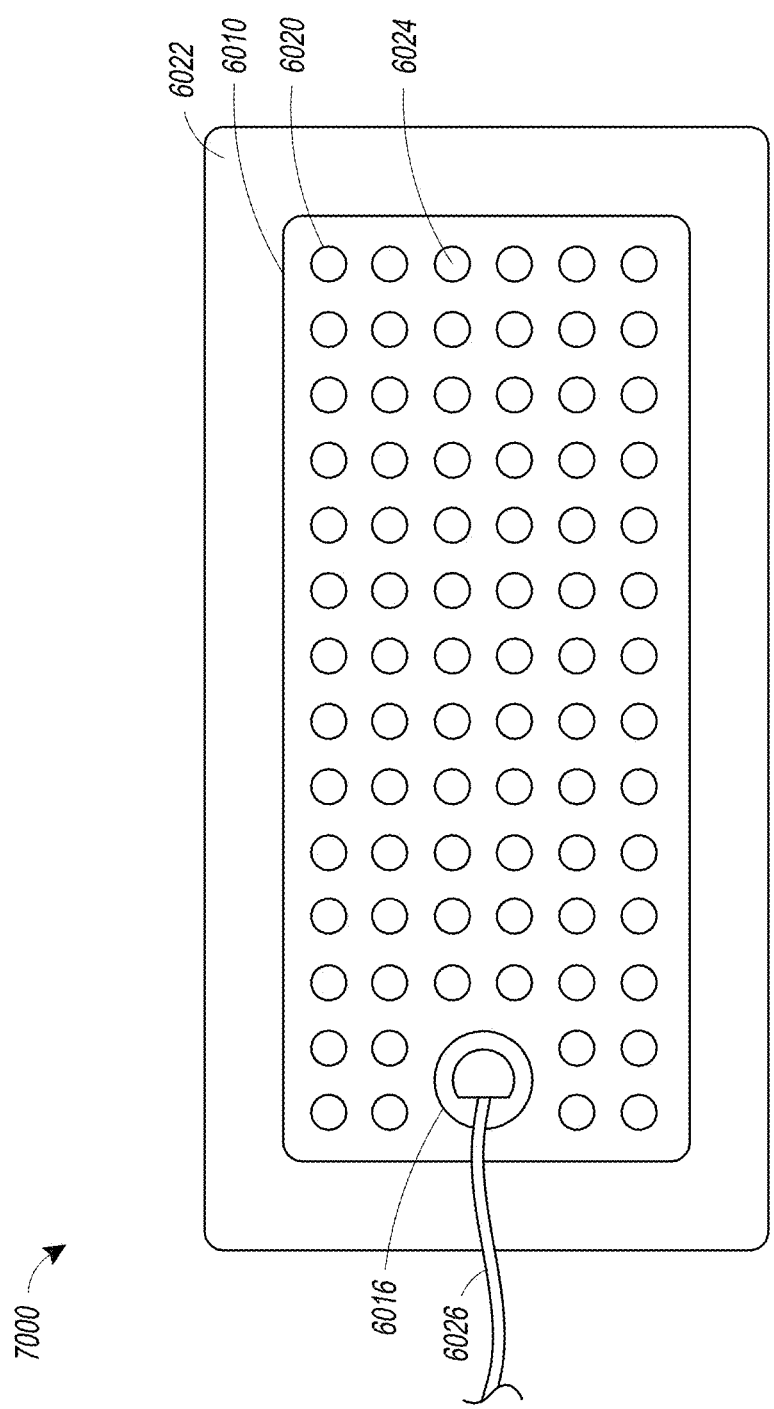
FIG. 39 is a top view illustration of an embodiment of a wound dressing comprising an absorbent layer with through holes.

FIG. 39 depicts a top view of an embodiment of a wound dressing 7000 configured for enhanced tissue visibility, similar to the wound dressing embodiment of FIG. 38. The wound dressing 7000 can be located over a wound site or potentially wound-forming tissue site to be treated as described above. In some embodiments, the dressing 7000 comprises a cover layer attached to a tissue contact layer, for example any of the cover layer or tissue contact layer embodiments described elsewhere in the specification. These two layers can be joined or sealed together around a perimeter 6022 so as to define an interior space or chamber in which therapeutic negative pressure can exist. This interior space or chamber may include absorbent layer 6010, which can be any of the absorbent materials described herein this section or elsewhere in the specification. A port 6016 and conduit 6026 can be attached to the dressing 7000.

As described elsewhere in the specification, the absorbent layer 6010 may include a number of through holes 6020 arranged in a repeating pattern. The through holes provide viewing portals 6024 through to the internal layers of the dressing 7000. In some embodiments, the optional ADL (6008 of FIG. 38) may not be included, be transparent, or contain aligned through holes. In such embodiments, since the stabilizing structure (not shown in FIG. 39) comprises a matrix with open vertical pathways, the viewing portals may provide a clear view through the dressing. As described above, some or all of the through holes in the absorbent layer may comprise a transparent plug material. Thus, due to the transparency or translucency of the cover layer and tissue contact layer, in embodiments the viewing portals 6024 can permit viewing of tissue beneath the wound dressing through the wound cover when the wound dressing is applied to a patient, for example enabling a clinician to assess characteristics of and changes in tissue underlying the dressing 7000.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. A negative pressure wound treatment apparatus, comprising:
    a wound dressing comprising a backing layer and a stabilizing structure positioned below the backing layer, the stabilizing structure comprising a plurality of cells and configured for placement over intact skin surrounding the wound;
    a port for communicating negative pressure to the wound dressing;
    an absorbent layer positioned between the stabilizing structure and the backing layer, the absorbent layer comprising a plurality of through holes, each through hole extending linearly from a top to a bottom of the absorbent layer and aligned with a corresponding cell, the through holes configured such that the absorbent layer collapses horizontally to a greater extent compared to an absorbent layer without through holes;
    a wound contact layer positioned beneath the stabilizing structure, the stabilizing structure positioned between the wound contact layer and the backing layer; and
    wherein the stabilizing structure is configured to be placed over an area of intact body surface adjacent the wound at least partially enclosing the wound area and collapse significantly more within a horizontal plane than within a vertical plane to apply a horizontal closing force through the wound contact layer over the intact skin surrounding the wound in the direction of a center of the wound when the wound dressing is placed under negative pressure.

2. The apparatus of claim 1, wherein the stabilizing structure comprises a first row of intervening members configured to rotate in a first direction and a second row of intervening members configured to rotate in a second direction, the first direction opposite the second direction.

3. The apparatus of claim 1, wherein the stabilizing structure comprises:
    a plurality of elongate strips;
    a plurality of intervening members connecting the elongate strips, wherein the plurality of intervening members are configured to pivot relative to the strips to allow the plurality of elongate strips to collapse relative to one another;
    wherein the intervening members between a first strip and a second strip are configured to pivot independently of the intervening members between a second strip and a third strip; and
    wherein the plurality of elongate strips and the plurality of intervening members connecting the elongate strips form a plurality of cells defined by one or more walls.

4. The apparatus of claim 3, wherein the intervening members are connected to the elongate strips via at least one joint.

5. The apparatus of claim 4, wherein the joint is a hinge.

6. The apparatus of claim 5, wherein the hinges are configured to collapse in one direction.

7. The apparatus of claim 4, wherein the joints are configured to restrict the movement of the intervening members.

8. The apparatus of claim 3, wherein the elongate strips are rigid.

9. The apparatus of claim 1, wherein the stabilizing structure is in the shape of an oval.

10. The apparatus of claim 1, wherein the wound dressing further comprises an acquisition distribution layer between the stabilizing structure and the backing layer.

11. The apparatus of claim 1, further comprising an adhesive configured to attach the wound dressing to the skin surrounding the wound.

12. The apparatus of claim 1, wherein the wound dressing is configured to relieve stress applied to sutures applied to the wound.

13. The apparatus of claim 1, wherein the backing layer is transparent or translucent.

14. The apparatus of claim 1, wherein the stabilizing structure is less than 20% as thick as it is wide or long.

15. A method of treating a wound with the apparatus of claim 1, comprising:
- placing the wound dressing over the wound with the stabilizing structure positioned over the skin surrounding the wound;
- applying negative pressure to the wound through the port; and
- wherein the stabilizing structure applies a horizontal force to the skin surrounding the wound when placed under negative pressure.

16. A negative pressure wound treatment apparatus, comprising:
- a wound dressing comprising a backing layer and a stabilizing structure positioned below the backing layer, the stabilizing structure comprising a plurality of cells and configured for placement over intact skin surrounding the wound;
- a port for communicating negative pressure to the wound dressing;
- an absorbent layer positioned between the stabilizing structure and the backing layer, the absorbent layer comprising a plurality of through holes, each through hole extending linearly from a top to a bottom of the absorbent layer, the through holes configured such that the absorbent layer collapses horizontally to a greater extent compared to an absorbent layer without through holes;
- a wound contact layer positioned beneath the stabilizing structure, the stabilizing structure positioned between the wound contact layer and the backing layer;
- an acquisition distribution layer, the acquisition distribution layer comprising a plurality of through holes, each through hole extending linearly from a top to a bottom of the acquisition distribution layer and aligned with a corresponding cell; and
- wherein the stabilizing structure is configured to be placed over an area of intact body surface adjacent the wound at least partially enclosing the wound area and collapse significantly more within a horizontal plane than within a vertical plane to apply a horizontal closing force through the wound contact layer over the intact skin surrounding the wound in the direction of a center of the wound when the wound dressing is placed under negative pressure.

17. The apparatus of claim 16, wherein the through holes in the acquisition distribution layer are aligned with the through holes in the absorbent layer.

* * * * *